(12) United States Patent
Clancy et al.

(10) Patent No.: US 11,749,383 B2
(45) Date of Patent: Sep. 5, 2023

(54) METHODS AND SYSTEMS OF PREDICTING AGENT INDUCED EFFECTS IN SILICO

(71) Applicant: The Regents of the University of California, Oakland, CA (US)

(72) Inventors: Colleen Clancy, Davis, CA (US); Pei-Chi Yang, Davis, CA (US); Kevin DeMarco, Davis, CA (US); Igor V. Vorobyov, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 694 days.

(21) Appl. No.: 16/089,331

(22) PCT Filed: Mar. 28, 2017

(86) PCT No.: PCT/US2017/024617
§ 371 (c)(1),
(2) Date: Sep. 27, 2018

(87) PCT Pub. No.: WO2017/172825
PCT Pub. Date: Oct. 5, 2017

(65) Prior Publication Data
US 2021/0074434 A1    Mar. 11, 2021

Related U.S. Application Data

(60) Provisional application No. 62/377,493, filed on Aug. 19, 2016, provisional application No. 62/314,337, filed on Mar. 28, 2016.

(51) Int. Cl.
*G16C 20/50* (2019.01)
*G16H 50/50* (2018.01)
(Continued)

(52) U.S. Cl.
CPC ............. *G16C 20/50* (2019.02); *G06N 20/00* (2019.01); *G16C 20/30* (2019.02); *G16C 20/70* (2019.02); *G16H 50/50* (2018.01)

(58) Field of Classification Search
CPC ........ G16H 50/50; G16C 99/00; G16C 20/50; G16C 20/30
(Continued)

(56) References Cited

U.S. PATENT DOCUMENTS 9,141,756 B1    9/2015  Hillis et al.
2004/0204862 A1  10/2004 Wainer et al.
(Continued)

FOREIGN PATENT DOCUMENTS

WO    WO-2008/027912 A2    3/2008

OTHER PUBLICATIONS

Clancy, et al., "Multiscale Modeling in The Clinic: Drug Design and Development", Annals of biomedical engineering, Feb. 17, 2016, vol. 44, No. 9, pp. 1-37; abstract; p. 4, fourth paragraph, p. 4, sixth paragraph. DOI: 10.1007/s10439-016-1563-0.
(Continued)

*Primary Examiner* — Thinh T Nguyen
(74) *Attorney, Agent, or Firm* — Foley & Lardner LLP

(57) ABSTRACT

The disclosure presents a new computer based model framework to predict drug effects over multiple time and spatial scales from the drug chemistry to the cardiac rhythm. The disclosure presents a new computer based model framework to predict drug effects from the level of the receptor interaction to the cardiac rhythm.

11 Claims, 46 Drawing Sheets

(51) Int. Cl.
 G06N 20/00 (2019.01)
 G16C 20/30 (2019.01)
 G16C 20/70 (2019.01)

(58) Field of Classification Search
 USPC .......................................................... 703/11
 See application file for complete search history.

(56) References Cited

U.S. PATENT DOCUMENTS

| 2015/0164878 | A1 | 6/2015 | Helson et al. | |
|---|---|---|---|---|
| 2015/0193575 | A1 | 7/2015 | Houghton et al. | |
| 2018/0224427 | A1* | 8/2018 | Abi Georges et al. | G01N 33/5008 |

OTHER PUBLICATIONS

International Search Report and Written Opinion dated Oct. 19, 2017, from application No. PCT/US2017/024617.

Brennan, et al., "Multiscale modelling of drug-induced effects on cardiac electrophysiological activity" European Journal of Pharmaceutical Sciences, vol. 36, No. 1, Jan. 31, 2009, pp. 62-77.

Carpenter, et al., "Identification of a Possible Secondary Picrotoxin-Binding Site on the GABA A Receptor", Chemical Research in Toxicology, vol. 26, No. 10, Oct. 2, 2013, pp. 1444-1454.

Clancy, et al., "Multiscale Modeling in the Clinic: Drug Design and Development", Annals of Biomedical Engineering, vol. 44, No. 9, Sep. 2016, pp. 2591-2610.

Collins, et al., "Modeling and Simulation Approaches for Cardiovascular Function and Their Role in Safety Assessment", CPT: Pharmacometrics & Systems Pharmacology, vol. 4, No. 3, Mar. 1, 2015, pp. 175-188.

Davis, et al., "RosettaLigand Docking with Full Ligand and Receptor Flexibility", Journal of Molecular Biology, vol. 385, No. 2, Jan. 16, 2009, pp. 381-392.

Extended European Search Report dated Oct. 9, 2019, from application No. 17776497.4.

Helson, et al., "Liposome mitigation ofcurcumin inhibition of cardiac potassium delayed-rectifier current", Journal of Receptor, Ligand and Channel Research, Nov. 1, 2012, pp. 1-8.

Sliwoski, et al., "Computational Methods in Drug Discovery", Pharmacological Reviews, vol. 66, No. 1, Jan. 1, 2014, pp. 334-395.

Villoutreix, et al., "Computational investigations of hERG channel blockers: New insights and current predictive models", Advanced Drug Delivery Reviews, vol. 86, Mar. 12, 2015, pp. 72-82.

Yarov-Yarovoy, et al., "Computational Models for Predictive Cardiac Ion Channel Pharmacology", Drug Discovery Today: Disease Model's, Jan. 1, 2017, pp. 3-10.

* cited by examiner

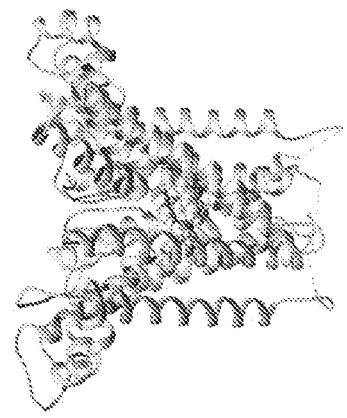
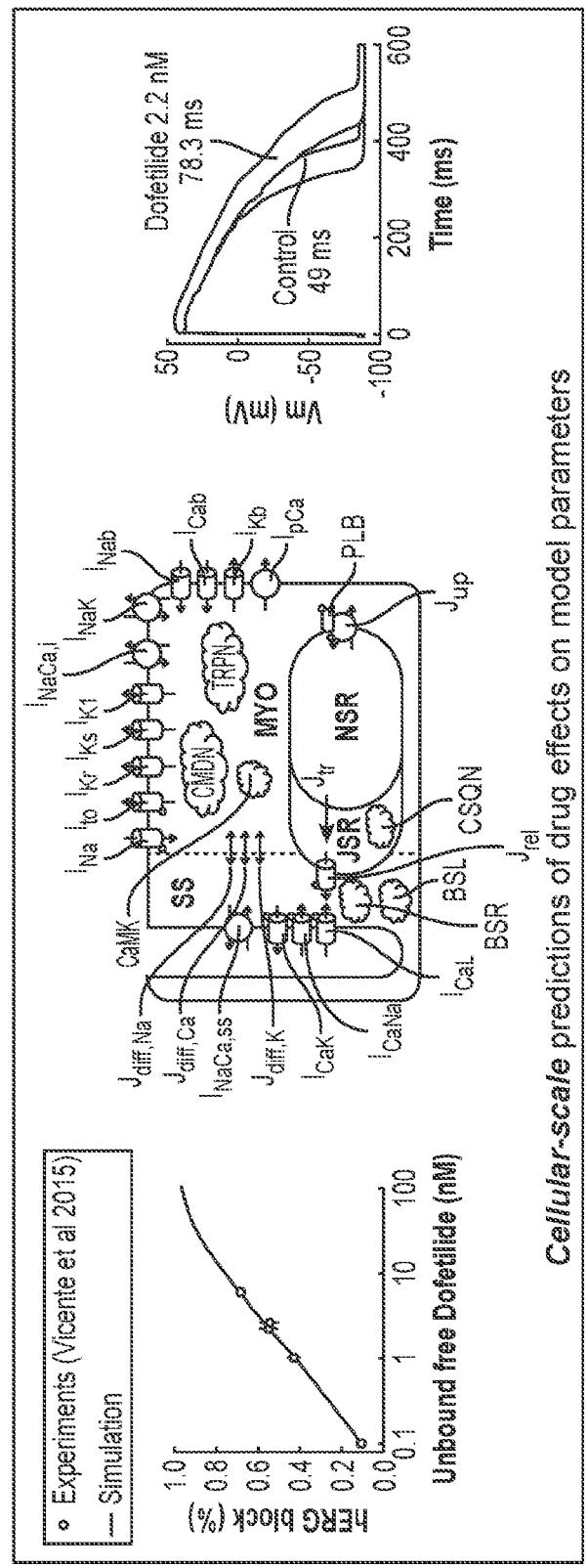
FIG. 2B (Cont. 1)

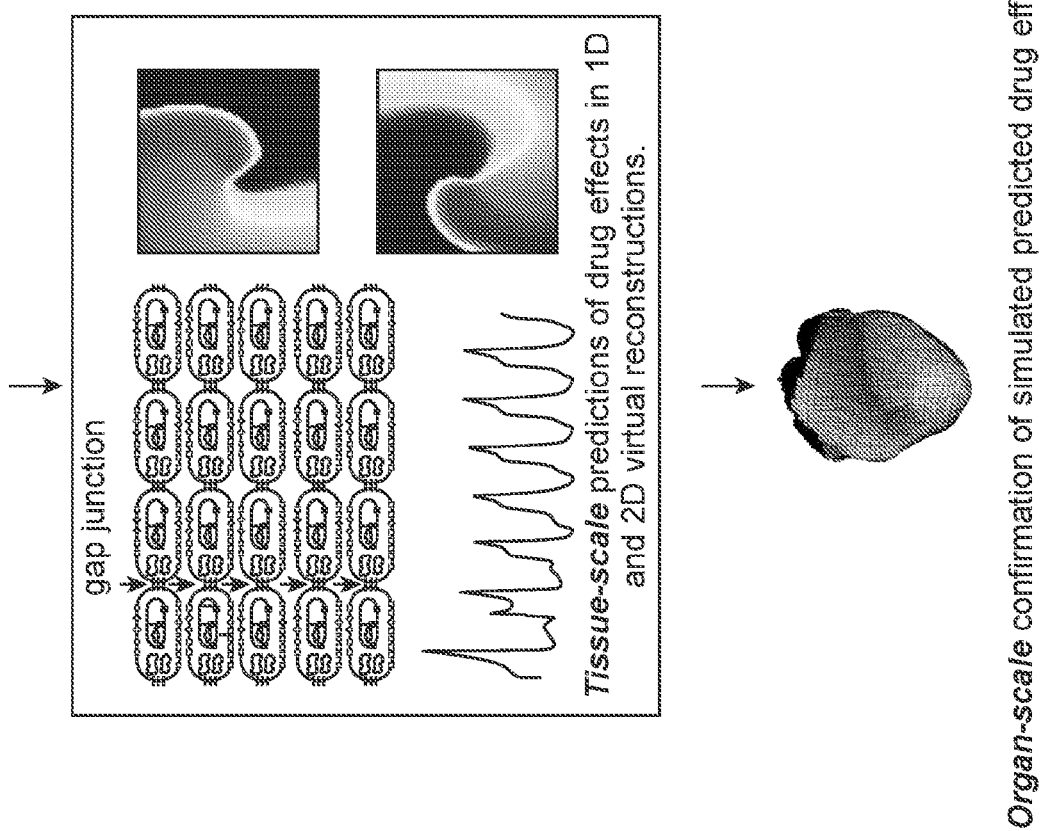
FIG. 2B (Cont. 2)

FIG. 23A  FIG. 23B

Open-inactivated

Dofetilide

FIG. 25A
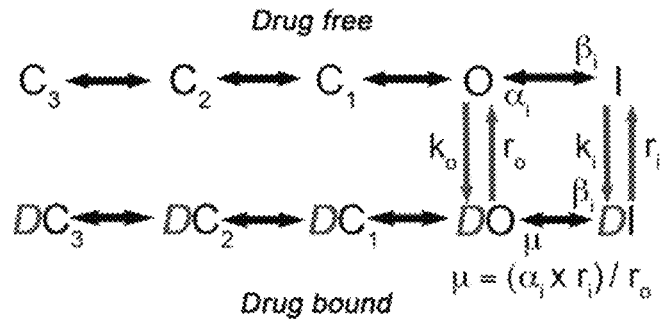
FIG. 25B
| Transition rates | Open (O) | Inactivated (I) |
|---|---|---|
| $k_x$ (nM$^{-1}$ ms$^{-1}$) | 0.02 | 0.02 |
| $r_x$ (ms$^{-1}$) | 0.028 | 1.586 |
| MD predicted kinetics (nM) | $K_{Do}$ = 1.4 | $K_{DI}$ = 79.3 |
FIG. 25C
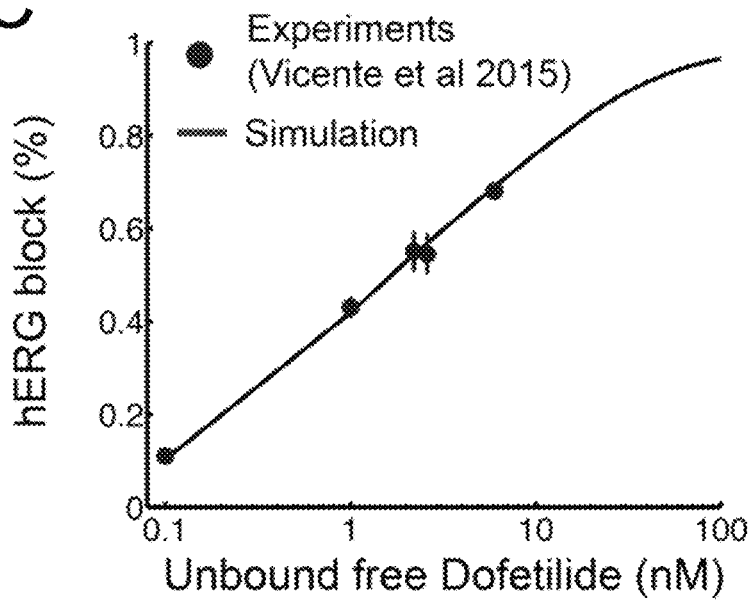

METHODS AND SYSTEMS OF PREDICTING AGENT INDUCED EFFECTS IN SILICO

CROSS-REFERENCE TO RELATED APPLICATIONS

This application claims priority under 35 U.S.C. § 119(e) to U.S. Provisional Application No. 62/314,337, filed Mar. 28, 2016, and U.S. Provisional Application No. 62/377,493, filed Aug. 19, 2016, the contents of each of which is hereby incorporated by reference in its entirety.

STATEMENT OF GOVERNMENT SUPPORT

This invention was made with government support under Grant No. R01HL1 28537-01A1 and U01 HL126273 awarded by National Institutes of Health. The government has certain rights in the invention.

BACKGROUND

Cardiotoxicity in the form of deadly abnormal rhythms is one of the most common and dangerous risks for drugs in development. Drug-induced proarrhythmia and prolongation of the QT interval have been so tightly associated that the QT interval has become widely accepted as a surrogate marker for arrhythmia. The problem with this approach is that it is neither sensitive nor selective, resulting in many potentially useful drugs eliminated early in the drug discovery process. There is an urgent need for new approaches to screen and predict the effects of drugs on cardiac rhythms.

Cardiotoxicity is a common risk for drugs in development, often manifesting as prolongation of the QT interval in the ECG and an increased likelihood for life-threatening ventricular arrhythmias (Roden, D. M. (2004) N Engl J Med 350:1013-1022; Hondeghem, L. M. (2008) Heart Rhythm 5:1210-1212; Sager, P. T. et al. (2014) Am Heart J. 167: 292-300). In this context of drug induced cardiac arrhythmia, the vital hindrance to prevention of electrical rhythm disturbances is a lack of meaningful approaches to predict effective or harmful actions of drugs. An important example is the use of QT interval prolongation as a surrogate marker for proarrhythmia (Hondeghem, L. M. (2008) Heart Rhythm 5(8):1210-1212). QT interval prolongation, is the metric for "Thorough QT Studies (TQT)" that are performed for preclinical drug candidates to assess potential for proarrhythmia (International Conference on Harmonisation (2005) Notice. Fed Regist. 70(61134-61135)). QT interval prolongation typically arises from hERG block in ventricular myocytes and hERG interaction must be analyzed for all drug candidates to determine their potential for proarrhythmia (International Conference on Harmonisation (2005) Notice. Fed Regist. 70(61134-61135)). Since 2005, the regulatory process for preclinical drug candidates includes a dedicated clinical study in healthy volunteers, the so-called "Thorough QT Study." A drug that results in greater than 5 ms QT prolongation above normal in healthy humans indicates "regulatory concern" (www.fda.gov/downloads/drugs/guidancecomplianceregulatoryinformation/guidances/ucm073153.pdf).

Abnormal cardiac electrical activity is most often a side effect from unintended block of the promiscuous drug target hERG, the pore-forming domain of the delayed rectifier $K^+$ channel in the heart. Block of hERG leads to prolongation of the QT interval on the ECG, a phase of the cardiac cycle that corresponds to underlying cellular repolarization.

A limitation of this approach is that many potentially useful drugs are eliminated early in the drug discovery process and development because they block hERG and thereby may cause acquired Long-QT syndrome. Numerous drugs with potential for high therapeutic value never make it to the market because of their hERG positive signal. Here the disclosure considers an alternative approach that involves addition of an additional drug that selectively blocks late Na current ($I_{NaL}$) in order to "cancel" the hERG blocking effect. This approach, if useful, may be warranted in instances where a hERG positive therapy is uniquely indicated for disease and no alternative therapies exist.

The problem is that many useful drugs that were approved prior to the 2005, including even the commonly used anti-arrhythmic agents verapamil, ranolazine and amiodarone to name a few, all fail the Thorough QT test—they all block hERG and prolong QT interval. Indeed, there exist numerous examples of safe and effective drugs (including antiarrhythmics, antipsychotics and antibiotics) that gained FDA approval prior to TQT implementation (Roden, D. M. (2004) N Engl J Med. 350(10):1013-1022; Hondeghem, L. M. (2008) Heart Rhythm 5(8):1210-1212; Hondeghem, L. M. (2006) J Cardiovasc Electrophysiol. 17(3):337-340). If screened today, these safe drugs would fail the test.

Not all hERG block is proarrhythmic. But, at present, there is no way to distinguish unsafe hERG blockers from safer drugs. There are at least two distinct classes of hERG blockers that prolong QT interval (Roden, D. M. (2004) N Engl J Med. 350(10):1013-1022). In the first group are drugs that block hERG, prolong QT interval and increase proclivity to potentially deadly torsades de pointer (TdP) arrhythmias. The second group consists of hERG blockers that prolong QT interval and do not carry risk for ventricular arrhythmias. There have been many attempts to distinguish the two classes of hERG blockers via "top-down" approaches including studies devoted to analytical methods aimed at assessing the relationship between rate corrected QT "morphology" and arrhythmia risk (Vila, J. A. et al. (2000) IEEE Trans Biomed Eng. 47(6):764-772; Jie, X. et al. (2010) Conf Proc IEEE Eng Med Biol Soc. 2010:2565-2568; Couderc, J. P. (2010) J Electrocardiol. 43(6):595-600; Couderc, J. P. (2010) Cardiol J. 17(4):416-419). Unfortunately none of these approaches have yet been proven sufficiently effective to justify their widespread implementation.

The exploration of adjunctive therapy to mitigate drug side effects is with strong precedent (Johannesen, L. et al. (2016) Clin Pharmacol Ther. 99:214-223; Vicente, J. et al. (2015) J Am Heart Assoc 4:e001615; Johannesen, L. et al. (2014) Clin Pharmacol Ther. 96:549-558). A longstanding example can be found in effective antiarrhythmic drugs, which while categorized by their primary mechanism of action, exhibit off-target effects that apparently mitigate proarrhythmia risk. Included in this group is the most effective therapeutic for treating cardiac ventricular arrhythmias, amiodarone, a dirty drug whose multiple off-target effects likely underlie its efficacy.

SUMMARY

The present disclosure discusses systems and methods for determining the effects induced by agents in silico. Drug screening can often use surrogate markers or proxies to predict drug side effects on a patient. The present system can be used for preclinical drug screening to identify agents that may cause actual drug side effects rather than relying on the surrogate markers. The present system can use a bottom-up, multi-scale model to predict the side-effects of drugs. The present system can model and determine the kinetics of primary and major off-target agent interactions at the atomic scale. This information can be integrated into a model to predict ion channel states at the protein function scale. This information can be integrated into a model to predict action potential characteristics at the cellular level. The information from the models can also be integrated into a tissue-scale model to predict drug efficacy.

The disclosure proposes that the fundamental mode of drug interaction derived from each drug's unique structure activity relationship determines the resultant effects on cardiac electrical activity in cells and tissue. By capturing the intrinsic complexity of drug channel interactions in a model, a system executing the various models is expected to be able to predict drug safety or electro-toxicity in the heart.

The system described herein can be used to predict the effects of many different agents. In some implementations, the agent is an agent that blocks hERG and prolongs a QT interval. In some implementations, the agent can cause Torsades de pointes (TdP). In other implementations, the agent is an agent that blocks hERG and prolongs a QT interval, but does not cause TdP. The agent can be a drug, an antibody, a small molecule agent, a pharmaceutical composition, a therapeutic peptide or protein, among others. The present disclosure provides details relating to K and Na channels, and it should be appreciated by one of ordinary skill in the art that similar techniques can be employed for Ca channels as well.

The disclosure presents a new computer based model framework to predict drug effects over multiple time and spatial scales from the drug chemistry to the cardiac rhythm. The disclosure presents a new computer based model framework to predict drug effects from the level of the receptor interaction to the cardiac rhythm. The disclosure presents a computational pipeline to predict cardiotoxicity over multiple temporal and spatial scales from the drug chemistry to the cardiac rhythm. This disclosure provides a model framework for predictions from atomic hERG structure simulations to generate kinetic parameters of function scale hERG ion channel models that capture dynamical interactions of drugs and ion channels. The computational components are then integrated into predictive models at the channel, cell and tissue scales to expose fundamental arrhythmia vulnerability mechanisms and complex interactions underlying emergent behaviors. Experimental and clinical data from the literature are used to validate model predictions. The disclosure sets out to test the hypothesis that the fundamental mode of hERG drug interaction derived from each drug's unique structure activity relationship determines the resultant effects on cardiac electrical activity in cells and tissue. The model framework represents a proof-of-concept development. The disclosure demonstrates its usefulness by applying the new framework to predict electro-toxicity in the heart for the prototype drug dofetilide.

According to one aspect of the disclosure, a method of predicting agent induced effects in silico can include performing, by a computing system that includes one or more processors, structure atomic scale modeling to predict a first impact of an agent on one or more ion channels. The method can include performing, by the computing system, protein function scale modeling to predict a second impact of the agent on the one or more ion channels. The protein function scale modeling can use agent concentration and agent diffusion rates and the first impact of the agent on the one or more ion channels. The method can include performing, by the computing system, cellular scale modeling to determine a third impact of the agent on a cellular level model using the second impact of the agent on the one or more ion channels. The method can include performing, by the computing system, tissue scale modeling to predict a fourth impact of the agent on a tissue level model. The method can include generating, by the computing system, an output that can indicate a likelihood that the agent induces the particular effect using the predicted first impact, second impact, third impact, and fourth impact of the agent.

In some implementations, performing, by the computing system, protein function scale modeling can include performing modeling of multiple states of pore-forming and voltage sensing domains. Performing cellular scale modeling to determine a third impact of the agent on a cellular level model can include calculating a triangulation of an action potential based upon the agent concentration. The method can include calculating a temporal dispersion of the action potential based on the agent concentration. The method can include simulating ventricular myocytes using action potential duration (APD) adaptation curves based on a plurality of agent concentrations to determine reverse use dependent agent effects. The method can include determining beat-to-beat instability for a duration of time.

In some implementations, performing tissue scale modeling to predict a fourth impact of the agent on a tissue level model can include using a one-dimensional simulation. The method can include determining parameter regimes of interest based on the one-dimensional modeling. In some implementations, performing tissue scale modeling to predict a fourth impact of the agent on a tissue level model can include using a two-dimensional simulation. Performing tissue scale modeling to predict a fourth impact of the agent on a tissue level model can include using a three-dimensional simulation.

In some implementations, the method can include simulating a transmural fiber. The method can include calculating an ECG computation based on the simulating the transmural fiber. The method can include modifying discrete transition rates of ion channels. The output indicating a likelihood that the agent induces the particular effect can include a likelihood score.

The method can include performing risk factor modeling to identify agent induced diseases or sensitivity. Performing the risk factor modeling to identify agent induced diseases or sensitivity can include performing targeted mutagenesis by modifying discrete transition rates in computational models of ion channels that result in targeted modification of channel activation, inactivation, deactivation or recovery from inactivation.

In some implementations, the one or more ion channels is a cardiac ion channel. In some implementations, the one or more ion channels is a hERG channel. In some implementations, the one or more ion channels is one of a Potassium ion channel, a Sodium ion channel or a Calcium ion channel.

In some implementations, generating an output indicating a likelihood that the agent induces the particular effect using the predicted first impact, second impact, third impact, and fourth impact of the agent can include generating an output indicating a likelihood that the agent induces an arrhythmia using the predicted first impact, second impact, third impact, and fourth impact of the agent.

The agent can be an agent that blocks hERG and prolongs a QT interval and causes Torsades de pointes (TdP) or other arrhythmia. The agent can be an agent that blocks hERG and prolongs a QT interval and does not cause TdP.

The method can include calculating an arrhythmia proclivity score based on a high-dose agent model and an agent-free model. The method can include establishing a range of the arrhythmia proclivity score, the range extending from a first number corresponding to an absence of the agent and a second number corresponding to a positive control induced by an agent known to cause arrhythmia. The agent can be a drug. The agent can be an antibody. The agent can be a small molecule agent. The agent can be a pharmaceutical composition.

According to another aspect of the disclosure, a method of predicting channel open probabilities of ion channels responsive to interactions with agents in silico. The method can include performing, by a computing system including one or more processors, for an agent, structure atomic scale modeling to predict kinetic on rates and kinetic off rates corresponding to one or more states of an ion channel. The method can include performing, by the computing system, for the agent, protein function scale modeling using the predicted kinetic on rates and kinetic off rates of the one or more ion channels to predict a channel open probability of the ion channel.

Performing the structure atomic scale modeling to predict kinetic on rates and kinetic off rates corresponding to one or more states of an ion channel can include performing the structure atomic scale modeling to predict kinetic on rates and kinetic off rates of an ion channel while the one or more ion channels is in an open state, a closed state and an inactivated state.

In some implementations, the method can include using the predicted kinetic on rates and the kinetic off rates of the one or more ion channels and agent concentration and agent diffusion rates to determine a constant that is used as an input to perform the protein function scale modeling. The kinetic on rates and kinetic off rates can be used to determine agent binding rate constants and agent unbinding rate constants used in the protein function scale modeling. The method can also include determining a dissociation rate constant based on a ratio of a function of the kinetic off rates to a function of the kinetic on rates. The method can include using the predicted channel open probability of the one or more ion channels to perform cellular scale modeling to determine an impact of the agent on a cellular level model.

In some implementations, the method can include performing, by the computing system, tissue scale modeling to predict a second impact of the agent on a tissue level model. The method can also include generating, by the computing system, an output indicating a likelihood that the agent induces a particular effect using the first impact and second impact of the agent. The one or more ion channels can be one of a Potassium ion channel, a Sodium ion channel or a Calcium ion channel. The one or more ion channels can be cardiac ion channels or hERG channels. The agent can be a drug, an antibody, a small molecule agent, or a pharmaceutical composition.

According to another aspect of the disclosure, a method of predicting agent induced effects in silico includes identifying, by a computing system including one or more processors, one or more channel open probabilities of one or more states of at least one ion channel. The method can include performing, by the computing system, cellular scale modeling or tissue scale modeling using the channel open probabilities of the one or more states of the at least one ion channel to predict an impact of an agent.

In some implementations, identifying, by the computing system, one or more channel open probabilities of an ion channel can include performing, by the computing system, for the agent, structure atomic scale modeling to predict kinetic on rates and kinetic off rates corresponding to one or more states of the ion channel. The method can include performing, by the computing system, for the agent, protein function scale modeling using the predicted kinetic on rates and kinetic off rates of the one or more ion channels to predict the channel open probabilities of the one or more states of the at least one ion channel.

The method can include performing, by the computing system, protein function scale modeling by performing modeling of multiple states of pore-forming and voltage sensing domains. The method can include calculating the triangulation of an action potential based upon the agent concentration. The method can include calculating the temporal dispersion of an action potential based upon the agent concentration. The method can include simulating ventricular myocytes using action potential duration (APD) adaptation curves based on a plurality of agent concentrations to determine reverse use dependent agent effects. The method can include determining beat-to-beat instability for a duration of time.

In some implementations, performing tissue scale modeling can include predicting a fourth impact of the agent on a tissue level model using a one-dimensional simulation by calculating the spatial dispersion of an action potential based upon the agent concentration and tissue composition. The method can include determining parameter regimes of interest based on the one-dimensional simulation. Performing tissue scale modeling can include predicting a fourth impact of the agent on a tissue level model using a two-dimensional simulation. Performing tissue scale modeling to predict the fourth impact of the agent on the tissue level model can use a three-dimensional simulation. The method can include simulating a transmural fiber or tissue. The method can include generating an ECG computation based on the simulating the transmural fiber.

The method can include modifying discrete transition rates of the at least one ion channel. The method can include generating an output indicating a likelihood that the agent induces a particular effect, wherein the output includes a likelihood score. The method can include performing risk factor modeling to identify agent induced diseases or sensitivity. Performing the risk factor modeling to identify agent induced diseases or sensitivity can include performing targeted mutagenesis by modifying discrete transition rates in computational models of ion channels that result in targeted modification of channel activation, inactivation, deactivation or recovery from inactivation.

The at least one ion channel can be a cardiac ion channel or a hERG channel. The at least one ion channel can include be one of a Potassium ion channel, a Sodium ion channel or a Calcium ion channel. The method can include determining a likelihood that the agent induces an arrhythmia.

The agent can be an agent that blocks hERG and prolongs a QT interval and causes Torsades de pointes (TdP) or other arrhythmia. The agent can be an agent that blocks hERG and prolongs a QT interval and does not cause Torsades de pointes (TdP) or other arrhythmia. The method can include calculating an arrhythmia proclivity score based on a high-dose agent model and an agent-free model. The method can include establishing a range of the arrhythmia proclivity score. The range can extend from a first number corresponding to an absence of the agent and a second number corresponding to a positive control induced by an agent known to cause arrhythmia. The agent can be a drug, an antibody, a small molecule agent, or a pharmaceutical composition.

According to another aspect of the disclosure, a system for predicting agent induced effects includes one or more processors and a memory. The system can be configured to calculate structure atomic scale modeling to predict a first impact of an agent on one or more ion channels. The system can be configured to perform protein function scale modeling to predict a second impact of the agent on the one or more ion channels using agent concentration and agent diffusion rates and the first impact of the agent on the one or more ion channels. The system can be configured to perform cellular scale modeling to determine a third impact of the agent on a cellular level model using the second impact of the agent on the one or more ion channels. The system can be perform tissue scale modeling to predict a fourth impact of the agent on a tissue level model. The system can be configured to generate an output indicating a likelihood that the agent induces the particular effect using the predicted first impact, second impact, third impact, and fourth impact of the agent.

In some implementations, the system can be configured to perform protein function scale modeling by performing modeling of multiple states of pore-forming and voltage sensing domains. The system can calculate the triangulation of an action potential based on the agent concentration. The system can the calculate temporal dispersion of an action potential based upon the agent concentration. The system can simulate ventricular myocytes using action potential duration (APD) adaptation curves based on a plurality of agent concentrations to determine reverse use dependent agent effects. The system can determine beat-to-beat instability for a duration of time.

The system can perform tissue scale modeling to predict a fourth impact of the agent on a tissue level model using a one-dimensional simulation. The system can determine parameter regimes of interest based on the one-dimensional simulation. The system can perform tissue scale modeling to predict a fourth impact of the agent on a tissue level model using a two-dimensional simulation by calculating a spatial dispersion of an action potential based upon the agent concentration and tissue composition. The system can perform tissue scale modeling to predict a fourth impact of the agent on a tissue level model using a three-dimensional simulation.

The system can receive a signal comprising a stimulation of a transmural fiber. The system can generate an ECG computation based on the stimulation of the transmural fiber. The system can modify discrete transition rates of ion channels. The output indicating the likelihood that the agent induces the particular effect includes a likelihood score. The system can perform risk factor modeling to identify agent induced diseases or sensitivity. To system can perform the risk factor modeling to identify agent induced diseases or sensitivity the one or more processors are configure to target mutagenesis by modifying discrete transition rates in computational models of ion channels that result in targeted modification of channel activation, inactivation, deactivation or recovery from inactivation.

The one or more ion channels can be cardiac ion channels or hERG channels. The one or more ion channels can be one of a Potassium ion channel, a Sodium ion channel or a Calcium ion channel. The likelihood can indicate a likelihood that the agent induces an arrhythmia using the predicted first impact, second impact, third impact, and fourth impact of the agent.

The agent can be an agent that blocks hERG and prolongs a QT interval and causes Torsades de pointes (TdP) or other arrhythmia. The agent can be an agent that blocks hERG and prolongs a QT interval and does not cause Torsades de pointes (TdP) or other arrhythmia. The system can calculate an arrhythmia proclivity score based on a high-dose agent model and an agent-free model. The system can establish a range of the arrhythmia proclivity score. The range can extend from a first number corresponding to an absence of the agent and a second number corresponding to a positive control induced by an agent known to cause arrhythmia. The agent can be a drug, an antibody, a small molecule agent, or a pharmaceutical composition.

According to another aspect of the disclosure, a system for predicting channel open probabilities of ion channels responsive to interactions with agents can include one or more processors and a memory. The system can be configured to perform, for an agent, structure atomic scale modeling to predict kinetic on rates and kinetic off rates corresponding to one or more states of an ion channel. The system can perform, for the agent, protein function scale modeling using the predicted kinetic on rates and kinetic off rates of the one or more ion channels to predict a channel open probability of the ion channel.

In some implementations, the system can perform structure atomic scale modeling to predict kinetic on rates and kinetic off rates of an ion channel while the one or more ion channels is in an open state, a closed state, and an inactivated state. The system can use the predicted kinetic on rates and the kinetic off rates of the one or more ion channels and agent concentration and agent diffusion rates to determine a constant that is used as an input to perform the protein function scale modeling. The system can use the kinetic on rates and kinetic off rates to determine agent binding rate constants and agent unbinding rate constants used in the protein function scale modeling.

The system can determine a dissociation rate constant based on a ratio of a function of the kinetic off rates to a function of the kinetic on rates. The system can use the predicted channel open probability of the one or more ion channels to perform cellular scale modeling to determine an impact of the agent on a cellular level model. The system can perform tissue scale modeling to predict a second impact of the agent on a tissue level model. The system can generate an output indicating a likelihood that the agent induces a particular effect using the first impact and second impact of the agent.

The ion channels can be one of a Potassium ion channel, a Sodium ion channel or a Calcium ion channel. The ion channels can be cardiac ion channels or hERG channels. The agent can be a drug, an antibody, a small molecule agent, or a pharmaceutical composition.

According to another aspect of the disclosure, a system for predicting agent induced effects can include one or more processors and a memory. The system can be configured to identify one or more channel open probabilities of one or more states of at least one ion channel. The system can perform cellular scale modeling or tissue scale modeling using the channel open probabilities of the one or more states of the at least one ion channel to predict an impact of an agent.

In some implementations, the system can perform for the agent, structure atomic scale modeling to predict kinetic on rates and kinetic off rates corresponding to one or more states of the ion channel. The system can perform for the agent, protein function scale modeling using the predicted kinetic on rates and kinetic off rates of the one or more ion channels to predict the channel open probabilities of the one or more states of the at least one ion channel.

The system can perform protein function scale modeling by performing modeling of multiple states of pore-forming and voltage sensing domains. The system can calculate the triangulation of an action potential based upon the agent concentration. The system can calculate the temporal dispersion of an action potential based upon the agent concentration. The system can simulate ventricular myocytes using action potential duration (APD) adaptation curves based on a plurality of agent concentrations to determine reverse use dependent agent effects. The system can determine beat-to-beat instability for a duration of time.

The system can perform tissue scale modeling by predicting a fourth impact of the agent on a tissue level model using a one-dimensional simulation. The system can determine parameter regimes of interest based on the one-dimensional simulation. To perform tissue scale modeling, the system can predict a fourth impact of the agent on a tissue level model using a two-dimensional simulation. The system can preform tissue scale modeling to predict the fourth impact of the agent on the tissue level model using a three-dimensional simulation. The system can receive a signal that can include a stimulation of a transmural fiber. The system can to generate an ECG computation based on the simulating the transmural fiber or tissue. The system can modify discrete transition rates of the at least one ion channel. The system can generate an output indicating a likelihood that the agent induces a particular effect and the output includes a likelihood score. The system can perform risk factor modeling to identify agent induced diseases or sensitivity. To perform the risk factor modeling to identify agent induced diseases or sensitivity the system can perform targeted mutagenesis by modifying discrete transition rates in computational models of ion channels that result in targeted modification of channel activation, inactivation, deactivation or recovery from inactivation.

The ion channel can be a cardiac ion channel or a hERG channel. The ion channel can be a Potassium ion channel, a Sodium ion channel or a Calcium ion channel. The system can determine a likelihood that the agent induces an arrhythmia. The agent can be an agent that blocks hERG and prolongs a QT interval and causes Torsades de pointes (TdP) or other arrhythmia. The agent can be an agent that blocks hERG and prolongs a QT interval and does not cause Torsades de pointes (TdP) or other arrhythmia. The system can calculate an arrhythmia proclivity score based on a high-dose agent model and an agent-free model. The system can establish a range of the arrhythmia proclivity score. The range can extend from a first number corresponding to an absence of the agent and a second number corresponding to a positive control induced by an agent known to cause arrhythmia. The agent can be a drug, an antibody, a small molecule agent, or pharmaceutical composition.

The disclosure hypothesizes that two drug factors determine promotion of TdP: 1) Multichannel block that may cancel hERG effects, as in the case of amiodarone, and 2) Conformation state specificity of hERG block and associated kinetics, may promote TdP as indicated by the TRIaD: Triangulation, reverse use dependence, beat-to-beat instability of action potential duration, temporal and spatial action potential duration dispersion. Here, the disclosure uses an integrative experimental and computational modeling approach that spans scales from the atom to the tissue to predict structure activity relationships that determine proarrhythmia for the prototype drug dofetilide.

Mathematical modeling and simulation constitutes one of the most promising methodologies to reveal fundamental biological principles and mechanisms, model effects of interactions between system components and predict emergent drug effects. Thus, the disclosure presents a novel multiscale approach based on drug-channel structural interactions and kinetics intended to predict drug-induced cardiotoxicity. It is expected the model framework may be expanded to impact in drug discovery, screening and regulatory processes.

A major factor plaguing drug development is that there is no preclinical drug screen that can accurately predict unintended drug induced cardiac arrhythmias. The current approaches rely on substitute markers such as QT interval prolongation on the ECG. Unfortunately, QT prolongation is neither specific nor sensitive to indicate likelihood of arrhythmias. There is an urgent need to identify a new approach that can predict actual proarrhythmia rather than surrogate indicators. Mathematical modeling and simulation constitutes one of the most promising methodologies to reveal fundamental biological principles and mechanisms, model effects of interactions between system components and predict emergent drug effects.

Thus, the disclosure proposes the development of a novel multi-scale approach based on drug-channel structural interactions and kinetics intended to predict drug-induced cardiotoxicity in the context of: 1) preclinical drug screening, 2) drug rehabilitation, and 3) prediction of the intersection of drug effects and coexistent risk factors. Applicants' underlying hypothesis is that the fundamental mode of drug interaction derived from each drug's unique structure activity relationship determines the resultant effects on cardiac electrical activity in cells and tissue. By capturing these complex drug channel interactions in a model, it is expected to be able to predict drug safety or electro-toxicity in the heart. Predictions from the atomic structure simulations can be used to inform the kinetic parameters of models that capture the complex dynamical interactions of drugs and ion channels. The computational components can then be studied in predictive models at the channel, cell and tissue scales to expose fundamental mechanisms and complex interactions underlying emergent behaviors. Experiments in mammalian cells and tissues can be undertaken to validate model predictions. Drug properties can be perturbed in models to rehabilitate dangerous drugs and reduce their potential toxicity. The multi-scale model for prediction of cardiopharmacology that the disclosure develops in this application can be applied to projects demonstrating its usefulness for efficacy or toxicity of drug treatments in the complex physiological system of the heart.

The pharmaceutical industry has spent hundreds of millions of dollars testing drug candidates preclinically and in humans using 'thorough QT studies' to assess the risk of potentially fatal proarrhythmias. Stakeholders in government, industry and academia have recognized that the current requirements fall short due to limitations in the ability to accurately predict the risk of cardiotoxicity that have led to drug candidates being abandoned or pursued erroneously (Chi, K. R. et al. (2013) Nat Rev Drug Discov 12:565-567). These statements aptly describe the major biomedical problem underlying the goals of Applicants' proposed work. There is an urgent need to develop new approaches for predicting how drugs with complex interactions and multiple subcellular targets can alter the emergent electrical activity in the heart and lead to unintended arrhythmias.

Abnormal cardiac electrical activity is a common side effect from unintended block of the promiscuous drug target hERG, the pore-forming domain of the delayed rectifier $K^+$ channel in the heart. Block of hERG leads to prolongation of the QT interval on the ECG, a phase of the cardiac cycle that corresponds to underlying cellular repolarization. Prolongation of the QT interval and proarrhythmia have been so tightly associated that the QT interval has become widely accepted as a surrogate marker for arrhythmia. Since 2005, the regulatory process for preclinical drug candidates includes a dedicated clinical study in healthy volunteers, the so-called "Thorough QT Study." A drug that results in greater than 5 ms QT prolongation above normal in healthy humans indicates "regulatory concern". The problem is that many useful drugs that were approved prior to 2005, including even the commonly used antiarrhythmic agents verapamil, ranolazine and amiodarone to name a few, all fail the Thorough QT test-they all block hERG and prolong QT interval. While for some drugs there is a clear association between prolonged QT interval and torsades de points (TdP) arrhythmias, there is another class of drugs for which QT interval prolongation is not associated with TdP. Many potentially useful drugs in the latter category are nevertheless eliminated by the Thorough QT test. The questions, "How can we distinguish QT prolonging proarrhythmic drugs from those that cause QT prolongation but not arrhythmias?" and "Can we predict when a QT prolonging drug is a proarrhythmic drug?" are what the disclosure intends to answer by assembly of a novel multiscale model for predictive cardiac pharmacology. The present disclosure can have major impact in drug discovery, screening and regulatory processes.

Here the disclosure tries to extend this idea to adjunctive therapy design to promote the concept of "virtuous promiscuity" (Haigney, M. C. (2014) Clin Pharmacol Ther. 96:534-536).

In this study the disclosure explores the basis for a novel adjunctive therapy aimed at mitigating acquired Long-QT as associated arrhythmia risk by pharmacological targeting of late Na current ($I_{NaL}$) using GS-458967, a potent and selective inhibitor of this current (Belardinelli, L. et al. (2013) J Pharmacol Exp Ther. 344:23-32). The first studies on the preclinical compound GS-458967 in 2013 showed potent selective targeting of $I_{NaL}$ (GS-458967, $IC_{50}$ for $I_{NaL}$=130 nM, compared to Kd for tonic block of peak $I_{Na}$=1500 μM (Belardinelli, L. et al. (2013) J Pharmacol Exp Ther. 344: 23-32)) allowing for specific therapeutic inhibition and study of the physiological and pathological role for $I_{NaL}$ in the heart.

The disclosure evaluates arrhythmia vulnerability by integrating data-based drug channel models into virtual ventricular myocyte and tissue models. On the system can provide predictions of emergent drug effects that modify individual elements of the TRIaD. This approach yielded novel and potentially important insights into the proarrhythmia markers at the myocyte and/or tissue scales. Thus, it is based on the fundamental biophysical and molecular pharmacological mechanisms underlying drug induced arrhythmia and their influence on electrophysiological parameters. Gaining reliable insights that inform arrhythmia risk is the first necessary step that must be taken to ultimately lead to development of specific in silico screening test for both assessing risk and then implementing practical risk reduction measures.

The present disclosure describes models that can be used to predict that selective pharmacological targeting of $I_{NaL}$ by inhibiting this current using GS-458967 improves all TRIaD related parameters in acquired Long-QT syndrome and consequently reduces arrhythmia risk.

BRIEF DESCRIPTION OF THE DRAWINGS

(FIG. 6A) Ion channel patch clamp experiments (Vicente, J. et al. (2015) J Am Heart Assoc 4:e001615) and the predicted hERG dose-response with model based on (FIG. 6B) MD predicted kinetics.

FIG. 12A shows experimentally measured $I_{Kr}$ (upper) (Berecki, G. et al. (2005) Biophys J. 88:566-578), and $I_{K1}$ (lower) (Shimoni, Y. et al. (1992) J Physiol. 448:709-727). FIG. 12B shows simulated $I_{Kr}$ (upper) and $I_{K1}$ (lower) compared. FIG. 12C shows experimental action potential clamp waveform (upper) and corresponding L-type $Ca^{2+}$ current (lower) from rabbit ventricular myocyte (Saegusa, N. et al. (2011) J Gen Physiol. 138:537-559). FIG. 12D shows simulated rabbit ventricular myocyte action potential and model generated L-type Ca' current. FIG. 12E shows experimentally recorded $Ca^{2+}$ transient during the AP (Shannon, T. R. et al. (2000) Biophys J. 78:322-333). FIG. 12F shows corresponding simulated $Ca^{2+}$ transient.

FIG. 13A shows $Na^+$ current activation curve derived from data generated in response to depolarizing voltage clamp pulses (Lee, H. C. et al. (1993) J Clin Invest. 91:693-701). FIG. 13B shows steady-state inactivation (Lee, H. C. et al. (1993) J Clin Invest. 91:693-701). FIG. 13C shows recovery from inactivation at −100 mV (Lee, H. C. et al. (1993) J Clin Invest. 91:693-701). FIG. 13D shows $I_{Na}$ waveform in drug free conditions at low gain normalized to peak current (Belardinelli, L. et al. (2013) J Pharmacol Exp Ther. 344:23-32). FIG. 13E shows drug free $I_{Na}$ at high gain (Belardinelli, L. et al. (2013) J Pharmacol Exp Ther. 344:23-32). FIG. 13F shows superimposition of model predicted and experimentally recorded drug free or baseline $I_{Na}$ in response to a slow depolarizing ramp voltage protocol.

FIG. 14A shows optimized model generated concentration-dependent data for GS-458967 on late Na current compared to two separate sets of experimental data—Blue asterisks indicate experimental data set #1 (n=4) (Belardinelli, L. et al. (2013) J Pharmacol Exp Ther. 344:23-32), and red circles are from experimental data set #2 (For 0 µM and 0.03 µM, n=3. For 0.1 µM and 0.3 µM, n=4. For 1 µM, n=6. For 3 µM, n=2). The effect of high concentration GS-458967 on peak $I_{Na}$ is indicated for experiments (blue square), and simulated $I_{Na}$ peak (black triangle). FIG. 14B shows behavior of a myocyte 'population' was simulated by randomly varying the amplitude of maximal conductances for $I_{Na}$, $I_{CaL}$, $I_{Ks}$, $I_{Kr}$, $I_{K1}$, $I_{to}$, $I_{NaK}$, $I_{NaCa}$ (to within 10% of their nominal values in the rabbit ventricular myocyte model). This approach allowed for efficient analysis of 100 distinct cell action potentials. $APD_{90}$ was calculated at 1 Hz for each case. These simulated myocyte properties were compared to experimental data set #1 (blue asterisks) and experimental data set #2 (red circles).

FIG. 15A shows simulated effects of GS-458967 on rabbit ventricular myocyte AP and FIG. 15B shows the corresponding effects of GS-458967 on late $I_{Na}$.

FIG. 16A shows experimental data from two distinct data sets from rabbit ventricular myocytes showing drug free conditions (left), the effect of 3 nM ATX-II (middle) and the combination of 3 nM ATX-II with 0.3 µM GS-458967 (right). FIG. 16B shows simulated effects on virtual rabbit ventricular myocyte showing drug free (left), simulated effect of ATX-II (middle) and ATX-II with co-treatment with GS-458967 0.3 µM (right).

FIG. 17A shows space-time plots of membrane potential (top) and pseudo ECGs (lower) computed from a 165-rabbit myocyte transmural cardiac preparation in the presence of ATX-II during a "short-long-short" pacing protocol. FIG. 17B shows 0.03 µM GS-458967 markedly diminishes QT interval prolongation and APD dispersion as indicated by reduced T-wave amplitude. FIG. 17C shows 0.1 µM GS-458967 further reduced QT interval prolongation and reversed the repolarization gradient as demonstrated by inversion of the T-wave.

(FIG. 18G) Instability of APD was quantified as the difference between the maximum and minimum of 1000 individual myocytes in the presence of physiological noise current as a function of prolongation of APD (shown in FIGS. 18A-18C). (FIG. 18H) Simulated beat-to-beat instability of rabbit ventricular myocyte action potentials to small perturbations before and after application of drugs. Poincaré plots of sequential APD pairs indicating beat-to-beat instability are shown for each case. (FIG. 18I) GS-458967 improved dofetilide induced reverse use dependence: Action potential adaptation curves show $APD_{90}$ at various pacing frequencies in the presence or absence of drugs.

(FIG. 19A) Shows the control or drug-free case, (FIG. 19B) with ATX-II, (FIG. 19C) with ATX-II and 0.3 µM GS-458967, (FIG. 19D) 16 nM Dofetilide, or (FIG. 19E) 16 nM Dofetilide and 0.3 µM GS-458967. Tissues (5 cm×5 cm) were stimulated (S1) along left edge (endocardium) and this followed by a premature stimulus (S2) applied in the vulnerable window (see Example 2 Methods). Six snapshots obtained following application of GS-458967, dofetilide or both at selected time points. Corresponding pseudo-ECGs are in the right panels. Membrane voltage values are indicated by the color gradient.

FIGS. 22A-22E show single APs from 3 different sites in the simulated tissues are shown for each case as in FIGS. 19A-19E. (FIG. 22A) Control. (FIG. 22B) With ATX-II. (FIG. 22C) ATX-II and GS-458967 µM. (FIG. 22D) Dofetilide 16 nM. (FIG. 22E) Dofetilide+GS-458967 0.3 µM.

FIGS. 23A-23F show hERG1 and dofetilide structures. (FIG. 22A and FIG. 22D) Structural homology models for the transmembrane regions for the pore domain (S5-S6) of open and (FIG. 22B and FIG. 22E) open-inactivated hERG1 shown as a side views and top views. (FIG. 22C and FIG. 22F) Chemical structure model of dofetilide.

(FIG. 24A) A schematic showing the process for potential of mean force (PMF) calculation for the movement of dofetilide. Different hERG1 subunits are shown by blue, red, orange and gray colors using cartoon representation. Dofetilide is shown by a molecular surface in bulk water (pink) and in the binding pocket of the channel (green). (FIG. 24B) Two dominant low energy wells were identified for open (black) and open-inactivated (red) hERG1. (FIG. 24C) Structural determinants of dofetilide (green molecular surface) interaction with hERG1 in open (black a and b) and open-inactivated (red a' and b') states (upper) and interaction details (lower). All atoms within 3.9 Å of dofetilide are shown with sticks. Water molecules are shown as red balls and the hydrogen bonds as cyan sticks. Molecular surfaces are shown for protein and bound water molecules and colored by an atom type (Blue—Nitrogen, Red—Oxygen, Gray—Carbon, and Yellow—Sulfur). Residue name coloring corresponds to different hERG1 subunits. (FIG. 24D) Diffusion coefficients for ingress of dofetilide for open and open-inactivated states showing that their values are similar during the binding process.

FIGS. 25A-25C show concentration and state-dependent block of hERG1 by dofetilide. (FIG. 25A) A map of the hERG1 channel functional states. Drug free (black) and drug bound (red) states are shown. (FIG. 25B) Model parameters for drug binding "on" (kg) and unbinding, "off" ($r_x$) rates derived from potential mean force calculations from molecular dynamics simulations of conformation state dependent dofetilide interaction with hERG1 open and open-inactivated states. (FIG. 25C) Experimentally measured dose dependent inhibition of hERG1 by dofetilide (symbols) (Vicente, J. et al. (2015) J Am Heart Assoc 4:e001615) and optimized computationally based results.

(FIG. 26A) A heart rate corrected pseudo ECG (QTC interval) was computed from a 1-dimensional strand of O'Hara-Rudy human cardiac ventricular myocytes for pacing frequencies between 43-75 bpm for a range of dofetilide concentration. (FIG. 26B) Comparison of human clinical data showing control and effect of simulated dofetilide (Vicente, J. et al. (2015) J Am Heart Assoc 4:e001615; Okada, Y. et al. (1996) J Am Coll Cardiol. 27:84-89) and simulated mean values under the same conditions. Green asterisk (*): subjects received a single dose of 0.5 mg (population's mean maximum concentration $C_{max}$ is 2.7+/−0.3 ng/mL). Blue asterisk (*): unbound free concentration 2 nM was used in the simulations. Black asterisk (*): subjects received 0.5 to 0.75 mg twice a day. (FIG. 26C) The clinically observed and predicted QT intervals over a wide range of preceding RR intervals after dofetilide application. Rate dependent changes in the QT interval were tracked as the slope of the linear regression line estimating the QT-$\sqrt{RR}$ relation.

(FIG. 27A) Predicted temporal APD dispersion of 1000 simulated O'Hara-Rudy human ventricular action potentials generated after incorporating physiological noise to induce beat-to-beat variability at 1 Hz in the drug-free control case and following simulated application of Dofetilide (2.2 nM). Dispersion of APD was quantified as the difference between the maximum and minimum of 1000 individual cells (Control −49 ms; Dofetilide 2.2 nM=78 ms). (FIG. 27B) Action potential triangulation as a function of APD prolongation for individual cells for control (slope=0.27), and Dofetilide 2.2 nM (slope=0.74). (FIG. 27C) Simulated beat-to-beat instability of action potentials to small perturbations before and after application of drugs. Poincaré plots of sequential APD pairs indicating beat-to-beat instability are shown. (FIG. 27D) Action potential adaptation curves show APD90 at various pacing frequencies with or without Dofetilide. (FIG. 27E) pseudo ECGs after a long pasue (5000 ms) are shown for control and dofetilide 2.2 nM. (FIG. 27F) Relative increased T-wave areas with dofetilide 2.2 nM.

(FIG. 30A) The sensitivity of the slope of the relationship between action potential triangulation and APD prolongation in O'Hara-Rudy computational myocytes plotted for a range of drug "on" ($k_o$ and $k_i$,) and "off" ($r_o$ and $r_i$,) model transition rates for open and open inactivated states (scale factor indicated on x axis). (FIG. 30B) Sensitivity of simulated beat-to-beat instability of action potentials for a range of rate constants. Average and standard deviation of $APD_{90}$ for each case are shown (left). Right panel shows scale factors beyond 1.0. (FIG. 30C) The sensitivity to changes in drug transition rates of the steepest recorded slope of $APD_{90}$ reverse use dependent curves (left) and the $APD_{90}$ at BCL=2000 ms (right). (FIG. 30D) Sensitivity of the T-wave area to model transition rates. Blue asterisk indicates baseline transition rates.

In FIG. 31A, temporal action potential duration dispersion was quantified in a cell population of 1000 individual simulated cardiac myocyte action potentials constructed by incorporating physiological noise (Sato, D. et al. (2013) PLoS One 8:e85365; Sato, D. et al. (2006) Circ Res. 99:520-527; Tanskanen, A. J. et al. (2007) Math Biosci. 208:125-146). Dispersion of APD was quantified as the difference between the maximum and minimum action potential duration. Dofetilide within the clinical dosing range has a clear effect to promote temporal action potential duration variability in the presence of the drug (Control −25 ms; Dofetilide 2.2 nM=35 ms). FIG. 31B illustrates the effect of dofetilide to promote triangulation of the action potential as a function of APD prolongation. In the absence of drug, control cells had a slope=0.37, while Dofetilide 2.2 nM increased the slope=0.55.

FIG. 31C shows Poincaré plots of sequential APD pairs indicating beat-to-beat instability following the application of small electrical perturbations in the absence of drug or with 2.2 nM dofetilide. Instability was assessed by applying small amplitude inward currents randomly between −0.1 to −0.2 pA/pF for 50 ms over the course of the action potential plateau at a pacing cycle length=1000 ms. Finally, in FIG. 31D, reverse use dependence induced by dofetilide was evaluated. The action potential adaptation curves were generated using APD90 values from human computational ventricular myocytes at steady-state at the indicated pacing frequencies. When dofetilide (red) was applied, there was a clear steepening of the APD adaptation curve compared to the baseline drug-free case (black).

(FIG. 34A) Rosetta model of local anesthetic interaction with cardiac NaV1.5 pore. View of NaV1.5—lidocaine model from the intracellular side of the membrane. Each domain is colored and labeled. Side chains of key residues for lidocaine binding shown in space-filling and stick representation. (FIG. 34B) MD simulation of benzocaine binding free energy surface mapped on NavAb channel structure (gray). Pore lumen and fenestration regions (colored red) have the lowest binding free energy values.

(FIG. 36A) Dose dependence of tonic block (TB) for peak (solid) and late (dashed) current. (FIG. 36B) Peak and late currents in WT and ΔKPQ mutant channels. (FIG. 36C) Steady-state channel availability. Currents measured at −10 mV in drug free conditions (dotted), or with 10 μM ranolazine (solid) pulsed from −120 mV to −40 mV in 5 mV increments (normalized to tonic block at −120 mV). (FIG. 36D) Dose-dependence of use-dependent block (UDB) from 300 pulses to −10 mV for 25 ms from −100 mV at 5 Hz. (FIG. 36E) Frequency of UDB 10 μM ranolazine. (FIG. 36F) Recovery from UDB. Yellow boxesindicate therapeutic ranolazine. From Moreno, J. D. et al. (2013) Circ Res. 113:e50-e61.

(FIG. 37A) Inactivated state block of L-type $Ca^{2+}$ channels. Whole cell current recorded during voltage clamp steps to 0 mV following conditioning pulses to membrane potentials between −90 and +30 mV before and after exposure to drug. From (Belevych, A. E. et al. (2002) Molecular Pharmacology 62:554-565) (FIG. 37B) Biphasic effect of drug stimulation on ventricular (APD). Action potentials recorded under control conditions (a) and following drug (b and c) (Harvey, R. D. et al. (1990) The Journal of General Physiology 95:1077-1102).

Figure 45:
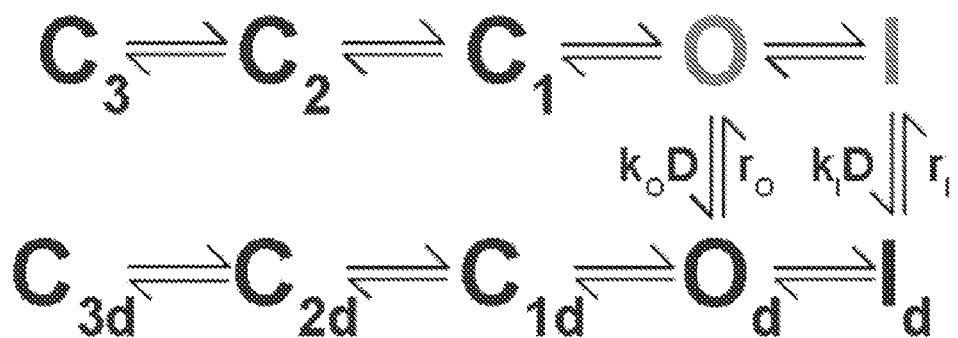

FIG. 45 shows Markov model of $I_{Kr}$ with dofetilide binding to open and inactivated states The model includes the observed 70-fold preferential binding to the inactivated state (Maltsev, V. A. et al. (1998) Circulation 98:2545-2552).

Figure 46:
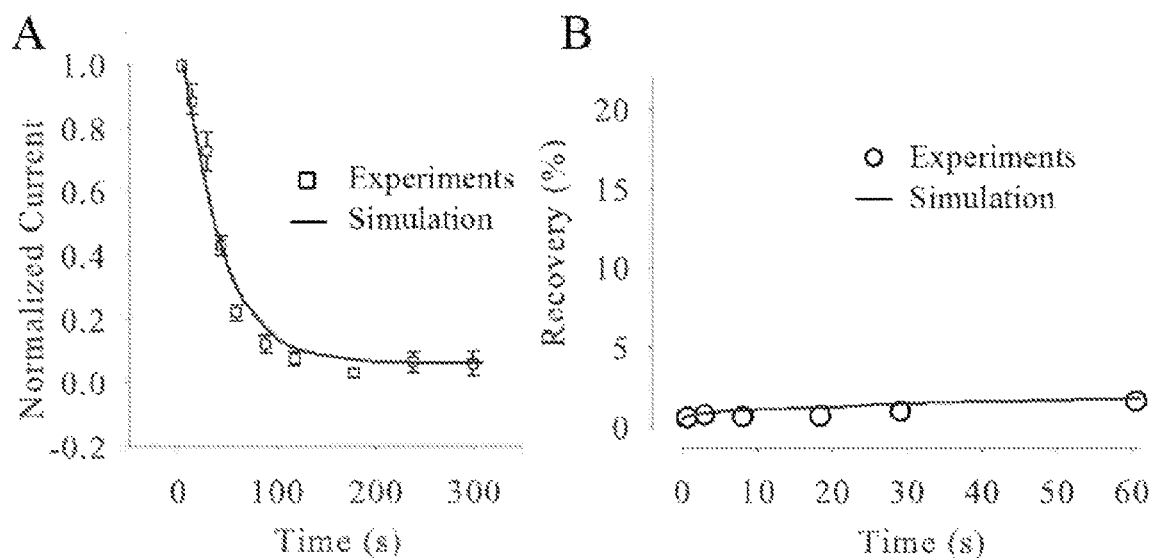

FIGS. 46A-46B show measured (symbols) and simulated (lines) timecourse of IKr block by 50 nM dofetilide (FIG. 46A) & 3 μM washout (FIG. 46B). Protocols as in 2. C Model reproduces the slow dissociation of dofetilide (Ishii, K. et al. (2003) Cardiovasc Res. 57:651-659; Ficker, E. et al. (1998) Circ Res. 82:386-395).

Figure 47A:
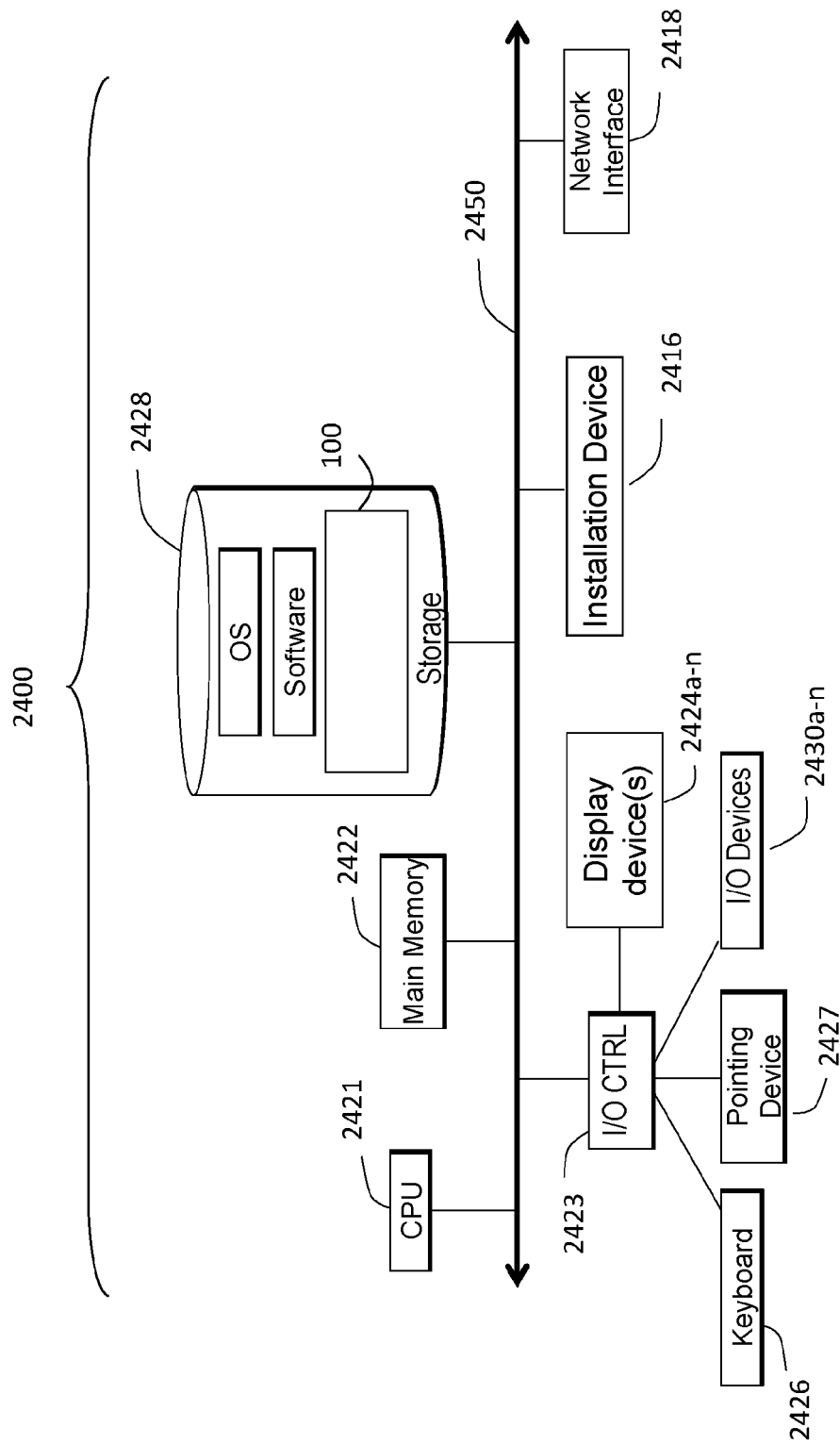
Figure 47B:
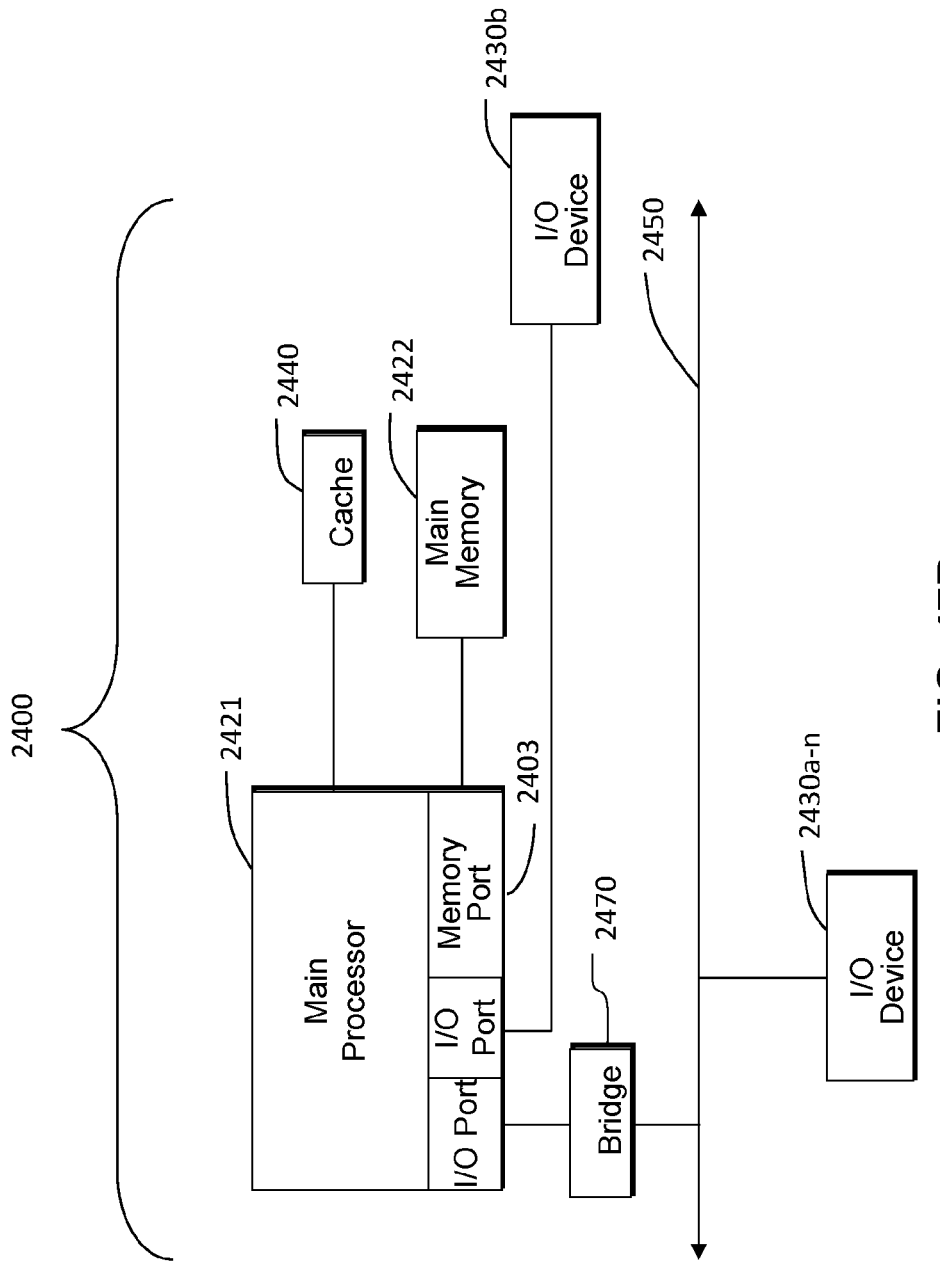

FIGS. 47A-47B are block diagrams depicting embodiments of computing devices useful in connection with the systems and methods described herein;

DETAILED DESCRIPTION

The present disclosure discusses systems and methods for determining the effects induced by agents in silico. Drug screening can often use surrogate markers or proxies to predict drug side effects on a patient. The present system can be used for preclinical drug screening to identify agents that may cause actual drug side effects rather than relying on the surrogate markers. The present system can use a bottom-up, multi-scale model to predict the side-effects of drugs. The present system can model and determine the kinetics of primary and major off-target agent interactions at the atomic scale. This information can be integrated into a model to predict ion channel states at the protein function scale. This information can be integrated into a model to predict action potential characteristics at the cellular level. The information from the models can also be integrated into a tissue-scale model to predict drug efficacy.

The disclosure proposes that the fundamental mode of drug interaction derived from each drug's unique structure activity relationship determines the resultant effects on cardiac electrical activity in cells and tissue. By capturing the intrinsic complexity of drug channel interactions in a model, a system executing the various models is expected to be able to predict drug safety or electro-toxicity in the heart.

The system described herein can be used to predict the effects of many different agents. In some implementations, the agent is an agent that blocks hERG and prolongs a QT interval. In some implementations, the agent can cause Torsades de pointes (TdP). In other implementations, the agent is an agent that blocks hERG and prolongs a QT interval, but does not cause TdP. The agent can be a drug, an antibody, a small molecule agent, a pharmaceutical composition, a therapeutic peptide or protein, among others. The present disclosure provides details relating to K and Na channels, and it should be appreciated by one of ordinary skill in the art that similar techniques can be employed for Ca channels as well. In particular, Ca channels can incorporate the techniques described in both the K and the Na channels.

Figure 1:
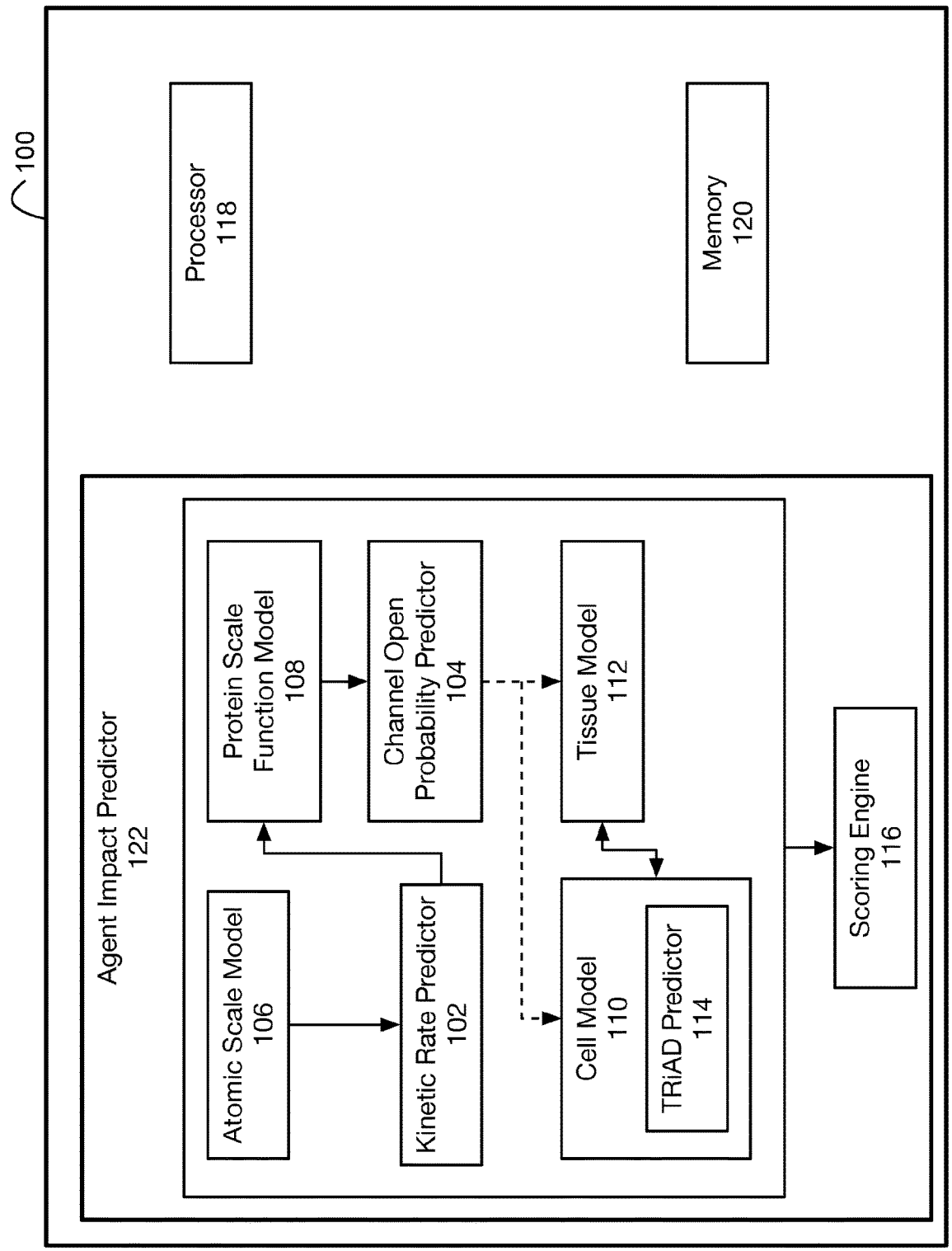
FIG. 1 illustrates a block diagram of an example system for predicting the effects of agents.

FIG. 1 illustrates a block diagram of an example system 100 for predicting the effects of agents. The system 100 can include one or more processors 118 and memory 120. The processors 118 can execute processor executable instructions to perform the methods and functions described herein. The processor executable instructions can be stored in the memory 120. Details with respect to the system are provided below with respect to FIGS. 47A and 47B.

The system 100 includes an agent impact predictor 122. The agent impact predictor 122 includes a plurality of models that estimate the effect of agent at different scales (e.g. from the atomic scale to the tissue scale). The agent impact predictor 122 can include an atomic scale model 106 that can inform a kinetic rate predictor 102. The kinetic rate predictor 102 can generate kinetic on and kinetic off rates of one or more ion channel states, which can be used to inform a protein scale function model 108. The protein scale function model 108 can generate an output that can be used to inform a channel open probability predictor 104. The channel open probability predictor 104 can inform at least one of the cell model 110 and the tissue model 112. The tissue model 112 and the cell model 110 can also exchange data used in the prediction of the agent effect. The cell model 110 can include a TRiAD predictor 114. The TRiAD predictor 114 can be used to determine various values using one or more functions, including but not limited to triangulation, reverse use dependence, beat-to-beat instability of action potential duration, temporal and spatial action potential duration dispersion. The output of the models is provided to a scoring engine 116 which can generate a score corresponding to a likelihood of an impact the agent can cause a particular condition or artifact.

The system 100 includes an atomic scale model 106. The atomic scale model 106 can be any script, file, program, application, set of instructions, or computer-executable code, that is configured to enable a computing device on which the atomic scale model 106 is executed to perform atomic scale modeling. In some implementations, the atomic scale model 106 can include one or more algorithms, functions, formulas, or equations. In some implementations, the atomic scale model 106 can be a script that executes the atomic scale model. In some implementations, the atomic scale model 106 and the kinetic rate predictor can be a single entity that informs the protein function scale model. The atomic scale model 106 can generate predictions about the integration between the agent and the ion channels at the atomic level. The atomic scale model 106 can estimate agent docking sites. The atomic scale model 106 can predict the state of the ion channels in the presence of the agent. The atomic scale model 106 can also estimate association and dissociation rates for ion blockers to ion channels in different states (e.g., a closed, open, or inactivated state of the channel). As described below, the atomic scale model 106 can provide these values to the kinetic rate predictor 102. The kinetic on and off rates that the kinetic rate predictor 102 predicts using information from the atomic scale model can be used to establish or determine constants that are used to initialize the subsequent models in the system 100, such as the protein function scale model.

In some implementations, the atomic scale model 106 can determine agent binding rate constants and agent unbinding rate constants. The atomic scale model 106 can also determine a dissociation rate constant. In some implementations, the atomic scale model 106 or the kinetic rate predictor can determine the dissociation rate constant for the agent by determining a ratio of the kinetic off rates to the kinetic on rates. The atomic scale model 106 can provide its output or otherwise inform the kinetic rate predictor 102. The output can include the agent binding and unbinding rates and dissociation rate constant. The output can also include the kinetic on rates and the kinetic off rates. Additional details to atomic scale modeling are described below in the Examples Section and specifically in relation to Example 1's "Structure Atomic Scale Modeling" section.

In further detail with respect to cardiac ion channels, full-atom modeling of hERG K channels can be performed using Rosetta-Membrane-Symmetry methods developed by the Baker and Yarov-Yarovoy labs. The X-ray structures of Kv1.2, KvAP, and KcsA (prokaryotic potassium) channels can be used as templates, and pairwise sequence alignments with hERG can be generated using a HHPred server (or any similar server).

Potassium channels are the most diverse group of the ion channel family. They are important in shaping the action potential, and in neuronal excitability and plasticity. The potassium channel family is composed of several functionally distinct isoforms, which can be broadly separated into 2 groups: the practically non-inactivating 'delayed' group and the rapidly inactivating 'transient' group.

These are all highly similar proteins, with only small amino acid changes causing the diversity of the voltage-dependent gating mechanism, channel conductance and toxin binding properties. Each type of $K^+$ channel is activated by different signals and conditions depending on their type of regulation: some open in response to depolarisation of the plasma membrane; others in response to hyperpolarisation or an increase in intracellular calcium concentration; some can be regulated by binding of a transmitter, together with intracellular kinases; while others are regulated by GTP-binding proteins or other second messengers. In eukaryotic cells, $K^+$ channels are involved in neural signalling and generation of the cardiac rhythm, act as effectors in signal transduction pathways involving G protein-coupled receptors (GPCRs) and may have a role in target cell lysis by cytotoxic T-lymphocytes. In prokaryotic cells, they play a role in the maintenance of ionic homeostasis.

All $K^+$ channels discovered so far possess a core of alpha subunits, each comprising either one or two copies of a highly conserved pore loop domain (P-domain). The P-domain contains the sequence (T/SxxTxGxG), which has been termed the $K^+$ selectivity sequence. In families that contain one P-domain, four subunits assemble to form a selective pathway for $K^+$ across the membrane. However, it remains unclear how the 2 P-domain subunits assemble to form a selective pore. The functional diversity of these families can arise through homo- or hetero-associations of alpha subunits or association with auxiliary cytoplasmic beta subunits. $K^+$ channel subunits containing one pore domain can be assigned into one of two superfamilies: those that possess six transmembrane (TM) domains and those that possess only two TM domains. The six TM domain superfamily can be further subdivided into conserved gene families: the voltage-gated (Kv) channels; the KCNQ channels (originally known as KvLQT channels); the EAG-like $K^+$ channels; and three types of calcium (Ca)-activated $K^+$ channels (BK, IK and SK). The 2TM domain family comprises inward-rectifying $K^+$ channels. In addition, there are $K^+$ channel alpha-subunits that possess two P-domains. These are usually highly regulated $K^+$ selective leak channels.

The Kv family can be divided into several subfamilies on the basis of sequence similarity and function. Four of these subfamilies, Kv1 (Shaker), Kv2 (Shab), Kv3 (Shaw) and Kv4 (Shal), consist of pore-forming alpha subunits that associate with different types of beta subunit. Each alpha subunit comprises six hydrophobic TM domains with a P-domain between the fifth and sixth, which partially resides in the membrane. The fourth TM domain has positively charged residues at every third residue and acts as a voltage sensor, which triggers the conformational change that opens the channel pore in response to a displacement in membrane potential. More recently, 4 new electrically-silent alpha subunits have been cloned: Kv5 (KCNF), Kv6 (KCNG), Kv8 and Kv9 (KCNS). These subunits do not themselves possess any functional activity, but appear to form heteromeric channels with Kv2 subunits, and thus modulate Shab channel activity. When highly expressed, they inhibit channel activity, but at lower levels show more specific modulatory actions.

The first Kv1 sequence (also known as Shaker) was found in *Drosophila melanogaster* (Fruit fly). Several vertebrate potassium channels with similar amino acid sequences were subsequently found and, together with the *D. melanogaster* Shaker channel, now constitute the Kv1 family. The family consists of at least 6 genes (Kv1.1, Kv1.2, Kv1.3, Kv1.4, Kv1.5 and Kv1.6) which each play distinct physiological roles. A conserved motif found towards the C terminus of these channels is required for efficient processing and surface expression. Variations in this motif account for the differences in cell surface expression and localisation between family members. These channels are mostly expressed in the brain, but can also be found in non-excitable cells, such as lymphocytes.

Kv1.2 channels are uniformly distributed in the heart and brain. They play diverse functional roles in several neuronal compartments, especially in the regulation of pre- and post-synaptic membrane excitability. Kv1.2 subunits can co-localise with other Kv1 subunits. For example, Kv1.2 colocalises with Kv1.1 in the nodes of Ranvier in myelinated axons, and in the brain, in particular, the axons and nerve terminals; Kv1.2 coassembles with Kv1.4 subunits. In addition, Kv1.2 assembles with the Kv-beta2 subunit resulting in the promotion of Kv1.2 transport to the cell surface. Although potassium channels are described herein, the present disclosure is not limited to the elements or ions described herein but can extend to ion channels of other elements, such as Sodium, Calcium, and others.

Figure 3A:
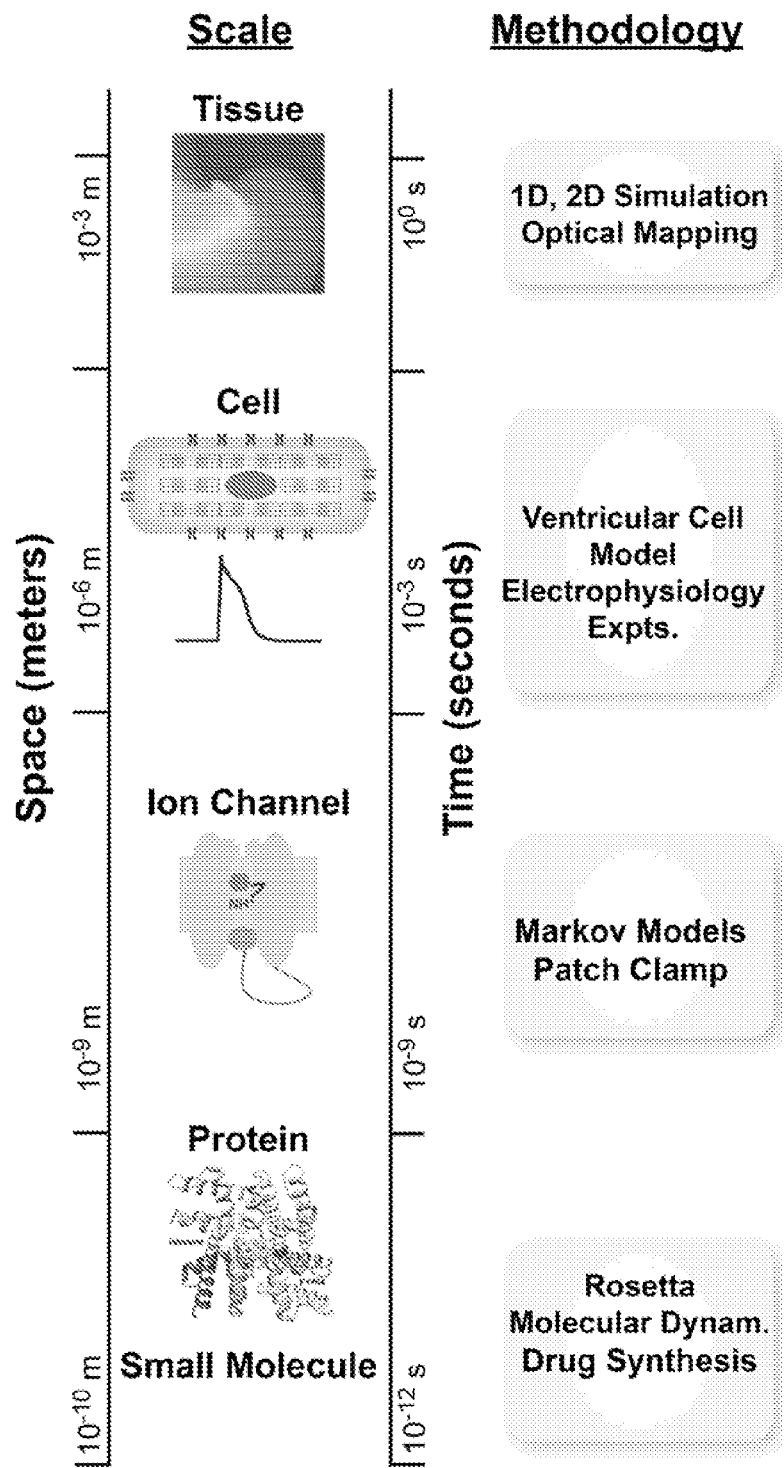
FIG. 3A shows time/space scales and methodologies.
Figure 3B:
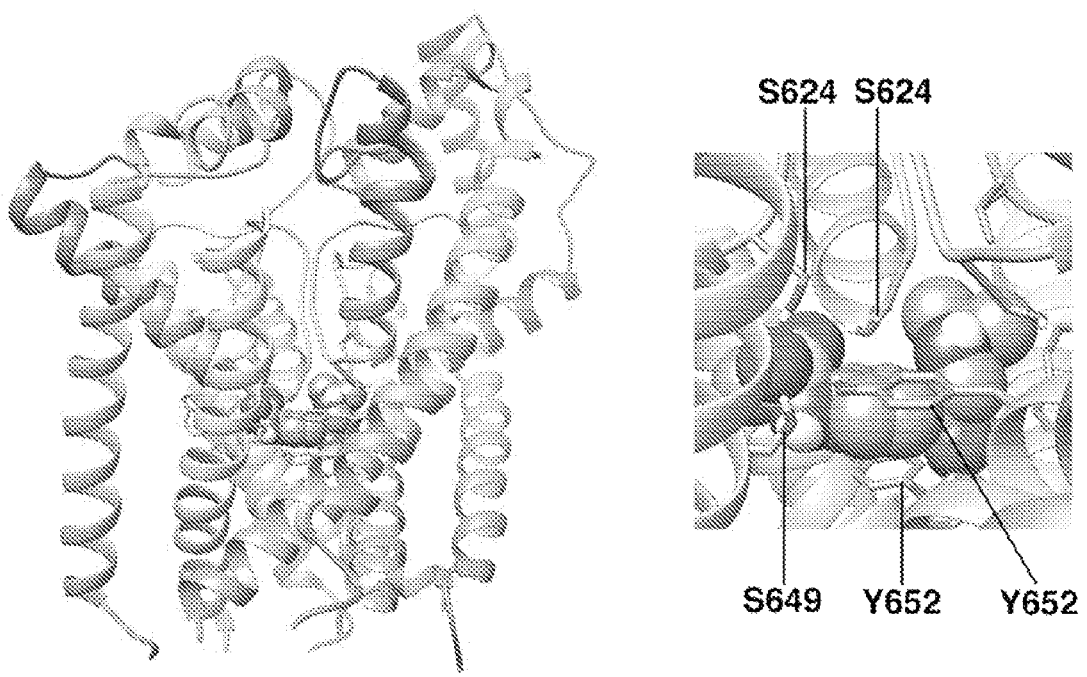
FIG. 3B shows Rosetta model of drug docking to hERG pore in the open inactivated state. Transmembrane view of hERG pore-forming and predicted d-sotalol docking in hERG using Rosetta Ligand is shown.

Preliminary structural models of hERG can be generated. The system can assess a state-dependent binding affinity of the drug to a channel in its open, closed and open-inactivated states (FIG. 3B).

In further detail of the Rosetta-Ligand model, the model can be used for drug docking to hERG channels. Determining high-resolution structures of closed, open, and inactivated states of the pore-forming (PD) and voltage sensing domains (VSD) of ion channels allows structural modeling of multiple states of hERG PD and VSD. The disclosure develops a set of hERG channel complexes with drugs using RosettaLigand methods as discussed below. Closed, open and inactivated state models of hERG can be used to predict docking of various agents, such as sotalol, dofetilide, ibutilide, moxifloxacin, ketaconozole and amiodarone (FIG. 3B).

The agent impact predictor 122 can include the kinetic rate predictor 102. The kinetic rate predictor 102 can be any script, file, program, application, set of instructions, or computer-executable code, that is configured to enable a computing device on which the kinetic rate predictor 102 is executed to predict the kinetic on and off rates of the ion channel in the presence of the agent. The kinetic rate predictor 102 can predict how the agent affects the kinetic rates of the ion channels. The kinetic rate predictor 102 can predict how the agent affects the kinetic rates of the ion channels when the ion channels are in different states. The states can include an open state, a closed state, and an inactivated state, such as an open-inactivated state. The kinetic rate predictor 102 can base the kinetic rate prediction on characteristics of the agent. A user can input the characteristics of the agent into the system. The characteristics of the agent can include the agent concentration, the agent diffusion rates, among other relevant characteristics. In some implementations, the user can provide an indication of the agent, and the system can automatically vary the agent characteristics. For example, the kinetic rate predictor 102 may run simulations that generate kinetic rate predictions for a plurality of agent concentrations. The tested agent concentrations can include a range of concentrations at which the agent may be delivered to a patient. The kinetic rate predictor 102 can determine the kinetically separated stable and unstable states of the ion channels using a Markov State analysis.

The agent impact predictor 122 can include the protein scale function model 108. The protein scale function model 108 can be any script, file, program, application, set of instructions, or computer-executable code, that is configured to enable a computing device on which the protein scale function model 108 is executed to model the gating of ion channels. The protein scale function model 108 can predict, for the agent, the gating of the ion channels use the predicted kinetic on and off rates from the kinetic rate predictor 102. In some implementations, the ion channels can be cardiac ion channels. The ion channels can be hERG channels. In some implementations, the ion channels can be Potassium, Sodium, or Calcium ion channels.

The protein scale function model 108 can perform the protein function scale modeling by modeling multiple states in the pore-forming and voltage sensing domains. The protein scale function model 108 can also receive agent concentrations and agent diffusion rates. In some implementations, the diffusion rates can be estimated by the atomic scale model 106. The protein scale function model 108 can modify the discrete transition rates of the ion channels. Additional details relating to the protein scale function model 108 are described below in the Examples Section and specifically in relation to Example 1's "Protein Function Scale Models."

The agent impact predictor 122 can include the channel open probability predictor 104. The channel open probability predictor 104 can be any script, file, program, application, set of instructions, or computer-executable code, that is configured to enable a computing device on which the channel open probability predictor 104 is executed to predict an ion channel's open probability. The protein scale function model 108 use the predicted kinetic on rates and the kinetic off rates for the ion channel to predict the ion channel's open probability. It should be appreciated that ion channels open and close in a stochastic fashion, following the laws of probability. However, the probability of finding the channel closed or open is not a fixed number but can be modified by some external stimulus, such as the voltage.

Figure 3C:
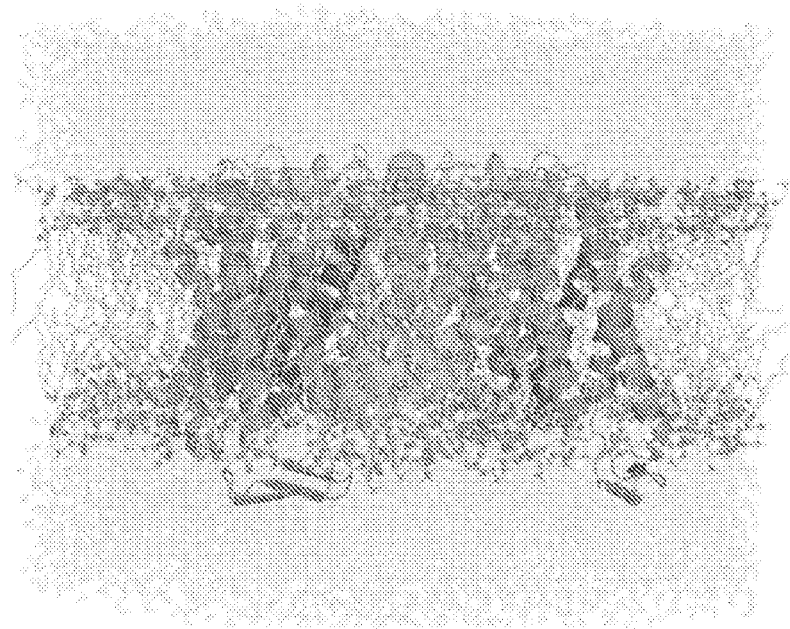
FIG. 3C shows Molecular Dynamics of hERG (Lees-Miller, J. P. et al. (2009) Biophys J. 96:3600-3610; Subbotina, J. et al. (2010) Proteins 78:2922-2934). Transmembrane view shows hERG model embedded into lipid bilayer after 10 ns equilibration. PD forming segments (S5, selectivity filter, and S6) are shown in a green color. VSD forming segments are shown in magenta (S1-S3) and blue (S4).

Starting with the lowest energy models for the drug-channel complexes from the Rosetta docking simulations, the system 100 can launch a library that can include hundreds of long (100 ns) molecular dynamics simulations (FIG. 3C). These simulations can enable the observation of unbiased trajectories of drug binding and unbinding with the ion channel. The system 100 can calculate the standard free energy of binding ($\Delta G°$) using $\Delta G° = -\Delta W - k_B T \log(V_b/V°)$, where $\Delta W$ is the depth of the potential of mean force (PMF), computed from the library of trajectories that have sampled an equilibrium distribution of drug-channel interactions, $k_B$ is the Boltzmann constant, T is the temperature, $V_b$ is the bound volume calculated as the integral of the Boltzmann factor of the potential mean force over the binding site, and $V°$ is the standard state volume. The system then carry out a Markov State analysis to determine the kinetically separated stable and metastable states. Analysis of the successful state crossings can provide yield statistics from which the system 100 can obtain kinetic rate constants. The system 100 can do this by using the mean first passage time (MFPT) for the ON and OFF reactions as $k_{off}=1/\text{MFPToff}$ and $k_{on}=1/(C^*\text{MFPT}_{on})$, where $k_{on}$ is inversely dependent on the ligand concentration, C. Knowledge of the free energies and rates of drug binding, combined with the extensive sampling of drug movements around the channel, can inform the mechanisms of drug interactions, understanding extents and rates of binding and unbinding of the different drugs to a particular state of the channel.

FIG. 3B illustrates drug orientation in the receptor cavity for d-sotalol binding to open-inactivated states of the hERG channel. FIG. 3B also provides direct evidence for differential targeting to open-inactivated state of the channel.

The binding constant for a drug can be calculated as:

$$K_D^{-1}(\text{binding}) = \pi R^2 \int_{z_{min}}^{z_{max}} dz\, e^{-PMF(z)/k_bT}$$

where PMF(z) is potential of mean force along the reaction coordinate and R is a confinement radius used to enhance relevancy sampling. In addition to the Markov model described above, the system 100 can use the Kramer's approach to kinetics of the drug unbinding. Kramer's rate theory describes the escape rate of the drug from a stable state to another state as:

$$\text{rate} = \frac{D\sqrt{K_b K_w}}{2\pi k_B T} \exp(-\Delta W(z)/k_B T)$$

where D is the approximate drug diffusion coefficient, which can be directly computed from PMF simulations. $\Delta W(z)$ is the free energy difference between the barrier and the well. $K_b$ and $K_w$ are the curvatures at the barrier and well, respectively. The method has been tested in ivabradine, KN93, and dofetilide binding to hERG. The system 100 can also sample by utilizing parallel tempering of multiple simulations with the drug bound and unbound to the ion channel. The spatially-resolved diffusion coefficient is used in the kinetic modelling. Molecular dynamic simulations can rely on the careful parameterization of new drug models.

For new compounds, the system uses a multistep protocol with Quantum Mechanical calculations for minimized coordinates, interactions with water molecules, adjustments to improve interactions in aqueous media, and dipole moments of neutral and charged drugs, and via modifications to Lennard-Jones potentials to approach experimental partitioning data, such as from water to the membrane interface mimetic, n-octanol. Statistical error minimization can be via exhaustive sampling of drug bound states, utilizing the Replica-Exchange method with parallel tempering and Markov state analysis.

The empirical measurements of the drug binding to heterologously expressed hERG channels can provide a link between the molecular and cell scale models. The system 100 can provide the state dependent affinities and kinetics of the hERG blockers. To generate experimentally constrained models of hERG blocker kinetics, the system can conduct measurements of binding kinetics to determine the molecular rate constants $k_{on}$ and $k_{off}$ for channels in closed, open and inactivated states. The resultant dissociation constants from steady state measurements can cross validate rate constant extractions by the relationship $KD=k_{off}/k_{on}$. The general framework of rate extraction can be used to determine drug-binding rates under conditions that bias the equilibrium between states towards the conformation for which affinity is measured. Appropriate voltage protocols enable extraction of state-dependent affinities for the conformation of hERG channels. Similar protocols can enabled the prediction of affinity changes between states of K+ channels that can be measured independently with optical recordings of fluorescently-labeled K+ channel inhibitors.

The system 100 can conduct drug binding kinetic experiments by patch-clamp electrophysiology using conventional manual patch clamp and with a Q-Patch medium-throughput electrophysiology workstation. The Q-Patch system can enable 16 simultaneous recordings with individual control over drug application and series resistance compensation. Both manual and Q-Patch recordings can be compensated for series resistance error by a maximal admissible voltage error criterion.

The system 100 can test compounds against a stable HEK-hERG cell line. Rate constants for different channel conformations can be extracted from drug wash-in and wash-out kinetics during stimulus protocols, that bias channel towards adopting closed, open and inactivated conformations. Closed channel affinity can be assessed using negative holding potentials with sparse test pulses to test channel inhibition. Open channel affinities can be deduced by including frequent pulses to maximally open the channels. Inactivated channel affinity can be assessed from current inhibition at depolarized holding potentials where channels are biased towards inactivated conformations.

To constrain drug rates for conformational states in the kinetic models, the system can use drug concentration (a model variable) and diffusion rates (D) to formulate drug on rates $k_{on}$=[drug]D. Affinity ($IC_{50}$) of the drug to discrete conformations determines drug off rates $k_{off}$=$IC_{50}$D. The diffusion constants can be extracted from the molecular dynamic simulations described herein or introduced as parametric variables. The system can derive the relative kinetic rates for the charged and neutral drug fractions from the atomic scale simulations described herein. These values can be compared to experimentally measured affinities and used to constrain the drug binding and unbinding rate constants in the Markov model. Drug "on" and "off" rates can be fixed to reduce the number of free parameters in the model. Rate constants can then be constrained via optimization to electrophysiological pacing protocols for each agent. Implicit methods can be used to solve ordinary differential equations. Nelder-Mead or Newton-Raphson optimization with random small (<10%) perturbations applied to local minimum can enable continued optimization to improve fits.

The agent impact predictor 122 can include the cell model 110. The cell model 110 can be any script, file, program, application, set of instructions, or computer-executable code, that is configured to enable a computing device on which the cell model 110 is executed to determine the impact of the agent on a cellular level model using inputs from the kinetic rate predictor 102, atomic scale model 106, and/or the protein function scale model 108. In some implementations, the cell model 110 can be a Sotis-Saucerman cardiac cell model. The cell model 110 can generate simulations of the action potentials generated by the simulated cells. The action potentials can be generated in response to the flux of ions into and out of the simulated cells. The agent impact predicted by the atomic scale model 106 and the protein scale function model 108 can be used to model the flux of ions into and out of the simulated cells. The cell model 110 can provide a series of simulated action potentials to the TRiAD predictor 114 in the form of a simulated ECG. The TRiAD predictor 114 can calculate the TRiAD of the simulated ECG. Calculating the TRiAD can include calculating the triangulation of an action potential within the ECG signal. The TRiAD calculation can also include calculating the reverse use dependence, the beat-to-beat instability of the action potentials. Calculating the TRiAD can also include calculating the temporal and spatial action potential duration dispersion.

The system 100 can use the Soltis-Saucerman rabbit cardiac model for initial simulations. This enables experimental validation of model predictions to ensure drug-receptor interactions are modeled accurately, followed by simulations in human models. For translational significance, following full validation in computational lower animal models, the models of drug-channel kinetics can be incorporated into models of ventricular cells. The system can use the Soltis-Saucerman for β—adrenergic/CAMKII signaling cascade and models for IKs, IKr, and ICa-L. The system can predict drug effects on action potentials (APs) for therapeutic concentrations of amiodarone 0.1 mg/L to 2.5 mg/L; d-sotalol 400 ng/mL to 2500 ng/mL; dofetilide 4 nM; moxifloxacin 5.9 µM.

In further detail of the TRiAD calculation, the system 100 can calculate triangulation of the action potential during simulated action potential as $ADP_{90}$-$ADP_{30}$. The system 100 can pace simulated ventricular myocytes to steady-state at a rate of about 60 to about 220 beats per minute (BPM) and APD adaptation curves can be constructed (BCL versus APD) for various drug concentrations within the clinical range for each drug. Steepening of the curve relative to drug free curves indicates reverse use dependent drug effects. The system 100 can calculate beat-to-beat instability of action potential duration by simulating 10000 normal ventricular myocytes (+/−drug) with randomly varying ionic conductances (GNa, GCaL, GCaT, GKs, GKr, GKl, GKp) within 20% of their nominal values. That is not meant to imply that the conductances vary by +/−20% on each beat, but is an efficient way to observe responses in a population of action potentials with varying parameters. The values can be uniformly distributed and new values randomized and applied prior to the stimulus and held constant for the duration of the ensuing action potential. $ADP_{90}$ can be calculated for each cell as the time from the maximum velocity of the action potential upstroke (dV/dtmax) until the time of 90% repolarization at 1 Hz. Temporal action potential duration dispersion can be calculated at the 500th paced beat (BCL=1000 ms) in single myocytes. The system can test the degree of $APD_{90}$ variability induced by small electrical perturbations that are present in any noisy physiological system, or that may result from an ectopic beat or triggered depolarization in nearby tissue. To simulate these perturbations, the system can small amplitude inward currents randomly between −0.1 to −0.2 pA/pF for 50 ms over the course of the action potential plateau at a pacing cycle length=1000 ms. The small inward current can also be applied randomly in time between 30 to 200 ms on the plateau phase for 1000 beats.

In addition to TRiAD, the system 100 can track additional parameters. The parameters can include cell excitability (max. upstroke velocity of the AP (V/s)), action potential duration (APD), early afterdepolarizations (EADs), cell refractoriness and APD restitution. The system 100 can simulate drug dose-dependent increases in APD compounds, but no reverse use dependence for moxifloxacin. It is expected that dofetilide, ibutilide, and sotalol (or other agents) can promote the TriAD and exhibit strong reverse use dependence. The influence of off-target drug effects (e.g. blocks by amiodarone) on cell parameters can be predicted in simulations with drugs on primary targets alone and/or with off-target effects. The system 100 can use sensitivity analysis to identify quantities underlying model dynamics, examine the limits on parameter estimation from experimental measurements, improve numerical stability, and test hypotheses. Variance based systematic sensitivity analysis using an orthonormal Hermite approximation (OHA) for parameter perturbations can produce sensitivity coefficients connecting parameters and outputs. Validation of the model predictions can be conducted in rabbit myocytes. The model predictions of changes to cell parameters after drug application can be experimentally tested in single rabbit ventricular myocytes.

Additional details about cellular scale modeling is described below in the Examples Section and specifically in relation to Example 1's "Cell Scale" section. Additional details for calculating the TRiAD are described below in the Examples Section and specifically in relation to Example 1's "Simulation of the TRiAD" section.

The agent impact predictor 122 can also include the tissue model 112. The tissue model 112 can be any script, file, program, application, set of instructions, or computer-executable code, that is configured to enable a computing device on which the tissue model 112 is executed to perform tissue scale modeling to predict a fourth impact of the agent on a tissue level model. In some implementations, the tissue model 112 can include a one-dimensional simulation. The tissue model 112 can determine parameter regimes of interest based on the one-dimensional modeling. In other implementations, the tissue model 112 can include a two-dimensional or a three-dimensional model.

In further detail of the tissue model, the system can carry out or execute one-dimensional simulations to coarsely identify parameter regimes of interest with a computationally tractable model. Regimes exhibiting compelling dynamics can be investigated in higher dimensions. The following parameter changes with drug application can be: APD restitution, conduction velocity (CV). CV can be calculated between cell 45 and 55 m (to avoid edge effects) at dV/dt-max. Because APD prolongation can trigger arrhythmias as well as conduction slowing, reentrant arrhythmias and wavebreak causing fibrillation, the system can predict the drug concentration for triggered activity, dispersion of repolarization, and conduction block (due to functional block caused by prolonged APD) and over 60 BPM to 220 BPM with escalating drug (0.5 µM increments) or an event occurs. A period of vulnerability exists when electrical stimulation can initiate self-sustaining spiral waves capable of degeneration into fibrillatory rhythms. The system can assess the "vulnerable window" to unidirectional block and retrograde conduction. The refractory period can be used to quantify drug-induced increase in arrhythmia risk.

Two-dimensional simulations can be used to determine if proarrhythmic phenomena occurred in lower dimensions, causing reentrant arrhythmias and/or spiral wave breakup. The change in voltage in space and time can be computed. As in the one-dimensional simulations, other parameters can be used in the two-dimensional simulations. 2D reentry can be induced after static pacing (S1) followed by an S2 within the vulnerable window. APD restitution, dispersion of repolarization and reentry wavelength can be tracked and compared to experiments before and after exposure to the agent. Sensitivity analysis can also be conducted. Because the PDE-based model is computationally expensive, the elementary effects can be used for sensitivity analysis of large perturbation combinations.

Figure 8:
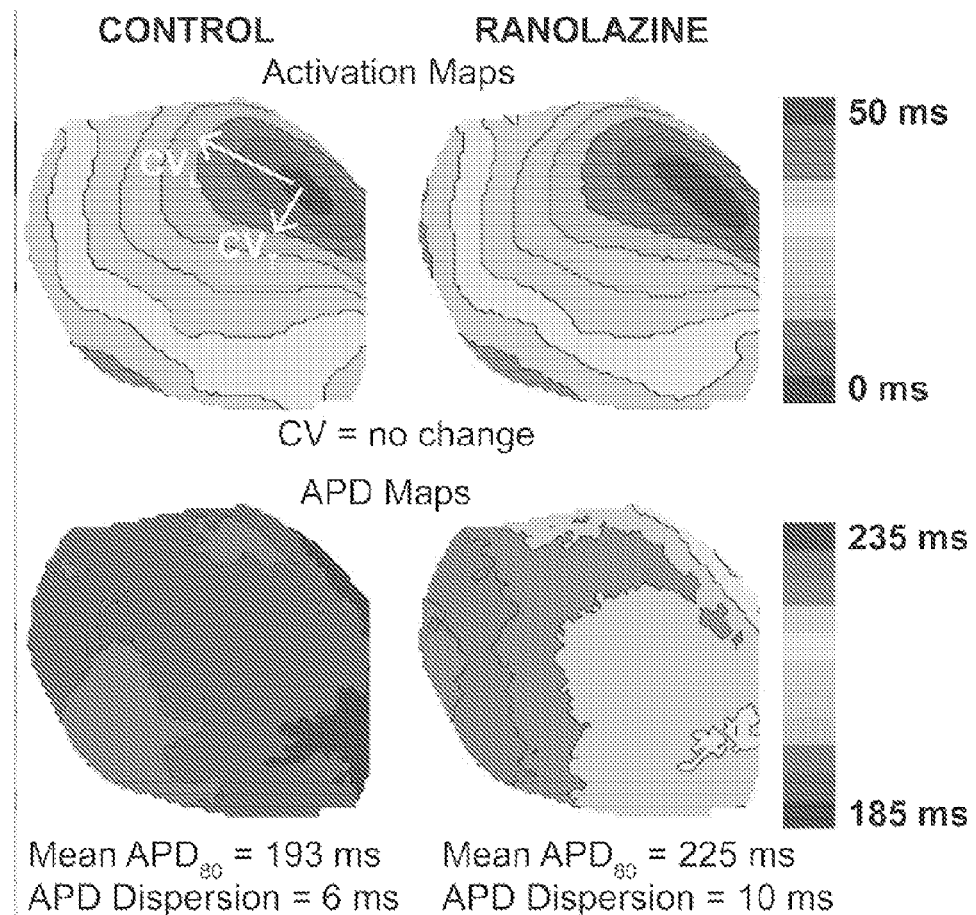
FIG. 8 shows an example of experimental tissue data for model validation. Activation and APD maps at baseline and following 10 μM ranolazine in the rabbit heart. Top) Conduction Velocity is unchanged. Lower) APD and spatial dispersion (range of 5-95 percentile of APD).

The tissue model can be experimentally validated. The tissue model can be experimentally validated with optical mapping experiments. The experiments can be performed in rabbit tissue to validate key parameter changes predicted by the tissue level simulations with no drug, dofetilide, sotalol, moxifloxacin, and amiodarone. Arrhythmia vulnerability parameters can be tracked (see FIG. 8) and compared to simulated parameters. The conduction velocity, conduction velocity restitution, APD restitution, dispersion of repolarization and reentry wavelength can also be tracked. Optical mapping experiments in Langendorff-perfused rabbit hearts can use voltage-(RH237) and calcium-(Rhod2-AM) sensitive dyes. The dyes can be excited with LED light sources (~530 nm). Emitted light can be collected with two MiCam Ultima-L CMOS cameras (SciMedia, USA) at a sampling rate of 1 kHz. The mapping field of view can be approximately 2.5×2.5 cm, resulting in a spatial resolution of ~250 gm/pixel. The AV node can be ablated to produce heart block, and hearts can be paced at rates of 60 BPM-220 BPM. APs can be recoded from the left ventricular epicardium and a lead I ECG can be continuously recorded. Pacing can be applied with a bipolar electrode on the epicardial surface. Arrhythmia incidence can be measured with a standard S1-S2 or S1-S2-S3 pacing protocol and can be compared to simulated arrhythmias. After a 10-20-minute period of equilibration, hearts can be exposed to vehicle (Tyrode's solution) or drug and then to increasing concentrations.

Additional details on the tissue model 112 are described below in the Examples Section and specifically in relation to Example 1's "Tissue Scale" section.

The system 100 can include the scoring engine 116. The scoring engine 116 can be any script, file, program, application, set of instructions, or computer-executable code, that is configured to enable a computing device on which the scoring engine 116 is executed to determine a likelihood that the agent induces a particular effect. Based on the output of above-described models, the scoring engine 116 can generate a score that the agent induced a particular effect. The scoring engine 116 can report the score as a likelihood score that indicates the probability that the effect would happen when the agent is administered to a patient. The scoring engine 116 can generate the output score that the agent induces the particular effect using the predicted impact calculated by each of the atomic scale model 106, the protein scale function model 108, the cell model 110, and the tissue model 112. The score can indicate the likelihood that the agent induces an arrhythmia.

In some implementations, the scoring engine 116 can perform risk factor modeling to identify agent induced diseases or sensitivity. The risk factor analysis can be performed by targeted mutagenesis by modifying discrete transition rates in computational models of ion channels that result in targeted modification of channel activation, inactivation, deactivation or recovery from inactivation. In some implementations, performing the risk factor modeling can include incorporating independent factors into the generation of the output score. The independent factors can include factors such as sex and age of the patient. The independent factors are factors that may not relate to the mechanism of the ion channels modeled by the tissue model 112.

The scoring engine 116 can also calculate an arrhythmia proclivity score. The arrhythmia proclivity score can be based on a high-dose agent model and an agent-free model. The arrhythmia proclivity score can be a range extending from a first number that corresponds to an absence of the agent and a second number that corresponds to a positive control induced by an agent known to cause arrhythmia.

In further detail of the proclivity score, to simulate effects of dofetilide, the system replaces the $I_{K_r}$ channel with a Markov model. For the TRiaD simulations, simulations were conducted as follows: First, Triangulation was calculated as the repolarization time from $APD_{30}$ to $APD_{90}$ from 1000 simulated cell with noise currents. Reverse-use-dependence was measured $APD_{90}$ at steady state for each pacing cycle length (from 3 Hz to 0.5 Hz) and APD adaptation curves were constructed. Instability was simulated by applying small amplitude inward currents randomly between −0.1 to −0.2 pA/pF for 50 ms over the course of the action potential plateau at a pacing cycle length=1000 ms. A small inward current was also applied randomly in time between 10 to 210 ms on the plateau phase for 1000 beats. Applicants modeled beat-to-beat APD variability by adding noise currents into membrane potential calculations, and simulated 1000 cells action potentials. Using the equation:

$$V_{t+\Delta t} = V_t - \frac{I(V_t)\Delta t}{C_m} + \xi n\sqrt{\Delta t}$$

where n is N(0,1) is a random number from a Gaussian distribution, and $\Delta t$ is the time step. $\xi$ is the diffusion coefficient, which is the amplitude of noise. In FIGS. 18A-18I, $\xi$ was set to 0.32. The noise current was generated and applied to membrane potential $V_t$ throughout the whole simulated time course.

For transmural fiber simulations, spatial dispersion of repolarization, corrected QT interval, and frequency dependence of QT interval was performed via the models described herein using transmural 1- or 2-dimensional tissue composed of 165 ventricular cells ($\Delta x=\Delta y=100$ μm) connected by resistances to simulate gap junctions. The fiber can contain an endocardial region and epicardial region, which shown a linear decreased in APDs. In the model, $G_{toSlow}$ was monotonically increased from 0.0615 to 0.078, and $G_{toFast}$ was linearly increased from 0.0095 to 0.026. The fiber was paced at BCL=1000 ms for 200 beats. The stimulus is applied to the first cell.

For the ECG computation, extracellular unipolar potentials ($\Phi_e$) generated by the fiber in an extensive medium of conductivity $\sigma_e$, were computed from the transmembrane potential $V_m$ using the integral expression:

In One-Dimension:

$$\Phi_e(x') = \frac{a^2 \sigma_i}{4\sigma_e} \int (-\nabla V_m) \cdot \left[\nabla \frac{1}{r}\right] dx$$

$$r = [(x-x')^2]^{1/2}$$

In Two-Dimension:

$$\Phi_e(x', y') = \frac{a^2 \sigma_i}{4\sigma_e} \int (-\nabla V_m) \cdot \left[\nabla \frac{1}{r}\right] dxdy$$

$$r = [(x-x')^2 + (y-y')^2]^{1/2}$$

where $\nabla V$ is the spatial gradient of $V_m$, a is the radius of the fiber, $\sigma_i$ is the intracellular conductivity, $\sigma_e$ is the extracellular conductivity, and r is the distance from a source point (x, y, z) to a field point (x', y', z'). $\Phi_e$ was computed at an "electrode" site 2.0 cm away from the distal end along the fiber axis.

The tissue was paced at varying basic cycle length (BCL) from 800 ms to 1400 ms for 200 beats. Pseudo ECGs were computed from the transmembrane potential $V_m$ using the integral expression. Heart rate corrected QT (QTc) was computed using Fridericia formula using the cubic root of RR interval:

$$QT_c = \frac{QT}{\sqrt[3]{RR}} \quad (8)$$

Spatial APD dispersion was measured using the T-wave area indicator, which was calculated as the T-wave amplitude on the computed pseudo-ECGs. For this purpose, a 1-dimensional model of the transmural wedge preparation was stimulated by applying a standard short-long protocol as follows: The transmural wedge preparation was stimulated by a train of pulses (S1) at 1000 ms pacing cycle length until the steady-state was reached followed by a premature beat (S1-S2 interval=800 ms) and then a delayed beat (S3) was delivered after a long pause (S2-S3 interval=5000 ms). T-wave area calculations were computed as follows:

(Eq. 2)

$$\sum_{t=t1}^{t2} |ECG(mV)| \cdot \Delta t \quad (8)$$

where $\Delta t=1$ 1 ms, $t_1$ is the time where ECG equals to $T_{peak}-0.9*(T_{peak}$=minimum of left side oft-wave) and $t_2$ is the time where ECG equals to $T_{peak}-0.9*(T_{peak}$=minimum of right side of t-wave).

For Frequency-dependent QT prolongation fiber was paced at 1 Hz for 1000 beats (S1) and then a second stimulus (S2) was applied after a varying RR interval (between 550 ms and 1150 ms). The QT interval, in response to S2, was recorded. The same simulations were carried out 11 times for both control and dofetilide 2 nM cases, and the relative changes in slope of relationship of QT and preceding RR intervals were calculated.

For transmural tissue simulations, a heterogeneous cardiac tissue assuming a 500 by 500 component grid $\Delta x=\Delta y=100$ μm. This tissue was assumed to contain an endocardial region and epicardial region, with a linear decrease in APDs. All ion channel conductances and gap junctions parameters are same as in the one-dimensional simulations. Current flow is described by the following equation:

$$\frac{\partial V(x,y,t)}{\partial t} = D_x \frac{\partial^2 V(x,y,t)}{\partial x^2} + D_y \frac{\partial^2 V(x,y,t)}{\partial y^2} - \frac{I_{ion}-I_{stim}}{C_m}$$

Where V is the membrane potential, x and y are distances in the longitudinal and transverse directions, respectively, $D_x$ and $D_y$ are diffusion coefficients in the x and y directions. $I_{stim}$ is 500 mA/cm² for 1 ms. Applicants also incorporated anisotropic effects by setting $D_x$ and $D_y$ such that the ratio of conduction velocity is 1:2.

The output scores from each of these simulations are utilized in a weighted average calculation (proarhythmia score) whereby the weighting is determined by the correlation between each parameter and arrhythmia. Arrhythmia is determined by an in silico diagnostic test in 2- or 3-dimensional tissue using an S1-S2 pacing protocol. Arrhythmia is indicated by 1) induction of a spiral wave, 2) the persistence (duration) of the spiral wave. Additional metrics may be tracked including spiral wave morphology and potential to break up.

The higher the score, the more "proarrhythmic" the agent. The score is within the range of 0 to 1, where 0 is the correlation in the absence of the drug and 1 is the correlation to the positive control induced by a high dose of dofetilide.

This ventricular tissue segment was first paced for 200 beats (S1) at BCL=1000 ms on the entire length of one side of tissue. A premature stimulus (S2) was then delivered at 330 ms in control case (FIG. 22A) after S1 in a 2.5 cm×2.5 cm area on the top edge of the endocardial region. (FIG. 22B) In ATX-II case, S2 paced at 450 ms, and at 465 ms in Dofetilide case (FIG. 22C) after S1 in a 2.5 cm×2.5 cm area on the top edge of the endocardial region. With GS-458967 applications, S2 was applied at 420 ms in ATX-II (FIG. 22D) and at 430 ms (FIG. 22E) in Dofetilide cases (FIGS. 22A-22E).

Additional details on the scoring engine 116 are described below in the Examples Section and specifically in relation to Example.

In some implementations, the system 100 can be provided validation data to validate the tissue model's models. For example, a transmural fiber can be stimulated and recorded. The models can compare the experimentally obtained stimulation results with action potentials generated with the agent impact predictor 122. Based on the recording of the stimulated transmural fiber, the models' parameters can be manipulated to provide a ECG computation that resembles the action potentials (and ECG) from the stimulation of the transmural fiber. Additional details on the validation of the model are described below in the Examples Section and specifically in relation to Example 1's "Simulation Methods" and "Model validation" sections.

Figure 2A:
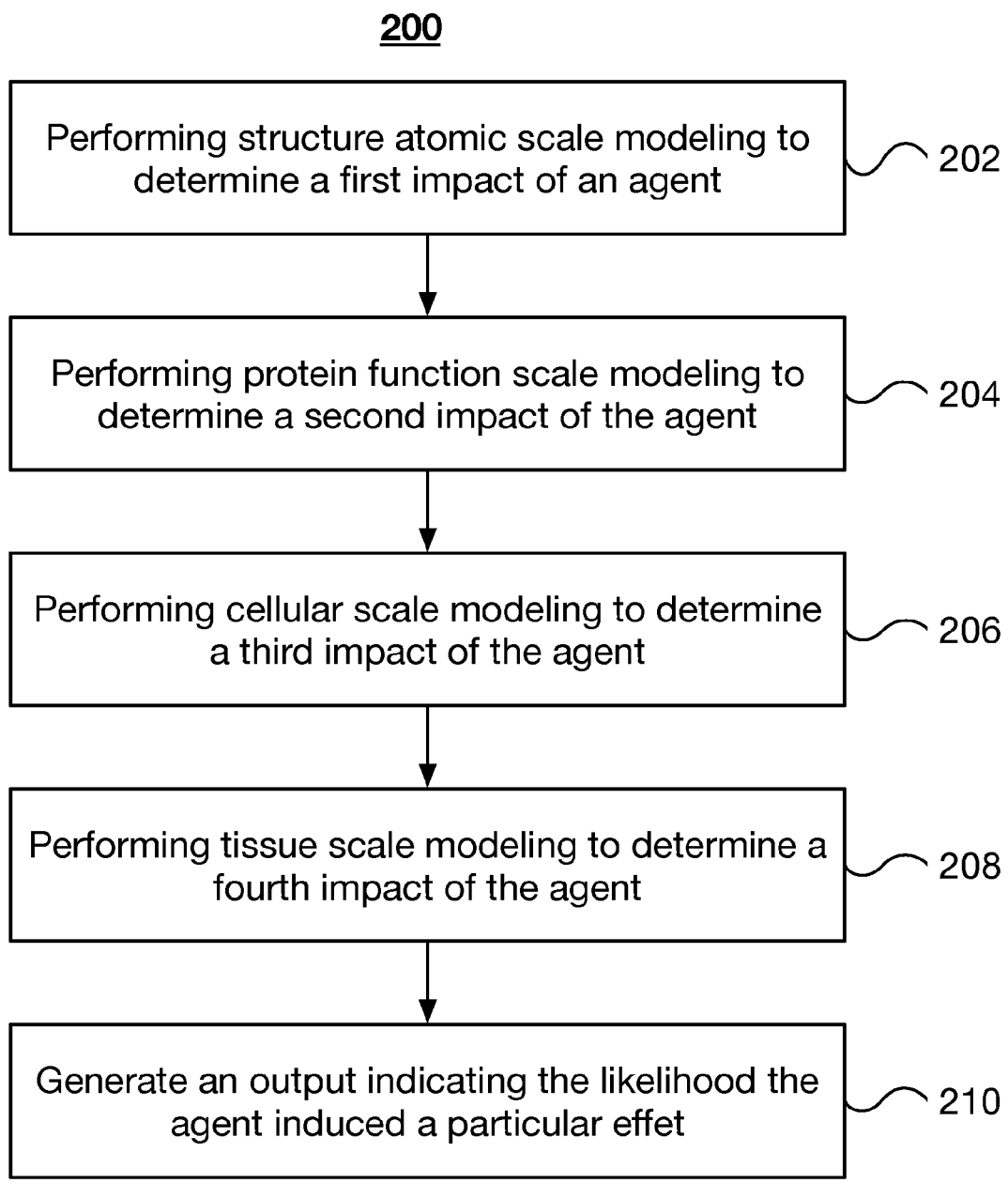
FIG. 2A illustrates a block diagram of an example method for predicting agent induced effects using the system illustrated in FIG. 1.

FIG. 2A illustrates a block diagram of an example method 200 for predicting agent induced effects in silico. The method 200 can include performing structure atomic scale modeling to predict a first impact of an agent (Block 202). The method 200 can include performing protein function scale modeling to predict a second impact of the agent on the ion channels (BLOCK 204). The method 200 can include performing cellular scale modeling to determine a third impact of the agent on a cellular level model (BLOCK 206). The method 200 can include performing tissue scale modeling to predict a fourth impact of the agent on a tissue level model (BLOCK 208). The method 200 can include generating an output indicating the likelihood that the agent induces a particular effect (BLOCK 210).

As set forth above, the method 200 can include performing structure atomic scale modeling to predict a first impact of the agent (BLOCK 202). The atomic scale modeling can predict the impact of the agent on one or more ion channels. The atomic scale model can provide the impact of the agent on the ion channels to a protein function model.

In some implementations, the atomic scale modeling can predict the kinetic on and off rates of the ion channels. The kinetic rates can be predicted for the ion channel in an open state, a closed state, and an inactive state. In some implementations, the atomic scale modeling can be performed to determine one or more kinetic parameters that can be used to inform one or more other models, such as the protein function scale model. The one or more kinetic models can include kinetic on rates and kinetic off rates of one or ion channels while the ion channels are in one or more states, such as an open state, a closed state, or an open-inactivated state.

The atomic scale model can also use the kinetic rates to predict agent binding rate constants and agent unbinding rate constants. The atomic scale model can also determine the kinetic on and off rates based on different agent concentrations and agent diffusion rates. The atomic scale model can provide the predicted kinetic rate information to the protein function scale model. In some implementations, the predicted kinetic rate information can be used to initiate one or more parameters or constants used in the protein function scale model.

The method 200 can include performing protein function scale modeling to predict a second impact of the agent on the ion channels (BLOCK 204). In some implementations, the protein function scale modeling can incorporate agent concentration and agent diffusion rates to predict the second impact of the agent on the ion channels. The protein function scale modeling can also incorporate the first impact of the agent that was determined by the atomic scale model. In some implementations, the protein function scale model can model multiple states of pore-forming and voltage sensing domains. In some implementations, the protein function model can modify discrete transition rates of the ion channels.

In some implementations, the protein function scale modeling can predict, based on the kinetic on and off rates provided by the atomic scale model, the channel open probabilities of one or more ion channels. It should be appreciated that ion channels open and close in a stochastic fashion, following the laws of probability. However, the probability of finding the channel closed or open is not a fixed number but can be modified by some external stimulus, such as the voltage.

In some implementations, the ion channels is a cardiac ion channel. The ion channels can be hERG channels. The ion channels can be potassium, sodium, or calcium ion channels. The agent can be a drug, antibody, small molecule agent, pharmaceutical composition, an agent that blocks hERG, an agent that prolongs a QT interval, an agent that causes TdP, or any combination thereof.

The method 200 can include performing cellular scale modeling to determine a third impact of the agent (BLOCK 206). The third impact can be the impact of the agent on a cellular level model. The cellular scale model can incorporate the second impact of the agent to determine the third impact of the agent.

In some implementations, the cellular scale model can determine the third impact of the agent based on one or more characteristics of a simulated action potential. The cellular scale model can calculate the third impact of the agent using action potential characteristics such as triangulation, action potential duration, and beat-to-beat instability. The cellular scale model can calculate the triangulation of the action potential based on the agent's concentration. The cellular scale model can calculate action potential duration adaptation curves to determine reverse use dependent agent effects. The action potential duration adaptation curves can be based on a plurality of different agent concentrations.

The method 200 can also include performing tissue scale modeling (BLOCK 208). The system can perform the tissue scale modeling on a tissue level model to determine a fourth impact of the agent. The tissue scale model can predict the fourth impact of the agent using a one-dimensional simulation, a two-dimensional simulation, or a three-dimensional simulation. In some implementations, the one-dimensional simulations can be performed to locate compelling dynamics. The compelling dynamics can be further investigated with the two-dimensional and the three-dimensional simulations.

The method 200 can include generating an output indicating the likelihood that the agent induces a particular effect (BLOCK 210). The output can be based on the fourth impact determined by the tissue scale model. In some implementations, the output can be based on the first impact, the second impact, the third impact, the fourth impact, or any combination thereof. The output can be a likelihood score that the agent can induce a particular effect given the first impact, the second impact, the third impact, or any combination thereof. The likelihood score can indicate the likelihood that the agent induces an arrhythmia. The method 200 can also include generating a range of likelihood scores. The range of likelihood scores can be the likelihood that the agent can induce an arrhythmia. The likelihood score can be an arrhythmia proclivity score that extends from a first number that corresponds to the absence of the agent to a second number that corresponds to a positive control induced by an agent known to cause arrhythmia.

In some implementations, the method 200 can also include performing risk factor modeling to identify agent induced diseases or sensitivity. For example, the risk factor modeling can determine is a specific sex, age, or race is more likely to be effected by the agent. The risk factor modeling can include performing targeted mutagenesis by modifying discrete transition rates in computational models of ion channels that result in targeted modification of channel activation, inactivation, deactivation or recovery from inactivation.

Figure 2B:
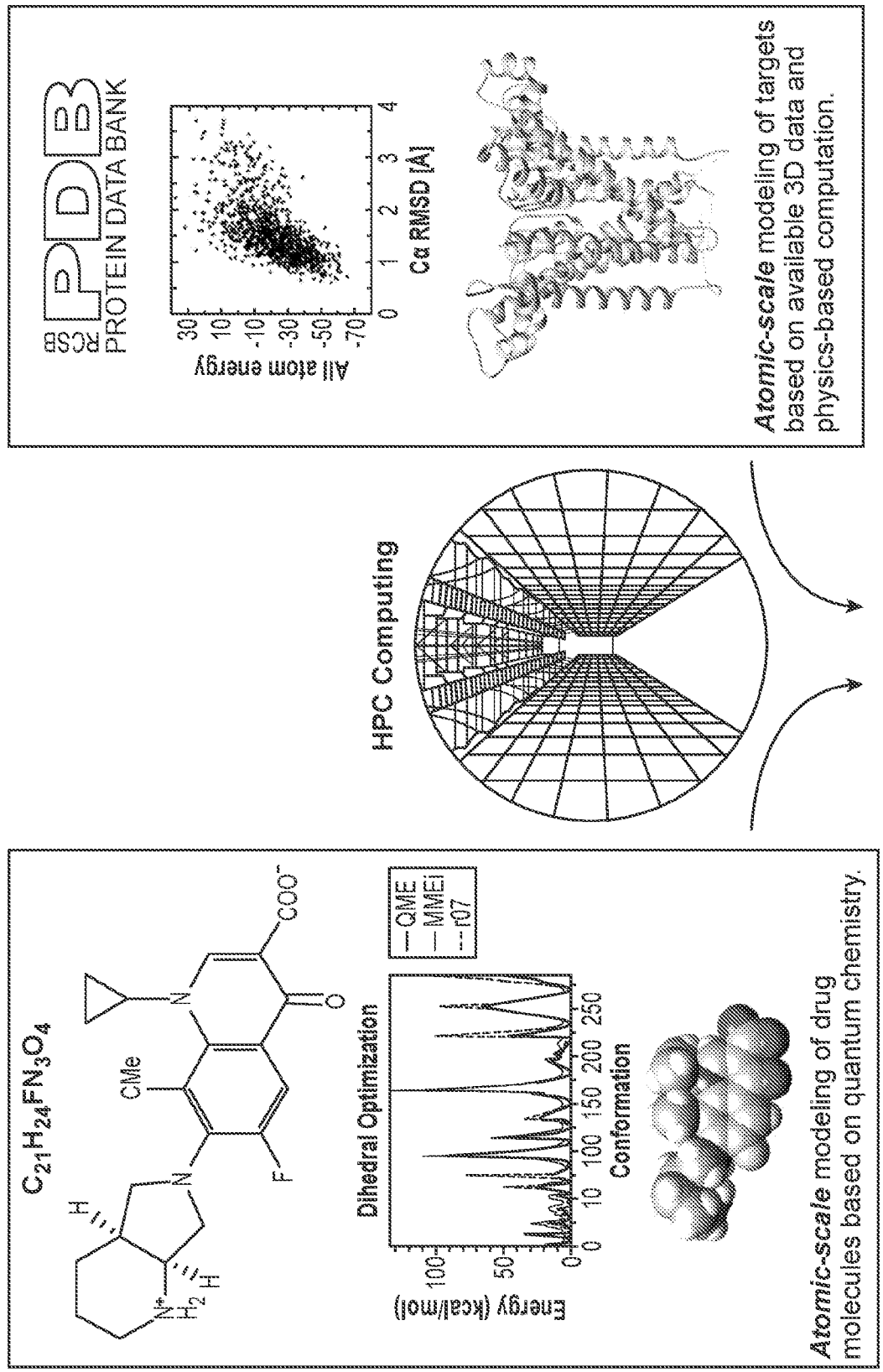
FIG. 2B illustrates a workflow diagram for modeling and predicting drug effects.

FIG. 2B illustrates a workflow diagram for modeling and predicting drug effects. The atomic-scale modeling can be based on the quantum chemistry of the agent. The atomic-scale modeling of targets can be based on 3D data of the ion channel and physics-based computations. The output of the atomic-scale modeling can be provided to a molecular-scale model. The molecular-scale model can derive state-dependent chemical kinetics. The output of the molecular-scale model can be provided to the cellular-scale model. The cellular-scale model can make predictions of the agent effects on the cellular-scale model. The output of the cellular-scale model can be provided to the tissue-scale model. The tissue-scale model can make predictions of the agent effects in 1D and 2D virtual reconstructions of the tissue. The results of the tissue-scale model can be used to make organ-scale simulations of the agent's effects.

EXPERIMENTAL EXAMPLES

A. Example 1

A major factor plaguing drug development is that there is no preclinical drug screen that can accurately predict unintended drug induced cardiac arrhythmias. The current approaches rely on substitute markers such as QT interval prolongation on the ECG. Unfortunately, QT prolongation is neither specific nor sensitive to indicate likelihood of arrhythmias. There is an urgent need to identify a new approach that can predict actual proarrhythmia rather than surrogate indicators. Mathematical modeling and simulation constitutes one of the most promising methodologies to reveal fundamental biological principles and mechanisms, model effects of interactions between system components and predict emergent drug effects. Thus, the disclosure proposes the development of a novel multiscale approach based on drug-channel structural interactions and kinetics intended to predict drug induced cardiotoxicity in the context of: 1) preclinical drug screening, 2) drug rehabilitation, and 3) prediction of the intersection of drug effects and coexistent risk factors. Applicants' underlying hypothesis is that the fundamental mode of drug interaction derived from each drug's unique structure activity relationship determines the resultant effects on cardiac electrical activity in cells and tissue. By capturing these complex drug channel interactions in a model, It is expected to be able to predict drug safety or electro-toxicity in the heart. Predictions from the atomic structure simulations can be used to inform the kinetic parameters of models that capture the complex dynamical interactions of drugs and ion channels. The computational components can then be studied in predictive models at the channel, cell and tissue scales to expose fundamental mechanisms and complex interactions underlying emergent behaviors. Experiments in mammalian cells and tissues can be undertaken to validate model predictions. Drug properties can be perturbed in models to rehabilitate dangerous drugs and reduce their potential toxicity. The multiscale model for prediction of cardiopharmacology that the disclosure develops in this application can be applied to projects demonstrating the usefulness for efficacy or toxicity of drug treatments in the complex physiological system of the heart.

Drug Prediction: To establish a prototype multiscale model for safety pharmacology. Not all hERG block is proarrhythmic. But, at present, there is no way to distinguish unsafe hERG blockers from safer drugs. Applicants' goal is to assemble, utilize and experimentally validate a proof-of-concept multiscale model to predict cardiac effects for two classes of prototypical drugs: (A) Drugs that block hERG, prolong QT and cause TdP (i.e., d-sotalol, dofetilide, ibutilide) and, (B) Drugs that block hERG, prolong QT and do not cause TdP (moxifloxacin, ketaconozole, amiodarone). The disclosure asserts that two drug factors determine promotion of TdP: 1) Multichannel block that may cancel hERG effects, and 2) Conformation state specificity of hERG block and associated kinetics, may promote TdP as indicated by the TRIaD: Triangulation, reverse use dependence, beat-to-beat instability of action potential duration, temporal and spatial action potential duration dispersion. The disclosure develops an integrative experimental and computational modeling approach that spans scales from the atom to cardiac rhythm to predict structure activity relationships that determine drug safety or proarrhythmia.

Drug Rehabilitation: To apply the model to design safer hERG blockers. The disclosure expands the multiscale model to carry out hERG blocker rehabilitation. Applicants' goal is to identify fundamental drug mechanisms that promote TdP as indicated by the TRIaD. The disclosure uses an in silico screen to identify the structural and kinetic properties of drugs that promote the TRIaD. Preliminary results indicate that hERG blockers with high affinity to the inactivated state, such as dofetilide, exhibit TRIaD-derived proarrhythmic properties, whereas drugs with predominant open state affinity (moxifloxacin) do not. The disclosure performs dofetilide rehabilitation using the structure guided RosettaLigandDesign computational approach in order to design a TRIaD-safer analog of dofetilide with reduced inactivated state block. The most promising compounds can be synthesized and then screened experimentally and in virtual ion channels, cells and tissues under arrhythmia provoking conditions to screen for improved drug safety. This can produce novel predictions of hERG based atomic determinants of TRIaD linked proarrhythmia.

Drug Risk Stratification: To predict the interaction of risk factors with hERGdependent cardiotoxicity. One of the goals this disclosure achieves is to assemble, utilize and test the multiscale model in the presence of concomitant risk factors for drug-induced acquired Long-QT Syndrome. Female sex is a profound independent risk factor for development of TdP in drug-induced LQTS, suggesting that the effect of sex hormones on arrhythmic risk may be related to cardiac ion channel mechanisms. The disclosure uses an interdisciplinary approach to test the hypothesis that estrogen is a hERG pore blocker that acutely increases QT interval and propensity for TdP arrhythmias. This hypothesis is based on published data showing that estrogen interacts with hERG, reduces hERG current, increases the rate of channel deactivation and makes hERG more sensitive to block by other drugs. As such, the system can apply the integrative multiscale approach to predict a role for estrogen in female-linked propensity for drug-induced arrhythmias.

There is a critical need to identify a better approach for preclinical drug screening that is both specific and sensitive, and that identifies actual "proarrhythmia", rather than substitute markers (Hondeghem, L. M. (2006) J Cardiovasc Electrophysiol. 17:337-340). This application proposes the development of a novel "bottom up" multiscale approach based on drug-channel structural interactions and kinetics intended to begin to solve this problem in the context of: 1) preclinical drug screening, 2) drug rehabilitation, and 3) prediction of the intersection of drug effects and coexistent risk factors. The disclosure proposes that the fundamental mode of drug interaction derived from each drug's unique structure activity relationship determines the resultant effects on cardiac electrical activity in cells and tissue. By capturing the intrinsic complexity of drug channel interactions in a model, it is expected to be able to predict drug safety or electro-toxicity in the heart.

The system can include multiscale models for predicting cardiac safety pharmacology from chemistry to rhythm (FIG. 1). The model can enable simulation and prediction from the small molecule scale of the drug, to protein structure, protein function, cell and tissue levels. Applicants have brought together the following established approaches to develop a novel paradigm for predictive safety pharmacology: 1) developed the Rosetta-Membrane computational method for ion channel structure prediction and recently for small molecule interactions with voltage-gated sodium and hERG channels; 2) developed tools for efficient prediction of binding free energy and Molecular Dynamics to provide molecular descriptions of K channel function and drug interactions; 3) established cardiac channel, cell and tissue modeling and simulation methods to predict the effects of ion channel drugs on ventricular rhythms; 4) specific expertise in modeling hERG channel gating and pharmacology; 5) extensively studied kinetics and mechanisms of drug interactions with K$^+$ channels; 6) expert in cardiac cellular electrophysiology and pharmacology; 7) developed high-resolution optical cardiac imaging at the tissue and whole heart scale; 8) medicinal chemist who has designed multiple channel modulators.

The first necessary step for predicting emergent drug effects on the heart is determining and modeling the kinetics of primary and major off-target drug interactions with subcellular targets. The bulk of drugs that target ion channels have complex interactions at the atomic scale. Moreover, changes in voltage result in changes to apparent affinities of drugs for their receptors at the protein function scale. Bi-directional feedback exists because drugs alter the cell scale action potential, which affects the potency of drugs. In order to predict drug efficacy, the dynamical complexity of the drug kinetics must be considered to predict the combined emergent effects in the tissue scale. Similarly, reentrant ventricular arrhythmias are emergent tissue scale phenomena that are influenced by coupling because of the ~mm electrical space constant of myocardium.

In Aim 1, the disclosure begins by modeling dofetilide, ibutilide and sotalol, which are prototypes of the proarrhythmic class associated with hERG block, QT prolongation and TdP (Van Opstal, J. M. et al. (2001) Eur J Pharmacol 412:67-76). These drugs can be compared to the hERG channel blockers moxifloxacin, ketaconozole and amiodarone that block hERG and prolong QT, but do not promote ventricular arrhythmias. The system can carry out multiscale model simulations to predict and compare the drugs' fundamental mechanisms (Alexandrou, A. J. et al. (2006) Br J Pharmacol. 147:905-916; Nalos, L. et al. (2012) Br J Pharmacol. 165:467-478; Thomsen, M. B. et al. (2006) Br J Pharmacol. 149:1039-1048). A novel link between scales can be established in Aim 1: Atomic scale predictions can estimate drug docking sites and association and dissociation rates for hERG blockers to closed, open and inactivated states of the channel. These values can inform the kinetic parameters for functional scale Markov models of drug interactions with cardiac channels. Simultaneous experimental measurements can be used to test and validate the model predictions. Drug-channel models can be integrated into virtual cardiac cell and tissue level models to predict emergent drug effects that promote elements of the TRiAD: Triangulation, reverse use dependence (increase in drug effects at slow heart rates), beat-to-beat instability of action potential duration, temporal and spatial action potential duration dispersion—proarrhythmia markers that emerge at cell and tissue scales. Experiments can test and validate the model predictions.

An essential and unique aspect of Applicants' approach is that the disclosure models the state-dependent kinetics of drug interactions with the channel, which have been proposed as critical determinants of hERG block-associated proarrhythmia (Di Veroli, G. Y. et al. (2013) J Cardiovasc Electrophysiol. 25(2):197-207; Di Veroli, G. Y. et al. (2013) Am J Physiol Heart Circ Physiol. 304:H104-H117; Hill, A. P. et al. (2014) Mol Pharmacol. 85:769-776). The driving hypothesis is that the proarrhythmic cellular manifestations of the TRiAD arise directly from the underlying kinetics of channel block. Identification of the specific kinetic interactions that give rise to components of the TRiAD can define new standards for preclinical testing that can be used to rule out compounds with these properties in early screening tests. For example, existing data and Applicants' preliminary simulations suggest that high affinity inactivated state block of hERG channels underlies proarrhythmic reverse use-dependence of hERG blockers. If Applicants' tests confirm this prediction, then the disclosure attempts removal or reduction in the affinity of inactivated state block in an attempt to rehabilitate known hERG blockers and test for reduced propensity to arrhythmias. Drugs that do not exhibit high affinity inactivated state block of hERG are moxifloxacin, ketaconozole and the selective-serotonin reuptake inhibitor CONA-437 (Alexandrou, A. J. et al. (2006) Br J Pharmacol 147:905-916; Alexandrou, A. J. et al. (2014) J Physiol Pharmacol 65:511-523). Critically, neither moxifloxacin nor CONA-437 relies strongly on binding to the S6 aromatic amino acid residues Y652 and F656 (Alexandrou, A. J. et al. (2014) J Physiol Pharmacol 65:511-523). Thus, the disclosure tests if the structural disruption of this molecular interaction in dofetilide atomic simulations reduces inactivated state block. Drug analogs designed in this way can be tested in silico, with the systems described herein, and if promising, can be synthesized and tested experimentally.

Another essential aspect of safety pharmacology that is often neglected in the drug discovery process is the consideration of coexistent risk factors. It is well-known that female sex is the most profound risk factor for acquired long-QT syndrome and associated torsade de pointer (TdP) arrhythmias (Bazett, H. C. (1920) The Journal of Physiology 53:320-339; Pham, T. V. et al. (2002) Cardiovasc Res. 53:752-762; Pham, T. V. et al. (2002) Cardiovasc Res. 53:740-751; Furukawa, T. et al. (2007) Pharmacol Ther. 115:106-115; Nakamura, H. et al. (2007) Circulation 116: 2913-2922; James, A. F. et al. (2007) Prog Biophys Mol Biol. 94:265-319; Nakagawa, M. et al. (2005) J Cardiovasc Electrophysiol. 16:278-284; Taira, C. A. et al. (2010) Curr Drug Saf. 5:65-72; Farkas, A. S. et al. (2010) Drugs 70:573-603). Recent clinical and experimental studies suggest that differences in arrhythmia vulnerability may stem from sex steroid hormones (Pham, T. V. et al. (2002) Cardiovasc Res. 53:740-751; Furukawa, T. et al. (2007) Pharmacol Ther. 115:106-115; Nakamura, H. et al. (2007) Circulation 116: 2913-2922; Nakagawa, M. et al. (2005) J Cardiovasc Electrophysiol. 16:278-284; Nakagawa, M. et al. (2006) Pacing and Clinical Electrophysiology 29:607-613; Korte, T. et al. (2005) Circulation 111:2282-2290; Verkerk, A. O. et al. (2005) Int Heart J. 46:1105-1118; Bai, C. X. et al. (2005) Circulation 112:1701-1710; Xiao, L. et al. (2006) Am J Physiol Heart Circ Physiol. 291:H570-H580; Di Diego, J. M. et al. (2002) Circulation 106:2004-2011; Fish, J. M. et al. (2003) J Electrocardiol. 36(Suppl):173-179; Pham, T. V. (2003) Cardiovasc Res. 57:591-593; Pham, T. V. et al. (2002) Cardiovasc Res. 53:752-762; Pham, T. V. et al. (2002) Circulation 106:2132-2136; Pham, T. V. et al. (2001) Circulation 103:2207-2212; Hara, M. et al. (1998) J Pharmacol Exp Ther. 285:1068-107234-46). Thus, in Aim 3, the system can determine if physiological concentrations of the female sex steroid hormone estrogen can exacerbate initiation of self-sustaining reentrant arrhythmias, a clinically significant precedent to lethal arrhythmias that have been observed with significantly higher incidence in women in the setting of acquired long QT (Regitz-Zagrosek, V. (2006) Nat Rev Drug Discov. 5:425-438). Applicants' working hypothesis is that estrogen can acutely increase arrhythmia vulnerability in the presence of hERG blockers. The disclosure tests this hypothesis by carrying out studies to determine if acute application of the sex steroid hormone estrogen modifies risk for cardiac arrhythmias and to reveal the mechanisms of modified risk. To realize the most basic biological mechanisms underlying sex-based differences in LQTs risk and susceptibility to TdP arrhythmias can set the stage for specific sex-based risk stratification and drug screening.

Despite attempts for more than 50 years, there is no way to predict how drugs can alter the emergent electrical behavior generated in the heart. The disclosure aims to assemble a novel multiscale model intended to begin to solve this problem and to demonstrate its usefulness for 1) drug prediction (Lu, H. R. et al. (2010) Br J Pharmacol. 160:60-76), 2) drug rehabilitation and, 3) to predict drug effects in the setting of associated risk factors. The system can include model simulations at the level of the atom—for the small molecule scale of the drug and the molecule scale of the channel—and simulations at the functional levels of the protein, cell, tissue and organ. The power of combining these scales in a predictive framework is that it can enable, for the first time, a way to derive on and off rates of drugs from atomic scale simulations and to then use these values to inform and build functional level channel models. Although cardiac simulations at the channel, cell and tissue level have been long developed and are not new techniques per se, the simulations have been repeatedly proven. The novel linkages of the present system can connect mature approaches to emerging modeling approaches at the atomic scales.

The multiscale model can be used to address key independent research questions in each Aim to drive model development and exemplify applications. Ultimately, the approach is a scalable framework with automation potential to interact with other developing technologies, including high-throughput electrophysiology measurements (Penniman, J. R. et al. (2010) J Pharmacol Toxicol Methods 62:107-118; Mo, Z. L. et al. (2009) J Pharmacol Toxicol Methods 60:39-44; Zeng, H. et al. (2008) Assay Drug Dev Technol. 6:235-241; Trepakova, E. S. et al. (2007) Assay Drug Dev Technol. 5:617-627; Ly, J. Q. et al. (2007) Clin Lab Med 27:201-208; Dubin, A. E. et al. (2005) J Biomol Screen. 10:168-181; Bridal, T. R. et al. (2010) Assay Drug Dev Technol. 8:755-765; Jow, F. et al. (2007) J Biomol Screen. 12:1059-1067; Harmer, A. R. et al. (2008) J Pharmacol Toxicol Methods 57:30-41; Bridgland-Taylor, M. H. et al. (2006) J Pharmacol Toxicol Methods 54:189-199; Sorota, S. et al. (2005) Assay Drug Dev Technol. 3:47-57; Schroeder, K. et al. (2003) J Biomol Screen. 8:50-64), drug development via progress in synthetic biology (Nattel, S. et al. (2006) Nature Reviews Drug Discovery 5:1034-1049), and even personalized medicine via drug screening in patients' own induced pluripotent stem (iPS) cell-derived cardiomyocytes (Braam, S. R. et al. (2010) Stem Cell Res. 4:107-116). All of these developing technologies are innovative but they can't each alone solve the fundamental problem—that the effects of multifaceted drug interactions are emergent. These technologies in conjunction with the multiscale models that the disclosure develops may form an interactive multiscale modeling and simulation driven process that can ultimately be used in the regulatory process prior to drug approval, in academia for research, in industry for drug and disease screening, and for patient oriented medicine in the clinic.

Specific Aim 1—Drug Prediction: To establish a prototype multiscale model for safety pharmacology. Aim 1 Rationale: Applicants' goal in this aim is to distinguish QT prolonging proarrhythmic drugs from those that cause QT prolongation but not arrhythmias. The disclosure confirms the predictive utility of the model by simulating prototype drugs, dofetilide, ibutilide, sotalol, moxifloxacin, ketaconozole and amiodarone. Dofetilide, ibutulide and sotalol are prototypes of the proarrhythmic class-associated with hERG block, QT prolongation and TdP (Van Opstal, J. M. et al. (2001) Eur J Pharmacol. 412:67-76). The disclosure hypothesizes that dofetilide, ibutilide and sotalol have structure activity relationships that underlie distinct drug-channel kinetics that promote the TRiAD: Triangulation, reverse use dependence, beat-to-beat instability of action potential duration, temporal and spatial action potential duration dispersion. In contrast, moxifloxacin, ketaconazole and amiodarone are members of the second class: They block hERG, prolong QT interval and are not associated with TdP (Thomsen, M. B. et al. (2006) Br J Pharmacol. 149:1039-1048; Shah, R. R. (2005) Drug Saf. 28:115-125). The disclosure hypothesizes that amiodarone is an effective antiarrhythmic because of its many off target effects that mitigate hERG block and that moxifloxacin and ketaconazole interaction modes with hERG improve their safety profile. The disclosure uses the multiscale model to predict the underlying structure activity mechanisms that promote or dissuade arrhythmias.

Figure 6:
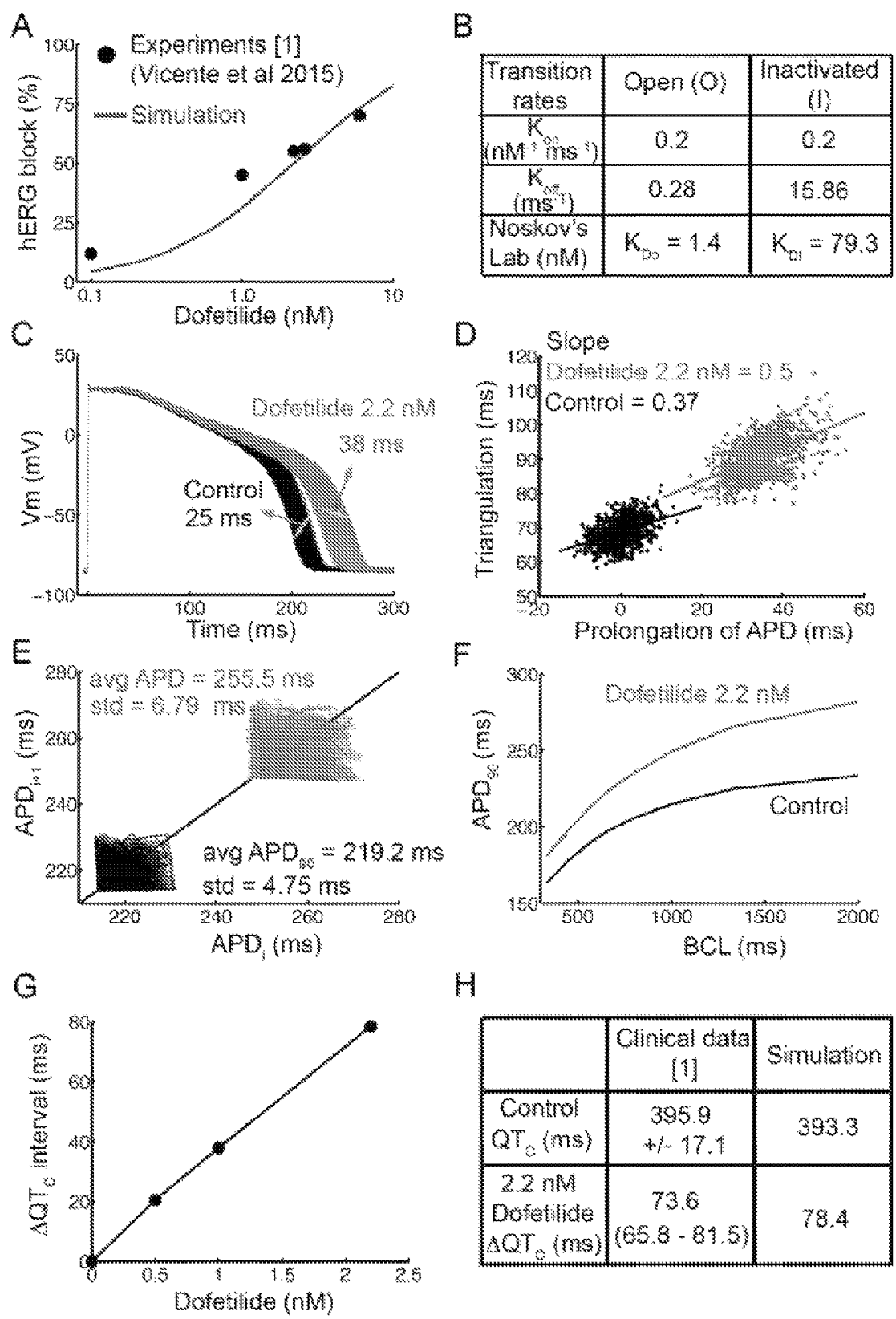
FIGS. 6A-6B show ofetilide block hERG potassium channel.
FIG. 6C shows predicted temporal action potential duration dispersion of 1000 simulated rabbit APs after Dofetilide (2.2 nM). Instability of APD was quantified as the difference between the maximum and minimum of 1000 individual cells (Control −25 ms; Dofetilide 2.2 nM=38 ms).
FIG. 6D shows action potential (rabbit) triangulation as a function of APD prolongation for individual cells for control (slope=0.37), and Dofetilide 2.2 Nm (slope=0.5).
FIG. 6E shows simulated beat-to-beat instability of rabbit APs to small perturbations (+/−) drug. Poincaré plots of sequential APD pairs indicating beat-to-beat instability.
FIG. 6F shows APD90 at various frequencies (+/−) drug.
FIG. 6G shows dofetilide-induced QTc prolongation. Pseudo ECG was computed in O'Hara-Rudy human tissue. Heart rates (HR) varied between 50-75 bpm.
FIG. 6H shows clinical data (Vicente, J. et al. (2015) J Am Heart Assoc. 4:e001615) and simulated mean values for control and Dofetilide 2.2 nM.

Aim 1 Expected Outcomes: Upon completion of Aim 1, it is expected to have assembled a prototype multiscale model for efficient prediction of: 1) Conformation state-specific atomic-scale determinants of drug interaction with hERG that cannot be determined experimentally without exhaustive crystallographic and/or mutagenesis experiments. 2) Rates from atomic scale simulations of interactions for hERG channel blocking drugs at the protein function scale. 3) High throughput prediction of emergent drug effects on channel, cell and tissue level cardiac electrical behavior for which no comparable experiment exists. 4) Emergent behaviors that can be mapped back to underlying parameters through component dissection, to reveal mechanisms of pro- or anti-arrhythmic emergent behaviors, for which there is no experimental counterpart. An example of the full integration is shown in FIG. 6 showing a model parameterized from kinetics obtained from the molecular dynamics. Multiscale simulations allow prediction up to the ECG, which is validated by clinical data.

Aim 1 General Plan: The present disclosure describes techniques that can assemble, utilize and validate the multiscale model to predict cardiac effects of hERG K$^+$ channel blockers sotalol, dofetilide, moxifloxacin, and amiodarone. Molecular docking simulations using RosettaLigand method can be used to realize drug-binding conformations of the hERG channel in multiple states. Empirically determined kinetics can guide Molecular Dynamics simulations to predict association and dissociation rates of sotalol, dofetilide, moxifloxacin, and amiodarone to discrete states of the cardiac hERG K$^+$ channel. Then, in a novel link between scales, atomic scale predictions can inform rate constants for constructing computational channel scale kinetic models for sotalol, ibutilide, dofetilide, moxifloxacin, ketaconozole and amiodarone interaction with hERG channels. Atomic scale Rosetta predictions of free energy of drug binding can be translated to drug on and off rates through an existing molecular dynamics based approach (Buch, I. et al. (2011) Proc Natl Acad Sci USA 108:10184-10189). High yield batch predictions of drug trajectories in the binding site can allow calculation of an equilibrium distribution of free energies of interactions to inform kinetic rates of drug-channel interactions with discrete states in the Markov functional models. Drug-channel models can be integrated into virtual cardiac cell and tissue scale models to predict emergent combined drug effects.

Experiments to determine cardiac drug targets can be carried out using methods from the Harvey lab. Ventricular myocytes can be isolated from adult rabbits using enzymatic techniques described previously (Harvey, R. D. et al. (1989) Am J Physiol. 257(6 Pt 1):C1177-C1181). Evidence for off-target drug effects can be obtained using the AP clamp sequential dissection technique (Horvath, B. et al. (2013) J Mol Cell Cardiol. 64:59-68; Banyasz, T. et al. (2011) J Mol Cell Cardiol. 50:578-581). With this approach, the steady-state action potential recorded under current clamp conditions is used to generate the command potential for voltage clamp experiments in the same cell. Subsequent application of the compound in question results in a drug-sensitive current. Reduction of the drug sensitive current in the presence of blockers of other known currents ($I_{Na}$ inhibition with 30 µM TTX, $I_{CaL}$, 1 µM nifedipine; $I_{to}$, 200 µM 3,4-diaminopyridine; $I_{Ks}$, 10 µM chromanol-293B; $I_{Kr}$, 1 µM E4031; and $I_{K1}$, 50 µM Ba$^{2+}$) would be used to identify channels affected. Traditional voltage clamp techniques can be used to quantify specific drug actions on identified targets for model optimization (Harvey, R. D. et al. (1989) Am J Physiol. 257(6 Pt 1):C1177-C1181; Harvey, R. D. et al. (1988) J Gen Physiol. 91:593-615) as described below.

Structure Atomic Scale Modeling. Rosetta modeling of cardiac voltage gated hERG channel (Kv11.1) (FIG. 3B). Homology, de novo, and full-atom modeling of the hERG K channels can be performed using Rosetta-Membrane-Symmetry methods developed by the Baker and Yarov-Yarovoy labs (Yarov-Yarovoy, V. et al. (2006) Proteins 62:1010-1025; Barth, P. et al. (2007) Proc Natl Acad Sci USA 104:15682-15687; Andre, I. et al. (2007) Proc Natl Acad Sci USA 104:17656-17661). The X-ray structures of Kv1.2 (Long, S. B. et al. (2007) Nature 450:376-382), KvAP (Jiang, Y. et al. (2003) Nature 423:33-41), and KcsA (Zhou, Y. et al. (2001) Nature 414:43-48) channels can be used as templates, and pairwise sequence alignments with hERG can be generated using HHPred server (Soding, J. (2005) Bioinformatics 21:951-960) as described previously (Wang, C. et al. (2007) J Mol Biol. 373:503-519; Mandell, D. J. et al. (2009) Nat Methods 6:551-552). Preliminary structural models of hERG were generated (Lees-Miller, J. P. et al. (2009) Biophys J. 96:3600-3610; Subbotina, J. et al. (2010) Proteins 78:2922-2934). Recently they have been tested with studies of 27 common hERG1 blockers. Additional refinement of the flexible structural elements (linkers and loops) can be performed with Rosetta. The present disclosure utilizes techniques that already can assess a state-dependent binding affinity of the drug to a channel in its open, closed and open-inactivated states (Durdagi, S. et al. (2012) J Chem Inf Model. 52:2760-2774; Guo, J. et al. (2014) PLoS One 9:e105553) (FIG. 3B).

Rosetta-Ligand drug docking to hERG channels. Progress in determining high-resolution structures of closed, open, and inactivated states of the pore-forming (PD) and voltage sensing domains (VSD) of ion channels (Long, S. B. et al. (2007) Nature 450:376-382; Jiang, Y. et al. (2003) Nature 423:33-41; Zhou, Y. et al. (2001) Nature 414:43-48; Tao, X. et al. (2010) Science 328:67-73; Long, S. B. et al. (2005) Science 309:897-903; Cuello, L. G. et al. (2010) Nature 466:203-208; Cuello, L G. et al. (2010) Nature 466:272-275; Li, Q. et al. (2014) Nat Struct Mol Biol. 21:244-252; Tang, L. et al. (2014) Nature 505:56-61; Payandeh, J. et al. (2012) Nature 486:135-139; Payandeh, J. et al. (2011) Nature 475:353-358; Zhang, X. et al. (2012) Nature 486:130-134; Shaya, D. et al. (2014) J Mol Biol. 426:467-483; Bagneris, C. et al. (2013) Nat Commun. 4:2465; McCusker, E. C. et al. (2012) Nat Commun. 3:1102) now allows structural modeling of multiple states of hERG PD and VSD. The disclosure develops a set of hERG channel complexes with drugs using RosettaLigand methods (Tinberg, C. E. et al. (2013) Nature 501:212-216; Davis, I. W. et al. (2009) J Mol Biol. 385:381-392; Davis, I. W. et al. (2009) J Mol Biol. 385: 381-392; Meiler, J. et al. (2006) Proteins 65:538-548). Closed, open and inactivated state models of hERG can be used to predict docking of sotalol, dofetilide, ibutilide, moxifloxacin, ketaconozole and amiodarone (FIG. 3B).

Molecular dynamics (MD) simulations. Starting with the lowest energy models for the drug-channel complex from Rosetta docking simulations, the system launches a library consisting of hundreds of long (100 ns) MD simulations (FIG. 3). These simulations can be used to observe unbiased trajectories of drug binding and unbinding with the channel. The disclosure adopts the approach used by Buch et al. (Buch, I. et al. (2011) Proc Natl Acad Sci USA 108:10184-10189) to estimate the kinetics of protein-ligand binding. The Standard free energy of binding ($\Delta G°$) can be calculated using $\Delta G° = -\Delta W - k_B T \log(V_b/V°)$, where $\Delta W$ is the depth of the potential of mean force (PMF), computed from the library of trajectories that have sampled an equilibrium distribution of drug-channel interactions, kB is the Boltzmann constant, T is the temperature, $V_b$ is bound volume calculated as the integral of the Boltzmann factor of the potential mean force over the binding site, and V° is the standard state volume. The system then carry out a Markov State analysis (Noe, F. et al. (2008) Curr Opin Struct Biol. 18:154-162) to determine the kinetically separated stable and metastable states. Analysis of successful state crossings can yield statistics from which the system cans obtain kinetic rate constants (Buch, I. et al. (2011) Proc Natl Acad Sci USA 108:10184-10189). The system does this by using the mean first passage time (MFPT) for the ON and OFF reactions as $k_{off}=1/\text{MFPT}_{off}$ and $k_{on}=1/(C^*\text{MFPT}_{on})$, where $k_{on}$ is inversely dependent on the ligand concentration, C. Knowledge of the free energies and rates of drug binding, combined with the extensive sampling of drug movements around the channel, can inform the mechanisms of drug interactions, understanding extents and rates of binding and unbinding of the different drugs to a particular state of the channel. In some implementations, the system can perform initial PMF computations for dofetilide, ivabradine, KN-93 and d-sotalol binding to open- and open-inactivated states of hERG using techniques from the Noskov Lab. FIG. 3B illustrates drug orientation in the receptor cavity for d-sotalol binding to open-inactivated states of the hERG channel. It provides direct evidence for differential targeting to open-inactivated state of the channel.

The binding constant for drug:

$$K_D^{-1}(\text{binding}) = \pi R^2 \int_{z_{min}}^{z_{max}} dz\, e^{-PMF(z)/k_B T}$$

where PMF(z) is potential of mean force along the reaction coordinate and R is a confinement radius used to enhance relevancy sampling. In addition to the Markov model described above, the system attempts to use the simple Kramer's approach to kinetics of the drug unbinding. Kramer's rate theory describes the escape rate of the drug from a stable state to another state (Hanggi, P. et al. (1990) Rev. Mod. Phys. 62:251-341; Crouzy, S. et al. (1994) Biophys J. 67:1370-1386) as:

$$\text{rate} = \frac{D\sqrt{K_b K_w}}{2\pi k_B T} \exp(-\Delta W(z)/k_B T)$$

where D is the approximate drug diffusion coefficient, which can be directly computed from PMF simulations. $\Delta W(z)$ is the free energy difference between the barrier and the well. $K_b$ and $K_w$ are the curvatures at the barrier and well, respectively. The method has been tested in studies of ivabradine, KN93 and dofetilide binding to hERG (Durdagi, S. et al. (2014) BMC Pharmacology & Toxicology 15:14). The disclosure furthers improve the system's sampling by utilizing parallel tempering of multiple simulations with the drug bound and unbound to the channel. The spatially-resolved diffusion coefficient is critically important for the kinetic modelling. MD simulations can rely on the careful parameterization of new drug models. For new compounds, the disclosure uses a multistep protocol with Quantum Mechanical calculations for minimized coordinates, interactions with water molecules, adjustments to improve interactions in aqueous media, and dipole moments of neutral and charged drugs, and via modifications to Lennard-Jones potentials to approach experimental partitioning data, such as from water to the membrane interface mimetic, n-octanol. Statistical error minimization can be via exhaustive sampling of drug bound states, utilizing the Replica-Exchange method with parallel tempering and Markov state analysis (Buch, I. et al. (2011) Proc Natl Acad Sci USA 108:10184-10189).

Figure 4:
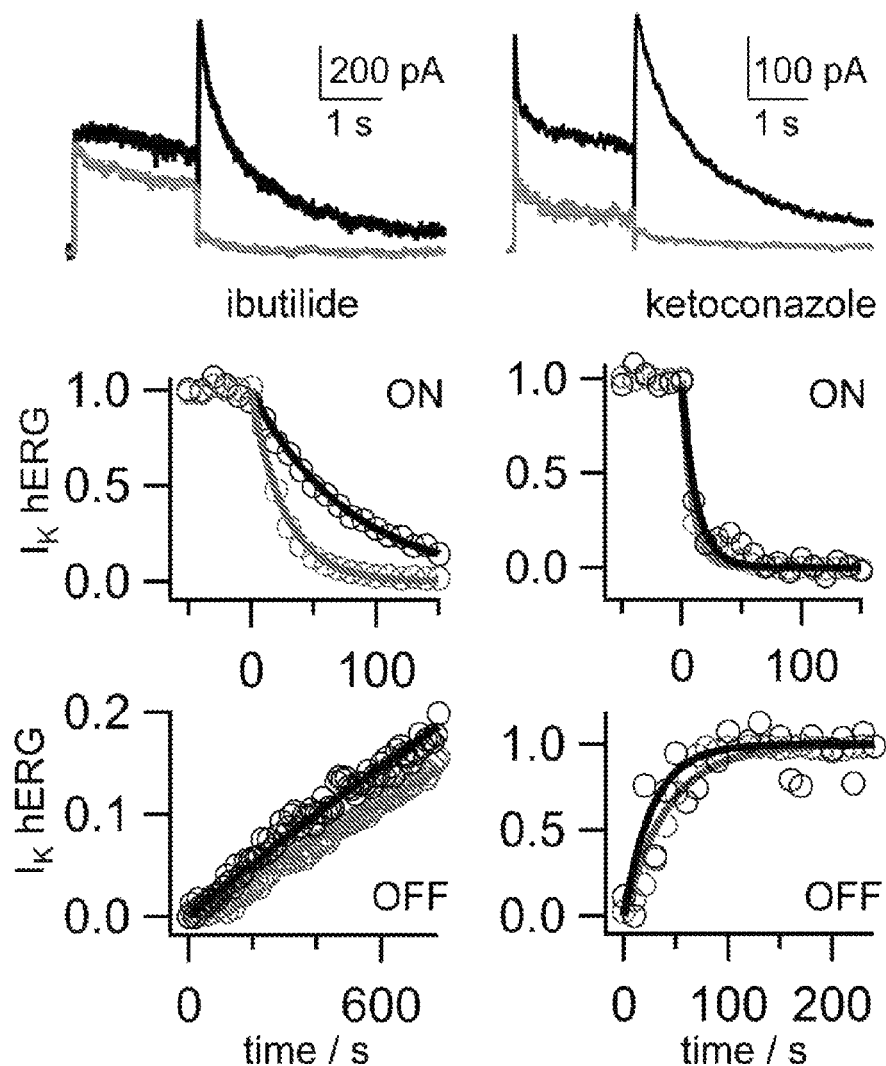
FIG. 4 shows state dependent hERG block. Ibutilide, but not ketoconazole block is altered by holding potential. Left) 300 nM ibutilide, Right) 10 uM ketoconazole. Top) hERG current from HP=−80 to 40 mV for 2 s then −60 mV for 4 s to relieve inactivation and elicit outward tails. Red is with hERG blocker. Middle) Drug kinetics from normalized peak hERG tail currents at −50 mV, drug applied at 0 s. HP=−80 mV (black) or 0 mV (blue). Ibutilide $\tau_{ON}$–80 mV=78±2 s, TON 0 mV=19.7±0.5 s. Ketoconazole $\tau_{ON}$–80 mV=12±2 s, $\tau_{ON}$–0 mV=8.5±0.8 s. Bottom) Dissociation kinetics after wash-out. Ibutilide $\tau_{OFF}$–80 mV=3990±80 s, $\tau_{OFF}$ 0 mV=4490±50 s. Ketoconazole $T_{OFF}$–80 mV=20±10 s, $\tau_{OFF}$–0 mV=32±2 s.

Model validation. Experimental data for mapping residues important for drug-channel interactions can be used to evaluate the accuracy of the drug-channel model predictions. Drug binding sites within the hERG pore lumen have been mapped in detail (Trudeau, M. C. et al. (1995) Science 269:92-95; Numaguchi, H. et al. (2000) Circ Res. 87:1012-1018; Durdagi, S. et al. (2011) J. Chem. Inf. Model. 51:463-474; Hancox, J. C. et al. (2008) Pharm. Therapeutics 119: 118-132; Witchel, H. J. (2011) Cardiovasc. Ther. 29:251-259; Numaguchi, H. et al. (2000) Circ. Res. 87:1012-1018; Kamiya, K. et al. (2005) Biophys. J. 88:608-609; Ficker, E. et al. (2001) Mol. Pharmacol. 60:1343-1348; Lees-Miller, J. P. et al. (2000) Mol. Pharmacol. 57:367-374; Gintant, G. A. (2008) Pharm. Therapeutics 119:199-209; Anwar-Mohamed, A. et al. (2014) Toxicol Lett. 230:382-392). Kinetic parameters from MD simulations can inform Markov models. Model outputs can be compared to experimentally measured drug affinities and on and off rates (FIG. 4). The results shown in FIG. 4 are based on the neutral form of dofetilide.

Limitations and alternatives. If predictions of on and off rates deviate from experimentally determined affinities for the same drug for specific hERG channel states, then alternative channel conformations can be explored with Rosetta-Membrane-Symmetry relax (Yarov-Yarovoy, V. et al. (2012) Proc Natl Acad Sci USA 109:E93-E102). These alternative hERG states can be used to find alternative lowest energy binding conformations of drugs. Force field and statistical errors may lead to kcal/mol-level errors in calculated free energies. However, the system keeps these errors to a minimum by: 1) focusing on relative drug binding affinities for similar drugs; 2) using force field models that target high level quantum mechanical and experimental data; and 3) sampling long times, as described above. The system can be extended to varied hERG subunit compositions (Abi-Gerges, N. et al. (2011) Br J Pharmacol. 164:419-432; Sale, H. et al. (2008) Circ. Res. 103:e81-e95.

Protein Function Scale. Experimental assessment of kinetics of ion channels-drug interactions: Empirical measurements of drug binding to heterologously expressed hERG channels can provide a link between the molecular and cell scales. Measurements based on methods from the Sack lab can validate or suggest refinement of the atomistic simulations and provide the thermodynamic underpinnings of block kinetics for drug-hERG interaction models (FIG. 4). The goal of these experiments is to establish the state dependent affinities and kinetics of the hERG blockers, as the disclosure hypothesizes differences in these properties underlie proarrythmic risk (Thomsen, M. B. et al. (2006) Br J Pharmacol 149:1039-1048; Di Veroli, G. Y. et al. (2013) J Cardiovasc Electrophysiol 25(2):197-20). To generate experimentally constrained models of hERG blocker kinetics, the system conducts measurements of binding kinetics to determine the molecular rate constants $k_{on}$ and $k_{off}$ for channels in closed, open and inactivated states, with resultant dissociation constants from steady state measurements cross validating rate constant extraction by the relationship $K_D = k_{off}/k_{on}$. The general framework of rate extraction can be to determine drug-binding rates under conditions that bias the equilibrium between states towards the conformation for which affinity is measured. Appropriate voltage protocols enable extraction of state-dependent affinities for the conformation of hERG channels (Alexandrou, A. J. et al. (2006) Br J Pharmacol 147:905-916; Hill, A. P. et al. (2014) Mol Pharmacol 85:769-776; Stork, D. et al. (2007) Br J Pharmacol. 51:1368-1376). Similar protocols have enabled predicting affinity changes between states of K+ channels that Applicants have recently measured independently with optical recordings of fluorescently-labeled K+ channel inhibitors (Tilley, D. C. et al. (2014) Proc Natl Acad Sci USA 111: E4789-E4796). Drug binding kinetic experiments can be conducted by patch-clamp electrophysiology using conventional manual patch clamp and with UC Davis' recently acquired Q-Patch medium-throughput electrophysiology workstation. The Q-Patch system allows 16 simultaneous recordings with individual control over drug application and series resistance compensation. Both manual and Q-Patch recordings can be compensated for series resistance error by a maximal admissible voltage error criterion. The disclosure tests compounds against a stable HEK-hERG cell line (Preliminary data is shown in FIG. 4), obtained from Craig January (Kikuchi, K. et al. (2005) Br J Pharmacol. 144:840-848; Harvey, A. J. et al. (2006) J Med Chem. 49:1433-1441). Rate constants for different channel conformations can be extracted from drug wash-in and wash-out kinetics during stimulus protocols, that bias channel towards adopting closed, open and inactivated conformations (Alexandrou, A. J. et al. (2006) Br J Pharmacol 147:905-916; Hill, A. P. et al. (2014) Mol Pharmacol 85:769-776; Stork, D. et al. (2007) Br J Pharmacol. 51:1368-1376). Closed channel affinity can be assessed using negative holding potentials with sparse test pulses to test channel inhibition; open channel affinities can be deduced by including frequent pulses to maximally open the channels; inactivated channel affinity can be assessed from current inhibition at depolarized holding potentials where channels are biased towards inactivated conformations (Hill, A. P. et al. (2014) Mol Pharmacol 85:769-776; Smith, P. L. et al. (1996) Nature 379:833-836).

Figure 5:
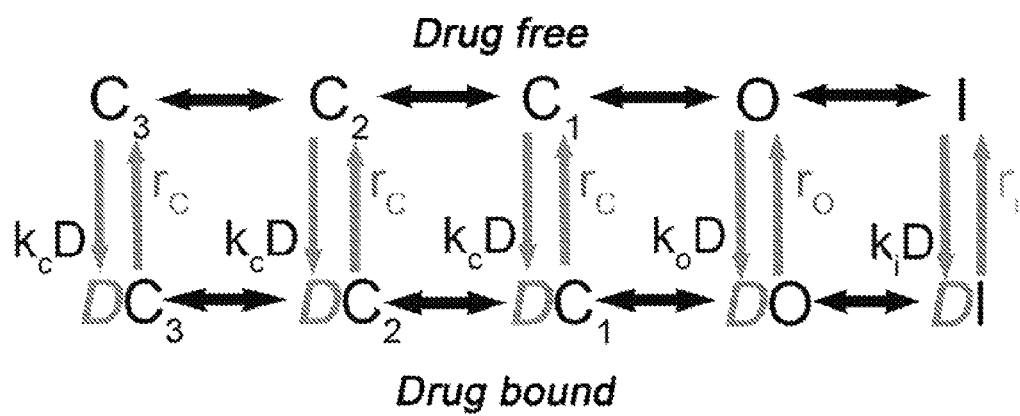
FIG. 5 shows drug-hERG interaction model with nondrug bound and drug bound states. $k_C$, $k_O$ and $k_I$ are the association rates constants in the closed, open and inactivated states, respectively, D is the drug concentration and $r_C$, $r_O$ and $r_I$ are the dissociation rate constants in the closed, open and inactivated states, respectively.

Protein Function Scale. Models for drug interaction with cardiac ion channels: Applicants have extensive experience developing gating models for cardiac ion channels (Fink, M. et al. (2008) Prog Biophys Mol Biol. 96:357-376; Clancy, C. E. et al. (2001) Cardiovasc Res. 50:301-313; Bett, G. C. et al. (2011) Biophys J. 101:631-642; Romero, L. et al. (2014) J Mol Cell Cardiol. 72:126-137; Moreno, J. D. et al. (2013) Circ. Res. 13:e50-e61; Moreno, J. D. et al. (2011) Sci Transl Med. 3(98):98ra83). Drug-bound states (Hille, B. (1977) J Gen Physiol. 69:497-515) for the hERG channel (Zhou, Z. et al. (1998) Biophys J. 74:230-241) model are shown in FIG. 5 (red).

To constrain drug rates for conformational states in the kinetic models, the system needs drug concentration (a model variable) and diffusion rates (D) to formulate drug on rates "$k_{on}$"=[drug]*D. Affinity ($IC_{50}$) of the drug to discrete conformations determines drug off rates "$k_{off}$"=$IC_{50}$*D. The diffusion constants can be extracted from MD simulations described above or introduced as parametric variables. Relative kinetic rates for the charged and neutral drug fractions can be derived from atomic scale simulations as described above. These values can be compared to experimentally measured affinities and used to constrain drug binding and unbinding rate constants in the Markov model. Drug "on" and "off" rates can be fixed to reduce the number of free parameters in the model. Rate constants can then be constrained via optimization to electrophysiological pacing protocols for each drug as described below. Details in Applicants' recent studies (Romero, L. et al. (2014) J Mol Cell Cardiol. 72:126-137; Moreno, J. D. et al. (2013) Circ. Res. 13:e50-e61; Moreno, J. D. et al. (2011) Sci Transl Med. 3(98):98ra83).

Numerical methods and parameter optimization for drug-free channels: Implicit methods can be used to solve ODEs (Moreno, J. D. et al. (2011) Sci Transl Med. 3(98):98ra83). Nelder-Mead or Newton-Raphson optimization with random small (<10%) perturbations applied to local minimum can allow continued optimization to improve fits (Moreno, J. D. et al. (2011) Sci Transl Med. 3(98):98ra83). Simultaneous optimization to experimental data can be performed (e.g., preliminary data FIGS. 4 and 6A-6H).

Modeling Dofetilide: Applicants' recent model of dofetilide interactions with hERG, is a starting point for comparison to the kinetic parameters generated by the MD simulations (Romero, L. et al. (2014) J Mol Cell Cardiol. 72:126-137). See preliminary data in FIGS. 6A-6H.

Modeling Ibutilide: The system can model ibutilide based on data from the Sack Lab.

Modeling D-sotalol: D-sotalol has been extensively characterized in terms of its pharmacokinetics and pharmacodynamics. The drug is not metabolized and is fully bioavailable (Funck-Brentano, C. (1993) Eur Heart J. 14(Suppl H):30-35). D-sotalol blocks all of the major repolarizing potassium currents in the heart including the delayed rectifier current Ix, and the inwardly rectifying current $I_{KI}$ (Carmeliet, E. (1985) J Pharmacol Exp Ther. 232:817-825; Nakaya, Y. et al. (1997) J. Cardiovasc Pharmacol Ther. 2:39-46). D-sotalol also inhibits cardiac Na current (Carmeliet, E. (1985) J Pharmacol Exp Ther. 232:817-825). Each of these interactions may contribute to reverse use-dependence (Nakaya, Y. et al. (1997) J. Cardiovasc Pharmacol Ther. 2:39-46; Peralta, A. O. et al. (2000) J Am Coll Cardiol. 36:1404-1410; Marschang, H. et al. (2000) J Cardiovasc Pharmacol. 35:443-450; Sharma, P. P. et al. (1999) J. Cardiovasc Pharmacol Ther. 4:15-21; Naitoh, N. et al. (1998) Jpn Heart J. 39:619-630; Lee, S. D. et al. (1997) J Am Coll Cardiol. 29:100-105; Kovoor, P. et al. (1996) Am J Cardiol. 78:247-250; Shimizu, W. et al. (1996) Am J Cardiol. 77:1004-1008; Wang, J. et al. (1994) Circulation 90:2032-2040; Wyse, K. R. et al. (1993) J Cardiovasc Pharmacol. 21:316-322; Schmitt, C. et al. (1992) J Cardiovasc Pharmacol. 19:487-492; Schmitt, C. et al. (1991) Am J Cardiol. 68:1183-1187; Wu, L. et al. (2011) Circulation 123:1713-1720). D-sotalol accesses hERG via the open state of the channel, and subsequent inactivation stabilizes the drug-receptor interaction (Numaguchi, H. et al. (2000) Circ Res. 87:1012-1018; Numaguchi, H. et al. (1999) Circulation 100:279-279; Numaguchi, H. et al. (1998) Circulation 98:231-231). Deactivation also traps the bound drug during hyperpolarization. Ancillary subunits did not affect binding or affinity (Numaguchi, H. et al. (2000) Circ Res. 87:1012-1018). Optimization for d-sotalol: D-sotalol interaction with hERG can be optimized to experimental data to the following protocols: tonic block, use-dependent block (Numaguchi, H. et al. (2000) Circ Res. 87:1012-1018), use-dependent block in the absence of inactivation (Numaguchi, H. et al. (2000) Circ Res. 87:1012-1018), recovery from UDB, frequency-dependence of UDB and dose-dependence of tail current amplitude (Carmeliet, E. (1985) J Pharmacol Exp Ther. 232:817-825). Interaction (for amiodarone and DEA) with hERG can be optimized to timecourse of tail current inhibition, dose-response of tail currents, frequency and dose dependence of use-dependent block (Zhang, Y. H. et al. (2010) J Electrocardiol. 43:440-448).

Modeling Amiodarone and active metabolite Desethylamiodarone (DEA): Although amiodarone is classified as class III due to inhibition of K$^+$ channels and prolongation of repolarization and QTc (Singh, B. N. et al. (1970) Br J Pharmacol. 39:657-667), amiodarone also blocks Na$^+$ and Ca$^{2+}$ currents. It exhibits noncompetitive ß-receptor antagonism that is additive to other B-blockers (Boutitie, F. et al. (1999) Circulation 99:2268-2275). DEA is the only metabolite identified in blood [0.3-4.7 µg/ml] (Kates, R. E. (1984) Ann. N.Y. Acad. Sci. 432:75-89; Kates, R. E. et al. (1984) Am J Cardiol. 53:248-251). Potassium channel affinities: Amiodarone acutely blocks native $I_{Ks}$ and exhibits open channel unblock with apparent affinity dependent on the pulse duration: 200 ms depolarization, $IC_{50}$=3.84 µM, 500 ms $IC_{50}$=1.74 µM, 2000 ms, $IC_{50}$=1.20 µM (Zankov, D. P. et al. (2005) J Cardiovasc Electrophysiol. 16:314-322). Amiodarone blocks IKr with an $IC_{50}$ between 0.8 and 0.047 µM (Zhang, Y. H. et al. (2010) J Electrocardiol. 43:440-448). N-Desethyl-amiodarone (N-DEA) also blocks IKr with $IC_{50}$=158 nM. DEA can also be modeled. DEA binding to $I_{Kr}$ is time and voltage dependent. DEA shifts activation (−9 mV) (Zhang, Y. H. et al. (2010) J Electrocardiol. 43:440-448). Sodium channel affinities: Both late ($IC_{50}$=3.0 µM) and peak $I_{Na}$ are inhibited by amiodarone (Wu, L. et al. (2008) Cardiovasc Res. 77:481-488). Tonic block of peak $I_{Na}$ by amiodarone is $IC_{50}$=178.1 nM (Wu, L. et al. (2008) Cardiovasc Res. 77:481-488). Calcium channel affinities: Amiodarone block of the L-type Ca channel is tonic (Hancox, J. C. (1997) Gen Pharmacol. 29:429-435). Affinity can be estimated from the 22% decrease in current after one pulse (Hancox, J. C. (1997) Gen Pharmacol. 29:429-435). Modeling noncompetitive β-receptor antagonism: Chronic amiodarone treatment ($IC_{50}$=8.7 µM) results in downregulation of the B-receptor (Chatelain, P. et al. (1995) Br J Pharmacol. 116:1949-1956; Nokin, P. et al. (1983) Biochem Pharmacol. 32:2473-2477). The timecourse of downregulation (Kadish, A. H. et al. (1990) J Am Coll Cardiol. 16:1240-1245) can be used to compute lost function for "chronic" amiodarone. Optimization for Amiodarone and DEA: Amiodarone with $I_{Na}$ can be optimized to data: steady state availability, tonic block, use-dependent block, recovery from UDB, frequency-dependence of UDB and onset of use-dependent block. Interaction (for amiodarone and DEA) with $I_{Kr}$ and $I_{Ks}$ can be optimized to timecourse of tail current inhibition, dose-response of tail currents, frequency and dose dependence of use-dependent block and unblock (Zhang, Y. H. et al. (2010) J Electrocardiol. 43:440-448; Zankov, D. P. et al. (2005) J Cardiovasc Electrophysiol. 16:314-322).

Modeling Moxifloxacin: Moxifloxacin inhibits ERG channels via a rate-independent open state blocking mechanism with an $IC_{50}$=65 µM at 22° C. and 29 µM at 35° C. (Kang, J. et al. (2001) Mol Pharmacol. 59:122-126; Alexandrou, A. J. et al. (2006) Br J Pharmacol 147:905-916). Critically important in support of Applicants' hypothesis, moxifloxcin does not interact with inactivated hERG channels (Alexandrou, A. J. et al. (2006) Br J Pharmacol 147:905-916).

Modeling Ketaconozole: The system can model ketaconozole based on data from the Sack Lab.

Limitations and alternatives: If Applicants are not able to fit experimental results with Applicants' proposed model schemes the system performs an iterative process to reconcile simulations and experiments: Alternate model topologies can be explored to minimize differences between the model and experiment. For example, complex kinetics of drug recovery may indicate additional drug states (i.e., fast and slow unbinding to open channels). Experiments can be performed to better constrain the model topology and kinetics as needed.

Cell Scale. Simulations: The Soltis-Saucerman rabbit cardiac model (Soltis, A. R. et al. (2010) Biophys J. 99:2038-2047) can be used for all initial simulations. This can allow experimental validation of model predictions to ensure drug-receptor interactions are modeled accurately, followed by simulations in human models. For translational significance, following full validation in computational lower animal models, the models of drug-channel kinetics can be incorporated into the three human models of ventricular cells including O'Hara-Rudy (O'Hara, T. et al. (2011) PLoS Comput. Biol. 7:e1002061), ten Tusscher (ten Tusscher, K. H. W. J. et al. (2006) Am J Physiol Heart Circ Physiol. 291:H1088-H1100), and Grandi-Bers (Grandi, E. et al. (2009) J Mol Cell Cardiol. 48:112-121) to minimize model dependence of Applicants' findings. Models of beta-adrenergic receptors: the disclosure uses the Soltis-Saucerman for β-adrenergic/CAMKII signaling cascade and Applicants' models for $I_{Ks}$, $I_{Kr}$, and $I_{Ca-L}$ (Saucerman, J. J. et al. (2003) J. Biol. Chem. 278:47997-48003; Nakamura, H. et al. (2007) Circulation 116:2913-2922; Terrenoire, C. et al. (2005) Circ Res. 96:e25-e34; Choe, C. U. et al. (2006) Hum Mol Gen. 15:2888-2902). Cellular level protocols: the disclosure predicts drug effects on action potentials (APs) for therapeutic concentrations of amiodarone 0.1 mg/L to 2.5 mg/L (Debbas, N. M. et al. (1984) Br Heart J. 51:316-320; Robinson, K. et al. (1990) Cardiovasc Drugs Ther. 4:529-530; Pollak, P. T. (1999) Am J Cardiol. 84:37R-45R); d-sotalol 400 ng/mL to 2500 ng/mL (Funck-Brentano, C. (1993) Eur Heart J. 14(Suppl H):30-35), dofetilide 4 nM (Redfern, W. S. et al. (2003) Cardiovasc Res. 58:32-45), moxifloxacin 5.9 µM (Kang, J. et al. (2001) Mol Pharmacol. 59:122-126) at 60-220 BPM.

Simulation of the TRIaD (Hondeghem, L. M. (2005) Novartis Found Symp. 266:235-244, discussion 244-250): See FIGS. 6C-6H. Triangulation: Triangulation of the action potential can be calculated during simulated action potential as $APD_{90}$-$APD_{30}$ (Hondeghem, L. M. (2005) Novartis Found Symp. 266:235-244, discussion 244-250; Romero, L. et al. (2010) Conf Proc IEEE Eng Med Biol Soc. 2010: 3253-3256). Reverse use dependence: Simulated ventricular myocytes can be paced to steady-state at a rate of 60-220 beats per minute (BPM) and APD adaptation curves constructed (BCL versus APD) for various drug concentrations within the clinical range for each drug. Steepening of the curve relative to drug free curves indicates reverse use dependent drug effects. Beat-to-beat instability of action potential duration: the system simulates 10000 normal ventricular myocytes (+/−drug) with randomly varying ionic conductances ($G_{Na}$, $G_{CaL}$, $G_{CaT}$, $G_{Ks}$, $G_{Kr}$, $G_{Kl}$, $G_{Kp}$) within 20% of their nominal values. That is not meant to imply that the conductances vary by +/−20% on each beat, but is an efficient way to observe responses in a population of action potentials with varying parameters. The values can be uniformly distributed and new values randomized and applied prior to the stimulus and held constant for the duration of the ensuing action potential. $APD_{90}$ can be calculated for each cell as the time from the maximum velocity of the action potential upstroke ($dV/dt_{max}$) until the time of 90% repolarization at 1 Hz. Temporal action potential duration dispersion: Simulated $APD_{90}$ can be calculated at the 500th paced beat (BCL=1000 ms) in single myocytes. The disclosure tests the degree of $APD_{90}$ variability induced by small electrical perturbations that are present in any noisy physiological system, or that may result from an ectopic beat or triggered depolarization in nearby tissue. To simulate these perturbations, the disclosure applies small amplitude inward currents randomly between −0.1 to −0.2 pA/pF for 50 ms over the course of the action potential plateau at a pacing cycle length=1000 ms. The small inward current can also be applied randomly in time between 30 to 200 ms on the plateau phase for 1000 beats.

Figure 7:
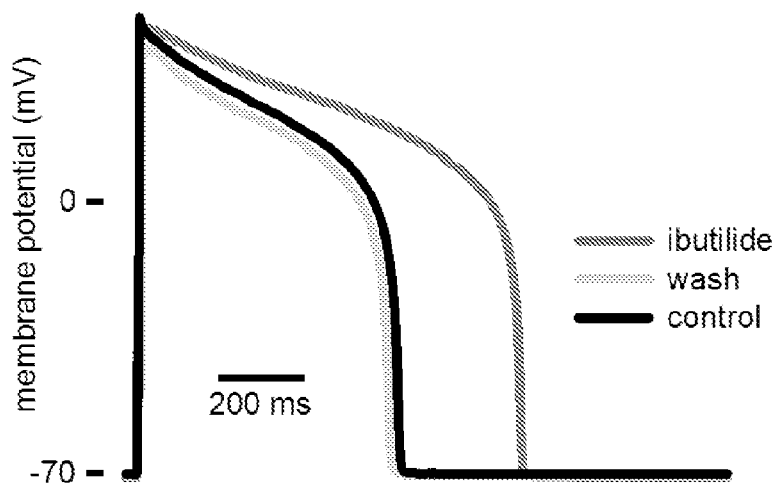
FIG. 7 shows action potentials at 1 Hz recorded under control conditions and following ibutilide (10 μM) and washout.

In addition to TRiAD, the following simulated parameters can be tracked: Cell excitability (max. upstroke velocity of the AP (V/s)), action potential duration (APD), early afterdepolarizations (EADs), cell refractoriness and APD restitution (Goldhaber, J. I. et al. (1997) Circulation 96:3756-3756). In WT cells, It is expected to observe drug dose-dependent increase in APD for all compound, but no reverse use dependence for moxifloxacin. It is expected dofetilide, ibutilide and sotalol to promote the TriAD and to exhibit strong reverse use dependence. It is expected to observe dose-dependent emergent early afterdepolarizations (EADs). The influence of off-target drug effects (i.e., $I_{Na}$ block by amiodarone) on cell parameters can be predicted in simulations with drug on primary targets alone and/or with off-target effects. Sensitivity analysis: Sensitivity analysis can be used to identify quantities underlying model dynamics, examine the limits on parameter estimation from experimental measurements, improve numerical stability, and test hypotheses. Variance based systematic sensitivity analysis using an orthonormal Hermite approximation (OHA) for parameter perturbations can produce sensitivity coefficients connecting parameters and outputs. The disclosure also conducts principal component analysis for parameter ranks (Wong, C. F. et al. (1991) J. Phys. Chem. 95:9628-9630). Validation of the model predictions in rabbit myocytes: Model predictions of changes to cell parameters after drug application can be experimentally tested in single rabbit ventricular myocytes (for example, in the Harvey Lab), see FIG. 7. Dr. Harvey is an expert in measuring changes to cellular electrophysiology induced by drugs and can carry out experiments to validate key parameter changes predicted by the model including the TRiAD for the therapeutically relevant concentration and pacing frequencies (60-220 beats per minute (BPM)). Parameters can be tracked: Cell excitability (max. upstroke velocity of the AP (V/s)), action potential duration (APD), early after depolarizations (EADs), cell refractoriness and APD restitution (Goldhaber, J. I. et al. (1997) Circulation 96:3756-3756). Validation of the models can also benefit from many published experiments (Zhang, Y. H. et al. (2010) J Electrocardiol. 43:440-448; Singh, B. N. et al. (1970) Br J Pharmacol. 39:657-667; Boutitie, F. et al. (1999) Circulation 99:2268-2275; Zankov, D. P. et al. (2005) J Cardiovasc Electrophysiol. 16:314-322; Wu, L. et al. (2008) Cardiovasc Res. 77:481-488; Hancox, J. C. (1997) Gen Pharmacol. 29:429-435; Chatelain, P. et al. (1995) Br J Pharmacol. 116:1949-1956; Nokin, P. et al. (1983) Biochem Pharmacol. 32:2473-2477; Kadish, A. H. et al. (1990) J Am Coll Cardiol. 16:1240-1245; Debbas, N. M. et al. (1984) Br Heart J. 51:316-320; Robinson, K. et al. (1990) Cardiovasc Drugs Ther. 4:529-530; Mason, J. W. et al. (1982) Circulation 66:292-292; Debbas, N. M. et al. (1983) Eur J Clin Invest. 13:123-127; Mason, J. W. et al. (1983) Pflugers Arch., EJP 396:79-81; Connolly, S. J. et al. (1984) J Cardiovasc Pharmacol. 6:531-535; Latini, R. et al. (1984) Biomed Mass Spectrom. 11:466-471; Latini, R. et al. (1984) Clin Pharmacokinet. 9:136-156; Mason, J. W. et al. (1984) Circ Res. 55:277-285; Balser, J. R. et al. (1987) Circulation 76:151-151; Bennett, P. B. et al. (1987) Circulation 76:150-150; Kohlhardt, M. et al. (1988) J Membr Biol. 102:105-119; Rosenheck, S. et al. (1990) Am J Cardiol. 66:229-230; Balser, J. R. et al. (1991) Circ Res. 69:519-529; Kodama, I. et al. (1992) Ann NY Acad Sci. 644:210-222; Sager, P. T. et al. (1993) Circulation 88:1063-1071; Finance, O. et al. (1995) J Cardiovasc Pharmacol. 26:570-576; Hodeige, D. et al. (1995) Eur J Pharmacol. 279:25-32; Manning, A. et al. (1995) J Cardiovasc Pharmacol. 25:252-261; Manning, A. S. et al. (1995) J Cardiovasc col. 26:453-461; Terada, Y. et al. (1995) Ann Thorac Surg. 60:1155; Balser, J. R. (1997) Anesthesiology 86:974-987; Campbell, T. J. (1997) Aust N Z J Med. 27:582-590; Kennedy, H. L. (1997) Am J Cardiol. 80:1208-1211; Kodama, I. et al. (1997) Cardiovasc Res. 35:13-29; Padrini, R. et al. (1997) Pharmacol Res. 35:409-416; Drouin, E. et al. (1998) J Am Coll Cardiol. 32:1063-1067; Knobloch, K. et al. (2000) Eur Heart J. 21:327-327; Balser, J. R. (2001) J Cardiothorac Vasc Anesth. 15:542-544; Omichi, C. et al. (2001) J Am Coll Cardiol. 37:114a; Wirth, K. J. et al. (2001) Circulation 104:47-48; Omichi, C. et al. (2002) Am J Physiol Heart Circ Physiol. 282:H1063-H1070; Doggrell, S. A. et al. (2004) Expert Opin Investig Drugs 13:415-426; Le Bouter, S. et al. (2004) Circulation 110:3028-3035; Xu, L. et al. (2008) Die Pharmazie 63:475-479; Liang, Y. L. et al. (2009) Ann Pharmacother. 43:134-138; Van Herendael, H. et al. (2010) Vasc Health Risk Manag. 6:465-472; Osaka, T. et al. (2011) J Cardiovasc Electrophysiol. 22:669-676Thomsen, M. B. et al. (2006) Br J Pharmacol 149:1039-1048; Kang, J. et al. (2001) Mol Pharmacol. 59:122-126).

Limitations and alternatives: Here Applicants have proposed multiple experiments to test the accuracy of the model predictions. The disclosure performs simulations in rabbit so that the system can directly compare effects of drugs in the WT simulations to experiments in cell and tissue level rabbit cardiac preparations. But, Applicants may find significant deviation from the rabbit model predictions and the experimental measurements. Thus, the disclosure undertakes an iterative process to reconcile simulations and experiments: Experimentally measured parameters that do not validate model predictions can be used in a feedback process to further refine and constrain the models via an iterative approach linking disparities in measured and simulated cellular level parameter to lower level model parameters (i.e., channel conductance, voltage dependence, time constants) that can be re-tuned in Applicants' optimization process. For example, if Applicants find that amiodarone causes more depression of cellular excitability in experiments (as indicated by maximum upstroke velocity of the AP (V/s)), the disclosure examines resting membrane potential and Na$^+$ current amplitude before and after drug application and then use these parameters to additionally constrain the computational model.

Tissue Scale. One-dimensional (1D) simulations: the system can carry out 1D simulations to coarsely identify parameter regimes of interest with a computationally tractable model as Applicants have described (Moreno, J. D. et al. (2011) Sci Transl Med. 3(98):98ra83).

Regimes exhibiting compelling dynamics can be investigated in higher dimensions. The following parameter changes with drug application can be predicted: APD restitution, conduction velocity (CV): CV is calculated between cell 45 and 55m (to avoid edge effects) at $dV/dt_{max}$ (Gomez, J. F. et al. (2014) PLoS One 9:e106602). Because APD prolongation triggered arrhythmias as well as conduction slowing, reentrant arrhythmias and wavebreak causing fibrillation (Weiss, J. N. et al. (2005) Circulation 112:1232-1240), the disclosure predicts the drug concentration for triggered activity, dispersion of repolarization and conduction block (due to functional block caused by prolonged APD) and over 60 BPM-220 BPM with escalating drug (0.5 µM increments) or an event occurs. A period of vulnerability exists when electrical stimulation can initiate self-sustaining spiral waves (Mines, G. (1914) Trans Roy Soc Can. 43-53; Allessie, M. A. et al. (1973) Circ Res. 33:54-62) capable of degeneration into fibrillatory rhythms. The disclosure assess the "vulnerable window" to unidirectional block and retrograde conduction, suggesting reentrant arrhythmia in higher dimensions (Starmer, C. F. et al. (1991) Circulation 84:1364-1377; Starmer, C. F. et al. (1993) Biophys J. 65:1775-1787; Starmer, C. F. (2002) Int J Bifurcat Chaos 12:1953-1968; Moreno, J. D. et al. (2011) Sci Transl Med. 3(98):98ra83). The refractory period can also be used to quantify drug-induced increase in arrhythmia risk (Starmer, C. F. (2002) Int J Bifurcat Chaos 12:1953-1968).

Two-dimensional (2D) simulations: 2D simulations can determine if proarrhythmic phenomena observed in lower dimensions cause reentrant arrhythmias and/or spiral wave breakup. The change in voltage in space and time can be computed as in (ten Tusscher, K. H. W. J. et al. (2006) Am J Physiol Heart Circ Physiol. 291:H1088-H1100). Other parameters are as in 1D simulations. 2D reentry can be induced after static pacing (S1) followed by an S2 within the vulnerable window. APD restitution, dispersion of repolarization and reentry wavelength can be tracked and compared to experiments before and after drug. Sensitivity analysis: Because the PDE-based model is computationally expensive, the elementary effects method can be used for sensitivity analysis of large perturbation combinations (Marino, S. et al. (2008) J Theor Biol. 254:178-196).

Tissue level experimental validation of the model predictions: Optical mapping experiments (for example in the Ripplinger Lab) can use rabbit tissue to validate key parameter changes predicted by the tissue level simulations with no drug, dofetilide, sotalol, moxifloxacin, and amiodarone. Arrhythmia vulnerability parameters can be tracked (see FIG. 8) and compared to simulated parameters: Conduction velocity, conduction velocity restitution, APD restitution, dispersion of repolarization and reentry wavelength. Optical mapping experiments in Langendorff-perfused rabbit hearts use voltage-(RH237) and calcium-(Rhod2-AM) sensitive dyes. Dyes are excited with LED light sources (~530 nm). Emitted light is collected with two MiCam Ultima-L CMOS cameras (SciMedia, USA) at a sampling rate of 1 kHz. The mapping field of view can be approximately 2.5×2.5 cm, resulting in a spatial resolution of ~250 µm/pixel. The AV node can be ablated to produce heart block, and hearts can paced at rates of 60 BPM-220 BPM. APs can be recoded from the left ventricular epicardium and a lead I ECG can be continuously recorded. Pacing can be applied with a bipolar electrode on the epicardial surface. Arrhythmia incidence can be measured with a standard S1-S2 or S1-S2-S3 pacing protocol and can be compared to simulated arrhythmias. After a 10-20-minute period of equilibration, hearts can be exposed to vehicle (Tyrode's solution) or drug and then to increasing concentrations.

Limitations and alternatives: Optical mapping limitations include the use of pharmacological excitation-contraction uncouplers to prevent motion artifacts in the optical recordings. However, the disclosure uses blebbistatin, which has been shown to have minimal effects on action potential and $Ca^{2+}$ handling characteristics (Fedorov, V. V. et al. (2007) Heart Rhythm 4:619-626). Optical signal recording is limited to a depth of ~1 mm, so it is not possible to record endocardial or transmural signals without excising portions of the heart tissue. Wide-field optical mapping signals represent average signals, so the system cannot discern single-cell activities. Experimentally, it is possible that arrhythmias can not be induced with an S1-S2 or S1-S2-S3 protocol. Then the disclosure uses a burst pacing approach to induce reentrant arrhythmias. The disclosure mays find differences in tissue model predictions and the experimental measurements. Thus, the disclosure undertakes an iterative process to reconcile simulations and experiments: Experimentally measured parameters that do not validate model predictions can be used in a feedback process to further refine and constrain the models via an iterative approach linking disparities in measured and simulated tissue level parameter to lower level model parameters (i.e., cellular APDs, cell coupling, upstroke velocity) that can be re-optimized. For example, if the disclosure finds that a drug causes more depression of conduction velocity in experiments the disclosure examines action potential upstroke velocity and cell coupling parameters in the model before and after drug application and then retune the model parameters.

Specific Aim 2—Drug Rehabilitation: To apply the model to design safer hERG blockers. Aim 2 Rationale: It is well-recognized that a critical determinant of hERG block-associated proarrhythmia is the state-dependent kinetics of drug interactions with the channel (Di Veroli, G. Y. et al. (2013) J Cardiovasc Electrophysiol 25(2):197-207; Di Veroli, G. Y. et al. (2013) Am J Physiol Heart Circ Physiol 304:H104-H117; Hill, A. P. et al. (2014) Mol Pharmacol 85:769-776). At present, preclinical assays do not consider this information in candidate screening. This is unfortunate since the proarrhythmic cellular manifestations of the TRiAD arise directly from the underlying kinetics of channel block. Just as slow kinetics of drug unblock from Na channels gives rise to use-dependent block and proarrhythmia (Starmer, C. F. et al. (1984) Biophys J. 46:15-27; Moreno, J. D. et al. (2011) Sci Transl Med. 3(98):98ra83), the disclosure hypothesizes that is it the slow kinetics of unblock from inactivated hERG channels (reflecting high affinity interaction) that underlies reverse use-dependence in hERG blockers. The logical extension of this hypothesis is that removal of high affinity inactivated state block may be safer. For drugs that do not exhibit high affinity inactivated state block of hERG, like moxifloxacin, ketaconozole and the selective-serotonin reuptake inhibitor CONA-437, block does not rely strongly on binding to the S6 aromatic amino acid residues Y652 and F656. The disclosure tests if structural disruption of this molecular interaction in dofetilide derivatives reduces reverse use-dependent block. Aim 2 Expected Outcomes: Upon completion of Aim 2, It is expected to have demonstrated the usefulness of the multi-scale model for efficient prediction of: 1) Effects of modified drug functional groups to change drug affinity to the hERG inactivated state, allowing for improved understanding of the atomic determinants of drug interactions. 2) Novel pharmacological compounds that cannot be readily determined experimentally without exhaustive screening libraries. 3) High throughput preclinical drug screening for emergent effects on channel, cell and tissue cardiac electrical behavior for which no comparable experiment exists.

Figure 9:
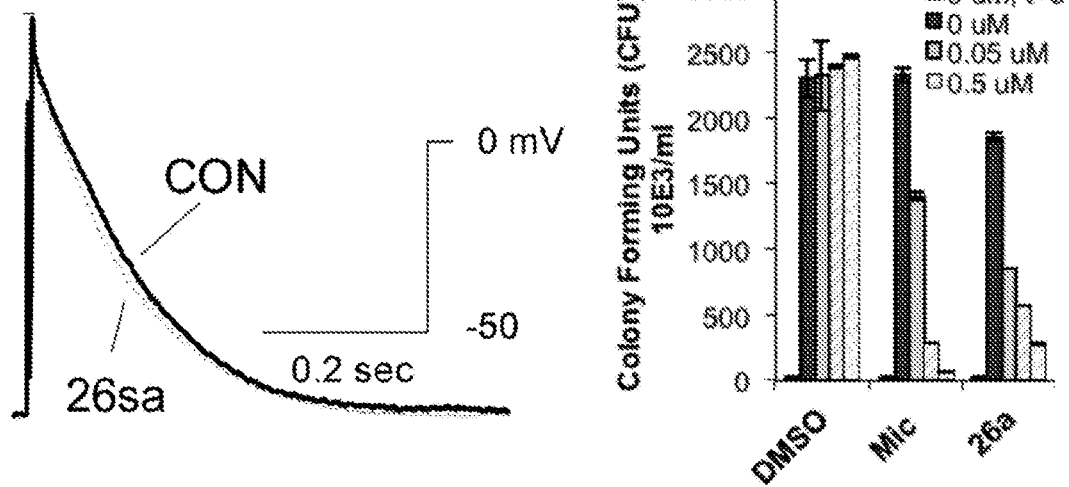
FIG. 9 shows new data showing rehabilitation of the antifungal miconazole, which blocks hERG, and is associated with acquired QT prolongation and ventricular arrhythmias (Kukuchi, K. et al. (2008) Br J Pharmacol. 144:840-848). Rehabilitated compounds were predicted by 3C-QSAR, protein and cell-level models developed in Noskov and Clancy labs. Compound 26 was synthesized and no cardiac electrophysiology AP effects observed (left), but antifungal activity was maintained (right).

Aim 2 General Plan: the disclosure performs atomic-scale simulations for dofetilide as described in Aim 1 to predict structure based drug channel interactions. These predictions can be used as the starting point for drug rehabilitation, which can consist of structural modifications to the drug to reduce inactivated binding. Molecular dynamics simulations can be used on drug analogs identified in the rehab procedure to inform rate constants of binding to discrete states of hERG in the channel function scale models. The disclosure carries out free energy perturbation (FEP) simulations to determine the relative free energies of drugs with similar structures allowing to pinpoint the molecular determinants of drug affinity for hERG channels. An example of a rehabilitated drug from the Noskov Group is shown in FIG. 9. As in Aim 1 drug-channel models can then be integrated into rabbit and human cellular and tissue level models to predict effects of drugs in higher dimensions. Model predictions can be validated experimentally in rabbit cells and tissues. The most promising analogs can be synthesized and modeled, followed by experimental tests of the predictions.

Structure Atomic Scale. Structural modeling of multiple hERG states, docking of dofetilide, and molecular dynamics (MD) simulations are as in Aim 1. Model validation: Kinetic parameters estimated from MD simulations can be compared with drug affinities from electrophysiological data dofetilide as in Aim 1 with additional kinetic experiments based on methods from the Sack Lab. Screening for drug analogs: The lowest interaction energy conformations of dofetilide in the hERG site (Rosetta) can be used to identify additional receptor contact points. Drug analogs can be rationally designed with RosettaLigandDesign according to the specific environment of drug molecule within the receptor site. For example, additional sites within the pore-forming domain structure are near the antiarrhythmic receptor that make up the binding domain for moxifloxacin and CONA-437 that do not include the S6 aromatic residues Y652 and F656 may comprise specific novel interaction sites. During each round, drug analogs can be docked to hERG channel states. The lowest interaction energy analogs can undergo MD simulations to estimate standard free energy of ligand binding and kinetic parameters as in Aim 1. Free Energy Perturbation (FEP) Simulations because of the anticipated structural similarity of dofetilide and the drug analogs that It is expected to test by employing FEP simulations that compute relative free energies of drug binding. Drugs can be alchemically transformed into analogs within the binding site, as well as in bulk electrolyte, with the free energy difference equal to the relative free energy of binding, via a thermodynamic cycle (e.g., Mobley, D. L. et al. (2012) J Chem Phys. 137:230901). Relative drug binding affinities of similar ligands can be far more efficient and accurate than absolute binding affinities, due to a cancellation of errors (Wang, K. et al. (2013) J Comput Aided Mol Des. 27:989-1007; Rocklin, G. J. et al. (2013) J Chem Phys. 139:184103; Rocklin, G. J. et al. (2013) J Chem Theory Comput. 9:3072-3083; Rocklin, G. J. et al. (2013) J Mol Biol. 425:4569-4583; Chodera, J. D. et al. (2013) Annu Rev Biophys. 42:121-142; Mobley, D. L. et al. (2007) J Mol Biol. 371:1118-1134; Mobley, D. L. et al. (2006) J Chem Phys. 125:084902; Deng, Y. et al. (2009) J Phys Chem B 113: 2234-2246), and have become a valuable tool for accurate screening of candidate drug compounds (Mobley, D. L. et al. (2012) J Chem Phys. 137:230901; Shirts, M. R. et al. Drug Design: Structure and Ligand-based Approaches. (Cambridge University Press, 2010)).

Synthesis of drug analogs: The SAR of dofetilide and related compounds for hERG inhibition has been previously studied and "do's and don'ts" for reducing hERG affinity have been developed such as reducing overall flexibility of the molecule or basicity of the central N (Shagufta et al. (2009) ChemMedChem 4:1722-1732; Carvalho, J. F. et al. (2013) J Med Chem. 56:2828-2840). However, most hERG inhibitors are screened only in binding assays such as [$^3$H]-astemizole displacement and no information is available about their kinetics or state-dependence of block. The disclosure uses these studies as a guide to suggest initial starting points for the simulations and then synthesize dofetilide analogues suggested to have reduced inactivated state potencies according to published procedures (Shagufta et al. (2009) ChemMedChem 4:1722-1732; Carvalho, J. F. et al. (2013) J Med Chem. 56:2828-2840). The Wulff laboratory is skilled in the design and synthesis of ion channel modulators including potent and selective K channel modulators (Sankaranarayanan, A. et al. (2009) Mol Pharmacol. 75:281-295; Wulff, H. et al. (2000) Proc Natl Acad Sci USA 97:8151-8156; Schmitz, A. et al. (2005) Mol Pharmacol. 68:1254-1270).

Limitations and Alternatives: As described for Aim 1.

Protein Function Scale. Experiments to assess drug kinetics with channels: Empirical measurements of drug binding kinetics to closed, open, and inactivated states can inform the atomistic models of drug-hERG interactions and test whether they predict accurate changes in relative affinity. State dependence of measured kinetics can be input into the kinetic models of rehabilitated compounds. Experiments are as in Aim 1.

Protein Function Scale. Models for drug interaction with cardiac ion channels: As described in Aim 1. Numerical methods and parameter optimization and Limitations and alternatives: As described in Aim 1.

Cell Scale. Simulations: Simulations can be carried out to assess cellular level parameters linked to the TRiAD as described in Aim 1. It is expected that modification of the inactivated state block affinities of dofetilide can reduce to reverse use dependence, temporal dispersion of repolarization at slow heart rates and emergence of EADs. Preliminary data on reverse use dependence is shown in FIGS. 6A-6H. The disclosure also tests the potential for dofetilide analogs to reduce cellular susceptibility to small electrical perturbations. The AP plateau is a phase of high resistance, rendering the cell vulnerable to perturbations that can arise from electrotonic influences of the surrounding tissue and arrhythmia triggers in the form of early and delayed after depolarizations. It is expected dofetilide analogs to reduce APD90 variability and reduce emergent EADs virtual cells in response to small electrical perturbation. Sensitivity analysis and error propagation: As in Aim 1. Experimental validation of the model predictions in rabbit myocytes: Predictions of changes in the WT rabbit cellular parameters after rehabilitated drug application can be as described in Aim 1. The disclosure also rehabbeds drugs on APD variability in cells compared to drug free as described in (Zaniboni, M. et al. (2000) Am J Physiol Heart Circ Physiol. 278:H677-H687). Action potentials can be recorded using non-dialyzing microelectrodes (Belevych, A. E. et al. (2000) J Physiol (Lond) 528:279-289). For each cell, 10 consecutive APs recorded after >2 minutes 0.5 Hz pacing can be used to calculate the coefficient of variability (CV), which is defined as the standard deviation/mean $APD_{90}$. APD variability, attributable to stochastic ion channel behavior, contributes to dispersion of refractoriness, a determinant of arrhythmogenesis (Zaniboni, M. et al. (2000) Am J Physiol Heart Circ Physiol. 278:H677-H687). Limitations and alternatives: As in Aim 1.

Tissue Scale. One-dimensional (1D) simulations: 1D simulations can be carried in rabbit and human ventricular virtual tissues as described in Aim 1. It is expected that dofetilide analogs without strong inactivated state block can lead to a reduction in spatial dispersion of repolarization due to a reduction in reverse use dependence. Two-dimensional (2D) simulations: 2D simulations can be as described in Aim 1. The disclosure hypothesizes that dofetilide analogs can be unable to promote functional lines of block following a pause protocol in tissue and can effectively reduce the size of the vulnerable window to unidirectional conduction block and reentry (Starmer, C. F. et al. (1991) Circulation 84:1364-1377; Starmer, C. F. et al. (1993) Biophys J. 65:1775-1787; Starmer, C. F. (2002) Int J Bifurcat Chaos 12:1953-1968). Thus, the disclosure assess the "vulnerable window" as in Aim 1 with and without varying concentrations of dofetilide analogs (Starmer, C. F. et al. (1991) Circulation 84:1364-1377; Starmer, C. F. et al. (1993) Biophys J. 65:1775-1787; Moreno, J. D. et al. (2011) Sci Transl Med. 3(98):98ra83). The refractory period can be considered to quantify drug-induced increase in arrhythmia risk (Starmer, C. F. (2002) Int J Bifurcat Chaos 12:1953-1968). Sensitivity analysis as for Aim 1 (Marino, S. et al. (2008) J Theor Biol. 254:178-196). Tissue level experimental validation of the model predictions: Optical mapping (based on methods from the Ripplinger Lab) can be performed with drug analogs following the same protocols as in Aim 1. Limitations and alternatives: Limitations are as in Aim 1.

Specific Aim 3—Drug Risk Stratification: To predict the interaction of risk factors with hERG dependent cardiotoxicity. Aim 3 Rationale: Female sex is the dominant risk factor for acquired LQT arrhythmias after puberty, with at least 70% incidence in females (Makkar, R. R. et al. (1993) JAMA 270:2590-2597). The disclosure uses an interdisciplinary approach to test the hypothesis that estrogen acts as a hERG pore blocker, interacts with other hERG blockers and increases the propensity for TdP arrhythmias. This hypothesis is based on published data showing that 17β-estradiol (E2) interacts directly with hERG and increases the rate of channel deactivation (Kurokawa, J. et al. (2008) J Physiol. 586(12):2961-2973). It has also been shown that in the presence of E2, hERG is markedly more sensitive to block by drugs (Kurokawa, J. et al. (2008) J Physiol. 586(12):2961-2973). The aromatic centroid of E2 may be responsible for increasing the sensitivity of hERG block by E4031 via interaction with the aromatic side chain of Phe$^{656}$ and aromatic rings of the hERG blocker (Kurokawa, J. et al. (2008) J Physiol. 586(12):2961-2973). Notably the concentration of E2 is not constant through the menstrual cycle, but rather fluctuates between 0.1 nM to 1 nM and has dramatic effects on sensitivity to hERG block within this range. Ibutilide exhibits clear sex and menstrual-cycle dependent effects (Rodriguez, I. et al. (2001) JAMA 285:1322-1326).

Aim 3 Expected Outcomes: Upon completion of Aim 3, It is expected to have demonstrated the usefulness of the multiscale model for novel prediction of: 1) Atomic-scale effects of estrogen interactions with hERG alone and in the presence of other hERG blockers that cannot be determined experimentally without onerous crystallographic and/or mutagenesis experiments. 2) Rates from atomic scale simulations of estrogen interactions with hERG channels for use at the protein function scale. 3) High throughput prediction of emergent drug effects in combined with risk factors on channel, cell and tissue cardiac electrical behavior for which no comparable experiment exists.

Aim 3 General Plan: The general approach to predict effects of antiarrhythmic drugs in diseased states is as follows: 1) Existing kinetic measurements can inform the development of computational models of estrogen effects on cardiac channels based on methods adapted from the Clancy Lab. 2) The cellular level models can form the basis for higher-scale 3) tissue simulations to predict how acute application of estrogen alone and in the presence of hERG blockers may underlie emergent arrhythmia susceptibility in coupled tissue. Experiments can inform and test model predictions.

Figure 10:
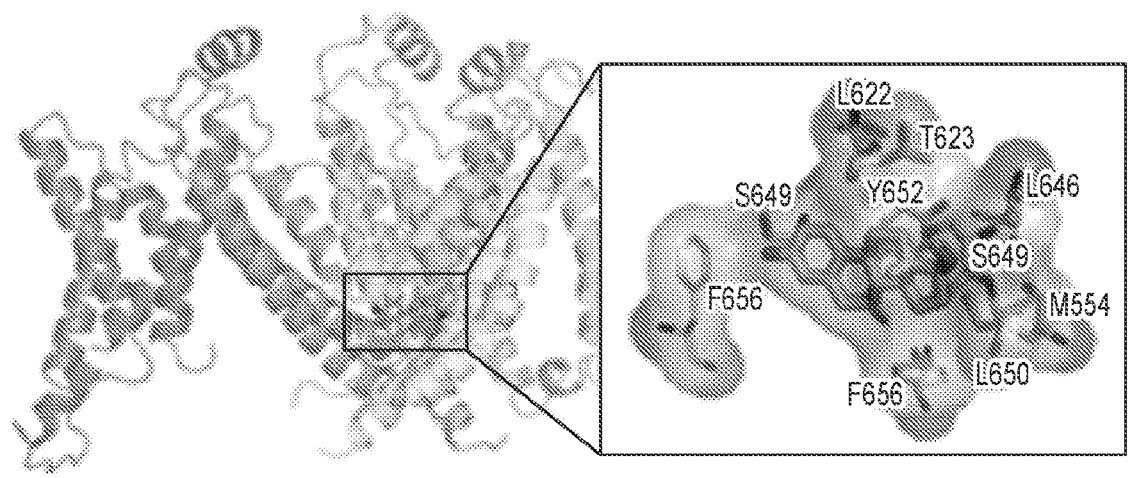
FIG. 10 shows top scoring docking poses for estradiol in the hERG WT model. A) E2 bound in the intracellular cavity (IFD score −8 kcal/mol), Estradiol is shown in Inset: E2 and relevant interacting residues with a hydrophobic surface overlay.

Protein Structure Scale. Rosetta modeling of hERG—estrogen—drug interactions. Closed, open and inactivated state models of hERG can be generated as in Aim 1 and used to predict state affinities of estrogen and to determine how estrogen may affect binding of the other drugs (ibutilide, sotaolol, moxifloxacin) to the binding site. Molecular dynamics simulations: Estrogen interactions with hERG can be modeled and simulated as described in Aims 1 and 2 for other drugs. See preliminary data in FIG. 10. Model validation: Kinetic parameters estimated from MD simulations can be compared with drug affinities from electrophysiological data for estrogen as described for the other drugs in Aim 1. Limitations and alternatives: As described for Aim 1.

Protein Function Scale. Experiments for assessing kinetics of drug interactions with ion channels: Empirical measurements as described in Aim 1 for drug binding kinetics to closed, open, and inactivated states can inform the atomistic models of hormone-hERG interactions and test whether they predict accurate changes in state-dependent affinity. Measured kinetics can be input into the kinetic models involving hormones.

Figure 11:
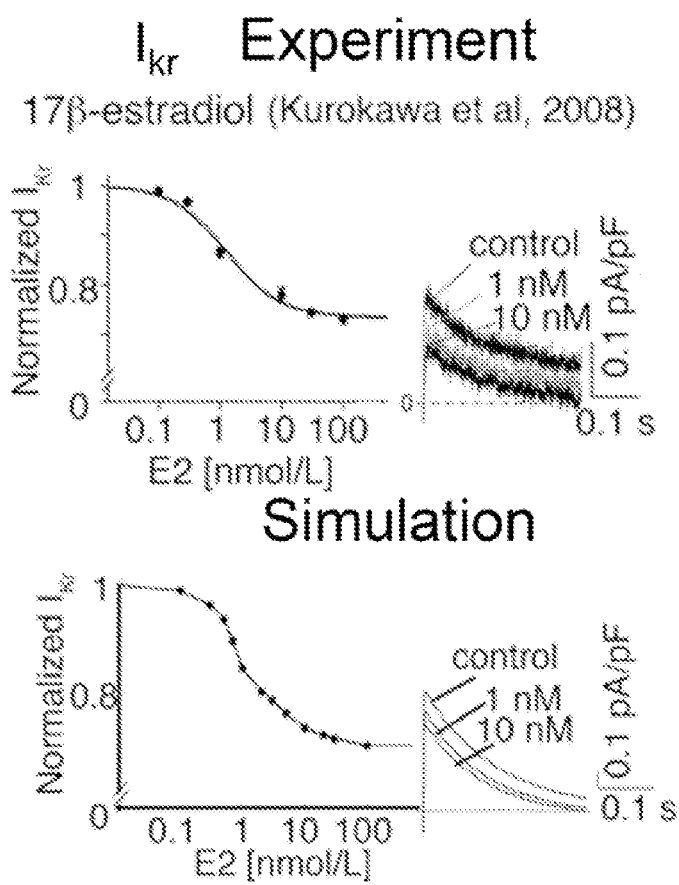
FIG. 11 shows effects of estrogen on $I_{Kr}$. The system simulated the $I_{Kr}$ current with addition of estrogen (lower panel) by scaling the conductance of current as indicated by experimental measurements (top panel) (Kurokawa, J. et al. (2008) J Physiol. 586(12):2961-2973).
Figure 12:
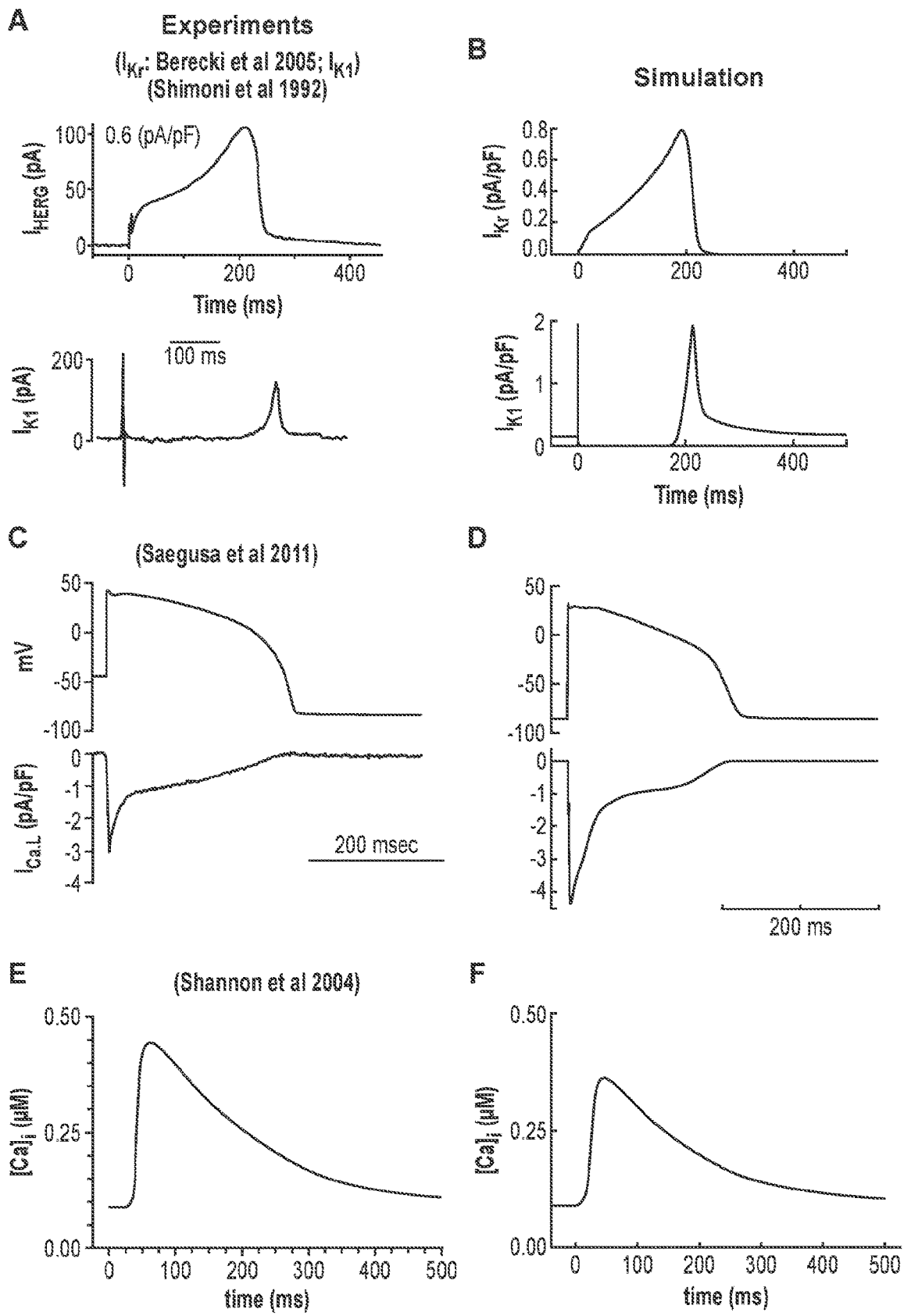
FIGS. 12A-12F show a comparison of experimentally recorded and model generated transmembrane ion currents from rabbit ventricular myocytes.

Protein Function Scale. Modeling effects of hormones on cardiac ion channels: Recent studies have demonstrated that sex steroid hormones act acutely and rapidly to directly modulate cardiac ion channel activity (Nakamura, H. et al. (2007) Circulation 116:2913-2922; Bai, C. X. et al. (2005) Circulation 112:1701-1710; Asada, K. et al. (2009) J Biol Chem. 284:6014-6020). The disclosure incorporates dose dependent effects of estrogen using the experimentally measured ratios (FIG. 11). Estrogen increases the rate of channel deactivation, which can reduce $I_{Kr}$ current. The disclosure also incorporates these kinetics effects on $I_{Kr}$ based on experimentally measured parameters at three physiological concentrations corresponding to various stages of the menstrual cycle: 0.1 nM (early follicular), 1.0 nM (late follicular) and 0.7 nM (luteal phase) (Kurokawa, J. et al. (2008) J Physiol. 586(12):2961-2973). Earlier studies have shown interaction of estrogen and drugs, the measured the scaling factors for conductance of IKr are: 0.93 with no hormone addition; 0.678 with E2 1 nM application (Kurokawa, J. et al. (2008) J Physiol. 586(12):2961-2973). The disclosure carries out similar experiments for dofetilide, analogs, sotalol and moxifloxacin (+/−) physiological concentrations of estrogen at stages of the menstrual cycle: 0.1 nM (early follicular), 1.0 nM (late follicular) and 0.7 nM (luteal phase). Ibutilide and estrogen can be systematically varied to predict combinations that produce arrhythmia triggers.

Cell Scale. In silico testing of estrogen mediated arrhythmia triggers in acquired Long-QT: To mimic conditions in acquired Long QT syndrome, the disclosure simulates transient exposure to dofetilide in the absence and presence of E2 and various pacing frequencies can be tested from 300 to 2000 ms. All possible combinations can be tested in order to construct a map indicating the cycle length and the type of trigger (e.g., alternans, early- or delayed-afterdepolarizations [EAD, DAD]). Short-long-short arrhythmia trigger: TdP arrhythmias may be triggered by pauses or short-long-short pacing sequences—especially in the setting of acquired long-QT syndrome resulting from $I_{Kr}$ block (Roden, D. M. et al. (2000) Heart 84:235-237). A sinus pause sets the stage for exaggerated heterogeneous action potential prolongation and even EADs. This can lead to triggered ectopy and the "cascade effect" leading to TdP. The disclosure tests for APD prolongation following a pause and/or EAD development. Estrogen effects can be determined as above. Conditions predicted to cause triggers can be tested in tissue simulations and experimentally. Validation of predictions for drug treatment of acquired Long-QT in rabbit myocytes: Drug effects on cell models of acquired Long-QT can be tested with acute application of estrogen as in Aims 1 and 2 in rabbit myocytes with dofetilide (10-100 nM) and moxifloxacin (Kiehn, J. et al. (1996) Circulation 94:2572-2579). Limitations and alternatives: As in the preceding aims.

Tissue Scale. One-dimensional (1D) simulations: 1D simulations can be carried out as in Aim 1. Compelling dynamics can be investigated in higher dimensions to limit computational expense. Following steady-state, drug/hormone can be applied and cells paced for a range of frequencies. Parameters can be tracked: Conduction velocity (CV): $I_{Kr}$ blocking drugs and sex steroid hormones can reduce CV by increasing APD so that Na channels have insufficient recovery time during diastolic intervals. CV depression can cause conduction block and reentry. Concentrations for conduction block (CB): the disclosure determines if conduction block occurs with static pacing over a range of physiological frequencies and drug/hormone concentrations. For each frequency (300-1000 ms), escalating drug and hormone concentrations (physiologically relevant increments) can be applied until the highest concentration is reached or block occurs. Calculation of the vulnerable window to unidirectional conduction block: the disclosure systematically determines the likelihood of arrhythmia induced by spontaneous ventricular stimuli with clinically relevant concentrations of hormones/drugs. Quantification of Arrhythmia Probability: The vulnerable window (VW) and refractory period (likely to be modified by estrogen and ibutilide) can be computed via the Starmer metric (Starmer, C. F. (2002) International Journal of Bifurcation and Chaos 12:1953-1968). Two-dimensional (2D) simulations: As in Aim 2 2D simulations can determine if proarrhythmic phenomena observed in lower dimensions cause reentrant arrhythmias and/or spiral wave breakup. Parameters can be compared to experiments as above and described in (Moreno, J. D. et al. (2011) Sci Transl Med. 3(98):98ra83; Nakamura, H. et al. (2007) Circulation 116:2913-2922; Zhu, Z. I. et al. (2007) Am J Physiol Heart Circ Physiol. 293: H3480-H3489; Yang, P. C. et al. (2010) PLoS Comput Biol. 6(1):e1000658). Experimental validation for drug treatment of acquired Long-QT in rabbit tissue: Tissue level model predictions of drug effects on acquired Long-QT can be tested in Optical mapping experiments in Langendorff perfused rabbit hearts: To test model predictions and determine the acute effects of estrogen in contributing to arrhythmia in the setting of acquired LQTS, the disclosure performs optical mappin. In order to study acute hormone effects, the disclosure eliminates chronic and fluctuating hormones in vivo via ovariectomy in female rabbits (Vertebrate Animals). Four weeks after ovariectomy, rabbits can be sacrificed and hearts excised for Langendorff perfusion. Atrioventricular node ablation via a fine tip thermal cautery to produce a slow intrinsic rhythm, can allow for pacing protocols including pauses and for the escape of ectopic activity. Optical mapping can be performed as described in Aim 1. As in the model simulations, the $I_{Kr}$ blocking drug as in Aims 1 and 2 ibutilide (10-100 nM) (Kiehn, J. et al. (1996) Circulation 94:2572-2579) and moxifloxacin can be applied in the absence and presence of physiological concentrations of estrogen corresponding to various stages of the menstrual cycle: 0.1 nM (early follicular), 1.0 nM (late follicular) and 0.7 nM (luteal phase). Pacing protocols, including dynamic and static restitution, and short-long-short can be applied as in model simulations to determine which conditions exhibit arrhythmogenic responses (e.g., alternans, EADs, DADs, reentrant arrhythmias). For each protocol, propensity to arrhythmogenic activity can be compared for different estrogen concentrations. The disclosure quantifys parameters as in the model (CV, APD restitution, APD dispersion, vulnerable window, reentry wavelength). Limitations and alternatives: These are as described in the preceding aims.

Vertebrate Animal Subjects Optical Mapping Studies

1. Adult New Zealand White rabbits can be used for optical mapping experiments in this project. Approximately 60 animals can be used for this project. A subset (approximately 25) of animals can undergo bilateral ovariectomy under sterile surgical conditions and allowed to recover for ~2-4 weeks. Then, animals can be euthanized and hearts excised for acute electrophysiological experiments.

2. Unfortunately no alternative to the use of animals in studies of arrhythmia has been found so far. Numerical approaches, like the studies proposed here, can undoubtedly decrease the number of animals needed in future studies, but computational models must be experimentally informed and validated, as can be done here. Additionally, the mechanisms of arrhythmia genesis and maintenance must be confirmed at the tissue-scale or higher, as it is impossible to predict how cell-level perturbations can translate to the tissue- or organ-scale.

The proposed research can use rabbits as experimental animals. There are several reasons justifying Applicants' choice of the rabbit experimental model:

a. This species has proven to be the most suitable model for in vitro research of arrhythmia due to its ability to sustain clinically relevant arrhythmias, which are not typically observed in smaller species. The rabbit heart has been found to be most similar to the human heart in terms of both the effective size and wave patterns during VT/VF, both of which are principal parameters for investigation of arrhythmia mechanisms.

b. The action potential characteristics of the rabbit heart are more similar to the human heart compared to smaller species (mouse and rat).

c. The size of the rabbit heart allows relatively deep penetration of reconstruction of electrical activity using optical mapping, compared with larger hearts.

Animal numbers: Based on Applicants' previous combined computational/experimental studies, the disclosure needs approximately 5 rabbits per experimental condition to validate model predictions. Therefore, animal numbers are as follows:

Aim 1: 5 conditions (no drug, dofetilide, ibutilide, sotalol, moxifloxacin, ketaconozole amiodarone)×5 animals/condition=35 rabbits
Aim 2: 2 conditions (2 most promising drug analogs)×5 animals/condition=10 rabbits
Aim 3: 4 conditions (all ovariectomy, 2 drugs, ±estrogen for each drug)×6 animals/condition (in case of surgical mortality)=24 rabbits
TOTAL=25+10+24=69 rabbits 3. Rabbits can be housed in a vivarium maintained by the Center for Lab Animal Science (CLAS) at UC Davis. The vivarium is located in the same building where the experiments and surgeries can be performed (Tupper Hall). These facilities are fully AAALAC accredited. Routine visits are made by veterinarians who are also available for emergencies at all times. The facilities are overseen by the Institutional Animal Care and Use Committee (IACUC). The guidelines of UC Davis are in accordance with policies of the National Institutes of Health and include mandatory periodic training for researchers, routine surveillance of animal facilities, periodic veterinarian visits, and the humane use of animals.

4. Bilateral ovariectomy can be performed in sterile surgical conditions under general anesthesia. Rabbits can be restrained in an approved rabbit restrainer or gently wrapped in a towel with head exposed. Anesthesia can be induced with a nosecone (mask) with 3-4% isoflurane and oxygen, and then moved to a nose cone with 1-2% isoflurane supplemented with oxygen. The following procedure can be used to assess adequacy of anesthesia: 1) eye blink reflex is present; 2) there is whisker movement; 3) paw withdraw upon pinch; 4) irregular or sudden changes in heart rate. If any of these signs are present, the isoflurane can be increased to 3-4%. The animal can be placed in a ventral recumbent position and a skin incision can be made from the second to fifth lumbar vertebrae. The skin incision can be retracted from one side to the other and each ovary and associated fat can be ligated and removed. The skin incision can then be closed. During recovery, heating can be provided as appropriate to ensure maintained body temperature. The narcotic buprenorphine (0.05 mg/kg) SQ can be given immediately post-op. Thereafter, buprenorphine or meloxicam (0.2 mg/kg) SQ can be given 2 times per day for 2 days, but additionally PRN to any animals whose behaviors suggest discomfort. Any animal that does not fully recover or appears to be in pain or distress can be euthanized.

Cardioectomy: For all experiments, cardioectomy can be performed. Rabbits can be brought to the laboratory approximately 1 hr prior to in vitro experiments to minimize stress. Rabbits can be anesthetized with pentobarbital sodium (50 mg/kg, IV). To administer anesthesia, rabbits can be securely restrained in a specially designed rabbit restrainer (Harvard Apparatus 520924 or similar). A butterfly needle can be inserted into the ear vein. 2000 Units of heparin can be administered IV followed immediately by pentobarbital sodium. The pain reflex (toe pinch) and respiration rate can be used as observable signs that adequate anesthesia is being applied. The heart can be quickly excised from the chest via midline thoracotomy and suspended on a Langendorff apparatus for retrograde perfusion and optical mapping studies. The rabbit should not experience anything more than momentary pain or discomfort throughout this procedure.

5. The most commonly used method of euthanasia by injection of a lethal dose of a drug is unacceptable in Applicants' experiments because it must result in cardiac arrest. Applicants' in vitro experiments require a normally excitable heart. Therefore, the disclosure uses the following procedure, which is consistent with the recommendation of the AVMA Panel on Euthanasia and is commonly accepted in the field: First, anesthesia is achieved by IV injection of 50 mg/kg sodium pentobarbital. Similar to clinical anesthesia, success of the procedure can be assured by the lack of corneal and nociceptive reflexes. Second, euthanasia can be performed by surgical removal of the heart, via a midsternal incision.

Vertebrate Animal Subjects Isolated Myocyte Studies

1. Adult rabbits of either sex can be used for the experiments in this project. Approximately 75 animals can be used each year at the University of Nevada, Reno.

2. The rabbit heart was chosen as the model for this project for several reasons: 1) the ionic basis and configuration of the ventricular action potential more closely resemble human than other species of similar size, 2) much of the background for the present studies was obtained using rabbit hearts, 3) the size of the rabbit heart is ideally suited for the proposed whole heart imaging studies being conducted by other investigators in this project, and 4) mathematical models of the rabbit ventricular action potential can be used as part of the project.

For single cell experiments, it is anticipated that it can be necessary to isolate myocytes an average of 2 days per week, 50 weeks per year in years 1 and 2. The number of animals used is reduced in subsequent years. It is anticipated that a total of 320 animals can be need over the 5 years of this project.

3. Animals used at the University of Nevada, Reno can be housed in the Animal Resource Center located in the Anderson Medical Science Building. These facilities are AAALAC approved and under the supervision of a licensed veterinarian.

4. Animals used in this project can only be exposed to acute procedures. They can be anesthetized, followed by removal of the heart. Therefore, the only discomfort or stress they may experience can be associated with the anesthesia procedure.

5. The methods of euthanasia employed are consistent with the recommendations of the Panel on Euthanasia of the American Veterinary Medical Association. The animals can be euthanized by removal of the heart following intravenous injection of a lethal dose of pentobarbital (20-60 mg/kg).

B. Example 2. A Computational Model Predicts Adjunctive Pharmacotherapy for Cardiac Safety Via Selective Inhibition of the Late Cardiac Na Current The QT interval is a phase of the cardiac cycle that corresponds to action potential duration (APD) including cellular repolarization (T-wave). In both clinical and experimental settings, prolongation of the QT interval of the electrocardiogram (ECG) and related proarrhythmia have been so strongly associated that a prolonged QT interval is largely accepted as surrogate marker for proarrhythmia. Accordingly, drugs that prolong the QT interval are not considered for further preclinical development resulting in removal of many promising drugs from development. While reduction of drug interactions with hERG is an important goal, there are promising means to mitigate hERG block. Here, the disclosure examines one possibility and test the hypothesis that selective inhibition of the cardiac late Na current ($I_{NaL}$) by the novel compound GS-458967 can suppress proarrhythmic markers.

New experimental data has been used to calibrate $I_{NaL}$ in the Soltis-Saucerman computationally based model of the rabbit ventricular action potential to study effects of GS-458967 on $I_{NaL}$ during the rabbit ventricular AP. Applicants have also carried out systematic in silico tests to determine if targeted block of $I_{NaL}$ would suppress proarrhythmia markers in ventricular myocytes described by TRIaD: Triangulation, Reverse use dependence, beat-to-beat Instability of action potential duration, and temporal and spatial action potential duration Dispersion.

Applicants' computer modeling approach based on experimental data, yields results that suggest that selective inhibition of $I_{NaL}$ modifies all TRIaD related parameters arising from acquired Long-QT syndrome, and thereby reduced arrhythmia risk. This study reveals the potential for adjunctive pharmacotherapy via targeted block of $I_{NaL}$ to mitigate proarrhythmia risk for drugs with significant but unintended off-target hERG blocking effects.

Methods

Experimental Methods

Recordings of late $I_{Na}$ and action potentials using whole-cell patch-clamp technique The conventional whole-cell configuration of patch clamp technique was used to record late $I_{Na}$ in voltage-clamp mode and action potentials (APs) in the current-clamp mode. All whole-cell data were acquired using a Multiclamp 700B amplifier with pClamp 10.2 software (Molecular Devices, Sunnyvale, Calif.). Data was analyzed using pClampfit 10, Microcal Origin 8 (OriginLab Corporation, Northampton, Mass.), and GraphPad Prism 5 (GraphPad Software, Inc., La Jolla, Calif.) software programs. Patch pipettes were pulled from borosilicate glass (World Precision Instruments, Sarasota, Fla.) using a DMZ Universal Puller (Dagan Corporation, Minneapolis, Minn.). Current-clamp experiments were performed at 36±1° C. using a temperature controlling system (TC-334B, Warner Instruments, Hamden, Conn.), whereas, the voltage-clamp experiments were done at 22±1° C. In all experiments, after a gigaseal was established in the whole-cell configuration, 5-10 minutes was allowed for stabilization before the experimental protocol was started.

In recordings of $I_{Na}$, myocytes were superfused with bath solution containing (in mM): 135 NaCl, 4.6 CsCl, 1.8 CaCl$_2$, 1.1 MgSO$_4$, 10 HEPES and 10 glucose supplemented with nitrendipine at a final concentration of 10 μM. The pH was adjusted to 7.4 with NaOH. The patch pipette resistances varied from 1.5-2 MΩ when they were filled with an internal solution containing (in mM): 120 aspartic acid, 20 CsCl, 1 MgSO$_4$, 4 ATPNa$_2$, 0.1 GTPNa$_3$ and 10 HEPES. The pH was adjusted to 7.3 with CsOH. Late $I_{Na}$ was recorded during a 1500 msec ramp voltage-clamp command starting from −90 mV and depolarizing to 0 mV once every 20 sec. Late $I_{Na}$ was measured as the maximum inward current during each ramp depolarization For microelectrode intracellular recordings of action potentials (APs), myocytes were superfused with bath solution containing (in mM): 140 NaCl, 4 KCl, 1.8 CaCl$_2$, 1 MgCl$_2$, 0.33 NaH$_2$PO$_4$, 5 HEPES and 7.5 glucose. The pH was adjusted to 7.4 with NaOH. Pipette resistances were in the range of 2-2.5 MΩ when using an internal solution containing (in mM) the following: 60 K aspartate, 80 KCl, 8 NaCl, 5 Mg-ATP, 0.25 Tris-GTP, and 5 HEPES was used. The pH was adjusted to 7.3 with KOH. APs were elicited by 3-3.5 ms depolarizing current pulses adjusted to approximately 1.5 time the threshold and applied every 5 sec (0.2 Hz). The APD was measured at 90% (APD$_{90}$) of full repolarization. Ten consecutive AP recordings were averaged for each experimental condition.

Simulation Methods

Cellular Simulations

A rabbit cardiac myocyte model was chosen in this study to align with the rabbit ventricular myocytes experimental data—unpublished and from (Belardinelli, L. et al. (2013) J Pharmacol Exp Ther. 344:23-32). The Sotis-Saucerman cardiac cell model (Soltis, A. R. et al. (2010) Biophys J. 99:2038-2047) was modified as follows: The $I_{Na}$ channel was replaced with Markov model described below and with full parameters in the accompanying supplement. The Na channel model structure was based on previously published models (Moreno, J. D. et al. (2013) Circ Res. 113:e50-e61; Yang, P. C. et al. (2015) J Physiol. 593:1429-1442). Recognizing that cardiac myocytes exhibit substantial variability in both current and action potential amplitudes and morphologies (Yang, P. C. et al. (2015) J Physiol. 593:1429-1442), Applicants then empirically tuned the Ca$^{2+}$ and K$^+$ current amplitudes to simultaneously recapitulate a representative rabbit experimental current data (Shimoni, Y. et al. (1992) J Physiol. 448:709-727; Shannon, T. R. et al. (2000) Biophys J. 78:322-333; Shannon, T. R. et al. (2004) Biophys J. 87:3351-3371) and action potential duration in experiments (Belardinelli, L. et al. (2013) J Pharmacol Exp Ther. 344:23-32) as follows:

TABLE 1

Current density changes in cardiac ventricular cell model. The maximum conductances were tuned to approximate the experimentally measured current amplitudes during the action potential. An action potential duration that was within the experimental range was determined.

| Ionic parameters | Scaling factors |
|---|---|
| pCa | 0.7 |
| Gto$_{slow}$ | 1.3 |
| Gto$_{fast}$ | 1.3 |
| G$_{K1}$ | 0.5 |

Optimization Procedure for Rabbit Sodium Channel

A computational Markov model of the drug-free (control) and GS-458967 drug channel interaction was formulated via numerical optimization from experimentally derived rate constants as previously described (Moreno, J. D. et al. (2013) Circ Res. 113:e50-e61; Moreno, J. D. et al. (2011) Sci Transl Med. 3:98ra83). Five pacing protocols were optimized: steady state availability at test potentials from −130 mV to −50 mV followed by depolarization to −35 mV, steady state activation (the holding potential was −120 mV and the testing potentials ranged from −60 to 20 mV in 5-mV steps) (Lee, H. C. et al. (1993) J Clin Invest. 91:693-701), recovery from inactivation at a holding potential of −100 mV (Lee, H. C. et al. (1993) J Clin Invest. 91:693-701), $I_{Na}$ time course current (Belardinelli, L. et al. (2013) J Pharmacol Exp Ther. 344:23-32), and ramp pulses from Gilead Sciences, Inc. (Please see the section above on Recordings of late $I_{Na}$ and action potentials using whole cell patch-clamp technique).

A cost function for each protocol was defined as the sum of squared differences between experiment and simulation. The total cost function (sum of the individual protocol errors) was then minimized and converged when a tolerance of 0.01 for the change of the cost function and 0.01 for the change in parameters was achieved.

All rate constants were allowed to change during the optimization. Post-optimization and Initial values are shown in Online Tables I and II, respectively.

Parameter Optimization for Drug-Bound Model

Figure 15A:
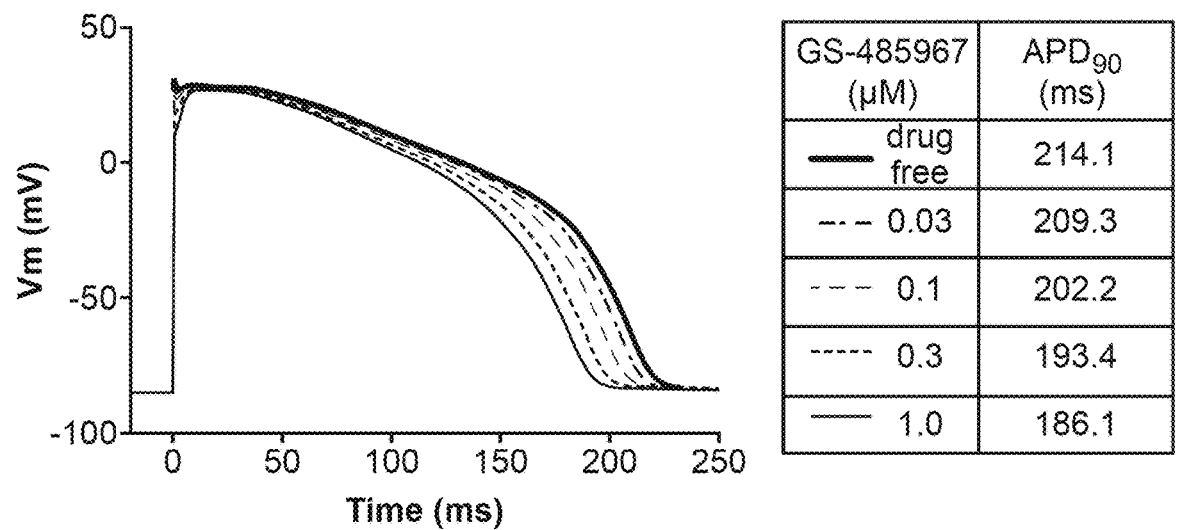
FIGS. 15A-15B show in silico prediction of GS-458967 induced reduction of $I_{NaL}$ and concentration-dependent shortening of APD in rabbit ventricular myocytes.

Simulations of GS-458967 dose-dependent effects on late Na current were optimized to fit the experimentally measured late Na$^+$ current with GS-458967 concentrations of 0.03, 0.1, 0.3 and 1 μM. The drug-bound rate constants (αx2, α13n, α_22, K$_{on}$, K$_{inactive}$, K$_{closed}$) were optimized to fit the experimentally measured late Na$^+$ current with GS-458967 concentrations of 0.03, 0.1, 0.3, 1 μM and 10 μM, and the peak Na$^+$ value at 10 μM (FIG. 15A). The optimized rate constants are shown in Online Table IV. Because GS-458967 is highly non-basic and cannot be protonated at physiological pH, the post-optimization values (αx2, α13n, α_22, β_33, K$_{on}$, K$_{inactive}$, K$_{closed}$) are shown in Online Table III, and initial guesses are shown in Online Table IV.

Introduction of variability in the cellular model to create cell populations

Simulated single action potentials (APs) were recorded at the 500$^{th}$ paced beat (BCL=1000 ms). Applicants have also simulated a cell 'population' by randomly varying the amplitude of maximal conductances for $I_{Na}$, $I_{CaL}$, $I_{Ks}$, $I_{Kr}$, $I_{Kl}$, $I_{to}$, $I_{NaK}$, $I_{NaCa}$ to within 10% (FIG. 14B) of their nominal values in the rabbit ventricular myocyte model, as is done in standard sensitivity analysis (Voit, E. O. (2000) Sensitivity Analysis. Computational Analysis of Biochemical Systems: A Practical Guide for Biochemists and Molecular Biologists. New York: Cambridge University Press, p. 222; Allen, L. et al. (2011) Int J Climatol. 31:1990-2005; Poleszczuk, J. et al. (2015) PLoS One 10:e0120007). This approach allowed for efficient analysis of 100 distinct cell action potentials. $APD_{90}$ was calculated at 1 Hz for each case. These simulated myocyte properties were compared to distinct experimental data sets #1 (blue asterisks) and #2 (red circles) as shown in FIGS. 14A-14B.

The numerical method used for updating the voltage was forward Euler. All the simulations were encoded in C/C++ and run on Mac Pro 3.06 GHz 12-Core computers. Numerical results were visualized using MATLAB R2014a by The Math Works, Inc.

Simulated Effects of ATX-II

Figure 14:
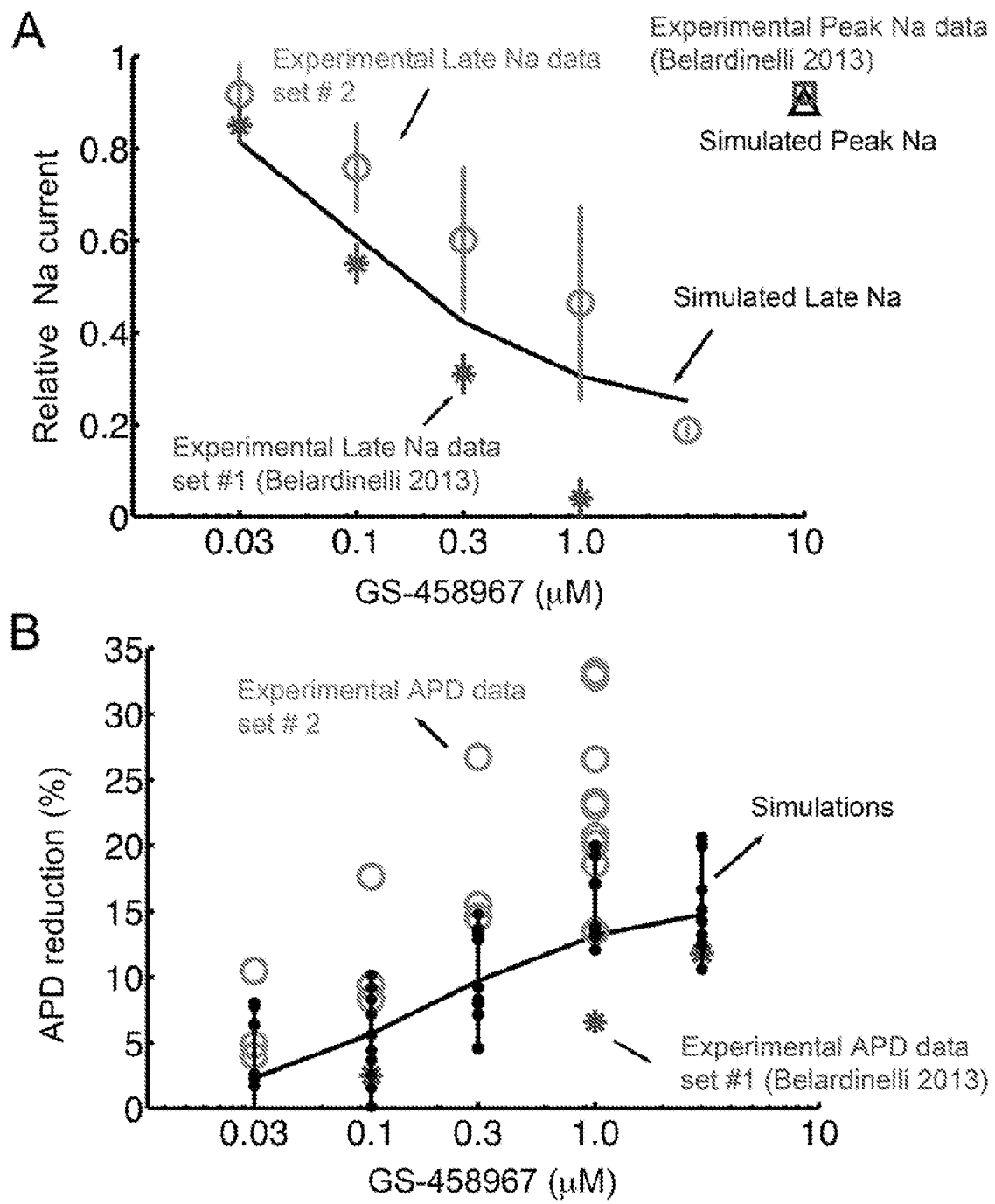
FIGS. 14A-14B shows experimentally measured and model predicted effect of GS-458967 on $I_{Na}$ in rabbit ventricle.

Applicants have also simulated a 'population' of 100 cells by randomly varying the amplitude of maximal conductances as in FIG. 14B. $APD_{90}$ was calculated at 0.2 Hz for each case in FIGS. 16A-16B.

where n is N(0,1) is a random number from a Gaussian distribution, and $\Delta t$ is the time step. $\xi$ is the diffusion coefficient, which is the amplitude of noise. In FIGS. 18A-18I, $\xi$ was set to 0.32 based on (Tanskanen, A. J. et al. (2007) Math Biosci. 208:125-146). The noise current was generated and applied to membrane potential $V_t$ throughout the whole simulated time course.

Transmural Fiber Simulations

Spatial dispersion of repolarization, corrected QT interval and frequency dependence of QT interval was performed via in silico transmural 1- or 2-dimensional tissue composed of 165 ventricular cells ($\Delta x = \Delta y = 100$ pm) connected by resistances to simulate gap junctions (Soltis, A. R. et al. (2010) Biophys J. 99:2038-2047). The fiber contains an endocardial region and epicardial region, which shown a linear decreased in APDs (Glukhov, A. V. et al. (2010) Am J Physiol Heart Circ Physiol. 299:H482-H491; Lou, Q. et al. (2011) Circulation 123:1881-1890). In the model, $G_{toSlow}$ was monotonically increased from 0.0615 to 0.078, and $G_{toFast}$ was linearly increased from 0.0095 to 0.026. The fiber was paced at BCL=1000 ms for 200 beats. The stimulus is applied to the first cell.

TABLE 2

Simulated and experimental measured $APD_{90}$. To simulate enhancement of late $I_{Na}$ with ATX-II, rate constant, µ2, was reduced by 40%.

| BCL = 5000 ms | Experimental $APD_{90}$ (ms) (mean values) | | Simulated $APD_{90}$ (ms) (mean values from |
|---|---|---|---|
| FIGS. 16A-16B | Cell 1 | Cell 2 | 1000 APs) |
| Control | 258.8 (n = 11) | 522 (n = 6) | 240.91 |
| ATX-II | 625.2 (n = 10) | 2305.2 (n = 12) | 497.02 |
| Relative change to ATX-II | 58.6% | 77.3% | 51.53% |

Figure 17:
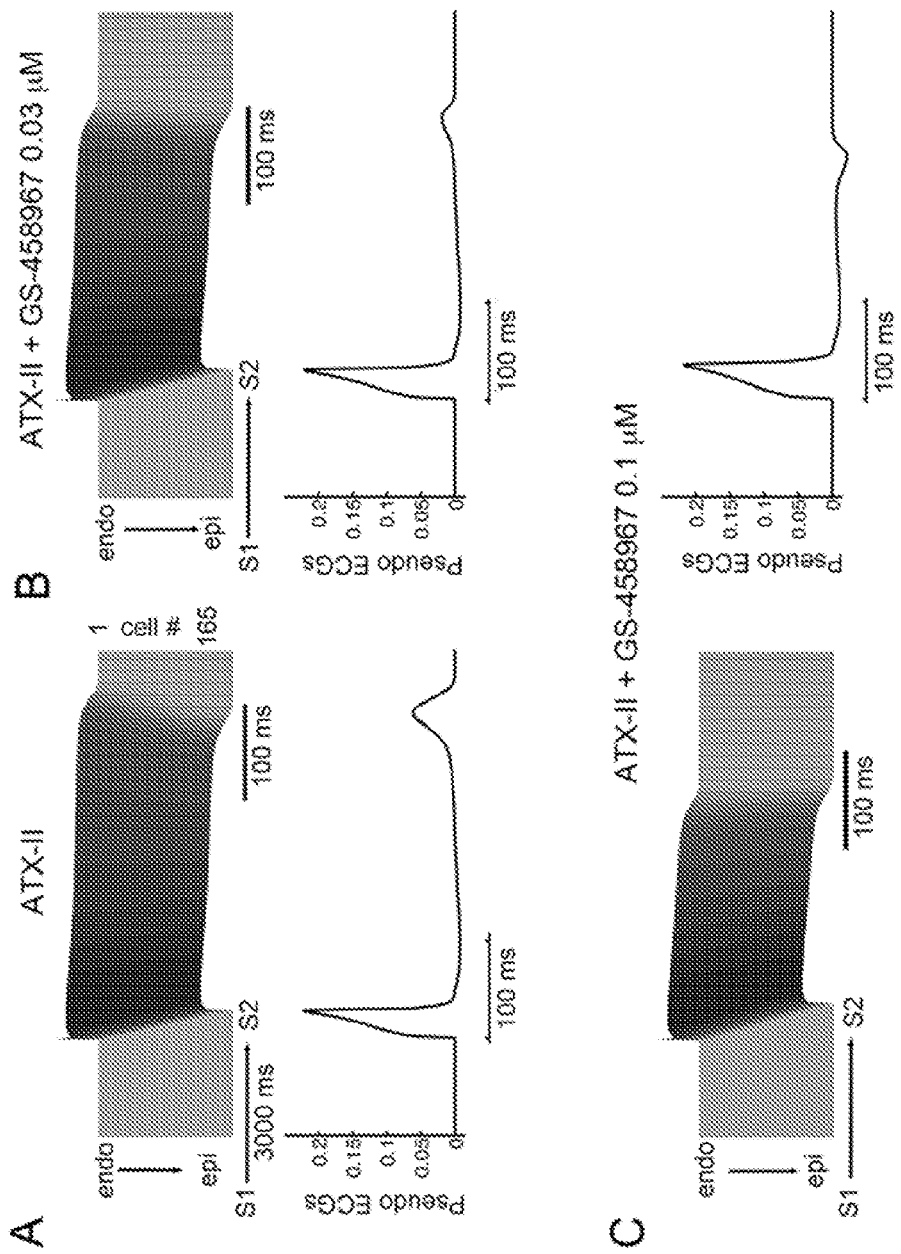
FIGS. 17A-17C show simulations showing that GS-458967 can effectively reduce spatial APD dispersion caused by ATX-II.

In FIGS. 17B and 17C, 1D cables were first paced at 1 Hz for 200 beats with simulated ATX-II effects only, added GS-458967 for next 10 beats at 1 Hz (s1) followed by a pause (3000 ms), and then applied a premature beat (s2).

Calculation of an Arrhythmia Proclivity Score:

Simulation of TRIaD in Drugged and Drug-Free Models

To simulate effects of dofetilide, the disclosure replacdes the $I_{Kr}$ channel with the previously published Markov model (Romero, L. et al. (2014) J Mol Cell Cardiol. 72:126-137). For the TRIaD simulations, simulations were conducted as follows: First, Triangulation was calculated as the repolarization time from $APD_{30}$ to $APD_{90}$ from 1000 simulated cell with noise currents. Reverse-use-dependence was measured $APD_{90}$ at steady state for each pacing cycle length (from 3 Hz to 0.5 Hz) and APD adaptation curves were constructed. Instability was simulated by applying small amplitude inward currents randomly between −0.1 to −0.2 pA/pF for 50 ms over the course of the action potential plateau at a pacing cycle length=1000 ms. A small inward current was also applied randomly in time between 10 to 210 ms on the plateau phase for 1000 beats. Applicants modeled beat-to-beat APD variability by adding noise currents into membrane potential calculations, and simulated 1000 cells action potentials. Using the equation from (Tanskanen, A. J. et al. (2007) Math Biosci. 208:125-146), $$V_{t+\Delta t} = V_t - \frac{I(V_t)\Delta t}{C_m} + \xi n \sqrt{\Delta t}$$

ECG Computation

Extracellular unipolar potentials ($\Phi_e$) generated by the fiber in an extensive medium of conductivity $\sigma_e$, were computed from the transmembrane potential $V_m$ using the integral expression as in Gima and Rudy (Gima, K. et al. (2002) Circ Res. 90:889-896):

In One-Dimension:

$$\Phi_e(x') = \frac{a^2 \sigma_i}{4\sigma_e} \int (-\nabla V_m) \cdot \left[\nabla \frac{1}{r}\right] dx$$
$$r = [(x - x')^2]^{1/2}$$

In Two-Dimension:

$$\Phi_e(x', y') = \frac{a^2 \sigma_i}{4\sigma_e} \int (-\nabla V_m) \cdot \left[\nabla \frac{1}{r}\right] dxdy$$
$$r = [(x - x')^2 + (y - y')^2]^{1/2}$$

where $\nabla V$ is the spatial gradient of $V_m$, a is the radius of the fiber, $\sigma_i$ is the intracellular conductivity, $\sigma_e$ is the extracellular conductivity, and r is the distance from a source point (x, y, z) to a field point (x', y', z'). $\Phi_e$ was computed at an "electrode" site 2.0 cm away from the distal end along the fiber axis.

The tissue was paced at varying basic cycle length (BCL) from 800 ms to 1400 ms for 200 beats. Pseudo ECGs were computed from the transmembrane potential $V_m$ using the integral expression as in Gima and Rudy (Gima, K. et al. (2002) Circ Res. 90:889-896). Heart rate corrected QT (QTc) was computed using Fridericia formula using the cubic root of RR interval (Fridericia, L. S. (1920) Acta Medica Scandinavica 53:469-486).

$$QT_C = \frac{QT}{\sqrt[3]{RR}} \qquad (8)$$

Spatial APD dispersion was measured using the T-wave area indicator, which was calculated as the T-wave amplitude on the computed pseudo-ECGs. For this purpose, a 1-dimensional model of the transmural wedge preparation, as described in (Yang, P. C. et al. (2012) Front Physiol. 3:360), was stimulated by applying a standard short-long protocol as follows: The transmural wedge preparation was stimulated by a train of pulses (S1) at 1000 ms pacing cycle length until the steady-state was reached followed by a premature beat (S1-S2 interval=800 ms) and then a delayed beat (S3) was delivered after a long pause (S2-S3 interval=5000 ms). T-wave area calculations were computed as follows:

(Eq. 2)

$$\sum_{t=t1}^{t2} |ECG(mV)| \cdot \Delta t \qquad (8)$$

where $\Delta t=1$ ms, $t_1$ is the time where ECG equals to $T_{peak}-0.9*(T_{peak}$=minimum of left side oft-wave) and $t_2$ is the time where ECG equals to $T_{peak}-0.9*(T_{peak}$=minimum of right side of t-wave).

Frequency-Dependent QT Prolongation

The fiber was paced at 1 Hz for 1000 beats (S1) and then a second stimulus (S2) was applied after a varying RR interval (between 550 ms and 1150 ms). The QT interval, in response to S2, was recorded. The same simulations were carried out 11 times for both control and dofetilide 2 nM cases, and the relative changes in slope of relationship of QT and preceding RR intervals were calculated.

Transmural Tissue Simulations

Applicants simulated a heterogeneous cardiac tissue assuming a 500 by 500 component grid $\Delta x=\Delta y=100$ pin. This tissue was assumed to contain an endocardial region and epicardial region, with a linear decrease in APDs (Glukhov, A. V. et al. (2010) Am J Physiol Heart Circ Physiol. 299:H482-H491; Lou, Q. et al. (2011) Circulation 123:1881-1890). All ion channel conductances and gap junctions parameters are same as in the one-dimensional simulations. Current flow is described by the following equation:

$$\frac{\partial V(x, y, t)}{\partial t} = D_x \frac{\partial^2 V(x, y, t)}{\partial x^2} + D_y \frac{\partial^2 V(x, y, t)}{\partial y^2} - \frac{I_{ion}\_I_{stim}}{C_m}$$

Where V is the membrane potential, x and y are distances in the longitudinal and transverse directions, respectively, $D_x$ and $D_y$ are diffusion coefficients in the x and y directions. $I_{stim}$ is 500 mA/cm$^2$ for 1 ms. Applicants also incorporated anisotropic effects by setting $D_x$ and $D_y$ such that the ratio of conduction velocity is 1:2 (Young, R. J. et al. (2010) Proc Natl Acad Sci USA 107:15063-15068).

The output scores from each of these simulations are utilized in a weighted average calculation (proarrhythmia score) whereby the weighting is determined by the correlation between each parameter and arrhythmia. Arrhythmia is determined by an in silico diagnostic test in 2- or 3-dimensional tissue using an S1-S2 pacing protocol. Arrhythmia is indicated by 1) induction of a spiral wave, 2) the persistence (duration) of the spiral wave. Additional metrics may be tracked including spiral wave morphology and potential to break up.

The higher the score, the more "proarrhythmic" the agent. The score is within the range of 0 to 1, where 0 is the correlation in the absence of the drug and 1 is the correlation to the positive control induced by a high dose of dofetilide.

This ventricular tissue segment was first paced for 200 beats (S1) at BCL=1000 ms on the entire length of one side of tissue. A premature stimulus (S2) was then delivered at 330 ms in control case (FIG. 22A) after S1 in a 2.5 cm×2.5 cm area on the top edge of the endocardial region. (FIG. 22B) In ATX-II case, S2 paced at 450 ms, and at 465 ms in Dofetilide case (FIG. 22C) after S1 in a 2.5 cm×2.5 cm area on the top edge of the endocardial region. With GS-458967 applications, S2 was applied at 420 ms in ATX-II (FIG. 22D) and at 430 ms (FIG. 22E) in Dofetilide cases (FIGS. 22A-22E).

Results

The starting point for this study compared the simulated main currents and Ca$^{2+}$ transient in the Soltis-Saucerman rabbit ventricular action potential model (Soltis, A. R. et al. (2010) Biophys J. 99:2038-2047) during the AP to those recorded experimentally from individual rabbit ventricular myocytes (FIGS. 12A-12F). Next the Soltis-Saucerman model parameters for the maximum conductances for Ca$^{2+}$ and K$^+$ currents were tuned to match the experimental data from rabbit ventricular myocytes (Shimoni, Y. et al. (1992) J Physiol. 448:709-727; Shannon, T. R. et al. (2000) Biophys J. 78:322-333; Shannon, T. R. et al. (2004) Biophys J. 87:3351-3371) including action potential durations (Belardinelli, L. et al. (2013) J Pharmacol Exp Ther. 344:23-32). Following these minor adjustments, the output of the model showed good agreement with the experimentally recorded currents.

Figure 13:
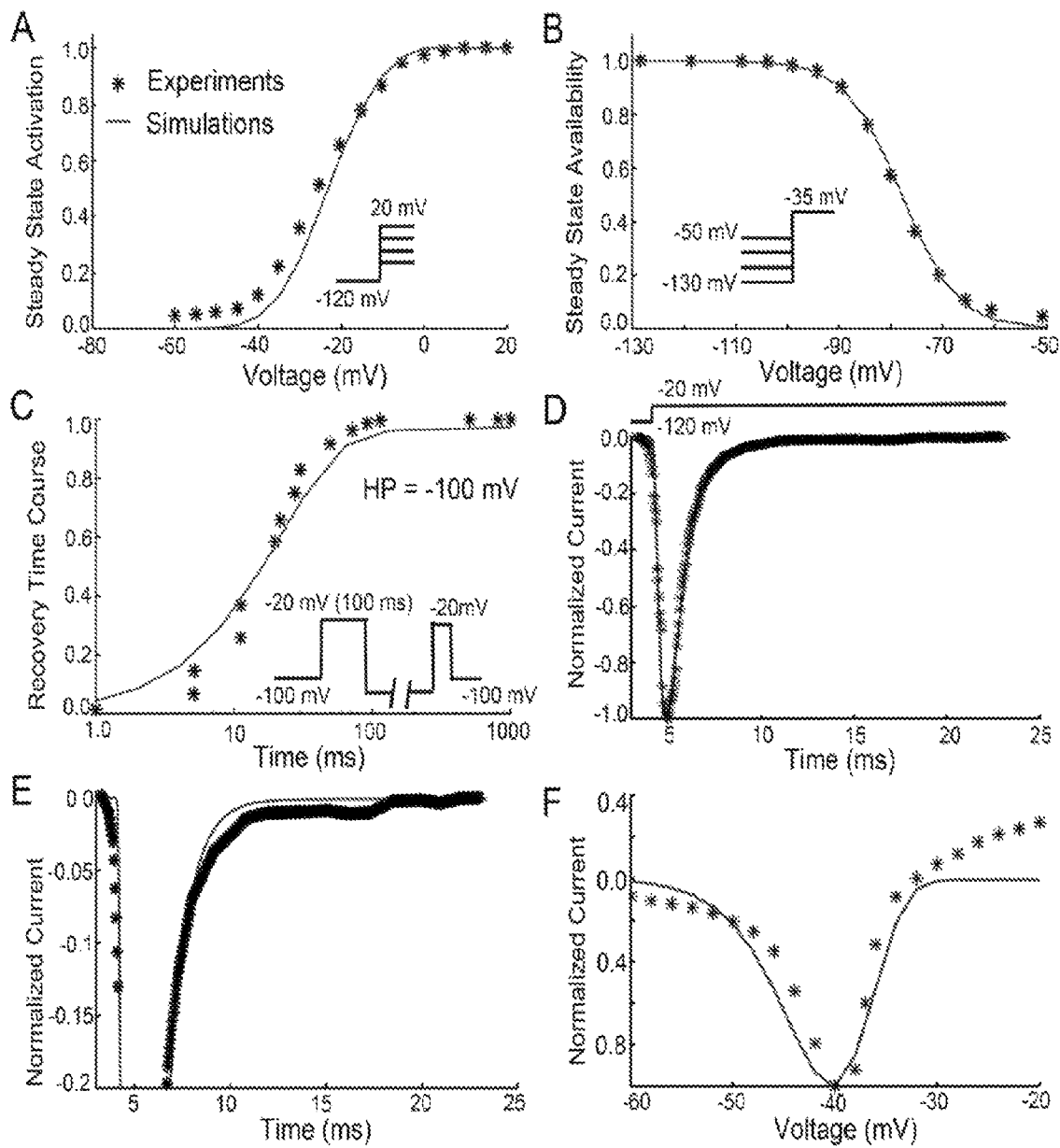
FIGS. 13A-13F show experimental (symbols) and model optimized (lines) drug free $Na^+$ current parameters in a rabbit ventricular myocyte.

Applicants next modeled the rabbit ventricular Na$^+$ current by re-optimizing the model parameters described in Moreno et al. (Moreno, J. D. et al. (2011) Sci Transl Med. 3(98):98ra83) to reproduce the time-course and kinetics of $I_{Na}$ that were experimentally recorded in rabbit ventricular myocytes patch clamping experiments. FIGS. 13A-13F show the adjusted, post-optimized, model-generated $I_{Na}$ (blue lines) superimposed on experimental records (black symbols). FIG. 13A shows the superimposition of model and experimentally generated voltage dependent activation curves. FIG. 13B shows the steady-state Na$^+$ channel availability (inactivation) relationship. FIG. 13C shows the recovery time course of current (or reactivation) at −100 mV generated using a standard double pulse voltage clamp protocol. The time-course of $I_{Na}$ is depicted in at low and high gain normalized to the peak $I_{Na}$ value (FIGS. 13D and 13E, respectfully). FIG. 13F shows $I_{Na}$ generated in response to a slow depolarizing voltage clamp ramp protocol. All protocols that are illustrated in the figure panels are described in detail in the Methods and Supplemental Methods section. It is interesting to note that rabbit ventricular myocytes exhibit a much smaller late $I_{Na}$ component measured during a square wave voltage depolarizing pulse, when compared to the current measured in guinea pig ventricular myocytes (Yang, P. C. et al. (2015) J Physiol. 593:1429-1442).

Concentration-Dependent Reduction in $I_{NaL}$ and APD by GS-458967

GS-458967 selectively inhibits endogenous $I_{NaL}$ and causes concentration-dependent shortening of APD in ventricular myocytes (Belardinelli, L. et al. (2013) J Pharmacol Exp Ther. 344:23-32; Sicouri, S. et al. (2013) Heart Rhythm 10:1036-1043; Song, Y. et al. (2012) Heart Rhythm Society 9:1909). Two independent experimental data sets from rabbit ventricular myocytes have been used as the basis for the model optimization to simulate the effects of GS-458967 on experimental data for rabbit $I_{NaL}$ during the AP and on APD. The blue asterisks indicate previously published experimental data set #1 (Belardinelli, L. et al. (2013) J Pharmacol Exp Ther. 344:23-32), and red circles are from Applicants' new (unpublished) experimental data set #2. Applicants incorporated their calibrated rabbit ventricular $Na^+$ channel model from FIGS. 13A-13F into the Soltis-Saucerman rabbit ventricular model of the cardiac ventricular action potential and then optimized the drug model parameters to fall within the independent experimental data sets. The results are shown in FIGS. 14A-14B. FIG. 14A shows the simulated effects of a 10-fold changes in concentrations of GS-458967 and selective $I_{NaL}$ block during the rabbit AP. The model accurately predicts the marked concentration-dependent shortening of the APD observed experimentally. Note that reduction of the large transient endogenous $I_{Napeak}$ in the optimized model simulations is minimal even after a very high concentration of GS-458967 (10 µM). This was also observed experimentally in rabbit ventricular myocytes (compare blue open square to black open triangle). The selectivity for block of $I_{NaL}$ compared to $I_{Napeak}$ was a key goal in the drug discovery process that resulted in selection of GS-458967 as a potential candidate compound.

FIG. 14B shows a model prediction of the concentration dependence of the simulated effects of GS-458967 on the APDs in a rabbit ventricular myocyte population. These data were tracked in a population of 100 virtual myocytes generated by randomly varying the amplitude of maximal conductances for $I_{Na}$, $I_{CaL}$, $I_{Ks}$, $I_{Kr}$, $I^{K1}$, $I_{to}$, $I_{NaK}$, $I_{NaCa}$ (to within (+/−) 10% of their nominal values in the rabbit ventricular myocyte model) prior to the upstroke of each action potential. $APD_{90}$ was calculated for each AP at a steady pacing frequency of 1 Hz. Note that the simulated $APD_{90}$ variability falls well within the range of experimentally recorded $APD_{90}$ from both data set #1 (blue asterisks) and data #2 (red circles).

Figure 15B:
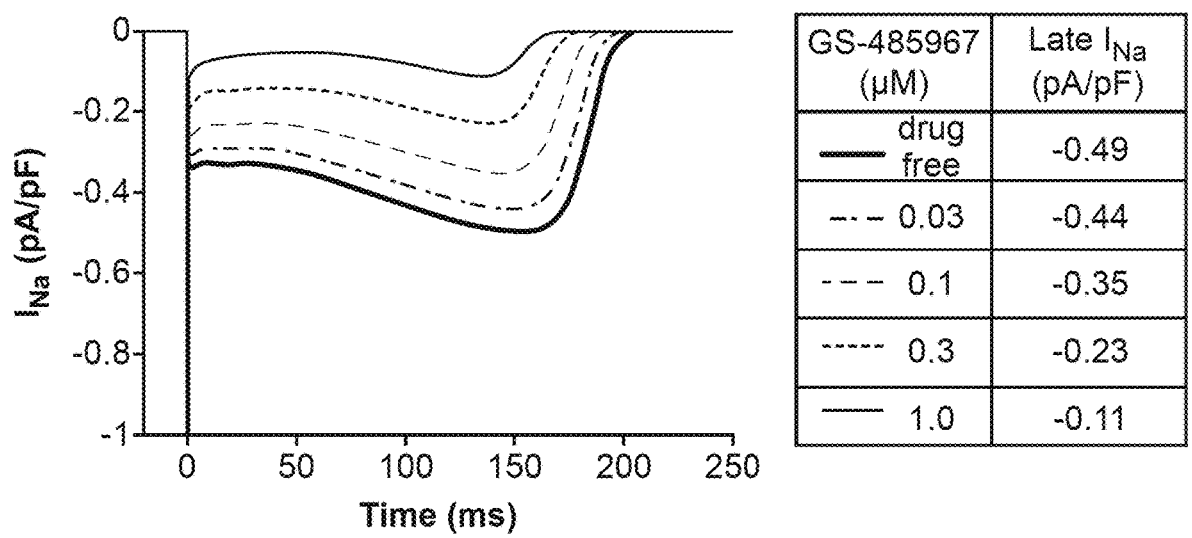

FIG. 15A shows the simulated time-course of the rabbit AP waveform. These results reveal the concentration-dependent effects of GS-458967 on rabbit ventricular repolarization. FIG. 15B shows the corresponding dose-dependent effects of GS-458967 on the time-course of the endogenous $I_{NaL}$. It is notable that although $I_{NaL}$ in the rabbit ventricular myocyte is very small in response to voltage clamp square wave depolarizing pulses (FIG. 13E), there is a detectable $I_{NaL}$ throughout the plateau of the AP. Note also that $I_{NaL}$ slowly increases during repolarization as expected from the progressively increasing electrochemical driving force.

GS-458967 Normalizes Drug Induced APD Prolongation

Figure 16:
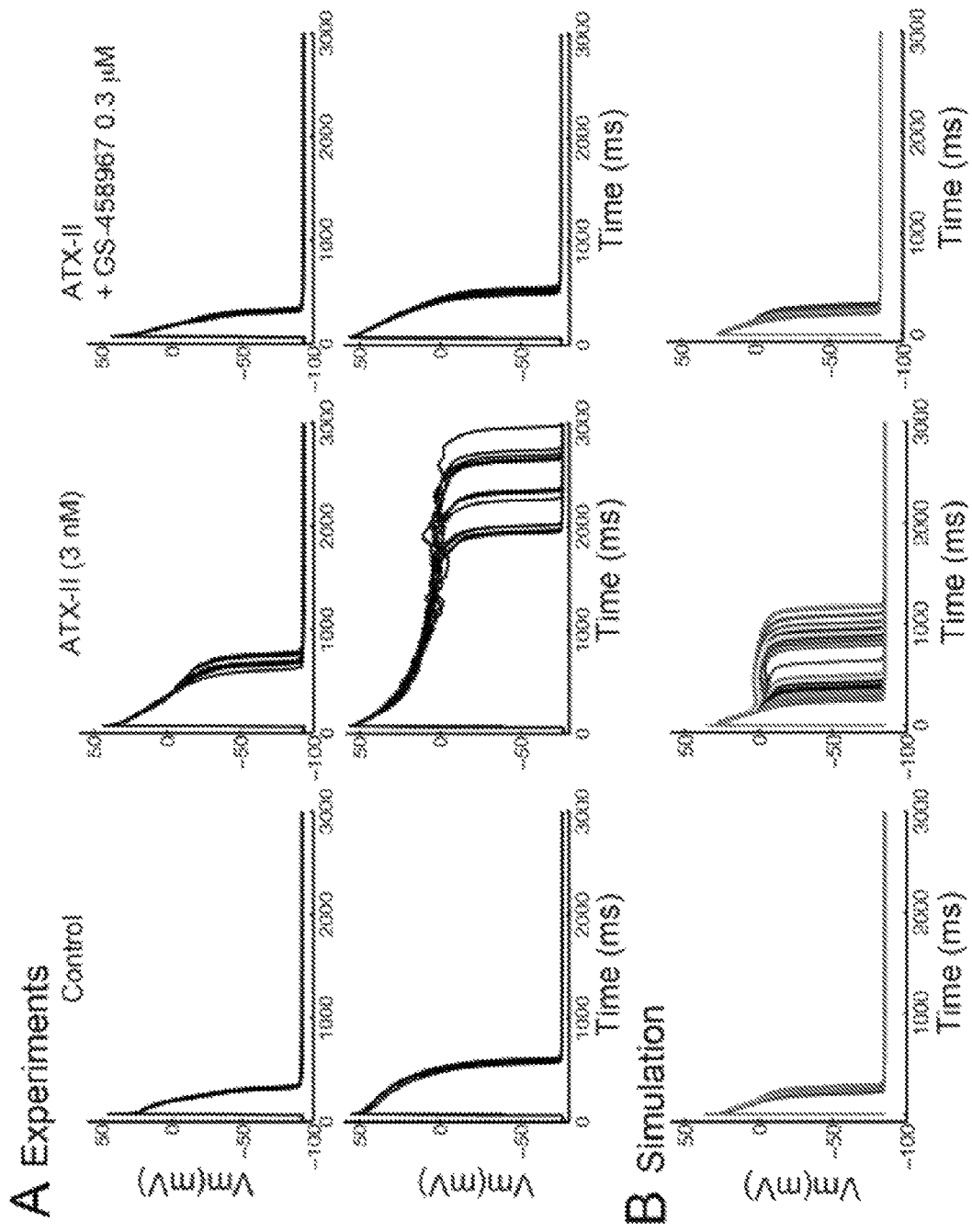
FIGS. 16A-16B show that GS-458967 can effectively attenuate APD prolongation by ATX-II in rabbit ventricular myocytes.

Applicants' experimental data show that GS-458967 is very effective in reversing APD prolongation by agents/toxins that selectively enhance $I_{NaL}$ (e.g., ATX-II). Applicants used these data as a basis for comparisons for the computational model predictions. Specifically, Applicants tested whether the selected drug concentrations would have similar effects when experimental data was compared to the model predictions, thereby acting as a model validation test and providing a basis for using the model for predictive testing. In FIG. 16A, experimental data from two different data sets from rabbit ventricular myocytes are shown in drug free conditions (left), and also following the application of 3 nM ATX-II (middle) as well as with combined 3 nM ATX-II with 0.3 µM GS-458967 application (right). FIG. 16B shows the predicted effects of these same conditions in the virtual rabbit ventricular myocyte population constructed by randomly vary the amplitude of maximal conductances for $I_{Na}$, $I_{CaL}$, $I_{Ks}$, $I_{Kr}$, $I^{K1}$, $I_{to}$, $I_{NaK}$, $I_{NaCa}$ to within (+/−) 10% of their nominal values in the rabbit ventricular myocyte model at a steady pacing frequency of 0.2 Hz with drug free (left), simulated effect of ATX-II (middle) and combined application of GS-458967 0.3 µM with ATX-II (right). This pattern of results clearly shows the same low concentration of GS-458967 is predicted to normalize the potent effect of ATX-II to prolong APD in the experiment and simulation (Table 2).

Having established that a reduction of $I_{NaL}$ (by GS-458967) can be protective against APD prolongation during exposure to ATX-II, Applicants focused on the effect of GS-458967 to normalize QT interval prolongation and reduce spatial dispersion of repolarization following application of ATX-II. FIGS. 17A-17C show membrane potential space-time plots and simulated electrograms (lower) computed using a one-dimensional 165-rabbit ventricular myocyte transmural cardiac strand preparation. FIG. 17A shows the effect of application of ATX-II alone during a short-long-short (S1-S2-S1) pacing protocol. Notice that ATX II causes high amplitude T-waves on the computed electrograms following application of the S2. This is an indication of spatial APD dispersion. In FIG. 17B, the effects of 0.03 µM GS-458967 both reduces QT interval prolongation and diminishes spatial APD dispersion as indicated by the marked reduction in T-wave amplitude. FIG. 17C shows that an increase in GS-458967 concentration to 0.1 µM further reduced QT interval prolongation. The higher concentration of GS-458967 also reversed the repolarization gradient. This is illustrated by inversion of the T-wave. This effect is a result of repolarization of the endocardial myocytes before the epicardial myocytes. This is due to the larger effect of block of $I_{NaL}$ on the background of smaller repolarizing currents intrinsic to the endocardial cells.

Reduction of $I_{NaL}$ by GS-458967 Reduces all Proarrhythmia-Linked Parameters in the TRIaD Detailed assessment of the effects of GS-458967 on the proarrhythmia parameters that form the TRIaD, systematic simulations to track each parameter were done (i) in the drug free control conditions, (ii) in the presence of dofetilide and (iii) with a combination of dofetilide and GS-458967. The results are shown in FIGS. 18A-18I.

Figure 18:
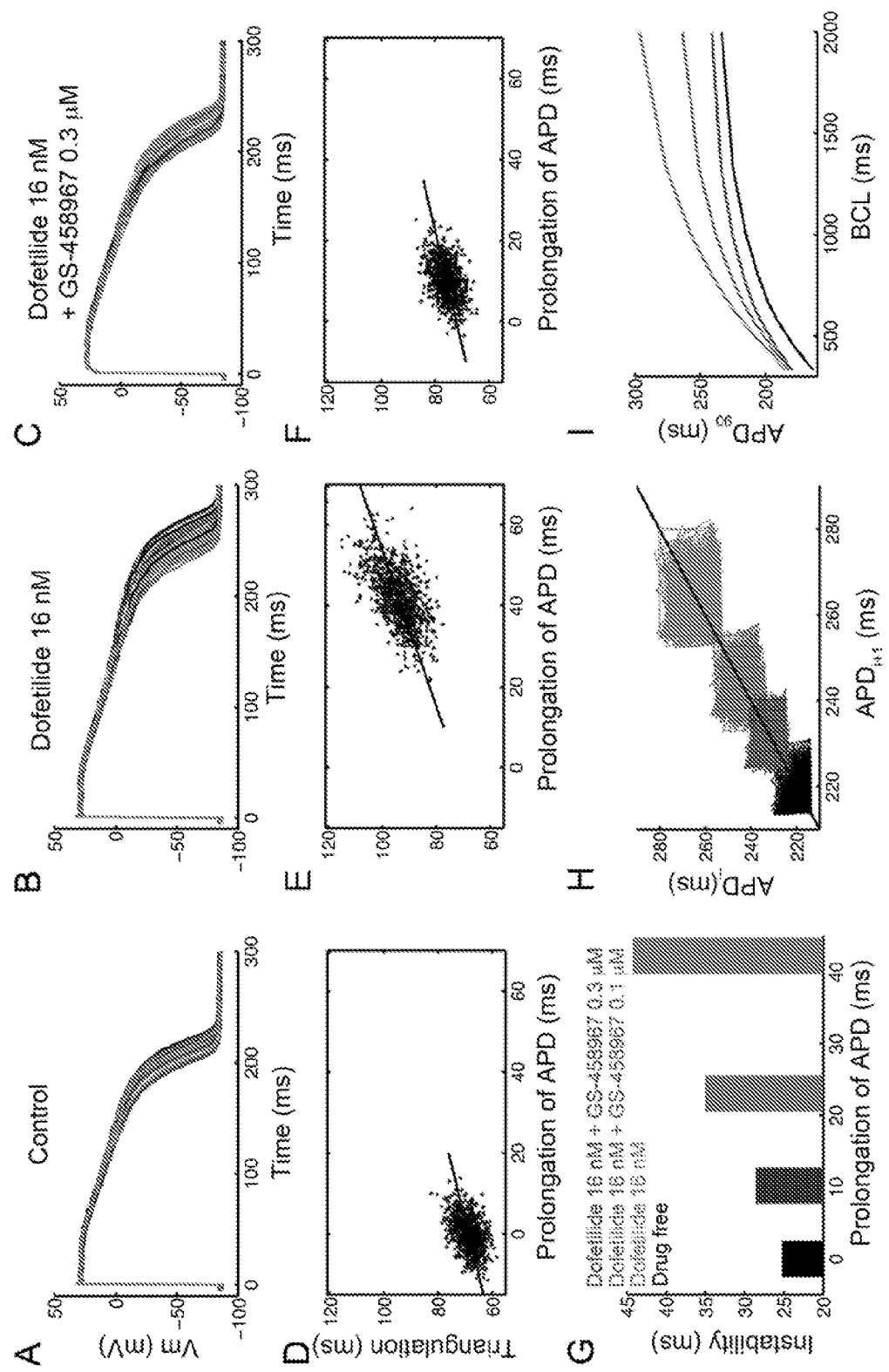
FIGS. 18A-18I show in silico pharmacological results suggesting that GS-458967 can reduce all proarrhythmia-linked parameters set out in the TRIaD approach: Triangulation, reverse use dependence, beat-to-beat instability of action potential duration, as well as temporal and spatial action potential duration dispersion. Predicted temporal action potential duration dispersion of 1000 simulated myocyte action potentials generated after incorporating physiological noise to induce beat-to-beat variability at 1 Hz in (FIG. 18A) the drug-free control case, (FIG. 18B) effects of simulated application of the $I_{Kr}$ blocker Dofetilide (16 nM) and (FIG. 18C) predicted effects of 0.3 µM GS-458967 with Dofetilide 16 nM. Action potential triangulation as a function of APD prolongation for individual myocytes for (FIG. 18D) control (slope=0.37), (FIG. 18E) Dofetilide 16 nM (slope=0.52) and (FIG. 18F) Dofetilide 16 nM+GS-458967 0.3 µM (slope=0.35).

The effects of GS-458967 to improve temporal action potential duration dispersion were assessed first. Applicants conducted a "computational experiment" using a myocyte sample consisting of 1000 action potentials generated after incorporating physiological noise (Sato, D. et al. (2013) PLoS One 8:e85365; Tanskanen, A. J. et al. (2007) Math Biosci. 208:125-146; Sato, D. et al. (2006) Circ Res. 99:520-527). This produces quite pronounced beat-to-beat variability at 1 Hz pacing rate as shown in FIG. 18A the drug-free control case (mean=214.76 ms, standard deviation=4.17 ms), (FIG. 18B) following simulated application of the $I_{Kr}$ blocker dofetilide (16 nM) (mean=256.27 ms, standard deviation=6.89 ms) and (FIG. 18C) predicted effects of 0.3 µM GS-458967 with dofetilide 16 nM (mean=236.87 ms, standard deviation=5.24 ms). The noisy current was generated as described in (Tanskanen, A. J. et al. (2007) Math Biosci. 208:125-146) and in the Methods. Following pacing to steady-state at a stimulation frequency of 1 Hz, the physiological noise was applied throughout the duration of the ensuing simulation of 1000 paced beats. The action potentials for each beat during this noise protocol were recorded.

Applicants next predicted the extent of action potential triangulation in silico as a function of APD prolongation in the myocyte population as described above for FIGS. 18A-18C. In FIGS. 18A-18I control (slope=0.37) is shown in FIG. 18D. FIG. 18E shows the effect of dofetilide 16 nM (slope=0.52) and in (FIG. 18F) dofetilide 16 nM in combination with GS-458967 0.3 µM (slope=0.35) is shown. Dofetilide increased both the $APD_{90}$ as indicated by the right shift and increase in area of the APD prolongation "cloud" (indicating more APD dispersion). In addition, dofetilide increased the triangulation slope, defined as $APD_{90}-APD_{30}$. When dofetilide was applied in combination with GS-458967, the model predicted a return to baseline as measured by the $APD_{90}$ "cloud" and a reduction in triangulation.

The effect of the drugs on instability of APD (FIG. 18G) was detected and quantified as the difference between the maximum and minimum of 1000 individual cells with physiological noise current as a function of prolongation of APD shown in FIGS. 18A-18C.

The beat-to-beat instability of rabbit ventricular myocyte action potential duration was assessed based on the sensitivity of virtual myocytes to small electrical perturbations before and after the application of drugs. A small inward current (between 0.1 and 0.2 pA/pF for 50 ms) was applied randomly during the AP plateau between 10-210 ms after AP initiation. FIG. 18H are Poincaré plots of sequential APD pairs indicating the beat-to-beat instability for each case. For the control case, shown in black, the mean $APD_{90}$ was 219.17 ms and the standard deviation was 4.75 ms, whereas the max and min $APD_{90}$ was 231.17 ms and 213.49 ms, respectively. The case for dofetilide 16 nM is shown in red with (mean=263.31 ms, standard deviation=7.67 ms, max $APD_{90}$=282.25 ms, min $APD_{90}$=252.37 ms). The case for dofetilide 16 nM in combination with 0.1 µM GS-458967 is shown in green and has $APD_{90}$ values as follows: mean=242.91 ms, standard deviation=6.12, max=257.92 ms, min $APD_{90}$=232.33 ms. In blue is the effect of a higher concentration of GS-458967 (0.3 µM) in combination with 16 nM dofetilide resulting in a mean $APD_{90}$ of 230.41 ms, standard deviation of 4.84, max and min $APD_{90}$=242.76 ms and 222.47 ms, respectively.

Lastly, as shown in FIG. 18I, the potential for GS-458967 to decrease reverse use dependence induced by dofetilide was evaluated. The action potential adaptation curves were generated using APD90 values from myocytes at steady-state at the indicated pacing frequencies. When dofetilide (red) was applied, there was a clear steepening of the APD adaptation curve compared to the baseline drug-free case (black). GS-458967 at 0.1 µM (green) flattened the curve, and the application of the higher dose of 0.3 µM of GS-458967 (blue) had a marked effect caused mainly by reducing the slow rate dependent APD prolongation.

Figure 19A:
FIGS. 19A-19E show that GS-458967 can prevent spiral wave reentry in the setting of acquired Long-QT Syndrome. A two-dimensional simulated heterogeneous anisotropic rabbit ventricular tissue was activated using a paired stimulus (S1-S2) protocol.
Figure 19B:
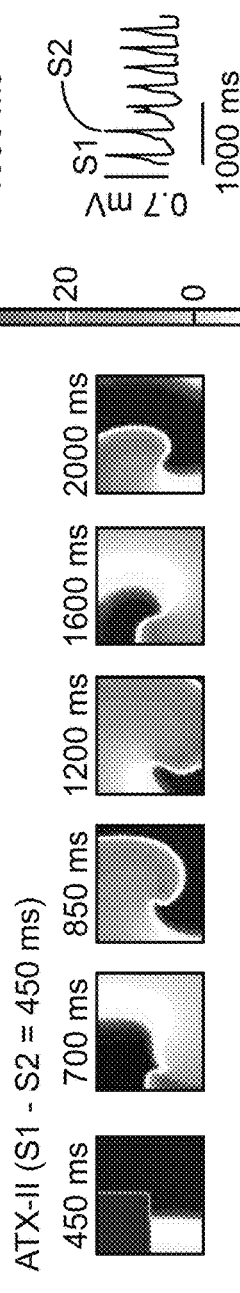
Figure 19C:
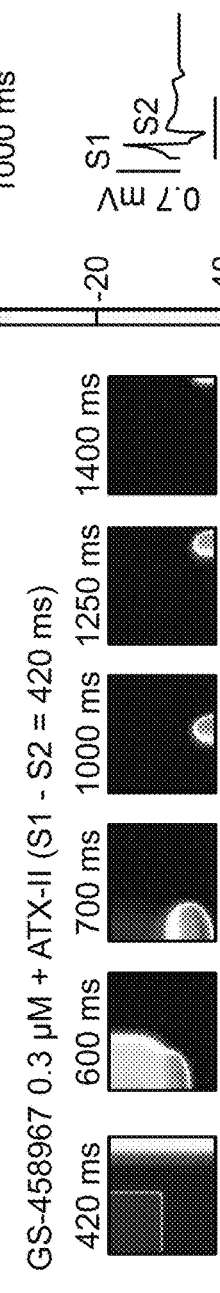
Figure 19D:
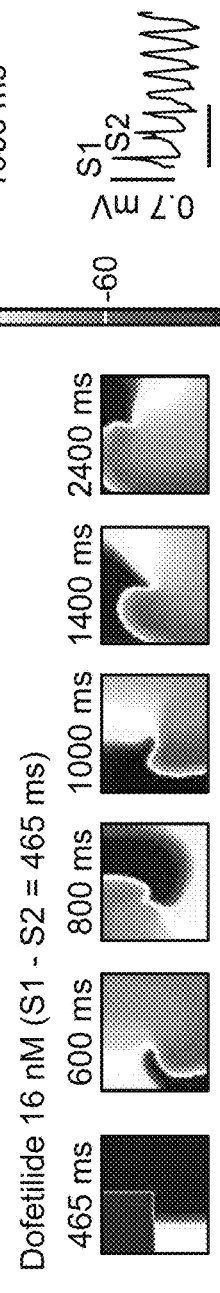
Figure 19E:
Figure 20:
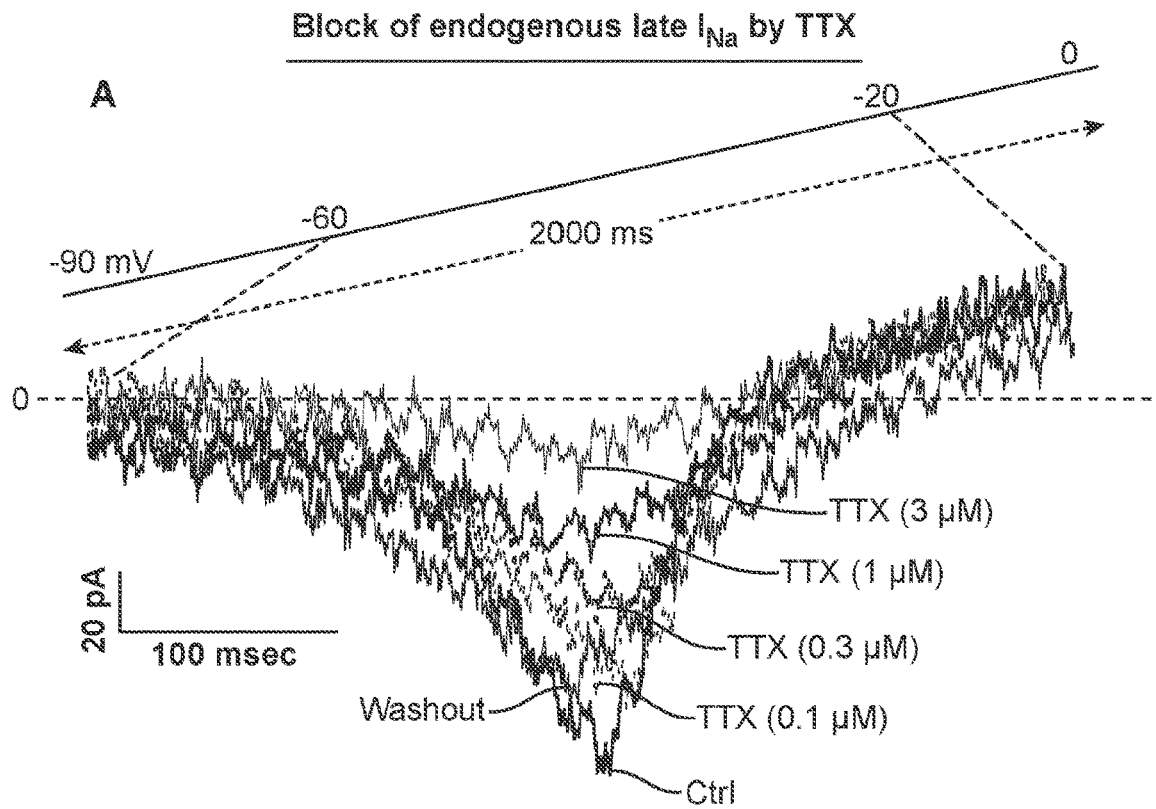
FIG. 20 shows representative endogenous late Na$^+$ current (late $I_{Na}$) tracings activated by ramp pulses in the absence (control; Ctrl) and presence of increasing concentrations of TTX (0.1, 0.3, 1, and 3 µM) and following washout (wash).
Figure 21:
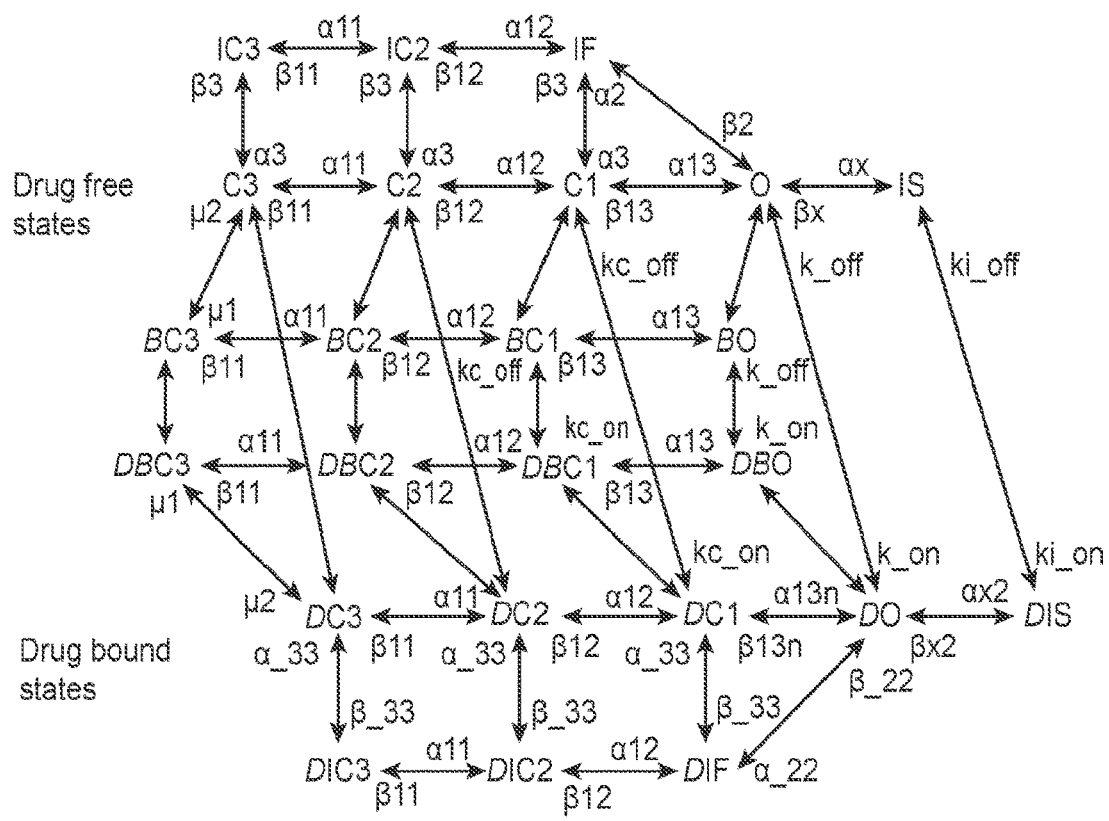
FIG. 21 shows the Markovian model representation of the drug free Na channel and the drug bound Na channel and the transitions between these two forms. The drug free channel has 12 distinct states (in black) including bursting states, denoted by a B. Any of the channel states in the model can exist as a drug-bound conformation (states denoted by a D). Green arrows indicate entry or egress from drug-bound states. Transition arrows were omitted from IC3→DIC3, IC2→DIC2, IF→DIF for clarity (blue boxes).
Figure 22:
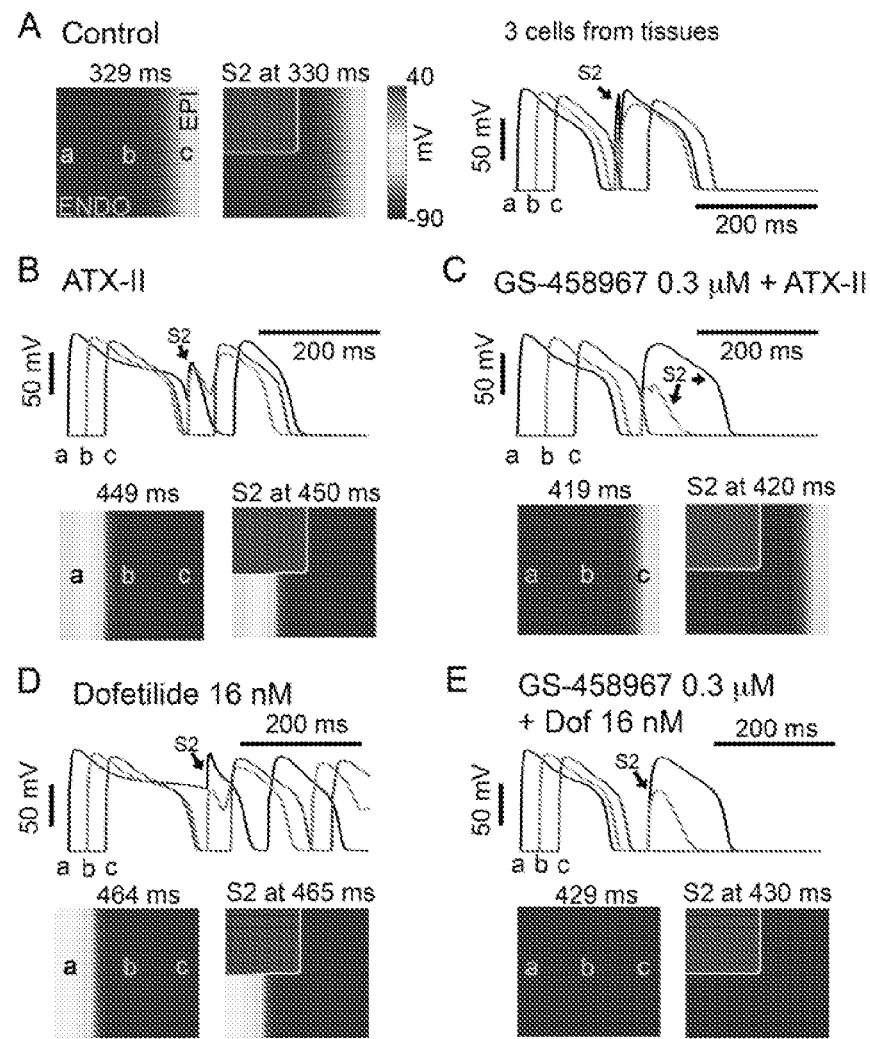

Arrhythmia can be considered a fundamental emergent spatial phenomenon. Accordingly, simulations to determine whether GS-458967 could prevent reentrant arrhythmias in the setting of an in silico acquired Long-QT Syndrome were performed. In this study a two-dimensional heterogeneous anisotropic rabbit ventricular in silico tissue composed of (5 cm×5 cm) myocytes was employed (FIGS. 19A-19E). Simulations were conducted using a paired stimulus (S1-S2) protocol where the S2 was applied (following 200 paced beats initiated along the left endocardial edge of the tissue) following the preceding S1 in the computed vulnerable window for reentry. Time snapshots are shown on the left for phase maps (Bray, M. A. et al. (2002) Phys Rev E Stat Nonlin Soft Matter Phys. 65:051902). These maps were constructed following the last planar wave (S1) (FIG. 19A) and throughout termination of the most persistent wave after S2 (FIG. 19E). Membrane voltages are indicated by the color gradient. The corresponding pseudo-ECGs are shown in the right panels. FIG. 19A illustrates the control or drug-free baseline condition. In the absence of any drug, there was no persistent reentry. In FIG. 19B the effect of ATX-II is shown, which promoted a persistent reentrant arrhythmia. FIG. 19C shows that ATX-II combined with 0.3 µM GS-458967 prevented the persistent reentry observed with ATX-II alone. When 16 nM dofetilide was applied (FIG. 19D), persistent reentry was induced, but this was prevented by co-treatment with 0.3 µM GS-458967 (FIG. 19E).

DISCUSSION

Recently, new chemical entities (NCEs) have been developed that specifically target the slowly inactivating component of the cardiac Na current, that is, the late Na current ($I_{NaL}$). Such compounds are now being evaluated as therapeutics in inherited and acquired cardiac diseases (Bennett, P. B. et al. (1995) Nature 376:683-685; Wang, Q. et al. (1995) Cell 80:805-811; Maltsev, V. A. et al. (1998) Circulation 98:2545-2552; Maltsev, V. A. et al. (2006) Cardiovasc Res. 69:116-127; Song, Y. et al. (2006) J Pharmacol Exp Ther. 318:214-222; Sossalla, S. et al. (2010) J Am Coll Cardiol. 55:2330-2342; Hund, T. J. et al. (2008) J Mol Cell Cardiol. 45:420-428. One promising preclinical candidate first described in 2013 is GS-458967. GS-458967 specifically and potently inhibits $I_{NaL}$ ($IC_{50}$ for $I_{NaL}$=130 nM) (Belardinelli, L. et al. (2013) J Pharmacol Exp Ther. 344: 23-32).

In order to begin to understand the potential for selective inhibition of $I_{NaL}$ to mitigate arrhythmia risk associated with acquired Long-QT Syndrome, Applicants have utilized experimental data describing the kinetics of the cardiac $Na^+$ channel in rabbit ventricular cells models in order to modify the Soltis-Saucerman model of the rabbit ventricular myocyte action potential model. Applicants then modeled the interaction of GS-458967 with the rabbit $Na^+$ channel and the concentration-dependent effect of this novel preclinical compound to affect electrophysiological parameters in rabbit cells. Results of the simulations were in good agreement with experimental findings with both approaches showing potent concentration-dependent reduction in $I_{NaL}$ and action potential duration. In these experiments and model simulations, GS-458967 did not affect myocyte excitability or conduction velocity in ventricular tissues, respectively (Belardinelli, L. et al. (2013) J Pharmacol Exp Ther. 344:23-32). Although $I_{NaL}$ is small compared to peak ($I_{Napeak}$) (~1-3%), the magnitude of this current is similar to that of other currents that are active during the action potential plateau phase, including $I_{Kr}$, the rapidly activated component of the delayed rectifier $K^+$ current.

Abnormal cardiac electrophysiological activity is a common effect caused by block of hERG, the alpha subunit of $I_{Kr}$. Block of hERG leads to prolongation of the QT interval on the ECG, a phase of the cardiac cycle that corresponds to ventricular cell repolarization. Prolongation of the QT interval and proarrhythmia have been so strongly associated that the QT interval has become widely used as a surrogate marker for arrhythmia risk. Since 2005, the regulatory process for clinical drug candidates includes a dedicated clinical study in healthy volunteers, the so-called "Thorough QT Study". A drug that causes greater than 5 ms QT prolongation above normal in healthy humans triggers a "regulatory concern". In the present work, Applicants asked the question, "Can we mitigate the risk of QT prolonging proarrhythmic drugs with targeted adjunctive therapy by the $I_{NaL}$ inhibitor GS-458967". In the current study, Applicants undertook a combined modeling and experimental approach in an attempt to improve the rationale for predictive Cardiac Safety Pharmacology.

One way to prevent acquired Long-QT based arrhythmias is to screen and eliminate compounds that fail the Thorough QT test. An alternative solution is to identify derivative analogs of promising drugs that can retain therapeutic efficacy with reduced hERG block (Windisch, A. et al. (2011) Br J Pharmacol. 162:1542-1552; Sasmal, P. K. et al. (2011) MedChemComm. 2:385-389; Zhang, S. et al. (1999) Circ Res. 84:989-998; Durdagi, S. et al. (2014) BMC Pharmacology & Toxicology 15:14). Another approach is to capitalize on the well-known fact that most effective antiarrhythmic drugs are "dirty"—they exhibit multiple channel effects (Haigney, M. C. (2014) Clin Pharmacol Ther. 96:534-536). By co-administering or co-formulating a specific $I_{NaL}$ blocker in the setting of unintended hERG block, it may be possible to create a situation of "virtuous promiscuity", where the two drug effects counter each and thus reduced or eliminate electrophysiological abnormalities, including prolongation of the action potential duration (APD) and lengthening of the QT interval (Haigney, M. C. (2014) Clin Pharmacol Ther. 96:534-536; Wang, L. et al. (1993) J Pharmacol Exp Ther. 264:1056-1062).

There is substantial precedent for the empirical mixing and matching of drugs to mitigate risk or reduce side effects (Van Opstal, J. M. et al. (2001) Eur J Pharmacol. 412:67-76; Johannesen, L. et al. (2014) Clin Pharmacol Ther. 96:549-558). Moreover, it is notable that the most successful on-market antiarrhythmic drugs exhibit multiple off-target or "dirty" effects. Examples include amiodarone, dronedarone and verapamil (Roden, D. M. (2004) N Engl J Med 350: 1013-1022; Hondeghem, L. M. (2008) Heart Rhythm 5:1210-1212). Here, Applicants have expanded this concept in an attempt to develop a way to inform and predict the therapeutic benefit of mixing drugs to mitigate cardiotoxic side effects. Applicants have focused on the common example of unintended hERG based cardiotoxicity. Applicants' model predicts substantial reduction of all acquired Long-QT proarrhythmia-linked parameters through adjunctive administration using GS-458967 to specifically inhibit $I_{NaL}$ and "cancel" or diminish the effect of hERG block.

Applicants tested the potential for targeted inhibition of $I_{NaL}$ by GS-458967 to improve cardiac safety in the setting of acquired long-QT Syndrome induced by dofetilide. Dofetilide is a prototype of the proarrhythmic class—associated with hERG block, QT prolongation and TdP (Van Opstal, J. M. et al. (2001) Eur J Pharmacol. 412:67-76). Applicants recently developed a detailed kinetically based model of the hERG blocker dofetilide by extending the consensus five-state Markov chain model that includes three closed states ($C_3$, $C_2$ and $C_1$), a conducting open state and (O) an inactivation state (I) (Romero, L. et al. (2014) J Mol Cell Cardiol. 72:126-137; Fink, M. et al. (2008) Prog Biophys Mol Biol. 96:357-376; Clancy, C. E. et al. (2001) Cardiovasc Res. 50:301-313; Bett, G. C. et al. (2011) Biophys J. 101:631-642). This expanded $I_{Kr}$ model that includes dofetilide interactions was incorporated into the Soltis-Saucermann rabbit ventricular action potential (AP) models (Soltis, A. R. et al. (2010) Biophys J. 99:2038-2047). Dofetilide has a distinct structure activity relationship that underlies drug-channel interaction kinetics that promotes the TRIaD: Triangulation, reverse use dependence, beat-to-beat instability of action potential duration, temporal and spatial action potential duration dispersion. Thus, Applicants simulated the effects of dofetilide as a "positive control" against which Applicants could systematically predict effects of GS-458967 on each parameter of the TRIaD linked proarrhythmia.

In a previous study (Yang, P. C. et al. (2015) J Physiol. 593:1429-1442), Applicants carried out a simulation showing the effects of GS-458967 application on Na loading at different frequencies. Applicants also showed the effect of the nominal changes to intracellular Na concentration on the amplitudes of the NCX and NaK currents during the action potential. These effects were minimal. Applicants' results are not surprising. Previous studies have suggested that even pathological increases in late $I_{Na}$ are not sufficient to account for substantial Na loading and that other mechanisms must also be contributing to Na loading during pathological states like heart failure (Wagner, S. et al. (2011) Circ Res. 108: 555-565; Grandi, E. et al. (2007) Biophys J. 93:3835-3847; Moreno, J. D. et al. (2013) Circ Res. 113:e50-e61).

There is a critical need to identify a more efficient and better approach for preclinical drug screening that is both specific and sensitive, and that also identifies actual "proarrhythmia", rather than surrogate markers (Hondeghem, L. M. (2006) J. Cardiovasc. Electrophysiol. 17:337-340). Here, Applicants applied a multiscale modeling approach based on experimentally determined drug-channel interactions and kinetics intended to predict drug safety or electro-toxicity in the heart. Electrophysiological measurements were used to inform the kinetic parameters for functional scale Markov models of drug interactions with cardiac ion channels. Drug-channel models were then integrated into virtual cardiac cell and tissue level models to predict emergent drug effects to promote specific elements of the TRIaD, comprising the proarrhythmia markers that emerge at cell and tissue levels. Experiments were then used to test and validate the predictions of the model. Such a combined analysis could be used along with the proposed early QT assessment (Darpo, B. et al. (2014) Ann Noninvasive Electrocardiol. 19:70-81) in order to replace the so-called thorough QT study.

the disclosure suggests that the in silico TRIaD analysis performed here may be useful to finally remove some of the "art" that has been implicit in defining experimental conditions and ensuing tests that have been used to provoke arrhythmic responses (Stockbridge, N. et al. (2004) J Electrocardiol. 37:40-41). Not only does the systematic application of the TRIaD tests allow the tracking of numerous proarrhythmic parameters, this approach also accounted for cell-to-cell variability and physiological noise that likely contribute to the random and rare amalgam of conditions that must be concomitantly present to allow a rare arrhythmia event to occur. The in silico screen presented in this study can be readily expanded with low cost and high efficiency to comprehensively examine any number of arrhythmia provoking conditions or additional electrophysiological parameters for preclinical drug testing.

Supplemental Material

Optimization Procedure for Rabbit Sodium Channel

A computational Markov model of the drug-free and GS-458967 drug channel interaction was formulated via numerical optimization from experimentally derived rate constants as previously described (Moreno, J. D. et al. (2013) Sci Transl Med. 3(98):98ra83; Moreno, J. D. et al. (2013) Circ Res. 113(7):50-61). Five pacing protocols were optimized: steady state availability at test potentials from −130 mV to −50 mV followed by depolarization to −35 mV, steady state activation (the holding potential was −120 mV and the testing potentials ranged from −60 to 20 mV in 5-mV steps) (Lee, H. C. et al. (1993) J Clin Invest. 91(2):693-701), recovery from inactivation at a holding potential of −100 mV (Lee, H. C. et al. (1993) J Clin Invest. 91(2):693-701), $I_{Na}$ time course current (Belardinelli, L. et al. (2013) J Pharmacol Exp Ther. 344(1):23-32), and ramp pulses from Gilead Sciences, Inc. (Please see Recordings of late $I_{Na}$ and action potentials using whole cell patch-clamp technique).

A cost function for each protocol was defined as the sum of squared differences between experiment and simulation. The total cost function (sum of the individual protocol errors) was then minimized and converged when a tolerance of 0.01 for the change of the cost function and 0.01 for the change in parameters was achieved.

All rate constants were allowed to change during the optimization. Post-optimization and Initial values are shown in Online Tables I and II, respectively.

ONLINE TABLE I

Post-optimization values.
Transition rates (ms$^{-1}$)
Drug free WT Na$^+$ channel

| | |
|---|---|
| IC3 →IC2, C3→C2, BC3 →BC2 | α11 = 13.668176/(0.1157*exp(-V/17.0) + 0.0659*exp(-V/150)) |
| IC2→IF, C2→C1, BC2→BC1 | α12 = 13.668176/(0.1157*exp(-V/15.0) + 0.0659*exp(-V/150)) |
| C1→O, BC1→BO | α13 = 13.668176/(0.1157*exp(-V/12.0) + 0.0659*exp(-V/150)) |
| IC2→IC3, C2→C3, BC2→BC3 | β11= 0.424557*exp(-V/20.3) |
| IF→IC2, C1→C2 BC1→BC2 | β12 = 5.071782*exp(-(V − 5)/20.3) |
| O→C1, BO→BC1 | β13 = 2.053124*exp(-(V − 10)/20.3) |
| IC3→C3, IC2→C2, IF→C1 | α3 = 1.07891e−07*exp(-V/6.85714) |
| C3→IC3, C2→IC2, C1→IF | β3 = 0.3035996*exp(V/21.9244) |
| O→IF | α2 = 18.727355*exp(V/47.28666) |
| IF→O | β2 = (α13* α2* α3)/(β13* β3) |
| O→IS | αx = 0.02675*α2 |
| IS→O | βx = 0.018316*α3 |
| C3, C2, C1, O → BC3, BC2, B1, BO | μ1 = 3.86944e−07; |
| BC3, BC2, BC1, BO → C3, C2, C1, O | μ2 = 0.00054755855; |

ONLINE TABLE II

Initial values.
Transition rates (ms$^{-1}$)
Drug free WT Na$^+$ channel

| | |
|---|---|
| IC3 →IC2, C3→C2, BC3 →BC2 | α11 = 12.693784/(0.113848 *exp(-V/17.0) + 0.1011820 *exp(-V/150)) |
| IC2→IF, C2→C1, BC2→BC1 | α12 = 12.693784/(0.113848 *exp(-V/15.0) + 0.1011820 *exp(-V/150)) |
| C1→O, BC1→BO | α13 = 12.693784/(0.113848 *exp(-V/12.0) + 0.1011820 *exp(-V/150)) |
| IC2→IC3, C2→C3, BC2→BC3 | β11 = 0.371233 *exp(-V/20.3) |
| IF→IC2, C1→C2, BC1→BC2 | β12 = 5.38768 *exp(-(V − 5)/20.3) |
| O→C1, BO→BC1 | β13 = 1.73128 *exp(-(V − 10)/20.3) |
| IC3→C3, IC2→C2, IF→C1 | α3 = 1.20541 − 07*exp(-V/6.3300159) |
| C3→IC3, C2→IC2, C1→IF | β3 = 0.473262 *exp(V/26.40821) |
| O→IF | α2 = 16.450126 *exp(V/44.017677) |
| IF→O | β2 = (α13* α2* α3)/(β13* β3) |
| O→IS | αx = 0.0265370*α2 |
| IS→O | βx = 0.01359195*α3 |
| C3, C2, C1, O → BC3, BC2, BC1, BO | μ1 = 3.03926e−07; |
| BC3, BC2, BC1, BO → C3, C2, C1, O | μ2 = 0.000643067; |

Parameter Optimization for Drug-Bound Model

Simulations of GS-458967 dose-dependent effects on late Na current was optimized to fit the experimentally measured late Na$^+$ current with GS-458967 0.03, 0.1, 0.3 and 1 μM. The drug-bound rate constants (αx2, α13n, α_22, β_33, K$_{on}$, K$_{inactive}$, K$_{closed}$) were optimized to fit the experimentally measured late Na$^+$ current with GS-458967 0.03, 0.1, 0.3, 1 μM and 10 μM, and the peak Na+value at 10 μM (FIG. 14A). The optimized rate constants are shown in Online Table IV below. Because GS-458967 is highly non-basic and cannot be protonated at physiological pH, the post-optimization values (αx2, α13n, α_22, β_33, K$_{on}$, K$_{inactive}$, K$_{closed}$) are shown in Online Table III, and initial guesses are shown in Online Table IV.

ONLINE TABLE III

Post-optimization values.
Transition rates (ms$^{-1}$)
GS-458967 drug bound states

| | |
|---|---|
| k$_{on}$ | [D]*Diffusion |
| k$_{off}$ | 0.198550776e−6*Diffusion |
| k$_{inactivated, on}$ | k$_{on}$ |
| k$_{inactivated, off}$ | 0.09134199e−6*Diffusion |
| k$_{closed, on}$ | k$_{on}$ |
| k$_{closed, off}$ | 146.116659e−6*Diffusion |
| DIC3 →DIC2, DC3→DC2, DBC3→DBC2 | α11 |
| | α12 |
| DIC2→DIF, DC2→DC1, DBC2→DBC1 | β11 |
| DIC2→DIC3, DC2→DC3, DBC2→DBC3 | β12 |
| DIF→DIC2, DC1→DC2, DBC1→DBC2 | |
| DC3, DC2, DC1, DO → DBC3, BDC2, DBC1, DBO | μ1 |
| DBC3, DBC2, DBC1, DBO → DC3, DC2, DC1, DO | μ2 |
| DBC1→DBO | α13 |
| DBO→DBC1 | β13 |
| DO→DIS | αx2 = 0.611415679*αx |
| DC1→DO | α13n = 1.23167646e−5*α13 |

ONLINE TABLE III-continued

Post-optimization values.
Transition rates (ms$^{-1}$)
GS-458967 drug bound states

| | |
|---|---|
| DO→DC1 | b13n = (β13*kc_on*α13n*k_off)/(kc_off*α13*k_on) |
| DIS→DO | βx2 = (βx*k_on* αx2*ki_off)/(αx*ki_on*k_off) |
| DO→DIF | α_22 = 309739*α2 |
| DIF→DO | β_22 = (α_33*α13n*α_22)/(β_33*β13n) |
| DC3→DIC3, DC2→DIC2, DC1→DIF | β_33 = 2.15225592616 *β3 |
| DIC3→DC3, DIC2→DC2, DIF→DC1 | α_33 = (ki_off* α3*kc_on* β_33)/(ki_on*kc_off* β3) |
| Diffusion | 14475.16 M$^{-1}$ms$^{-1}$ |

ONLINE TABLE IV

Initial values.
Transition rates (ms$^{-1}$)
GS-458967 drug bound states

| | |
|---|---|
| k$_{on}$ | [D]*Diffusion |
| k$_{off}$ | 0.138368821e-6*Diffusion |
| k$_{inactivated, on}$ | k$_{on}$ |
| k$_{inactivated, off}$ | 0.042582434e-6*Diffusion |
| k$_{closed, on}$ | k$_{on}$ |
| k$_{closed, off}$ | 100.889947e-6*Diffusion |
| DIC3→DIC2, DC3→DC2, DBC3→DBC2 | α11 |
| | α12 |
| DIC2→DIF, DC2→DC1, DBC2→DBC1 | β11 |
| DIC2→DIC3, DC2→DC3, DBC2→DBC3 | β12 |
| DIF→DIC2, DC1→DC2, DBC1→DBC2 | |
| DC3, DC2, DC1, DO → DBC3, BDC2, DBC1, DBO | μ1 |
| DBC3, DBC2, DBC1, DBO → DC3, DC2, DC1, DO | μ2 |
| DBC1→DBO | α13 |
| DBO→DBC1 | β13 |
| DO→DIS | αx2= 1.074968412*αx |
| DC1→DO | α13n = 4.793971034e-5*α13 |
| DO→DC1 | b13n = (β13*kc_on*α13n*k_off)/(kc_off*α13*k_on) |
| DIS→DO | βx2 = (βx*k_on* αx2*ki_off)/(αx*ki_on*k_off) |
| DO→DIF | α_22 = 214808*α2 |
| DIF→DO | β_22 = (α_33*α13n*α_22)/(β_33*β13n) |
| DC3→DIC3, DC2→DIC2, DC1→DIF | β_33 = 2.654373839*β3 |
| DIC3→DC3, DIC2→DC2, DIF→DC1 | α_33 = (ki_off* α3*kc_on* β_33)/(ki_on*kc_off* β3) |
| Diffusion | 22650.95 M$^{-1}$ms$^{-1}$ |

ONLINE TABLE V

Calculated APD$_{90}$ of 3 cells from different locations
in the tissue with a linear decreased in APDs.

| | APD$_{90}$ (ms) | | |
|---|---|---|---|
| Cell site in the tissue | a (black) | b (red) | c (blue) |
| Control | 269 | 240 | 216 |
| ATXII | 548 | 351 | 280 |
| ATXII + GS458967 0.3 μM | 326 | 267 | 237 |
| Dofetilide 16 nM | 536 | 361 | 291 |
| Dofetilide 16 nM + GS458967 0.3 μM | 297 | 257 | 231 |

Figure 23C:
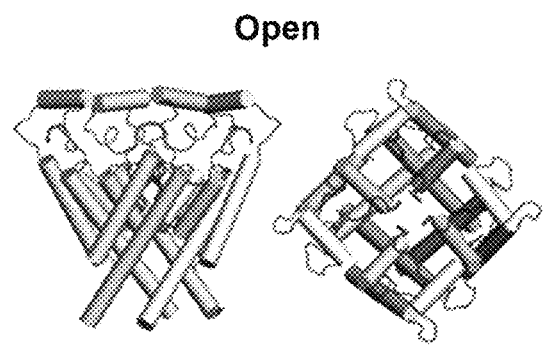
Figure 23C:
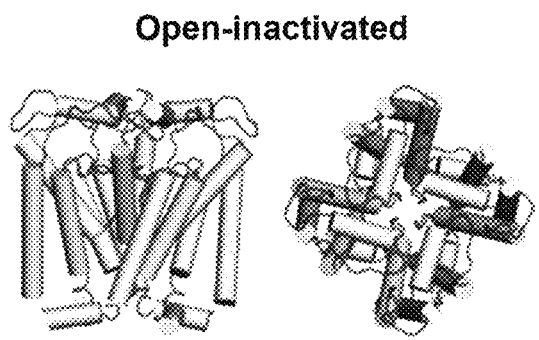
Figure 23C:
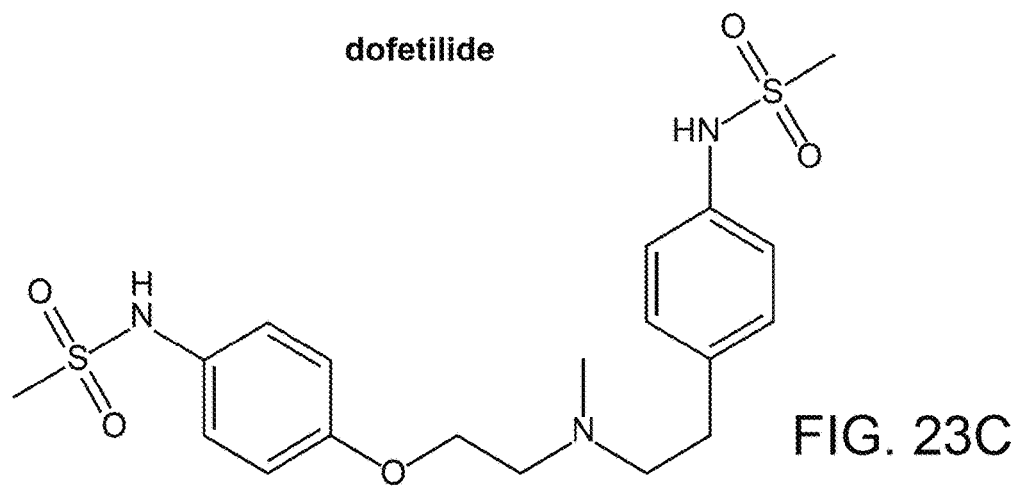
Figure 23D:
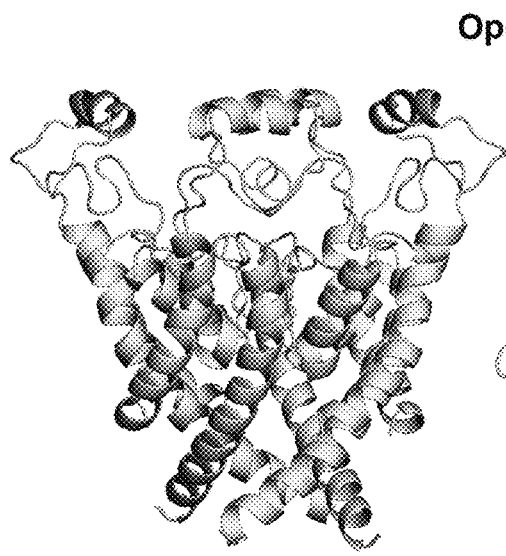
Figure 23D:
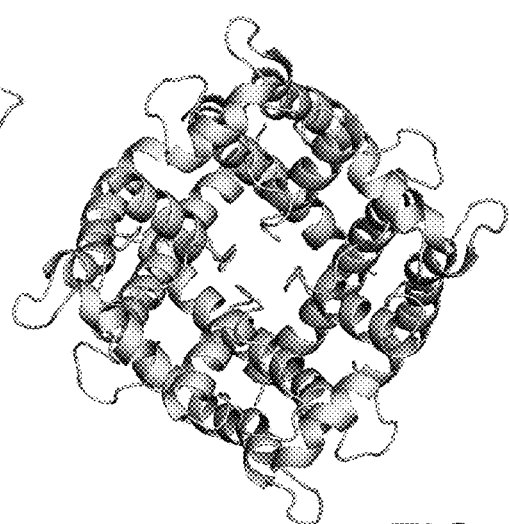
Figure 23E:
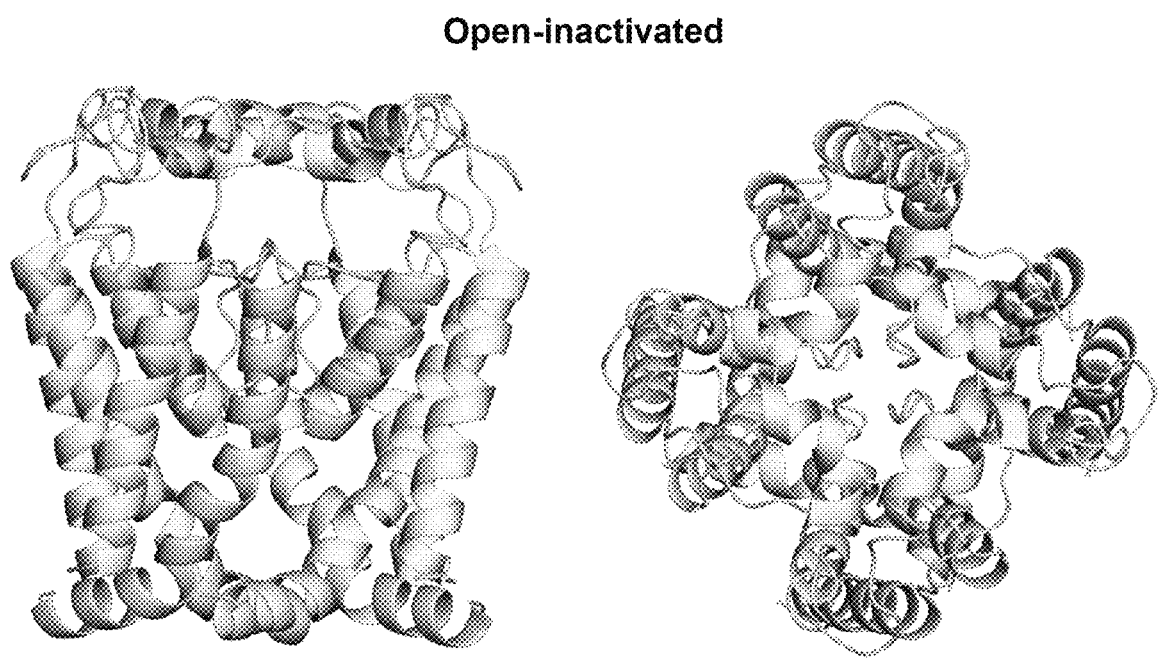
Figure 23F:
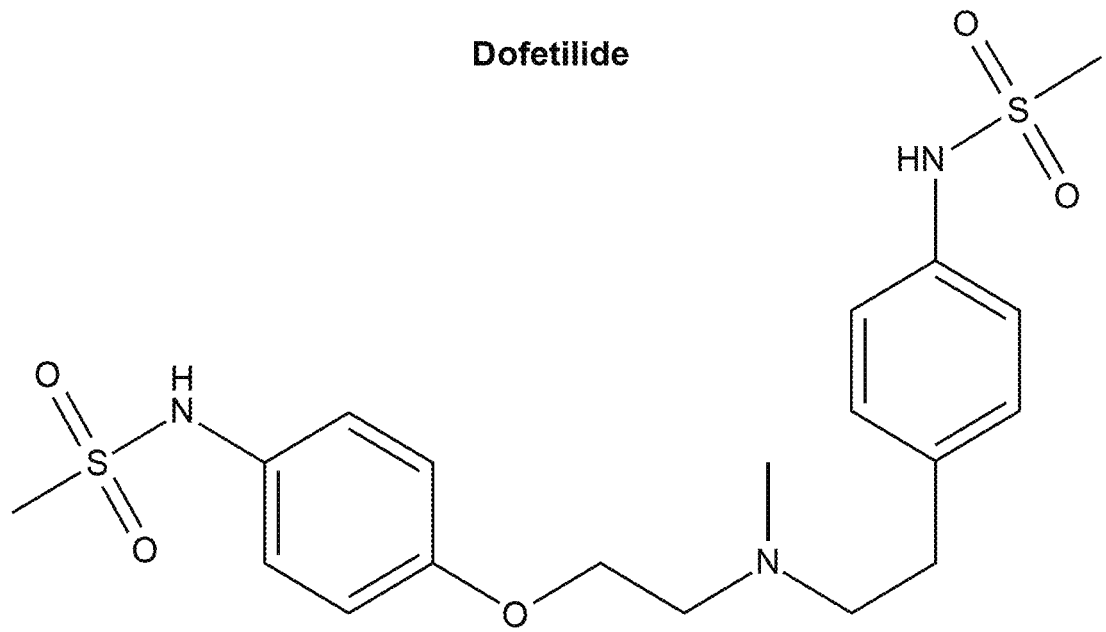

C. Example 3. A Computational Pipeline for Safety Pharmacology: From Atom to Rhythm Results The first steps Applicants took to build a computational pipeline for predictive pharmacology were to compute drug binding energetics from molecular simulations. Applicants then characterized key drug interactions with hERG1 pore-domain models of the open and open-inactivated states. The structural difference between open state and open-inactivated state is schematically illustrated in FIGS. 23A and 23B.

The structure of dofetilide (FIG. 23C) was obtained from the ZINC database of commercially-available chemical compounds (Irwin, J. J. et al. (2012) J. Chem. Inf. Model. 52:1757-1768).

Figure 24:
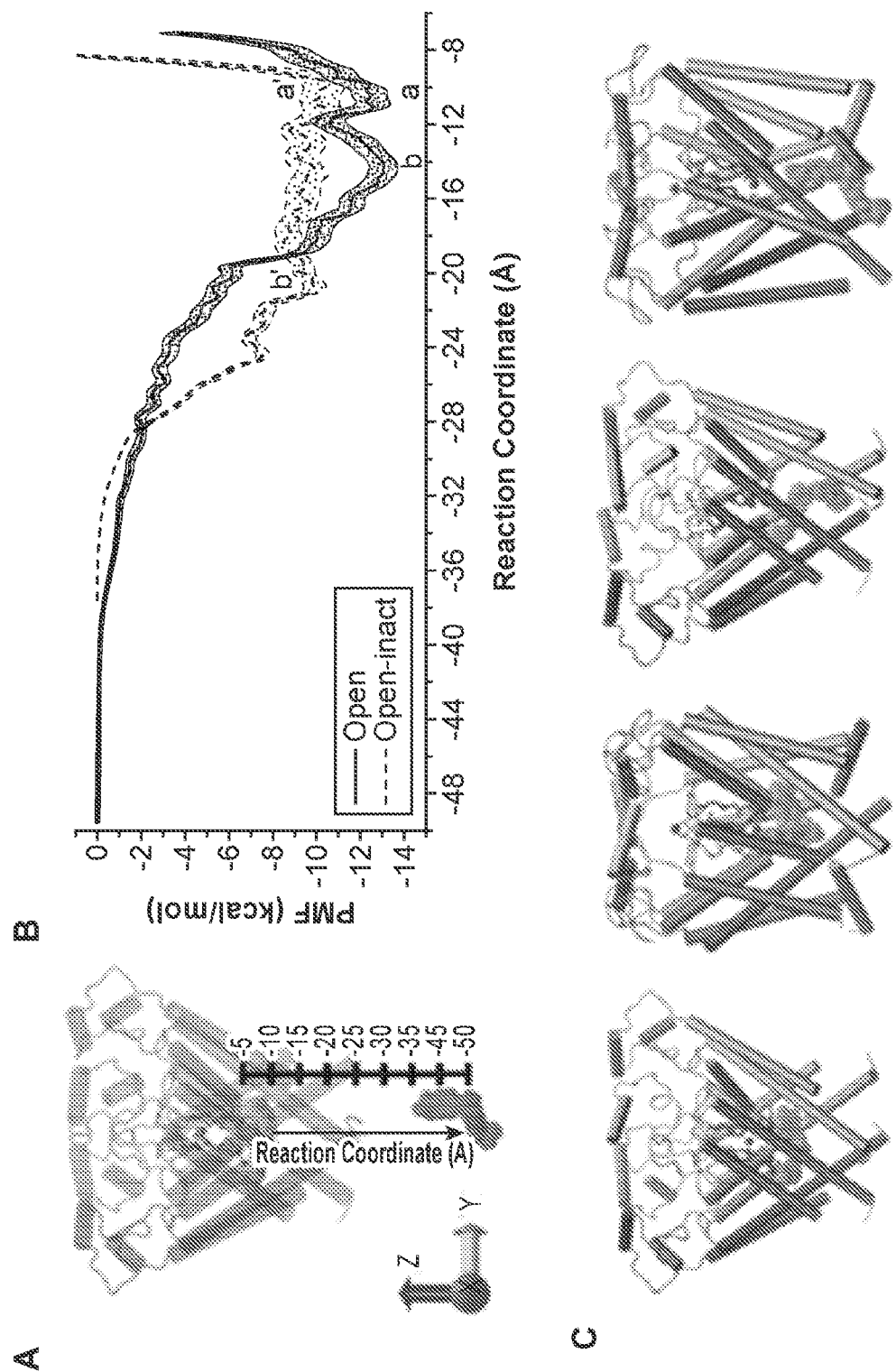
FIGS. 24A-24D show dofetilide binding to hERG1 from atomistic MD simulations.
Figure 24:
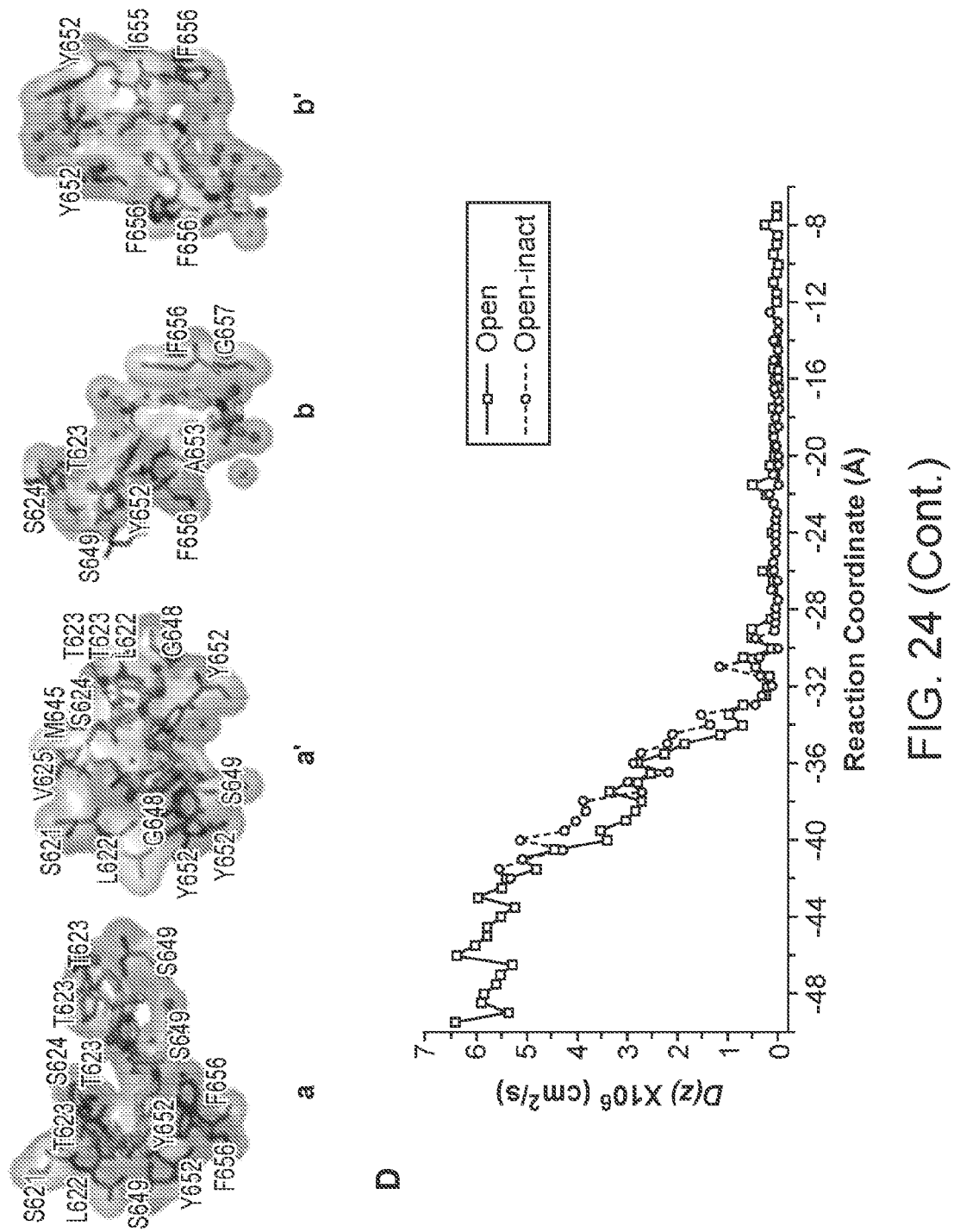

Applicants computed PMFs for dofetilide binding to discrete channel conformational states using the pore axis as the reaction coordinate (FIG. 24A). Both PMFs for open and open-inactivated states display well-pronounced state-dependent properties. As shown in FIG. 24B, the PMF shows two distinct energy wells for the open state hERG1 channel, suggesting that dofetilide has at least two binding sites in the cavity of the channel. These sites are well-localized in the open state of the channel, but less so in the open-inactivated pore, which is characterized by a broad and shallow binding surface at the bottom of the S6 helix. The free energy wells for dofetilide binding to the open state are around −12 kcal/mol for the inner binding site (point a in FIG. 24B) and −13 kcal/mol for the outer binding site (point b in FIG. 24B), while the free energy wells for dofetilide binding to the open-inactivated state are less negative than −10 kcal/mol in the cavity (points a' and b' in FIG. 24B). A more negative binding free energy of −12.56 kcal/mol, and the small equilibrium dissociation constant of $1.40 \times 10^{-9}$ M, suggest greater drug accessibility for the intra-cavity site in the open hERG1 channel (Table 3).

TABLE 3

Dissociation constants and binding Gibbs free energies for two states of hERG1.

|  | Open | Open-inactivated |
|---|---|---|
| $K_D$ (M) | $1.40 \times 10^{-9}$ | $7.93 \times 10^{-8}$ |
| $\Delta G_{bind}$ (kcal/mol) | −12.56 | −10.07 |

The topology of the binding pockets for dofetilide in open and open-inactivated states are shown in FIG. 24C. In the inner binding location (FIG. 24C-a) of open hERG1, dofetilide is stabilized by multiple interactions with the apex of the pore helix (formed by residues S621-S624) and cluster of residues from distal S6 helix including S649, Y652 and F656 in the cavity. One of the methanesulfonamide group formed hydrogen bonds with S649 and Y652. The other methanesulfonamide group is coordinated by T623 and water molecules. The tentative second binding site for neutral dofetilide (FIG. 24C-b) is located at the distal S6 helix. The ligand is primarily coordinated by the cluster of hydrophobic residues (Y652, A653 and F656) and polar residues (T623, S624 and S649). There are also multiple hydrogen bonds formed between the ethoxy- or methanesulfonamide-oxygens of dofetilide and S649 or water molecules. In the open-inactivated hERG1 cavity, the inner binding site is located between Y652 and the selectivity filter. Both drug polar termini are coordinated by S649 and water molecules (FIG. 24C-a'). The outer binding site is at the gate and close to the hydrophobic residues Y652, F656 and I655 (FIG. 24C-b'). One arm of dofetilide points into the solvent.

The position-dependent diffusion coefficient of the dofetilide in open and open-inactivated states (FIG. 24D) shows little dependence of the dofetilide diffusion on the state of the channel. Once dofetilide reaches the gate, the diffusion coefficient decreases sharply. Therefore, the dofetilide binding process is treated here as a purely diffusion-limited reaction. According to the boundary condition assumption in the Debye-Smoluchowski diffusion equation, the reactive region radius R (from Eq. 4 in methods section) is defined as the distance between the energy barrier and well (Shoup, D. et al. (1982) Biophys J. 40:33-39), and this assumption allowed the system to constrain the $k_{on}$ and $k_{off}$ rates for dofetilide binding to hERG1 open and open inactivated states in simulations.

Figure 25D:
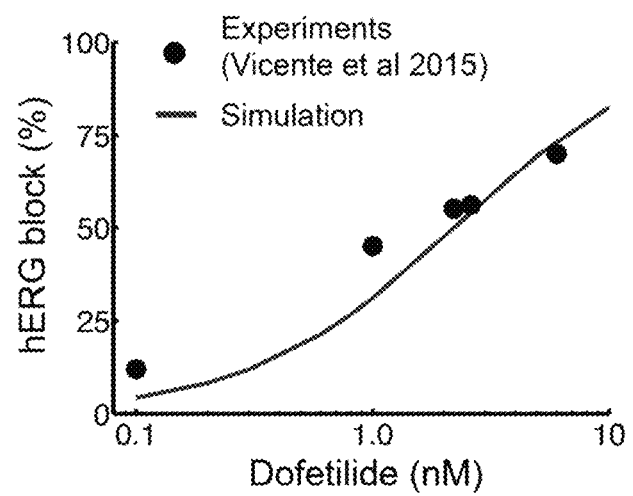
(FIG. 25D) Experimentally measured dose dependent inhibition of hERG1 by dofetilide.

The combination of calculated binding free energy profiles and diffusion rates of dofetilide into the open and open-inactivated states allowed for the constrained optimization of rate constants that were used to populate a state dependent hERG1 function scale model shown in FIG. 25A. To simulate drug interactions with hERG1, Applicants used drug diffusion rates D (~$5.77 \times 10^{-6}$ cm²/s for both states) and affinities (dissociation constants $K_{Do}$ and $K_{DI}$, Table 1) from the PMF calculation to constrain the drug "on" ([drug]*$k_x$) and "off" ($r_x$) rates. The "off" rate from the open state was calculated as $r_o = k_o * K_{Do}$, where $K_{Do}$ was from the PMF calculation (FIG. 25B and Table 3). Similarly, $r_i = k_i * K_{DI}$ (FIG. 25B and Table 3). The rates were optimized to the experimentally obtained IC$_{50}$ curve from Vicente et al. (Vicente, J. et al. (2015) J Am Heart Assoc 4:e001615) assuming $k_i = k_o$ (based on the similar calculated diffusion coefficients), shown in FIG. 25C. In both experiment and simulations, peak $I_{Kr}$ was recorded at the end of the 3-s activating step to 0 mV with drug concentrations from 0 to 6 nM. Percentage of drug block was calculated by ($I_{control} - I_{drug}$)*100/$I_{control}$ and compared to experimental data (Vicente, J. et al. (2015) J Am Heart Assoc 4:e001615).

Figure 26:
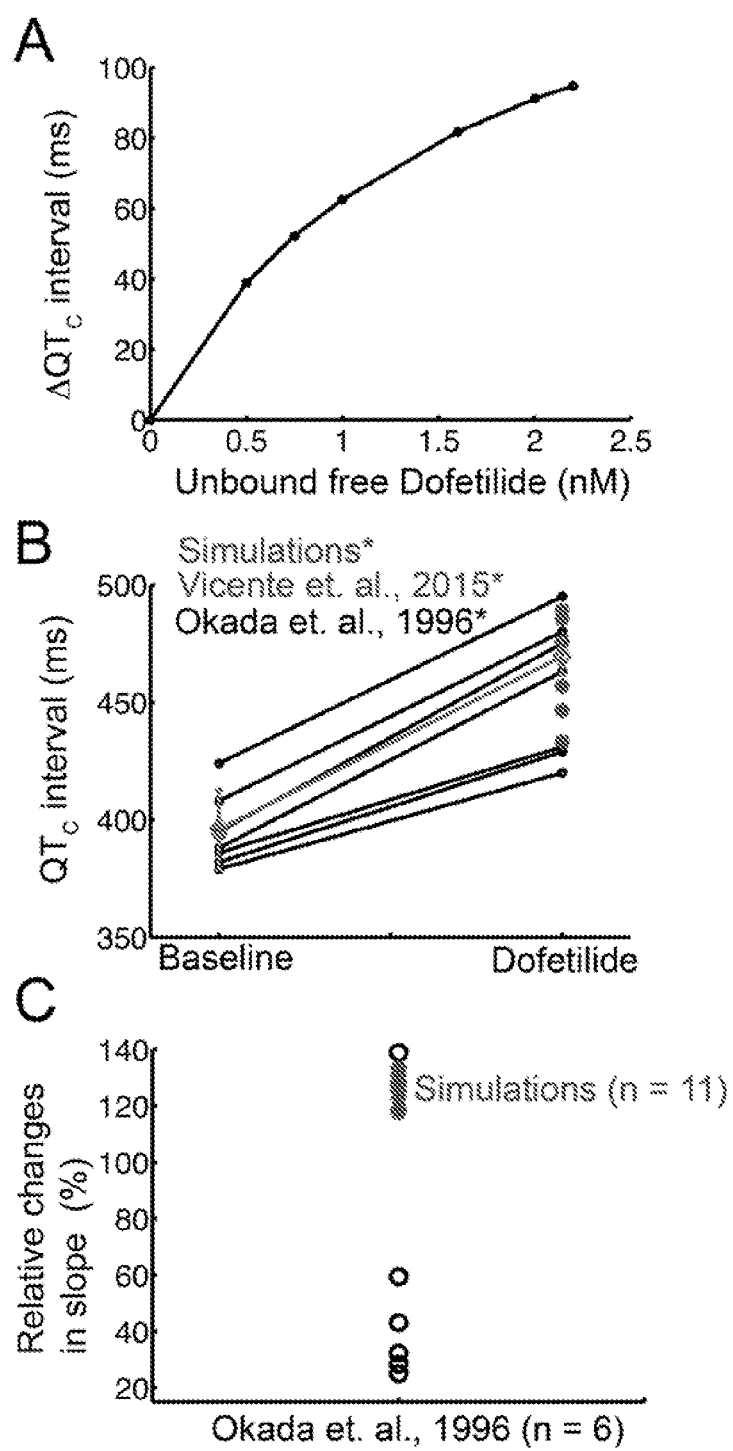
FIGS. 26A-26C show validation of the dofetilide prototype pipeline with human clinical data.

Next, Applicants subjected their computational pipeline for safety pharmacology to a validation test using the gold standard data: Human clinical data from electrocardiograms in the absence and presence of dofetilide. To do so, Applicants first constructed a one-dimensional strand of O'Hara-Rudy human cardiac ventricular myocytes (O'Hara, T. et al. (2011) PLoS Comput. Biol. 7:e1002061) by connecting them via simulated resistive elements to represent gap junctions. Applicants applied a simulated stimulus current at one end to initiate a propagating one-dimensional wave at a mean heart rate ~56 beats per minute. FIG. 26A shows the calculation of the spatial and temporal gradients of electrical activity used to construct a heart rate corrected pseudo ECG (QTc interval) for a range of dofetilide concentrations.

FIG. 26B shows the comparison of human clinical data under drug free conditions and following application of 2 nM dofetilide (Vicente, J. et al. (2015) J Am Heart Assoc 4:e001615; Okada, Y. et al. (1996) J Am Coll Cardiol. 27:84-89). The simulated mean values compared to clinically obtained data from humans are in excellent agreement, thereby providing an indication of the validity and predictive value of the computational pipeline to recapitulate the effect of a drug on the human QT interval.

Finally, as shown in FIG. 26C, Applicants simulated QT intervals over a wide range of preceding RR intervals after dofetilide application and compared to the clinically observed changes (Okada, Y. et al. (1996) J Am Coll Cardiol. 27:84-89). Each cell in the simulated tissue was subjected to a physiological noise current in order to introduce variability. Rate dependent changes in the QT interval were tracked as the slope of the linear regression line estimating the QT–$\sqrt{RR}$ relation. Again, the predicted relationship falls within the range of clinical data, indicating that the model can reproduce rate dependent changes in drug-induced QT interval.

Applicants next carried out computational screening in O'Hara-Rudy human computational ventricular myocytes for the effect of dofetilide to promote proarrhythmia by tracking the parameters comprising the TRIaD. Applicants tracked each parameter in the absence of drug (control conditions in black) and in the presence of 2.2 nM dofetilide (red). This approach was also carried out in simulated rabbit ventricular myocytes to explore the effects of species differences. The predicted results in rabbit were very similar to human and are shown in FIGS. 31A-31D.

Figure 27:
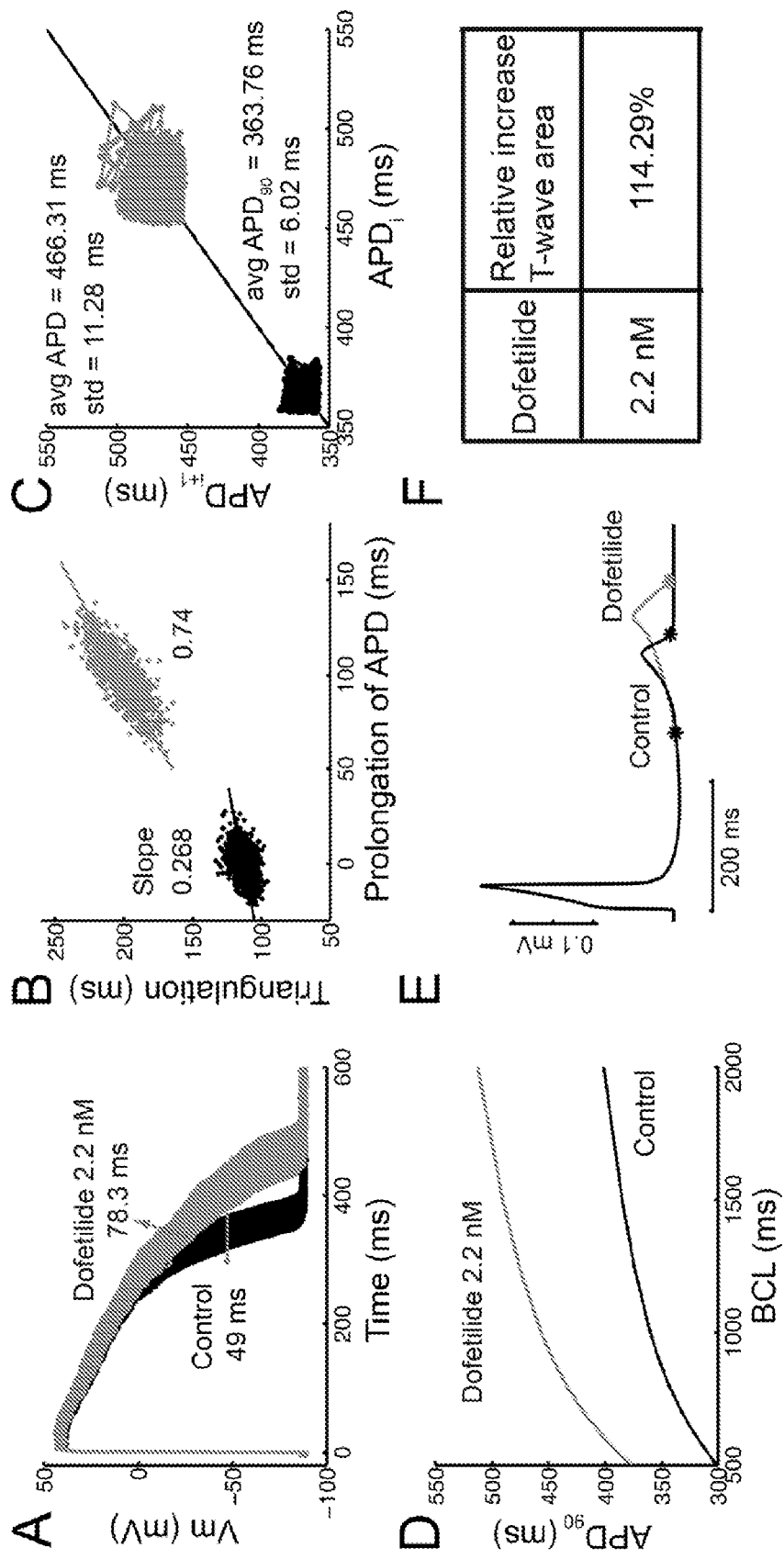
FIGS. 27A-27F show computational screen of arrhythmia vulnerability.

In FIG. 27A, temporal APD dispersion was quantified in a cell population of 1000 individual simulated cardiac myocyte action potentials constructed by incorporating physiological noise (Sato, D. et al. (2006) Circ Res. 99:520-527; Tanskanen, A. J. et al. (2007) Math Biosci. 208:125-146; Sato, D. et al. (2013) PLoS One 8:e85365). APD temporal dispersion was quantified as the difference between the maximum and minimum APD. Dofetilide within the clinical dosing range has a clear effect to promote temporal APD variability in the presence of the drug (Control −49 ms; 2.2 nM Dofetilide −78 ms). FIG. 27B illustrates the effect of dofetilide to promote triangulation of the action potential as a function of APD prolongation. In the absence of drug, control cells had a slope of 0.27, while 2.2 nM Dofetilide increased the slope to 0.74. FIG. 27C shows Poincaré plots of sequential APD pairs indicating beat-to-beat instability following the application of small electrical perturbations in the absence of drug or with 2.2 nM dofetilide. Instability was assessed by applying small amplitude inward currents randomly between −0.1 to −0.2 pA/pF for 50 ms over the course of the action potential plateau at a basic cycle length of 1000 ms. In FIG. 27D, reverse use dependence induced by dofetilide was evaluated. The action potential adaptation curves were generated using $APD_{90}$ values from human computational ventricular myocytes at steady-state at the indicated pacing frequencies. When dofetilide (red) was applied, there was a clear steepening of the APD adaptation curve compared to the baseline drug-free case (black). FIG. 27E shows spatial dispersion of APD that was quantified in tissue by integrating the area under predicted T-wave following a long pause (5000 ms). See methods section for details. The table in FIG. 27F shows the quantified increase in area (114.29%) under the T-wave when dofetilide is applied.

Figure 28:
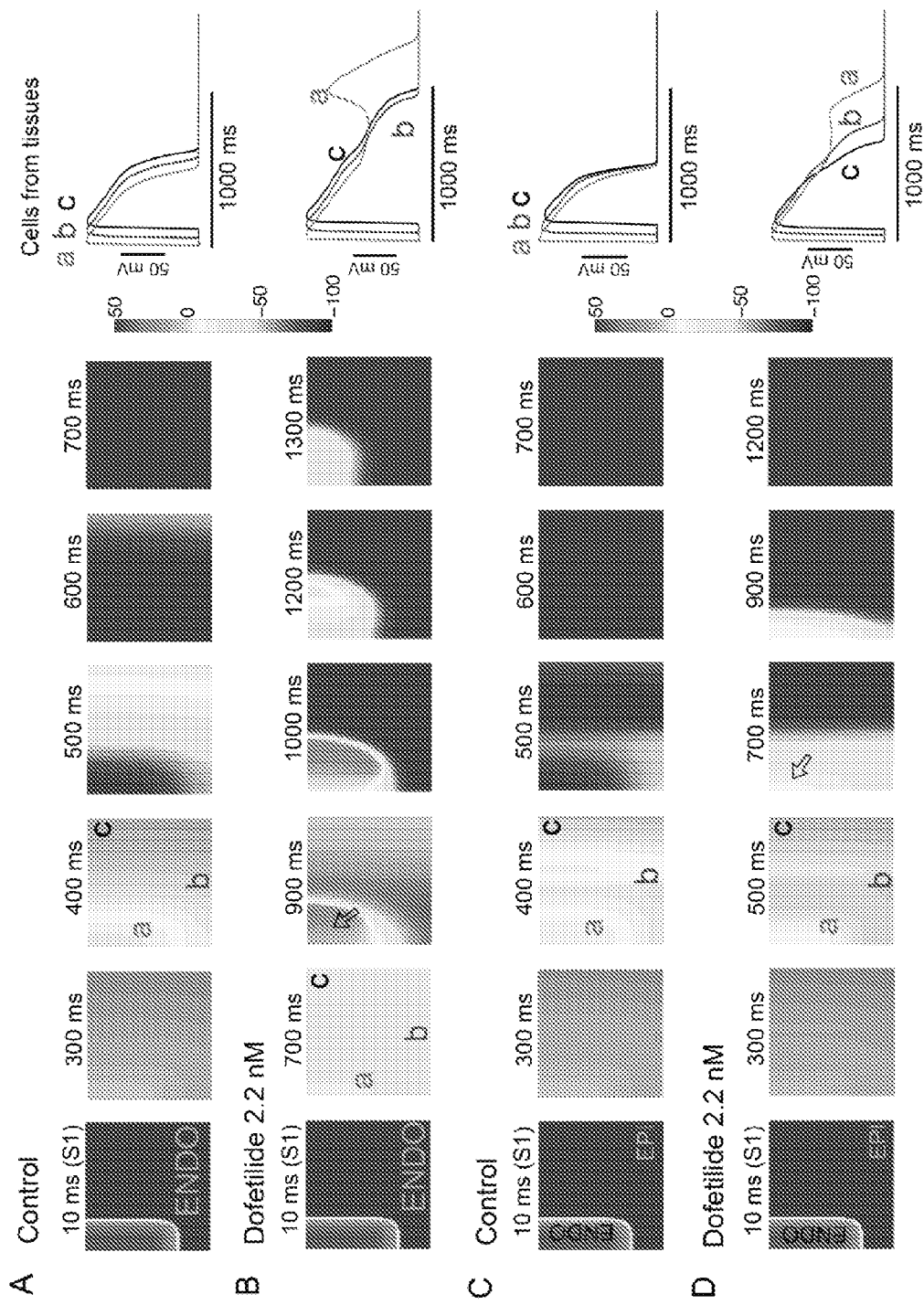
FIGS. 28A-28D show in silico diagnostic test in tissue reveals arrhythmia triggers with dofetilide. Time snapshots (panels) with voltage gradients are shown for two-dimensional simulated tissue as described. Membrane voltages are indicated by the color gradient. Two-dimensional homogeneous (FIGS. 28A and 28B, endocardial cells) and heterogeneous (FIGS. 28C and 28D, endocardial region (cells 1 to 180) and epicardial region (cells 181 to 300)) anisotropic human ventricular in silico tissue composed of (3 cm×3 cm) simulated myocytes.

Arrhythmia is fundamentally an emergent spatial phenomenon. Accordingly, simulations to determine if dofetilide promotes reentrant arrhythmias and their mechanisms were performed. The results are shown in FIGS. 28A-28D. Two-dimensional homogeneous (FIGS. 28A and 28B, endocardial cells) and heterogeneous (FIGS. 28C and 28D, endocardial region (cells 1 to 180) and epicardial region (cells 181 to 300), with a linear decrease in APD as indicated by experimental data (Lou, Q. et al. (2011) Circulation 123:1881-1890; Glukhov, A. V. et al. (2010) Circ Res. 106:981-991)) anisotropic human ventricular in silico tissues (3 cm×3 cm) were simulated. Each simulated tissue contained randomized spatial heterogeneity imposed by the application of low amplitude perturbations in the form of small inward currents, which were randomly applied between −0.1 to −0.44 pA/pF to each cell in the tissue at each time step for the duration of the simulation. In FIGS. 28A and 28B, the homogeneous tissue simulations showed that the presence of 2.2 nM dofetilide resulted in the emergence of early afterdepolarizations in some cells and not others, resulting in spatial dispersion of repolarization. As shown in FIGS. 28C and 28D, the effect persisted when the tissue was heterogeneous (to mimic transmural heterogeneity), with considerable reduced dispersion of repolarization in the heterogenous case (as epicardial cells fire last, but repolarize first) and profound spatial repolarization gradients in the setting of dofetilide only.

Figure 29:
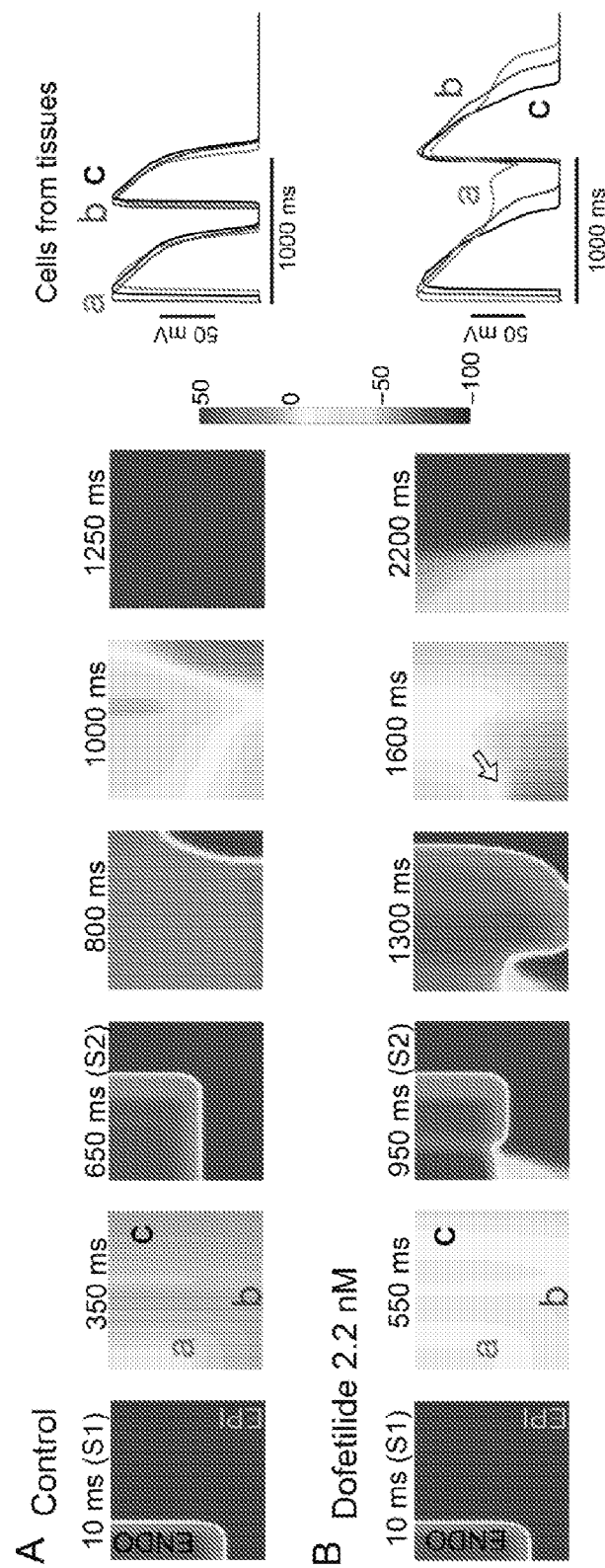
FIGS. 29A-29B show in silico diagnostic test to reveal vulnerability to reveal torsades de points arrhythmias by extrasystoles. Time snapshots (panels) with voltage gradients are shown for two-dimensional simulated tissue as described. Membrane voltages are indicated by the color gradient. The corresponding action potentials from three points in space are shown in the right panels. In the absence of drug (top row), there was no persistent reentry. In the bottom row the effect of dofetilide is shown, which promoted numerous persistent arrhythmia triggers observed as afterdepolarizations in the cellular action potentials (right).

Applicants next set out to test the effect of dofetilide in the setting of extrasystolic excitable triggers as shown in FIGS. 29A-29B. The 2D tissue was simulated using a typical S1-S2 protocol. The tissue was first paced (S1) (first panel) in a 0.5 cm×1.1 cm area on the left edge of the endocardial region, and a premature stimulus S2 (third panel) was then applied in a 1.8 cm×1.5 cm area on the top left corner of the endocardial region. As described above, spatial heterogeneity was applied via small amplitude inward currents randomly applied between −0.1 to −0.44 pA/pF to each cell in heterogeneous tissues after 0.5 ms. Time snapshots (panels) with voltage gradients indicated by the color map are shown. These maps were constructed following the last planar wave (S1) (first panel) and throughout termination of the most persistent wave after S2 (last panel). The corresponding action potentials from three points in space are shown in the right panels. In the absence of drug (top row), there was no persistent reentry. In the bottom row the effect of dofetilide is shown, which reproducibly (n=5 simulations) promoted numerous persistent arrhythmia triggers observed as afterdepolarizations in the cellular action potentials (right).

Figure 30:
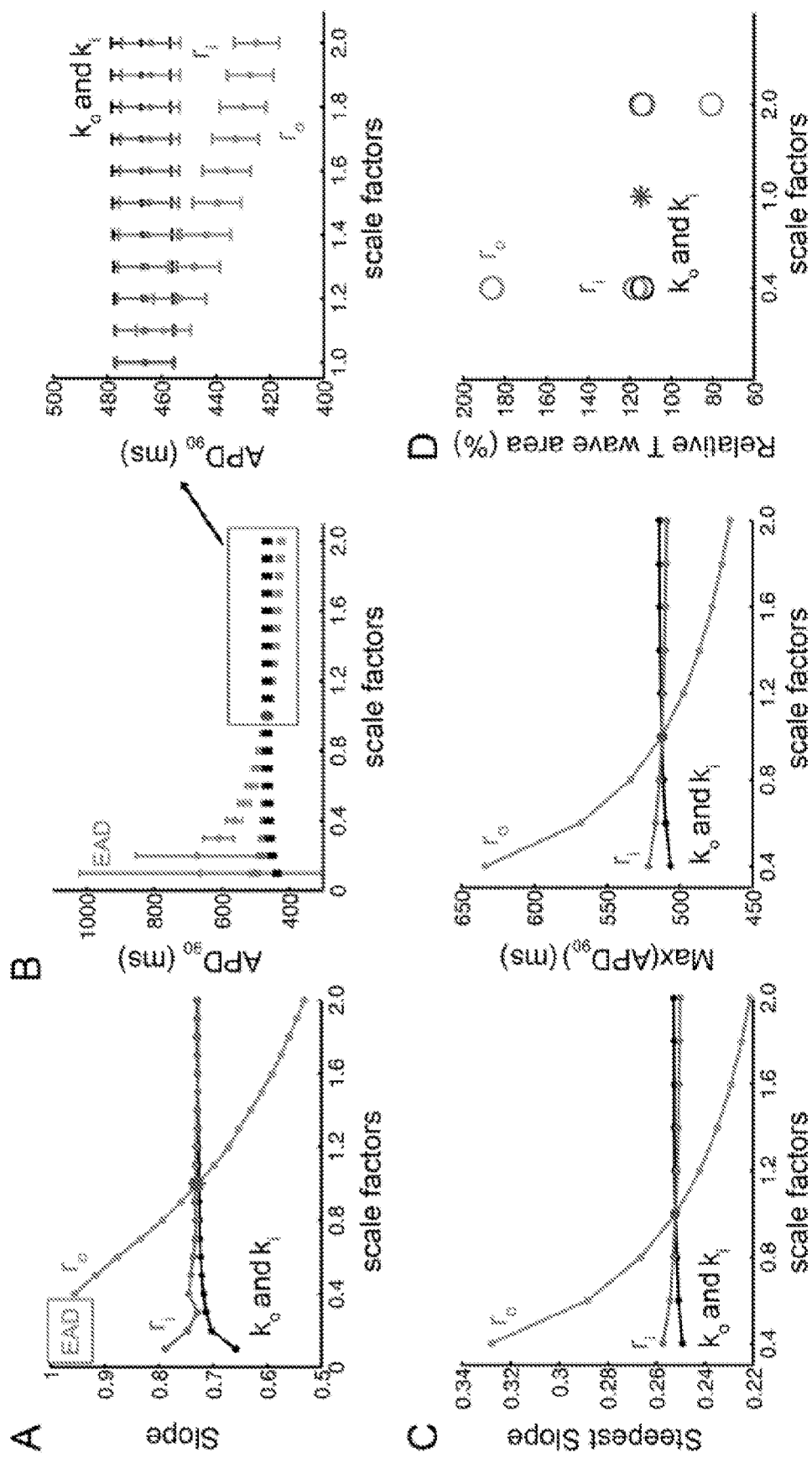
FIGS. 30A-30D show sensitivity analysis of arrhythmia vulnerability parameters from the TRIaD.
Figure 31:
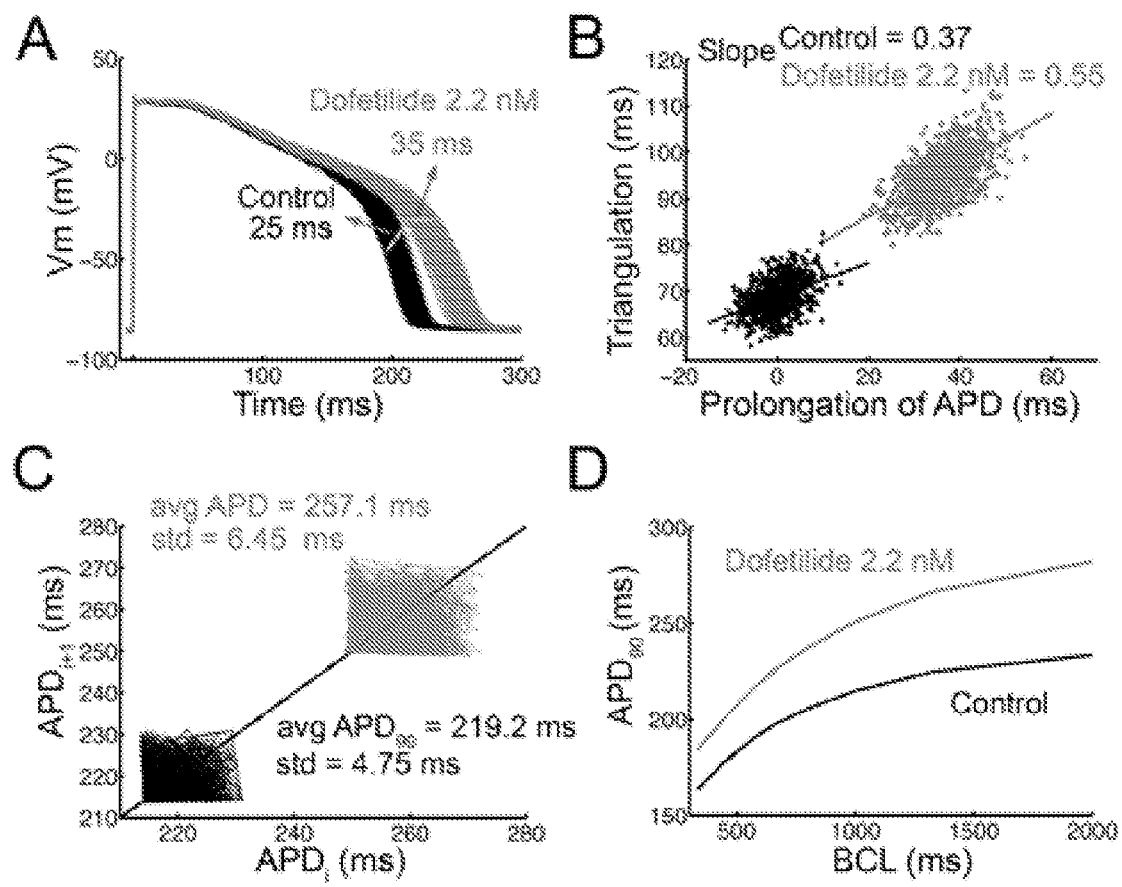
FIGS. 31A-31D show computational screen of arrhythmia vulnerability in rabbit model.

Finally, in order to assess the specific drug channel interactions that comprise the dofetilide structure-activity relationship and the link to proarrhythmia, Applicants undertook sensitivity analysis of arrhythmia vulnerability parameters from the TRIaD based simulations (FIGS. 30A-30D). As shown in FIG. 30A, Applicants first carried out an in silico test of the sensitivity of the slope of the relationship between action potential triangulation and APD prolongation in O'Hara-Rudy computational myocytes plotted for a range of drug "on" ($k_o$ and $k_i$,) and "off" ($r_o$ and $r_i$,) model transition rates for open and open inactivated states by multiplying each rate by a scale factor between 0.1 and 2.0. The analysis showed that this parameter is sensitive to drug unbinding to the open state, but insensitive to other transition perturbations. Similarly, in FIG. 30B, simulated beat-to-beat instability of action potentials only showed sensitivity to changes to drug unbinding rates to the open state (right panel is scale factors >1.0). The average and standard deviation of $APD_{90}$ for each case are shown. FIG. 30C illustrated the sensitivity to changes in drug transition rates of the steepest recorded slope of APD90 reverse use dependent curves (left) and APD90 at 0.5 Hz pacing rate (right). Again, these parameters were sensitive only to changes in the drug unbinding rate to the open state. Finally, FIG. 30D, shows the sensitivity of the T-wave area to drug unbinding rates to the open state only. Blue asterisk indicates baseline transition rates.

DISCUSSION

In this study Applicants take the first steps to construct a computational pipeline for predictive safety pharmacology. The goal of this study was to develop a framework that can allow the detection of unsafe hERG1 blockers early in the preclinical screening process. Thus, Applicants have assembled the process and utilized clinical data to demonstrate the utility for a proof-of-concept multiscale computational model to predict cardiac effects of dofetilide.

Applicants began by developing physics based computer models that can account for conformation state-specific atomic-scale determinants of dofetilide interaction with hERG1. This was accomplished through homology, de novo, and full-atom modeling of the hERG1 $K^+$ channels using Rosetta molecular modeling suite (Lees-Miller, J. P. et al. (2009) Biophys J. 96:3600-3610; Subbotina, J. et al. (2010) Proteins 78:2922-2934; Yarov-Yarovoy, V. et al. (2006) Proteins 62:1010-1025; Barth, P. et al. (2007) Proc Natl Acad Sci USA 104:15682-15687; Andre, I. et al. (2007) Proc Natl Acad Sci USA 104:17656-17661). The models were based on the templates of available X-ray structures of Kv1.2 (Long, S. B. et al. (2007) Nature 450:376-382), KvAP (Jiang, Y. et al. (2003) Nature 423:33-41), and KcsA (Zhou, Y. et al. (2001) Nature 414:43-48; Mandell, D. J. et al. (2009) Nature Methods 6:551-552; Wang, C. et al. (2007) J Mol Biol. 373:503-519). Molecular docking simulations were used to predict drug-binding conformations of the hERG1 channel in multiple states Molecular Dynamics Yields Novel Insights of Dofetilide Interaction with hERG1

Next, Applicants undertook molecular dynamics simulations to predict association rates and affinities of dofetilide to discrete open and open inactivated states of the hERG1 K$^+$ channel. Interestingly, this approach yielded novel information about the nature of dofetilide interactions with hERG1. The molecular dynamics simulations suggest that dofetilide interacts more strongly with the open state versus inactivated state of the hERG1 channel (FIG. 25B). Applicants' previous function scale dofetilide model (Romero, L. et al. (2014) J Mol Cell Cardiol. 72:126-137) was based on interpretation of experimental data, some of which suggested a 70-fold preferential binding to the inactivated state relative to the open state (Perrin, M. J. et al. (2008) Mol Pharmacol. 74:1443-1452; Weerapura, M. et al. (2002) Pflug Arch Eur J Phy. 443:520-531; Ishii, K. et al. (2003) Cardiovasc Res. 57:651-659; Ficker, E. et al. (1998) Circ Res. 82:386-395).

Interestingly, Applicants' older model required higher doses of dofetilide to cause prolongation of the QT interval, but the model generated from the MD parameters was able to reproduce dose-dependent prolongation of the QT interval in very close agreement to the clinical data (FIGS. 26A-26C). These results serve as an important reminder for the difficulty in empirically deconstructing state dependent drug mechanisms from experimental data. This is because the drug interaction often occurs on the same timescale (ms) as channel gating. In the physics based approach that Applicants used, the channel is held in a static conformation, allowing for an unambiguous calculation of drug-channel affinity for discrete channel conformations.

Computational Ion Channel Structure to Function

In this study Applicants have attempted to make a novel link between ion channel structure and function. Applicants utilized atomic scale predictions to inform rate constants for constructing computational channel scale kinetic models for dofetilide interaction with hERG1 channels. Potential mean force calculations from drug—channel binding trajectories allowed for the calculation of dissociation constants $K_D$ for dofetilide interactions with hERG1 for open and open inactivated states of the channel. These simulated data combined with predicted diffusion coefficients from the same atomistic MD runs allowed for drug "on" and "off" rates to discrete states to be introduced into the function scale Markov model of hERG1.

Connection Between Structure Activity Relationship and Proarrhythmia

Computational models of dofetilide interaction with the hERG1 receptor was integrated into virtual cardiac cell and tissue level models to predict emergent drug effects to promote elements of the TRIaD: Triangulation, reverse use dependence, beat-to-beat instability of APD, temporal and spatial APD dispersion—proarrhythmia markers that emerge at cell and tissue scales.

The driving hypothesis underlying the goals of this study is that the proarrhythmic cellular manifestations of the TRIaD arise directly from the underlying kinetics of channel block. Identification of the specific kinetic interactions that give rise to components of the TRIaD is essential to define new standards for preclinical compounds that can be used to rule out compounds with these properties in early screening tests. Applicants' sensitivity analysis (FIGS. 30A-30D) suggests that as a general principle, reducing the affinity of hERG1 blocking drugs in the open state can reduce the propensity to arrhythmias linked to TRIaD mediated arrhythmia vulnerability parameters. In all of the sensitivity tests that Applicants performed, Applicants observed a reduction in arrhythmia vulnerability when the dofetilide off rate from the open state was increased. The converse was also true: an increase in dofetilide binding the open state, accomplished in the simulation by reducing the rate of drug unbinding, increased arrhythmia vulnerability.

The manifestation of the TRIaD parameters can be observed in the tissue level simulations. In FIGS. 28A-28D, the model predictions show the emergence of arrhythmia triggers in the presence of dofetilide, even in the absence of external stimuli. The increase in instability and triangulation of the action potentials make cells "pre-treated" with dofetilide extremely vulnerable to small random spatial noise. It is the net effect of spontaneous depolarization that causes increased spatial and temporal APD dispersion, combined with the profound reverse use-dependence of dofetilide that results in the extrasystolic induction of a reentrant wave following a one second pause in the presence of dofetilide as shown in FIGS. 29A-29B. Thus, simulations in the multiscale computational pipeline for safety pharmacology suggest that high affinity open state block by dofetilide is the fundamental arrhythmia provoking mechanism. The effect could be presumably mitigated in drug congeners that display lower affinity open state binding. Future studies must specifically test this concept in order to prove the mechanism and ultimately improve preclinical drug screening approaches.

Structure based models of hERG 1 generated from crystal structures of closely related Kv channels have been enormously helpful to understand receptor-ligand interactions (Durdagi, S. et al. (2012) J. Chem. Inf. Model. 52:2760-2774; Stary, A. et al. (2010) ChemMedChem 5:455-467). The models have effectively captured the structural diversity of the channel, which may constitute the fundamental reason that Kv11.1 is so promiscuous in its drug binding capacity.

While widespread consensus has been reached concerning the structural elements of the hERG1 S6 and the selectivity filter, which are the regions that are most conserved among Kv channels (Yellen, G. (2002) Nature 419:35-42), the S5 segment structure is not resolved. There are two distinct possibilities of how S5 helix is arranged relative to S6 and the voltage sensing domains (Lees-Miller, J. P. et al. (2009) Biophys J. 96:3600-3610; Ju, P. et al. (2009) J Biol Chem. 284:1000-1008). In this work, Applicants minimized the effect of this limitation by focusing Applicants' prototype on dofetilide, a drug type that targets aromatic clusters in S6 in both the open and open-inactivated states.

Another limit is a force-field for dofetilide itself. Applicants have tested its solvation thermodynamics and lipid partitioning and found it to be consistent with various experimental studies involving similar compounds, as expected for parameters developed to reproduce physiochemical properties or drug-like compounds (CGenFF). However, one would have to parameterize specifically to target both solvation and/or partitioning thermodynamics and transport properties. Providing lacking experimental data on many common therapeutics, e.g., lipid or solvent partitioning coefficients, transport (diffusion coefficients and permeabilities), hydration free energies, etc., the targeted force-field development for near-experimental modeling accuracy remains very challenging task.

A limitation of Applicants' current approach is that Applicants assume that the membrane potential is zero. In the future, studies should attempt MD simulations of drug—channel interactions under different membrane voltages. A number of biologically relevant heterogeneous membrane compositions should also be considered to allow for the calculation of the impact of the lipid composition on drug effects. Future studies should also move towards polarizable force fields that can be critical for accurate simulation of charged drug species (Allen, T. W. et al. (2006) Biophys J. 90:3447-3468; Li, H. et al. (2015) J Phys Chem B. 119: 9401-9416).

In this study, Applicants have brought together model simulations at the atomistic level for hERG1 channel structure and dynamics and channel—drug interactions and simulations at the functional levels of the protein, cell and tissue. The power of combining these scales in a predictive framework is that it has allowed, for the first time, a way to derive on and off rates of drugs from atomic scale simulations and then use these values to inform and build functional level channel models. These function scale drug-channel models were then integrated into cellular and tissue level model to reveal mechanistic links between structure-activity relationships of ion channels and drugs with higher order emergent electrical phenomena such as cardiac rhythm disturbances. Applicants' approach can be expanded for varied genotypes and myriad risk factors, and even to predict individual responses to drug therapy.

Ultimately, Applicants hope that the presented approach represents a scalable framework with automation potential to interact with other developing technologies, including high-throughput electrophysiology measurements (Penniman, J. R. et al. (2010) J. Pharmacol. Toxicol. Methods 62:107-118; Mo, Z. L. et al. (2009) J. Pharmacol. Toxicol. Methods 60:39-44; Zeng, H. et al. (2008) Assay Drug Dev Technol. 6:235-241; Trepakova, E. S. et al. (2007) Assay Drug Dev Technol. 5:617-627; Ly, J. Q. et al. (2007) Clin Lab Med. 27:201-208; Dubin, A. E. et al. (2005) J Biomol Screen. 10:168-181; Bridal, T. R. et al. (2010) Assay Drug Dev Technol. 8:755-765; Jow, F. et al. (2007) J Biomol Screen. 12:1059-1067; Harmer, A. R. et al. (2008) J Pharmacol Toxicol Methods 57:30-41; Bridgland-Taylor, M. H. et al. (2006) J Pharmacol Toxicol Methods 54:189-199; Sorota, S. et al. (2005) Assay Drug Dev Technol. 3:47-57; Schroeder, K. et al. (2003) J Biomol Screen. 8:50-64), drug development via progress in synthetic biology (Nattel, S. et al. (2006) Nat Rev Drug Discov. 5:1034-1049), and even personalized medicine via drug screening in patients' own induced pluripotent stem (iPS) cell-derived cardiomyocytes (Braam, S. R. et al. (2010) Stem Cell Res. 4:107-116). All of these developing technologies are innovative but each of them cannot alone solve the fundamental problem—that the effects of multifaceted drug interactions are emergent. These technologies in conjunction with the multiscale models that the disclosure develops may form an interactive multiscale modeling and simulation driven process that can ultimately be used in the regulatory process prior to drug approval, in academia for research, in industry for drug and disease screening, and for patient oriented medicine in the clinic.

Materials and Methods

Homology Modeling and Docking

The 3D coordinates of the pore domain of hERG1 channel in the open and open-inactivated states were developed previously, based on an approach combining structure prediction using Rosetta molecular modeling suite (Lees-Miller, J. P. et al. (2009) Biophys J. 96:3600-3610; Subbotina, J. et al. (2010) Proteins 78:2922-2934; Yarov-Yarovoy, V. et al. (2006) Proteins 62:1010-1025; Barth, P. et al. (2007) Proc Natl Acad Sci USA 104:15682-15687; Andre, I. et al. (2007) Proc Natl Acad Sci USA 104:17656-17661) and molecular dynamics (MD) simulations as described in Applicants' previous publication (Durdagi, S. et al. (2012) J. Chem. Inf. Model. 52:2760-2774). This methodology has been validated in previous studies (Lees-Miller, J. P. et al. (2015) J Mol Cell Cardiol. 85:71-78; Durdagi, S. et al. (2014) BMC Pharmacol Toxicol. 15:14; Anwar-Mohamed, A. et al. (2014) Toxicol Lett. 230:382-392).

The topology and parameters of dofetilide (FIG. 23C) were constructed using CHARMM generalized force field (CGenFF) (Vanommeslaeghe, K. et al. (2010) J. Comput. Chem. 31:671-690). Dofetilide was then docked in-silico to the two hERG1 models representing the open and open-inactivated states of the channel using the Glide-XP (extra precision) docking program from Schrödinger (Ruan, Y. et al. (2009) Nat Rev Cardiol. 6:337-348), and the top-scoring intra-cavity binding poses for each representative state of hERG1 were chosen as initial structures for MD simulations in the next step.

Molecular Dynamics Simulation Protocol

The hERG1-dofetilide complexes from the docking study were embedded in a dipalmytoil-phosphatidylcholine (DPPC) bilayer. The membrane normal axis was aligned along the z-axis. The system was solvated in 150 mM aqueous KCl solution using TIP3P water model (Jorgensen, W. L. et al. (1983) J Chem Phys. 79:926-935) and CHARMM ion parameters (Beglov, D. et al. (1994) J Chem Phys. 100:9050-9063; Noskov, S. Y. et al. (2008) J Mol Biol. 377:804-818). Both systems (open and open-inactivated hERG1 with dofetilide, respectively) were built and pre-equilibrated with the CHARMM program (Brooks, B. R. et al. (2009) J Comput Chem. 30:1545-1614) using all-atom CHARMM force field (Noskov, S. Y. et al. (2008) J Mol Biol. 377:804-818; MacKerell, A. D. et al. (1998) J Phys Chem B 102:3586-3616; Mackerell, A. D. et al. (2004) J Comput Chem. 25:1400-1415; Klauda, J. B. et al. (2010) J Phys Chem B 114:7830-7843). After 10000 steps of Steepest-Descent minimization run with a 10 kcal/(mol·Å$^2$) harmonic restraint on heavy atoms, each system was equilibrated for 1 ns with a gradually decreasing from 10 to 1 kcal/(mol·Å$^2$) harmonic restraint, applied to backbone of the protein followed by 10 ns equilibration using the final value of this restraint. During the equilibration simulation, the backbone of the selectivity filter, two K$^+$ ions and three water molecules in the filter were restrained with a 8 kcal/(mol·Å$^2$) harmonic force constant. All equilibration simulations were run using NAMD2.9 program package with the time step of 2 fs (Phillips, J. C. et al. (2005) J Comput Chem. 26:1781-1802). A constant temperature and pressure (NPT) ensemble was used for all simulations with pressure set to 1 atm using the Nose-Hoover Langevin piston method and temperature set to 310.15 K with Langevin dynamics (Feller, S. E. et al. (1995) J Chem Phys. 103:4613-4621; Martyna, G. J. et al. (1994) J Chem Phys. 101:4177-4189). Long-range electrostatic interactions were treated by the particle mesh Ewald (PME) algorithm (Essmann, U. et al. (1995) J Chem Phys. 103:8577-8593). Non-bonded interactions were switched off between 10 to 12 Å, and systems were simulated with three-dimensional periodic boundary conditions (PBC). The last frame of each equilibration simulation was chosen as a starting point for the Umbrella Sampling simulations described below.

Potential of Mean Force for Dofetilide-hERG1 Binding

Applicants used Umbrella Sampling (US) simulations to evaluate Potentials of Mean Force (PMF) for drug binding to the hERG1 channel. In each US window, the initial structure was created and simulated using harmonic biasing potentials with a force constant of 10 kcal/(mol·Å$^2$) on the ligand. Meanwhile, force constants of 1 kcal/(mol·Å$^2$) on backbone of the protein, and 8 kcal/(mol·Å$^2$) on those of the selectivity filter, two K$^+$ ions and three water molecules in the filter were also applied to preserve a targeted channel state and permeant ion configuration. The reaction coordinate was defined (FIG. 24A) as a dofetilide center of mass (COM) position along the z-axis with respect to the COM of the Cα of residues 623-628 in the selectivity filter. A flat-bottom cylindrical constraint, with a radius of 10 Å, was used to cap lateral displacement of the bound drug in the xy plane. The sampling windows were spaced every 0.5 Å from −7.5 Å to −49.5 Å resulting in 85 windows for open hERG1 and from −8.5 Å to −38.0 Å resulting in 60 windows for open-inactivated hERG1. The simulation time per window was set to 22 ns. The total simulation time was 1.87 is and 1.32 μs for open and open-inactivated systems, respectively. The binding free energy profiles were obtained from the last 20 ns/window with the use of Weighted Histogram Analysis Method (WHAM) (Kumar, S. et al. (1992) J Comput Chem. 13:1011-1021), and tolerance set to $10^{-7}$ kcal/mol. The summary of the methods used for estimation of errors involved with PMF computations, the dissociation constant KD, and free energy estimations of the bound drug are collected in the supplementary materials section.

Diffusion Coefficient

The dynamics of dofetilide within each hERG1 model was analyzed in terms of its local diffusion along the pore axis z, D(z), which is inversely proportional to its local static friction coefficient $\xi(z)$. Thus, $$D(Z) = \frac{RT}{\xi(z)} \quad (1)$$

where R is the gas constant and T is the absolute temperature of the system.

Crucially, the fluctuation-dissipation theorem relates $\xi(z)$ to the time autocorrelation function of the fluctuation of constraint force acting on the molecule, ΔF, and is given by, $$\xi(z) = \frac{1}{RT}\int_0^\infty \langle \Delta F(z,t) \cdot \Delta F(z,0) \rangle dt$$

where, $$\Delta F(z,t) = F(z,t) - \langle F(z) \rangle_t$$

describes the deviation of the umbrella sampling constraint force acting on the molecule at time t, from the time-averaged force acting on the molecule at umbrella sampling window centered at z to remove a systematic biasing force.

The Equilibrium Dissociation Constant

The equilibrium dissociation constant of a single drug molecule, $K_D$ (single), was computed from PMF along z, ΔG(z), in the presence of a flat-bottom cylindrical restraint in the xy plane, and can be expressed as follows (Allen, T. W. et al. (2004) Proc Natl Acad Sci USA 101:117-122; Kim, I. et al. (2011) Proc Natl Acad Sci USA 108:17963-17968), $$K_d^{-1}(\text{single}) = \pi R^2 \int_{z_{min}}^{z_{max}} dz\, e^{-\Delta G(z)/k_B T} \quad (2)$$

where R is the radius of the cylindrical restraint oriented normal to the z-axis. The ΔG(z) was offset to zero for dofetilide in the bulk aqueous phase.

The binding free energy is calculated by $$\Delta G = RT \ln \frac{K_d}{C^0} \quad (3)$$

where $C^0$ is the standard concentration, which is 1 mol/L.

Dofetilide-hERG1 Interaction Function Scale Model

The wild-type drug-free hERG1 model was used as previously described in (Romero, L. et al. (2014) J Mol Cell Cardiol. 72:126-137) and shown in FIG. 25A. To simulate drug interactions with hERG1, Applicants used measured affinities and drug diffusion rates used to constrain the drug "on" ($k_o$ and $k_i$,) and "off" ($r_o$ and $r_i$,) model transition rates for open and open inactivated states (FIG. 25A).

TABLE 4

Transition rates for Dofetilide model.

| Transition rates | Open (O) | Inactivated (I) |
|---|---|---|
| On | $k_0$ * [drug] | $k_i$ * [drug] |
| Off | $k_0$ * $K_{Do}$ | $k_i$ * $K_{DI}$ |

$k_i = k_o$ was assumed in the model. Dissociation constants ($K_D$) of dofetilide for open and inactivated states hERG1 models, $K_{Do}$ and $K_{DI}$ are taken from MD predicted data (FIG. 25B). Then, using the relation, $$K_D = \frac{k_{off}}{k_{on}},$$

Applicants compute $k_{off}$. (4).

The initial value for $k_o$ used in the optimization is 0.005 $nM^{-1}$ $ms^{-1}$.

Calculated the Total Plasma Dofetilide Concentrations

Applicants used the population Cmax (plasma concentration) 2.72+/−0.3 ng/mL and unbound free fraction 2.2 nM from (Vicente, J. et al. (2015) J Am Heart Assoc 4:e001615) to calculate the maximal binding capacity (Bmax) (Toutain, P. L. et al. (2002) J Vet Pharmacol Ther. 25:460-463). Then the following equation (Toutain, P. L. et al. (2002) J Vet Pharmacol Ther. 25:460-463) was used to compute total plasma [Dofetilide].

$$\text{Total plasma [drug]} = \text{unbound free [drug]} + \frac{B\text{max} \times \text{unbound free [drug]}}{Kd + \text{unbound free [drug]}} \quad (5)$$

where $K_D$=1.4 nM and $B_{max}$=6.4812 nM.

Figure 32:
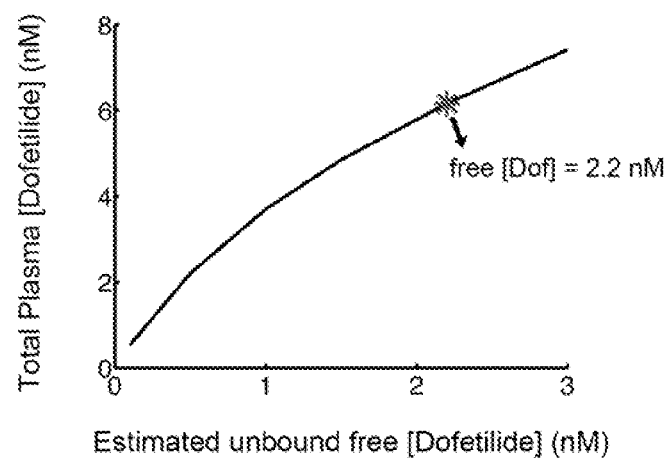
FIG. 32 shows the total plasma drug concentrations (y-axis above) is the concentration input in the dofetilide-hERG1 binding model.

The total plasma drug concentrations (y-axis above) is the concentration input in the dofetilide-hERG1 binding model (FIG. 32).

Simulation of TRIaD in Dofetilide and Control Case in O'Hara-Rudy Human Model

First, Triangulation was calculated as the repolarization time from $APD_{30}$ to $APD_{90}$ from 1000 simulated cell with noise currents. Reverse-use-dependence was measured $APD_{90}$ at steady state for each pacing cycle length (from 2 Hz to 0.5 Hz) and APD adaptation curves were constructed. Instability was simulated by applying small amplitude inward currents randomly between −0.1 to −0.2 pA/pF for 50 ms over the course of the action potential plateau at 1 Hz. A small inward current was also applied randomly in time between 10 to 700 ms on the plateau phase for 1000 beats. Applicants modeled temporal APD dispersion as beat-to-beat APD variability by adding noise currents into membrane potential calculations, and simulated 1000 cells action potentials. Using the equation from (Tanskanen, A. J. et al. (2007) Math Biosci. 208:125-146), $$V_{t+\Delta t} = V_t - \frac{I(V_t)\Delta t}{C_m} + \xi n \sqrt{\Delta t} \quad (6)$$

where n is a random number between 0 and 1 from a Gaussian distribution, and $\Delta t$ is the time step. $\xi$ is the diffusion coefficient, which defines the amplitude of noise. In FIGS. 27A-27F, $\xi$ was set to 0.3 based on (Tanskanen, A. J. et al. (2007) Math Biosci. 208:125-146). The noise current was generated and applied to the membrane potential $V_t$ throughout the simulated time course.

Fiber Simulations

Applicants simulated a transmural fiber composed of 165 O'Hara-Rudy human ventricular cells (O'Hara, T. et al. (2011) PLoS Comput. Biol. 7:e1002061) ($\Delta x=\Delta y=100$ µm) connected by resistances to simulate gap junctions (Faber, G. M. et al. (2000) Biophys J. 78:2392-2404). The fiber contains an endocardial region (cells 1 to 80) and epicardial region (cells 81 to 165), which showed a linear decrease in APDs (Lou, Q. et al. (2011) Circulation 123:1881-1890; Glukhov, A. V. et al. (2010) Circ Res. 106:981-991). $G_{Kr}$ was monotonically increased from 0.04 to 0.05. The heart was paced at 1 Hz to match the clinical observed QT intervals ~400 ms (Stramba-Badiale, M. et al. (1997) Eur Heart J. 18:1000-1006; Nakagawa, M. et al. (2005) J Cardiovasc Electrophysiol. 16:278-284; Ebert, S. N. et al. (1998) J Womens Health 7:547-557). AP simulations were carried out in epi/endocardial cells by changing various ion channel conductances (O'Hara, T. et al. (2011) PLoS Comput. Biol. 7:e1002061). The stimulus is applied to the first cell. Current flow is described by the following equation:

$$\frac{\partial V(x,t)}{\partial t} = D \frac{\partial^2 V(x,t)}{\partial x^2} - \frac{I_{ion\_}I_{stim}}{C_m} \quad (7)$$

where V is the membrane potential, t is time, D is the tissue diffusion coefficient (0.00092 cm$^2$/ms, calculated from Shaw and Rudy (Shaw, R. M. et al. (1997) Circ Res. 80:124-138)), $I_{ion}$ is the sum of transmembrane ionic currents, $I_{stim}$ is the stimulus current (300 µA/cm$^2$ for 0.5 ms), and $C_m$ is the membrane capacitance (1 µF/cm$^2$).

The fiber was paced at varying BCL from 800 ms to 1400 ms for 200 beats (mean heart rates=56 beats per minute (bpm)) in order to match the clinical data (56.8±6.4 bpm). Pseudo ECGs were computed from the transmembrane potential Vin using the integral expression as in Gima and Rudy (Gima, K. et al. (2002) Circ Res. 90:889-896). Heart rate corrected QT (QTc) was computed using Fridericia formula using the cubic root of RR interval (Fridericia, L. S. (1920) Acta Medica Scandinavica 53:469-486).

$$QT_C = \frac{QT}{\sqrt[3]{RR}} QT_C = \frac{QT}{\sqrt[3]{RR}} \quad (8)$$

Spatial APD dispersion was measured using the T-wave area indicator, which was calculated as the T-wave amplitude on the computed pseudo-ECGs. For this purpose, a 1-dimensional model of the transmural wedge preparation, as described in (Yang, P. C. et al. (2012) Front Physiol. 3:360), was stimulated by applying a standard short-long protocol as follows: The transmural wedge preparation was stimulated by a train of pulses (S1) at 1 Hz pacing rate until the steady-state was reached followed by a premature beat (S1-S2 interval=800 ms) and then a delayed beat (S3) was delivered after a long pause (S2-S3 interval=5000 ms). T-wave area calculations were computed as follows:

$$\sum_{t=t1}^{t2} |ecg(mV)| \cdot \Delta t \quad (9)$$

where $\Delta t=1$ ms, $t_1$ is the time where ECG equals to $T_{peak}-0.9*(T_{peak}$=minimum of left side oft-wave) and $t_2$ is the time where ECG equals to $T_{peak}-0.9*(T_{peak}$=minimum of right side of t-wave).

Frequency-Dependent QT Prolongation

The fiber was paced at 1 Hz for 1000 beats (S1) and then a second stimulus (S2) was applied after a varying RR interval (between 550 ms and 1150 ms). The QT interval, in response to S2, was recorded. The same simulations were carried out 11 times for both control and dofetilide 2 nM cases, and the relative changes in slope of relationship of QT and preceding RR intervals were calculated.

Two-Dimensional Simulations 2D simulations were performed to determine if proarrhythmic phenomena observed in lower dimensions cause reentrant arrhythmias.

$$\frac{\partial V(x,y,t)}{\partial t} = D_x \frac{\partial^2 V(x,y,t)}{\partial x^2} + D_y \frac{\partial^2 V(x,y,t)}{\partial y^2} - \frac{I_{ion\_}I_{stim}}{C_m} \quad (10)$$

where V is the membrane potential, x and y are distances in the longitudinal and transverse directions, respectively, $D_x$ and $D_y$ are diffusion coefficients in the x and y directions. Applicants simulated a heterogeneous and a homogenous cardiac tissues on a 300 by 300 pixel grid with $\Delta x=\Delta y=100$ µm. The heterogeneous tissue contains an endocardial region (fibers 1 to 180) and epicardial region (fibers 181 to 300). Applicants also incorporated anisotropic effects by setting $D_x$ and $D_y$ such that such that the ratio of conduction velocities is 1:2 (Young, R. J. et al. (2010) Proc Natl Acad Sci USA 107:15063-15068). A typical S1-S2 protocol was used for FIGS. 29A-29B. The tissue was first paced (s1) in a 0.5 cm×1.1 cm area on the left edge of the endocardial region, and a premature stimulus (s2) was then applied in a 1.8 cm×1.5 cm area on the top left corner of the endocardial region. Small amplitude inward currents were randomly applied between −0.1 to −0.44 pA/pF on each cell in both heterogeneous and homogenous tissues after 0.5 ms.

Supplementary Materials

Materials and Methods

The statistical uncertainties of the PMFs were estimated based upon the variance of the block-averaged reaction coordinate $\bar{z}_i$ for window i in umbrella sampling simulations according to Zhu and Hummer (Zhu, F. Q. et al. (2012) J Comput Chem. 33:453-465):

$$\text{var}[G(z)] = (k\Delta r)^2 \cdot \sum_{i=1}^{\frac{s-r_0}{\Delta r}} \text{var}(\bar{z}_i) \quad (S1)$$

where i is window number, k the force constant (10 kcal/mol·Å$^{-2}$ in simulations), dr the distance between the centers of the neighboring windows, $r_0$ the position of dofetilide in the bulk water phase and $G(r_0)$ was defined as zero. The variance of the reaction coordinate was obtained from block averaging (Rapaport, D.C. The Art of Molecular Dynamics Simulation. (Cambridge University Press, Cambridge, UK; New York, N.Y., ed. 2nd, 2004), pp. xiii, 54). The total number of sampled data M in each window simulation is divided into N (N=10 was used in this study) blocks of size B, $$M = N \cdot B \quad (S2)$$

The average in each block is given as $$\overline{z_n} = \frac{1}{B}\sum_{j=1}^{B} z_{j+(n-1)B} \text{ for } n = 1, \ldots, N \quad (S3)$$

And the corresponding variance var($\overline{x}$) is $$\mathrm{var}(\overline{z_t}) = \frac{1}{n(n-1)}\sum_{n=1}^{N}(\overline{z_n} - \overline{z_t})^2 \quad (S4)$$

Equations S1-S4 clearly show the accumulation of the statistical error along the reaction coordinate z.

D. Example 4. A Computational Pipeline for Cardiotoxicity Drug Screening

Applicants have an abundant set of computational tools available comprising the foundation of cellular level models. Included are three human models of ventricular cells including O'Hara-Rudy (O'Hara, T. et al. (2011) PLoS Comput. Biol. 7:e1002061), ten Tusscher (ten Tusscher, K. H. W. J. et al. (2006) Am J Physiol Heart Circ Physiol. 291:H1088-H1100), and Grandi-Bers (Grandi, E. et al. (2009) J Mol Cell Cardiol. 48:112-121), as well as the Soltis and Saucerman (Solstis, A. R. et al. (2003) Biophys J. 99:2038-2047) rabbit model that includes all the relevant components required for a detailed analysis, including accurate cellular electrophysiology, $Ca^{2+}$ handling (Shannon, T. R. et al. (2004) Biophys J. 87(5):3351-3371), and the cAMP-dependent protein kinase (PKA) (Saucerman, J. J. et al. (2003) J Biol Chem. 278(48):47997-48003) and $Ca^{2+}$/calmodulin-dependent protein kinase (CaMKII) (Soltis, A. R. et al. (2010) Biophys J. 99(7):2038-2047) phosphorylation pathways. Applicants have recently created a Grandi-Bers (Grandi, E. et al. (2009) J Mol Cell Cardiol. 48:112-121)-Soltis and Saucerman (Solstis, A. R. et al. (2003) Biophys J. 99:2038-2047) hybrid, which allows dynamic adrenergic signaling in adult human ventricular cells. Applicants have the Paci computational model of human pluripotent stem cell derived cardiomyocytes available for immediate use (Paci, M. et al. (2012) Biomed Eng Online 11:61) and are currently working to develop comprehensive computational models of atrial-like and ventricular-like iPSC-CMs based on data using methods based on the Wu lab. In addition to the cellular models Applicants have available an extensive set of in silico ion channel models for both wild-type and Long-QT mutants (Romero, L. et al. (2014) J Mol Cell Cardiol. 72:126-137; Moreno, J. D. et al. (2013) Circ Res. 113(7):e50-e61; Nawathe, P. A. et al. (2013) J Cardiovasc Electrophysiol. 24(9):1021-1027; Oren, R. V. et al. (2010) PLoS Comput Biol. 6(12):e1001041; Ahrens-Nicklas, R. C. et al. (2009) Cardiovasc Res. 82(3):439-447; Zhu, Z. I. et al. (2007) Am J Physiol Heart Circ Physiol. 293(6):H3480-H3489; Choe, C. U. et al. (2006) Hum Mol Genet. 15(19):2888-2902; Clancy, C. E. et al. (2003) Circulation 107(17):2233-2237; Clancy, C. E. et al. (2002) J Clin Invest. 110(9):1251-1262; Liu, H. et al. (2002) J Gen Physiol. 120(1):39-51; Clancy, C. E. et al. (2002) Circulation 105(10):1208-1213; Nuyens, D. et al. (2001) Nat Med. 7(9):1021-1027; Clancy, C. E. et al. (2001) Cardiovasc Res. 50(2):301-313; Clancy, C. E. et al. (1999) Nature 400(6744):566-569). More recently, Applicants have collected a rich set of models describing the interaction of drugs with cardiac ion channels and other receptors (Romero, L. et al. (2014) J Mol Cell Cardiol. 72:126-137; Moreno, J. D. et al. (2013) Circ Res. 113(7): e50-e61; Yang, P. C. et al. (2016) J Physiol. 594(3):567-593; Sihn, C. R. et al. (2016) J Biol Chem. 291(5):2499-2509; Perissinotti, L. L. et al. (2015) Biophys J. 108(6):1414-1424; Yang, P. C. et al. (2015) J Physiol. 593(6):1429-1442; Moreno, J. D. et al. (2011) Sci Transl Med. 3(98):98ra83; Clancy, C. E. et al. (2007) Am J Physiol Heart Circ Physiol. 292(1):H66-H75).

Tissue Scale. One-dimensional cable simulations: The cable equation can be solved to determine the change in membrane potential in time and space using the algebraic and differential equations described in (Luo, C. H. et al. (1991) Circ Res. 68(6):1501-1526).

the disclosure firsts simulate a homogenous fiber to elucidate the dynamical effects of electrotonic coupling in the presence of a given drug. Next, the components of $I_{ion}$ can be altered to investigate dynamics in a fiber comprised of endocardial, mid-myocardial (M), and epicardial cells as described for (Viswanathan, P. C. et al. (1999) Circulation 99:2466-2474; Viswanathan, P. C. et al. (2000) Circulation 101(10):1192-1198; Gima, K. et al. (2002) Circ Res. 90(8): 889-896) based on experimental observations (Sicouri, S. et al. (1991) Circ Res. 68(6):1729-1741; Antzelevitch, C. et al., Electrical Heterogeneity, the ECG, and Cardiac Arrhythmias, in Cardiac Electrophysiology: From Cell to Bedside, D. P. Zipes and J. Jalife, Editors. 2000, W. B. Saunders Company: Philidelphia:222-238; Laurita, K. R. et al. (2003) Circ Res. 92(6):668-675; Yan, G. X. et al. (1998) Circulation 98(18):1921-1927). One-dimensional (1D) simulations: 1D simulations can be carried out to coarsely identify parameter regimes of interest with a computationally tractable model as Applicants have described (Moreno, J. D. et al. (2011) Sci Transl Med. 3(98):98ra83).

Regimes exhibiting compelling dynamics can be investigated in higher dimensions. The following parameter changes with drug application can be predicted: APD restitution, conduction velocity (CV): CV is calculated between cell 49 and 50 at dV/dtmax. Because conduction block promotes reentrant arrhythmias and wavebreak causing fibrillation (Weiss, J. N. et al. (2005) Circulation 112(8): 1232-1240). the disclosure predicts the effect of drug to promote conduction block over 60 BPM-220 BPM to determine if block occurs. A period of vulnerability exists when electrical stimulation can initiate self-sustaining spiral waves (Mines, G. (1914) Trans Roy Soc Can. 4:43-53; Allessie, M. A. et al. (1973) Circ Res. 33(1):54-62) capable of degeneration into fibrillatory rhythms. The disclosure assess the "vulnerable window" to unidirectional block and retrograde conduction, suggesting reentrant arrhythmia in higher dimensions (Starmer, C. F. et al. (1991) Circulation 84(3):1364-1377; Starmer, C. F. et al. (1993) Biophys J. 65(5):1775-1787; Starmer, C. F. (2002) Int J Bifurc Chaos 12(9):1953-1968; Moreno, J. D. et al. (2011) Sci Transl Med. 3(98):98ra83). The refractory period can also be used to quantify drug specific increase in arrhythmia risk (Starmer, C. F. (2002) Int J Bifurc Chaos 12(9):1953-1968).

Two-dimensional (2D) simulations: 2D simulations can determine if proarrhythmic phenomena observed in lower dimensions cause reentrant arrhythmias and/or spiral wave breakup. Two-dimensional monolayer model: For two-dimensional simulations, the disclosure firsts simulate a homogeneous cardiac monolayer to elucidate the dynamical complexity introduced by a second dimension. The model can employ a partial differential equation realization of a network of coupled ventricular cells using the following equation with no-flux boundary conditions:

the disclosure incorporates anisotropy due to fiber orientation by setting $D_x$ and $D_y$ such that the longitudinal and transverse conduction velocities are 0.50 m/s and 0.25 m/s, respectively.

Transmural Tissue Simulations

Applicants simulated a transmural fiber composed of 360 ventricular cells ($\Delta x = \Delta y = 100$ μm) connected by resistances to simulate gap junctions (Faber, G. M. et al. (2000) Biophys J. 78(5):2392-2404). The fiber contains an endocardial region (cells 1 to 160) and epicardial region (cells 161 to 360), with a linear decreased in APD as indicated by experimental data (Lou, Q. et al. (2011) Circulation 123 (17):1881-1890; Glukhov, A. V. et al. (2010) Circ Res. 106(5):981-991). $G_{Kr}$ was used the index value of endocardium in the cell #1, and the index value of epicardium in cell #360. In the female model, $G_{Kr}$ was monotonically increased from 0.036 to 0.042. In the male model, $G_{Kr}$ was linearly increased from 0.046 to 0.05. AP simulations were carried out in epi-/endocardial cells by changing various ion channel conductance and gap-junctions (Yang, P. C. et al. (2012) Front Physiol. 3:360). The fiber was paced at BCL=1200 ms for 500 beats, and simulated arousal arrhythmias conditions (see above).

Applicants simulated a heterogeneous 2D cardiac tissue on 360 by 440 with $\Delta x = \Delta y = 150$ μm. The tissue contains an endocardial region (fibers 1 to 160) and epicardial region (fibers 161 to 360). Channel conductance and gap-junctions parameters are same as in the one-dimensional simulations. Current flow is described by the following equation:

$$\frac{\partial V(x, y, t)}{\partial t} = D_x \frac{\partial^2 V(x, y, t)}{\partial x^2} + D_y \frac{\partial^2 V(x, y, t)}{\partial y^2} - \frac{I_{ion} - I_{stim}}{C_m}$$

where V is the membrane potential, x and y are distances in the longitudinal and transverse directions, respectively, $D_x$ and $D_y$ are diffusion coefficients in the x and y directions. $I_{stim}$ is 180 mA/cm² for 0.5 ms. Applicants also incorporated anisotropic effects by setting $D_x$ and $D_y$ such that the ratio of conduction velocity is 1:2 (Young, R. J. et al. (2010) Proc Natl Acad Sci USA 107(34):15063-15068).

The tissue was first paced for 500 beats at BCL=1000 ms on the entire length of one side of tissue prior to application of SNS. And then the 501$^{th}$ beat was paced on the top left corner in an endocardial region with no PKA effects at BCL=1000 ms followed by PKA additions in the next beat paced in the same region.

Action potential duration mapping. Applicants construct "human transmural myocardial" based on data describing transmural action potential heterogeneity mapped from normal human left ventricle (Glukhov, A. V. et al. (2010) Circ Res. 106(5):981-991). First, ORd human model was used to generate a GKr lookup table corresponding to APD80. Next, experimental two-D APD80 map (100×100 virtual cells) was used to create a two-D Gkr Map using the GKr lookup table. Then the two-dimensional Gkr values (100×100) were used to simulate APD80. Applicants paced the female heart at 1 Hz and modified the length of APD80 to match the clinical observed QT intervals −400 ms (Stramba-Badiale, M. et al. (1997) Eur Heart J. 18(6):1000-1006; Nakagawa, M. et al. (2005) J Cardiovasc Electrophysiol. 16(3):278-284; Ebert, S. N. et al. (1998) J Womens Health 7(5):547-557). Applicants then construct a 3D wedge with $\Delta x = \Delta y = 200$ μm and $\Delta z = 500$ μm using this APD mapping data. Current flow is described by the following equation:

$$\frac{\partial V(x, y, z, t)}{\partial t} =$$
$$D_x \frac{\partial^2 V(x, y, z, t)}{\partial x^2} + D_y \frac{\partial^2 V(x, y, z, t)}{\partial y^2} + D_z \frac{\partial^2 V(x, y, z, t)}{\partial z^2} + -\frac{I_{ion} - I_{stim}}{C_m}$$

where V is the membrane potential. $D_x$, $D_y$ and $D_z$ are diffusion coefficients in the x, y and z directions. $I_{stim}$ is 150 mA/cm² for 0.5 ms. Applicants also incorporated anisotropic effects by setting $D_x$, $D_y$ and $D_z$ such that the ratio of conduction velocity is 2:4:1 (Young, R. J. et al. (2010) Proc Natl Acad Sci USA 107(34):15063-15068.).

Simulations and Predictions of Risk Factors

Apply computational modeling and simulation approaches to reveal genotype specific drug sensitivity and expose drug induced concealed disease. The disclosure applies high throughput computational approaches to carry out provocative screening tests for concealed disease derived from variants of unknown significance. The disclosure also predicts estrogen effects.

Specific methodology for provocative drug testing. The disclosure carrys out targeted "in silico mutagenesis" by modifying discrete transition rates in computational models of ion channels that result in targeted modification of channel activation, inactivation, deactivation or recovery from inactivation and resulting prolongation of the APD by 10 ms, 20 ms and 50 ms APD$_{90}$. An example of such changes to represent prototypical latent, mild and moderate allelic variants in hERG that may underlie a predisposition to aLQTs are shown at right. The same approach can be used for all subcellular targets. Provocative tests can be carried out with low and high concentrations of each simulated drug. For reproducibility, the low and high dose of each simulated drug is defined as the drug concentration that produced the same steady state (wild-type) WT APD$_{90}$ prolongation as 10 nM (as its therapeutic dose (Redfern, W. S. et al. (2003) Cardiovasc Res. 58(1):32-45)) and 40 nM dofetilide, respectively.

the disclosure applies computational modeling and simulation approaches to predict genotype specific therapeutic efficacy. The disclosure utilizes computational approaches to screen potential drugs for use to treat genotype specific excitable disorders in the heart. Here Applicants apply the computational framework to predict the effects of promising genotype-specific therapeutic candidates for inherited LQT-linked arrhythmias as well as acquired arrhythmia syndromes on emergent electrical activity in virtual cells and tissue. Computational analyses of disease-specific ion channel gating alterations and pharmacology present an opportunity to address which drug can best improve phenotype for a given genotype, and when it may exacerbate arrhythmogenic potential.

Drug-induced, or acquired Long-QT Syndrome (aLTQS), susceptibility which has recently been linked to normally benign DNA variants in the genes encoding hERG and its ancillary subunits that modify risk to drug-induced LQTS and arrhythmias (Bett, G. C. et al. (2006) J Physiol. 576(Pt 3):755-767; Sesti, F. et al. (2000) Proc Natl Acad Sci USA 97(19):10613-10618; Abbott, G. W. et al. (1999) Cell 97(2): 175-187; Yang, P. et al. (2002) Circulation 105(16):1943-1948). Large numbers of patients are exposed to numerous drugs with off-target effects that result in block of the major cardiac repolarizing current $I_{Kr}$, encoded by the gene hERG. Unfortunately, diagnosis based on baseline QT interval is not definitive (Rossenbacker, T. et al. (2007) Eur Heart J. 28(5):527-528) and genetic testing is difficult, expensive and is not always accessible (Shimizu, W. et al. (2003) J Am Coll Cardiol. 41(4):633-642). The potentially fatal outcome associated with aLQTS has led to black box warnings that limit the use of many drugs intended for treatment of cardiac dysrhythm, psychiatric disorders, gastrointestinal symptoms and infection (Drici, M. D. et al. (2000) Therapie 55(1): 185-193). Drugs have even been removed from the market due to unintended effects on cardiac repolarization (Redfern, W. S. et al. (2003) Cardiovasc Res. 58(1):32-45). Here, Applicants plan to reveal the pharmacological properties of $I_{Kr}$ blocking drugs that not only reveal predisposition to aLQTS, but also reveal the specific kinetic anomaly underlying the increased risk.

An example on the right is where model simulations predicted that a virtual drug that binds with low affinity to closed and high affinity to open states amplified action potential duration prolongation ($APD_{90}$) in simulated activation mutants (83 ms red) compared to WT cells (50 ms black). A drug with these properties was identified in the simulations to best unmask the mutant phenotype. Simulated addition of other virtual drugs failed to amplify APD differences and thus failed to unmask the mutant phenotype.

the disclosure systematicallys carry out "in silico mutagenesis" by altering discrete kinetic transition rates corresponding to activation, inactivation, deactivation and recovery from inactivation of $I_{Kr}$ channels. The disclosure thens identify the optimal properties of an $I_{Kr}$ blocker necessary to unmask the mutant phenotype for mild, moderate and severe mutants.

Additional Supplemental Methods for Risk Factors
Simulation of Genomic Sex Steroid Hormone Effects

TABLE 5

Sex-based differences in ion channel subunit expression from non-diseased ventricles (Gaborit, N. et al. (2010) J Mol Cell Cardiol. 49(4): 639-646). Ratios are relative to the male endocardial cell as Applicants published previously (Yang, P. C. et al. (2012) Front Physiol. 3: 360).

| Channels in the model | Gene | epi | | endo | |
|---|---|---|---|---|---|
| | | Male | Female | Male | Female |
| $I_{Ks}$ | KvLQT1 | 104.2 | 77.5 | 90.4 | 109.6 |
| | MinK (KCNE1) | 13.6 ± 1.4 *↑ | 7.3 ± 5 *↓ | 11.9 ± 4.2 **↑ | 5.8 ± 2.6 **↓ |
| | Ratio | 1.04 ± 0.04 | 0.87 ± 0.14 | 1 ± 0.12 | 0.83 ± 0.07 |
| | Functions | Co-express KvLQT1 & MinK shifts the voltage to more positive voltages. Also increase amplitude of expressed current. Only MinK shows significant differences between male and female. The stoichiometry of KCNE1:KCNQ1 in $I_{Ks}$ channels is a fixed 2:4 (Nakajo, K. et al. (2010) Proc Natl Acad Sci USA 107(44): 18862-18867). The ratio was calculated by modified the 1/3 of current activity according to MinK. | | | |
| $I_{Kr}$ | hERG (Kv11.1) | 179.5 ± 6.4 *↑ | 144.2 ± 41.1 *↓ | 164.8 ± 54.9 ↑ | 130.5 ± 65 ↓ |
| | Ratio | 1.09 ± 0.039 | 0.875 ± 0.25 | 1 ± 0.33 | 0.79 ± 0.39 |
| $I_{K1}$ | Kir2.1 | 94.5 | 93.8 | 104.1 | 79.7 |
| | Kir2.2 | 111.1 | 115.3 | 93.6 | 104.5 |
| | Kir2.3 | 91.2 ± 31.8 *↑ | 21.4 ± 10.6 f*↓ | 92.7 ± 26.8 ↑ | 55.2 ± 21.5 f↓ |
| | Ratio | 0.98 ± 0.12 | 0.74 ± 0.04 | 1 ± 0.09 | 0.86 ± 0.077 |
| | Functions | Kir2.x channels mediate cardiac $I_{K1}$ (Dhamoon, A. S. et al. (2004) Circ Res. 94(10): 1332-1339), however only Kir2.3 is significantly different. Kir2.3 changes the 1/3 of channel activity. | | | |
| $I_{to, s}$ | Kv1.4 | 12.1 ± 3.3 m *↑ | 5.4 ± 3.8 f * ↓ | 20.2 ± 4.0 m ** ↑ | 12.9 ± 5.2 f ** ↓ |
| | Ratio | 0.6 ± 0.16 | 0.26 ± 0.19 | 1 ± 0.2 | 0.64 ± 0.26 |
| $I_{NaK}$ | ATPase α1 | 207.7 ± 67 * ↓ | 513.4 ± 134.6 * ↑ | 269.0 ± 70.3 ** ↓ | 622.5 ± 287.7 ** ↑ |
| | α3 | 1481 ± 267 * ↑ | 917.8 ± 416.7 *↓ | 1547.6 ± 299.5 **↑ | 1014.2 ± 294.5 ** ↓ |
| | Ratio | 0.94 ± 0.18 | 0.7 ± 0.3 | 1.0 ± 0.2 | 0.79 ± 0.26 |
| | Functions | α3 is about 2-fold more activity than α1 in LV (Gaborit, N. et al. (2007) J Physiol. 582(Pt 2): 675-693). The ratio was calculated depended on 1/3 of α1 and 2/3 of α3. | | | |
| $I_{pCa}$ | PMCA1 | 31.7 | 46.4 | 44.1 | 48.1 |
| | PMCA4 | 377.0 ± 57.2 * ↓ | 682.1 ± 265.9 * ↑ | 426.8 ± 116.6 | 685.2 ± 379.7 |
| | Ratio | 0.88 ± 0.13 | 1.6 ± 0.6 | 1. ± 0.27 | 1.6 ± 0.89 |
| | Functions | PMCA1 serves a critical housekeeping function that requiring for the maintenance of basic cellular function. (Brini, M. (2009) Eur J Physiol. 457(3): 657-664). PMCA4 nearly ubiquitous distribution has similar role as PMCA1. PMCA4 was reported much more activity than PMCA1 in LV (Gaborit, N. et al. (2007) J Physiol. 582(Pt 2): 675-693), and there are no differences between genders in PMCA1. The ratio was calculated depended only on the PMCA4. | | | |

TABLE 5-continued

Sex-based differences in ion channel subunit expression from non-diseased ventricles (Gaborit, N. et al. (2010) J Mol Cell Cardiol. 49(4): 639-646). Ratios are relative to the male endocardial cell as Applicants published previously (Yang, P. C. et al. (2012) Front Physiol. 3: 360).

| Channels in the model | Gene | epi | | endo | |
|---|---|---|---|---|---|
| | | Male | Female | Male | Female |
| $I_{up}$ | SERCA2 | 4850.5 ± 146 m * ↓ | 6728.4 ± 1876.1 f * ↑ | 3410.4 ± 982.1 m | 3921.9 ± 1760.7 f |
| | Ratio | 1.42 ± 0.04 | 1.97 ± 0.55 | 1 ± 0.28 | 1.15 ± 0.5 |
| Calmodulin | CALM1 | 1329.5 | 991.9 | 879.8 | 1122.7 |
| | CALM3 | 1326.9 ± 220 * ↓ | 1955.5 ± 372.2 * ↑ | 1206.9 ± 187.7 ** ↓ | 1600.5 ± 242.9 ** ↑ |
| | Ratio | 1.07 ± 0.12 | 1.41 ± 0.2 | 1 ± 0.1 | 1.21 ± 0.14 |
| | Functions | CALM3 is more activity than CALM1 (~2-fold in LV) (Gaborit, N. et al. (2007) J Physiol. 582(Pt 2): 675-693). The ratio was obtained by changing the 2/3 of activity depends on CALM3. | | | |
| Gap-junction | Cx43 | 1124.1 ± 357 * ↑ | 728.6 ± 274.1 * ↓ | 1196.3 ± 311.7 ** ↑ | 810.9 ± 333.9 ** ↓ |
| | Ratio | 0.94 ± 0.3 | 0.61 ± 0.24 | 1.0 ± 0.26 | 0.68 ± 0.28 |

Simulation of Acute Sex Steroid Hormone Effects

The hormone concentrations used in the model simulations and their specific sources are as follows:

TABLE 6

The hormones 17β-estradiol (E2) concentrations used in the computational model.

| Early follicular stage | E2 = 0.1 nM |
|---|---|
| Late follicular stage | E2 = 1.0 nM |
| Luteal stage | E2 = 0.7 nM |

The E2 reference ranges are from Munro, C. J. et al. (1991) Clin Chem. 37(6):838-844 and Dighe, A. S. et al. (2005) Clin Biochem. 38(2):175-179.

TABLE 7

Progesterone concentrations used in the simulations.

| Early follicular stage | progesterone = 2.5 nM |
|---|---|
| Late follicular stage | progesterone = 2.5 nM |
| Luteal stage | progesterone = 40.6 nM |

Simulation of SNS-PKA Effects

Applicants simulated the effects of ISO on $I_{caL}$, $I_{ks}$, $I_{kb}$, $I_{Na}$, $J_{rel}$, $J_{up}$, troponin, and $I_{Nak}$, according to (O'Hara, T. et al. (2012) Heart Rhythm 9(2):275-282). In addition, progesterone and testosterone affect the conductance of $I_{Ks}$ but have no distinguishable effects on its kinetics under SNS stimulations. To model the effects of progesterone and testosterone on $I_{Ks}$, Applicants modified $G_{Ks}$ by scaling factors as indicated by the experimental data. In order to not overestimate the combined effects of DHT and SNS on $I_{Ks}$, Applicants assumed that the combined effects reached a saturating level that is less than an additive effect, as was shown for progesterone. If the combination were additive, Applicants would expect even more protection by testosterone in the setting of SNS.

Testosterone affect $I_{Ca,L}$ kinetics as shown in Table 8. DHT application during SNS stimulation affects the kinetics of $I_{Ca,L}$: the activation curve is less steep and is shifted to depolarized potentials compared to baseline (half maximal activation shifted $\Delta V_{1/2}$=5 mV and slop factor $\Delta k$=0.4 for DHT 100 nmol/L). The inactivation curve is shifted in the hyperpolarized direction and becomes steeper compared to baseline (half maximal inactivation shifted $\Delta V_{1/2}$=-2.1 mV and slope factor $\Delta k$=-0.3).

In the simulations, Applicants shifted the $I_{Ca,L}$ activation and inactivation curves by the same amount as above experimental data suggested to account for the different dosages of progesterone (baseline ISO: current conductance factor is 2.5, activation $1.0/(1.0+\exp((-(v+3.94+16))/4.23))$ and inactivation $1.0/(1.0+\exp((v+19.58+8.0)/3.396))$; Also the experimentally observed $I_{Ca,L}$ current reduction, the current reduction factor is 0.82 for DHT 35 nM (Table 9). Applicants used experimental data from 100 nM of DHT because DHT 35 nM is a maximally stimulating dose on $I_{Ca,L}$ (Table 10). Applicants then multiplied the basal conductance in control ISO conditions by these scaling factors for $I_{Ks}$ and $I_{Ca,L}$ when DHT is applied (see Table 10). The effects of progesterone on $I_{Ca,L}$ and $I_{Ks}$ shown in Table 11. Note that the ISO dose used in the experiments is a maximally stimulating dose.

TABLE 8

Experimental data for effects of testosterone on $I_{Ca, L}$.

| | Male | | | |
|---|---|---|---|---|
| Isoproterenol | $I_{max}$ (pA/pF) | $V_{1/2}$ (mV) | k | n |
| Activation | | -24.7 + 1.9 | 4.9 + 0.5 | 5 |
| ISO: | | -19.7 ± 5.3* | 5.3 ± 0.7 | |
| ISO + 100 nM DHT: | | | | |
| Inactivation | | | | |
| ISO: | -27.0 ± 3.6 | -26.8 ± 0.6 | 6.3 ± 0.3 | 7 |
| ISO + 100 nM DHT: | -19.9 ± 4.5 | -28.9 ± 0.7* | 6.0 ± 0.2 | |

TABLE 9

Experimental data for effects of DHT with cAMP + OA on $I_{Ca, L}$ current amplitude.

| DHT Concentrations | Normalized peak $I_{Ca,L}$ | | |
|---|---|---|---|
| | Mean (%) | SEM | N |
| 100 nM | 85.69788 | 2.228324 | 4 |
| 30 nM | 81.30512 | 10.62839 | 2 |
| 10 nM | 86.67992 | 8.337222 | 4 |
| 1 nM | 98.8005 | | 1 |

TABLE 10

Simulated effects of DHT on $I_{Ks}$ and $I_{Ca,L}$.

| Channel | Testosterone (DHT) 10 nM | Testosterone (DHT) 35 nM | DHT (SNS stimulation) 35 nM |
|---|---|---|---|
| $I_{Ks}$ | 1.38 | 1.4 | 3.52 |
| $I_{CaL}$ | 0.94 | 0.8 | 2.05 |
| Kinetics of $I_{CaL}$ | No effects | | dss = 1.0/(1.0 + exp((−(v + 3.94 + 16 − 5.0))/4.63)) fss = 1.0/(1.0 + exp((v + 19.58 + 8.0 + 2.7)/3.396)) |
| REF | (Bai, C. X. et al. (2005) Circulation 112(12): 1701-1710) | | Table 9 |

TABLE 11

Simulated effects of progesterone on $I_{Ks}$ and $I_{Ca,L}$.

| Channel | Progesterone (baseline) 2.5 nM | Progesterone (baseline) 40.6 nM | Progesterone (SNS stimulations) 2.5 nM | Progesterone (SNS stimulations) 40.6 nM |
|---|---|---|---|---|
| $I_{Ks}$ | 1.19 | 1.4 | 3.488 | 3.52 |
| $I_{CaL}$ | 1.0 | 1.0 | 2.4 | 2.05 |
| Kinetics of $I_{CaL}$ | No effects | | dss = 1.0/(1.0 + exp((−(v + 3.94 + 16 − 1.5))/4.73)) fss = 1.0/(1.0 + exp((v + 19.58 + 8.0 + 1.7)/3.596)) | dss = 1.0/(1.0 + exp((−(v + 3.94 + 16 − 4.4))/5.23)) fss = 1.0/(1.0 + exp((v + 19.58 + 8.0 + 3.7)/3.096)) |
| REF | (Nakamura, H. et al (2007) Circulation 116(25): 2913-2922) | | | |

TABLE 12

QT intervals at two pacing cycle lengths.

| | QT interval (ms) under SNS stimulus | | | |
|---|---|---|---|---|
| Cases | Early | Late | Luteal | DHT 35 nM |
| BCL = 800 ms | 534 | 550 | 526 | 403 |
| BCL = 1000 ms | 557 | 572 | 547 | 418 |

Pacing Protocol for Arousal Arrhythmias Conditions

Cells were paced for 400 beat (BCL=1000 ms or 1200 ms) with no PKA effects followed by 10 beats (BCL=800 ms) with PKA application. The Pg reference ranges (used in Applicants' initial study) are from Janse de Jonge, X. A. et al. (2007) Circulation 116(25):2913-2922 and Munro, C. J. et al. (1991) Clin Chem. 37(6):838-844.

Action potential duration mapping. Applicants reconstructed "human transmural myocardial" based on data describing transmural action potential heterogeneity mapped from normal human left ventricle (Glukhov, A. V. et al. (2010) Circ Res. 106(5):981-991. First, ORd human model was used to generate a $G_{Kr}$ lookup table corresponding to $APD_{80}$. Next, experimental two-D $APD_{80}$ map (100×100) was used to create a two-D $G_{kr}$ Map using the $G_{Kr}$ lookup table. Then the two-dimensional $G_{kr}$ values (100×100) were used to simulate $APD_{80}$. Applicants paced the female heart at 1 Hz and modified the length of $APD_{80}$ to match the clinical observed QT intervals ~400 ms (Stramba-Badiale, M. et al. (1997) Eur Heart J. 18(6):1000-1006; Nakagawa, M. et al. (2005) J Cardiovasc Electrophysiol. 16(3):278-284; Ebert, S. N. et al. (1998) J Womens Health 7(5):547-557). Applicants then contracted 3D wedge on 100 by 100 by 1 with Δx=Δy=200 μm and Δz=500 μm using this APD mapping data. Current flow is described by the following equation:

$$\frac{\partial V(x, y, z, t)}{\partial t} = D_x \frac{\partial^2 V(x, y, z, t)}{\partial x^2} + D_y \frac{\partial^2 V(x, y, z, t)}{\partial y^2} + D_z \frac{\partial^2 V(x, y, z, t)}{\partial z^2} + -\frac{I_{ion}\_I_{stim}}{C_m}$$

where V is the membrane potential. $D_x$, $D_y$ and $D_z$ are diffusion coefficients in the x, y and z directions. $I_{stim}$ is 150 mA/cm$^2$ for 0.5 ms. Applicants also incorporated anisotropic effects by setting $D_x$, $D_y$ and $D_z$ such that the ratio of conduction velocity is 2:4:1 (Young, R. J. et al. (2010) Proc Natl Acad Sci USA 107(34):15063-15068).

E. Example 5. In Silico Prediction of Cardiopharmacology: From Chemistry to Rhythm Methods Homology Modeling and Docking The 3D coordinates of the pore domain of hERG1 channel in the open- and open-inactivated states were built previously based on the combination study of ROSETTA-membrane de-novo, homology modelling and MD simulations (Durdagi, S. et al. (2012) J Chem Inf Model. 52(10):2760-2774). The structural difference between open state and open-inactivated states is schematically illustrated in FIGS. 23A and 23B.

The structure of dofetilide (FIG. 23C) was downloaded from ZINC database (Irwin, J. J. et al. (2012) J Chem Inf Model. 52(7):1757-1768). Dofetilide was docked in silica to the developed hERG1 models representing the open and open-inactivated states of the channel with Glide-XP (extra precision) docking program from Schrödinger (Schrödinger LLC, Portland, USA, www.schrodinger.com). The best-scored binding poses for dofetilide binding to an intra-cavitary site in the open and open-inactivated HERG1 were chosen as the initial structure for the next step.

Molecular Dynamic Simulation Protocol

The hERG1-dofetilide complexes from the docking study were embedded in a DPPC bilayer. The membrane normal axis was aligned along the z axis. The system was solvated in TIP3P water molecules with 150 mM KCl. Both systems (open and open-inactivated hERG1 with dofetilide, respectively) were built and pre-equilibrated with the CHARMM program using CHARMM27 force field (Brooks, B. R. et al. (2009) J Comput Chem. 30:1545-1614; MacKerell, A. D. et al. (1998) J Phys Chem B 102:3586-3616; Noskov, S. Y. et al. (2008) J Mol Biol. 377:804-818; Noskov, S. Y. et al. (2004) Nature 431(7010):830-834). The topology and parameters of dofetilide were initially generated with the CHARMM generalized force-fields (CGenFF) (Vanommeslaeghe, K. et al. (2010) J Comput Chem. 31(4):671-690) and then used to develop a specific force-field set using an automated force-field development protocol developed by Huang and Roux. After 10000 steps of Steepest-Descent minimization run, each system was equilibrated for I ns with a harmonic restraint, applied to backbone of the protein, gradually decreased from 10 to 1 kcal/(mol·Å$^2$). The systems were then equilibrated for 10 ns with the harmonic restraints of 1 kcal/(mol·Å$^2$) applied on the backbone of hERG1 using NAMD2.9 program package with the time step of 2 fs (Phillips, J. C. et al. (2005) J Comput Chem. 26:1781-1802). The NPaT ensemble was used for all simulations with pressure set to 1 atm using the Nose-Hoover Langevin piston method and temperature to 310.15 K with Langevin dynamics (Feller, S. E. et al. (1995) J Chem Phys. 103:4613-4621; Martyna, G. J. et al. (1994) J Chem Phys. 101:4177-4189). Long-range electrostatic interactions were treated by the particle mesh Ewald (PME) algorithm (Essmann, U. et al. (1995) J Chem Phys. 103:8577-8593). Non-bonded interactions were switched off at 10-12 Å. The systems were simulated with periodic boundary conditions applied in all directions. The last frame of each simulation was chosen to set up the Umbrella Sampling simulation in the next step.

Potential of Mean Force for Dofetilide Binding

To explore energetics of dofetilide binding Applicants used Umbrella Sampling simulations to evaluate Potential of Mean Force (PMF) for drug binding from the hERG 1 channel. It was performed with harmonic biasing potentials with a force constant of 10 kcal/(mol·Å$^2$) and the reaction coordinate was defined along the z-axis (see FIG. 24A). The zero position along the z-axis is the center of mass of the Cα of residues 623-628 in the filter. The flat-bottom cylindrical constraints with radius of 10 Å was used to cap lateral displacement of the bound drug. The reaction coordinate for each window was the distance along the z-axis between the center of mass of dofetilide and the zero position. The sampling windows were spaced every 0.5 Å from −7.5 Å to −49.5 Å resulting in 85 windows for open hERG1 and from −8.5 Å to −38.0 Å resulting in 60 windows for open-inactivated hERG I. The simulation time per window was set to 22 ns. The total simulation time was 1.87 μs and 1.32 μs for open and open-inactivated systems, respectively. The binding free energy profiles were rebuilt based on the last 20 ns/window with the use of Weighted Histogram Analysis Method (WHAM) ((Kumar, S. et al. (1992) J Comput Chem. 13:1011-1021)), and the tolerance for WHAM was set to 10$^{-7}$. The summary of the methods used for estimation of errors involved with PMF computations, KD, and Free energy estimations of the bound drug are collected in the supplementary materials section.

Diffusion Coefficient

The local diffusion coefficient is related to the local static friction coefficient ξ:

$$\xi = \int_0^\infty \xi(t)dt$$

as $$D(z) = \frac{RT}{\xi} = \frac{(RT)^2}{\int_0^\infty (\Delta F(z,t) \cdot \Delta F(z,0))dt}$$

where R is the gas constant, T is the absolute temperature, and the local time-dependent friction coefficient of the diffusant dofetilide ξ(C) is related to the time autocorrelation function of the fluctuations of the constraint force around its average over the simulation time:

$$\xi(t) = \frac{(\Delta F(z,t) \cdot \Delta F(z,0))}{RT}$$

where $$\Delta F(z,t) = F(z,t) - (F(z))_2$$

where $< >_t$ is the average over the time t.

Rate Constants

The estimation of association rate constant is based on the assumption that the binding process is a purely diffusion-controlled reaction. Debye derived the Smoluchiwski rate constant to $$k_{on}^{-1} = (4\pi)^{-1} \int_k^{on} \frac{e^{\beta \varphi \mu y(\tau)}}{r^2 D(r)} dr$$

where $\beta = (k_y T)^{-1}$ and D(r)=D as a constant (5.77×10$^{-6}$ cm$^2$/s in this study).[22, 23] And $k_{off}$ can be calculated based on $$k_v = \frac{k_{on}}{k_{on}}.$$

For full details of computational methods and experimental methods, please see Supplementary Information.

Results

State-Dependent Free Energy Profiles for Drug Unbinding

The computed PMFs for dofetilide binding to open and open-inactivated states display well-pronounced state-dependent properties. As shown in FIG. 24B, PMF shows two well-separated energy wells for the open state hERG1 channel. This suggests that dofetilide has at least two binding sites in the intra-cavitary site of the channel. These sites are well-localized in the open state of the channel, but inactivated pore resulted in a broad and shallow binding surface at the bottom of the distal S6. The energy wells for dofetilide binding to the open state are around −12 kcal/mol for the inner binding site and −13 kcal/mol for the outer binding site. At the same time PMF for dofetilide binding to open-inactivated state displays flat basin between two binding sites and the energy wells are less than −10 kcal/mol in the cavity of open-inactivated hERG1. The negative binding free energy with −12.56 kcal/mol and the small equilibrium dissociation constant with 1.40E-09 M suggest greater drug accessibility to the intra-cavitary site in the open hERG1 channel.

The position-dependent diffusion coefficient of the drug in open and open-inactivated states (FIGS. 25B and 25C) shows little dependence of the drug diffusion on the state of the channel. Once dofetilide reaches the gate, the diffusion coefficient sharply decreases to nearly 0. Therefore, the dofetilide binding process is considered as a purely diffusion-controlled reaction. According to the boundary condition assumption in the diffusion equation, the radius are defined as the distance between the energy barrier and well. Therefore, the rate constants are estimated as in Table 13:

TABLE 13

Rate Constants for two binding sites of each state of hERG1.

| | outer binding site (z = −14 Å) | inner binding site (z = −10 Å) |
|---|---|---|
| $k_{on}(M^{-1}*s^{-1})$ | 2.87E+09 | 1.09E+04 |
| $K_{off}(s^{-1})$ | 6.22E+00 | 1.52E−05 |
| $k_D$ (M) | 2.16E−09 | 1.40E−09 |

F. Example 6

Methods

Dofetilide Binding Model

The wild-type drug-free $I_{Kr}$ model was used as previously described in (Tanskanen, A. J. et al. (2007) Math Biosci. 208(1):125-146). The $I_{Kr}$ drug-channel model parameters for the $K_{on}$ and $K_{off}$ rates of dofetilide are taken from MD predicted data (FIG. 6B). To simulate drug interactions with $I_{Kr}$, Applicants used measured affinities and drug diffusion rates used to constrain the drug "on" and "off" rates. Drug on rates=[drug]*$K_{on}$ and drug off rates=[drug]*$K_{off}$.

1D Fiber Simulations

Applicants simulated a transmural fiber composed of 165 ventricular Human cells [4] ($\Delta x=\Delta y=100$ μm) connected by resistances to simulate gap junctions (Faber, G. M. et al. (2000) Biophys J. 78:2392-2404). The fiber contains an endocardial (cells 1 to 60), M-cell (cells 61 to 105) and epicardial (cells 106 to 165) regions, which described in (O'Hara, T. et al. (2011) PLoS Comput. Biol. 7:e1002061). The stimulus is applied to the first cell. Current flow is described by the following equation:

$$\frac{\partial V(x,t)}{\partial t} = D\frac{\partial^2 V(x,t)}{\partial x^2} - \frac{I_{ion}\_I_{stim}}{C_m}$$

where V is the membrane potential, t is time, D is the tissue diffusion coefficient (0.00092 cm²/ms, calculated from Shaw and Rudy (Shaw, R. M. et al. (1997) Circ Res. 80:124-138)), Lon is the sum of transmembrane ionic currents, $I_{stim}$ is the stimulus current (300 μA/cm² for 0.5 ms), and $C_m$ is the membrane capacitance (1 g/cm²).

The fiber was paced at varying BCL from 800 ms to 1200 ms for 200 beats (Heart rates varied between 50-75 bpm). Pseudo ECGs were computed from the transmembrane potential $V_m$ using the integral expression as in Gima and Rudy (Gima, K. et al. (2002) Circ Res. 90:889-896). Heart rate corrected QT (QTc) was computed using Fridericia formula using the cube-root of RR (Fridericia, L. S. (1920) Acta Medica Scandinavica 53:469-486).

$$QT_C = \frac{QT}{\sqrt[3]{RR}}$$

G. Example

It is increasingly apparent in the biomedical sciences that mechanisms of biological function cannot be observed or readily predicted solely through the study of constituent elements. This is especially clear in the longstanding failures of drug treatment in heart rhythm disturbances. The vital hindrance to pharmacological treatment of electrical rhythm disturbances is a persistent inability to predict the effective or harmful action of drugs. For example, the CAST (The Cardiac Arrhythmia Suppression Trial (CAST) Investigators (1989) N Engl J Med. 32:406-412) and SWORD (Waldo, A. L. et al. (1996) Lancet 348:7-12) clinical trials showed that common antiarrhythmic drugs increased mortality and risk of sudden cardiac death in patients. Almost thirty years later, there is still no way to differentiate useful or potentially harmful drugs for treating arrhythmia. In some implementations, the present disclosure describes proposes a novel multiscale model for predictive cardiac pharmacology intended to begin to solve this critical problem that can apply to 1) drug prediction 2) preclinical screening, and 3) drug therapy for specific clinical manifestations of excitable disease. Successful development of the framework can allow for future expansion to multiple cardiac disease states including inherited syndromes, ischemia and heart failure. The framework described herein is configured to serve purposes in governmental regulation, industry, academia and medicine.

Research endeavors to reveal arrhythmia and drug mechanisms have generally focused on specific temporal and spatial scales of the cardiac system.

Figure 33:
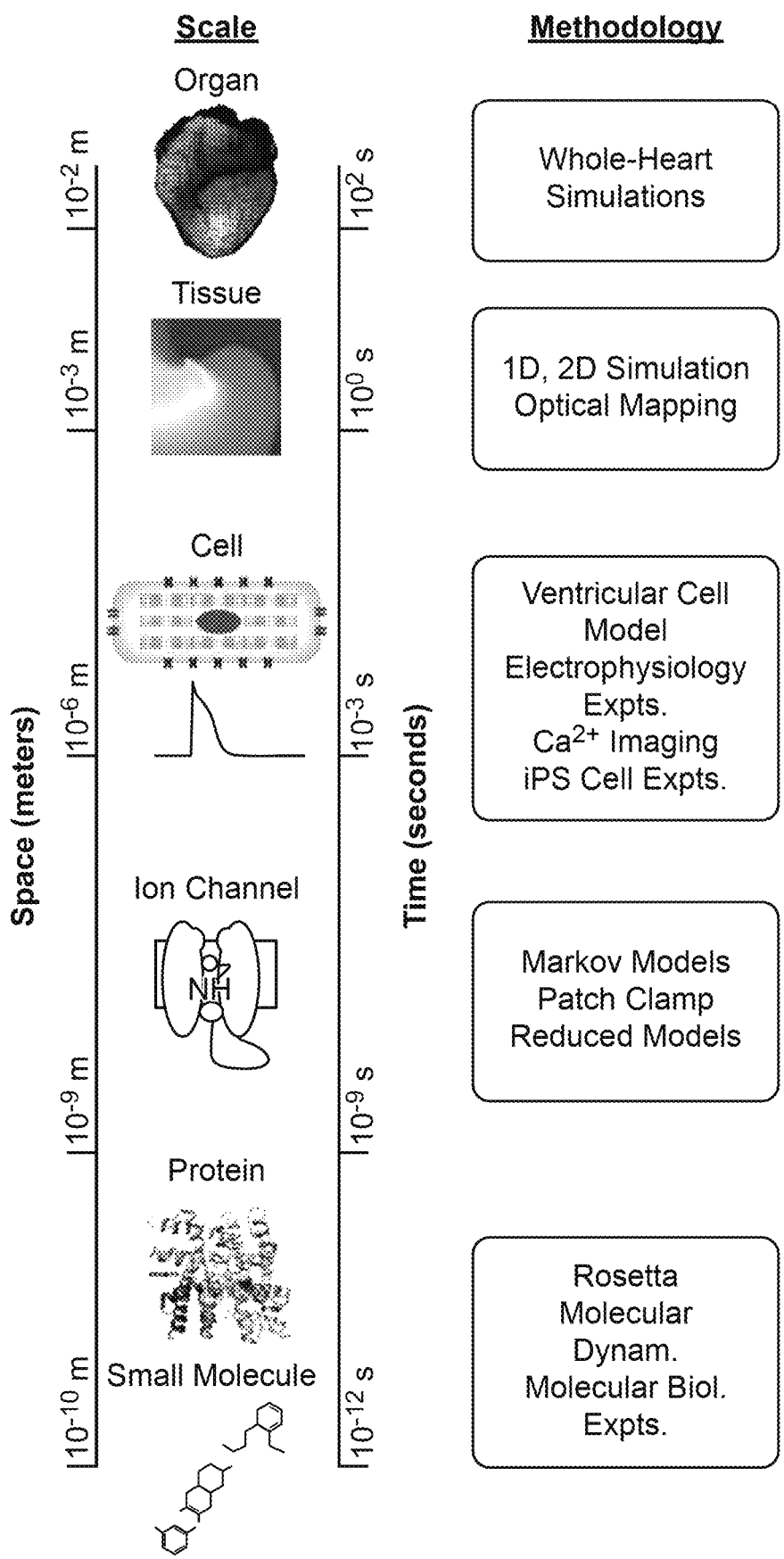
FIG. 33 shows investigators, time/space scales & methodologies. (CC=Colleen Clancy, TA=Toby Allen, VYY=Vladimir Yarov-Yaravoy, RH=Robert Harvey, DB=Don Bers, NC=Nipavan Chiamvimonvat, TL=Tim Lewis, CR=Crystal Ripplinger, NT=Natalia Trayanova, AM=Andrew McCulloch)

Referring now to FIG. 33, the system includes the Rosetta-Membrane computational method, which has expanded to modeling of small molecule interactions with voltage-gated Na and hERG channels. The system is configured to perform multimicrosecond molecular dynamics simulations to provide molecular-level descriptions of sodium channel function and drug interactions. The system described herein also utilizes a computational model, informed and validated by experimental data, predicting Na channel drug effects (Moreno, J. D. et al. (2011) Science Translational Medicine 3:98ra83; Greenemeier, L. (2011) Virtual Ventricle: Computer Predicts Dangers of Arrhythmia Drugs Better than Animal Testing, www.scientificamerican.com/article.cfm?id=computer-heart-simulation-arrhythmia; Stoye, E. (2011) Good News for Broken Hearts, www.thenakedscientists.com/HTML/content/news-archive/news/2361). Experiments in rabbit hearts performed in Crystal Ripplinger's Lab employing state-of-the-art highspeed, high-resolution optical imaging of transmembrane potential validated the model predictions. Simulations from Natalia Trayanova's Lab in image based 3-dimensional high-resolution MRI-based human reconstructed ventricles allowed generation of organ level model predictions.

Aim 1: To establish a multiscale model for predictive cardiopharmacology. The first step for predicting emergent drug effects on the heart is determining and modeling the kinetics of primary and off-target drug interactions with subcellular targets. The bulk of antiarrhythmics target ion channels and have complex interactions at the atomic scale, which may be altered by genetic polymorphisms and mutations. Moreover, changes in voltage result in changes to apparent affinities of drugs for their receptors at the protein function scale. Bi-directional feedback exists because drugs alter the cell scale action potential waveform, which affects the potency of drugs. In order to predict drug efficacy, the dynamical complexity of the drug kinetics should be considered to predict the combined emergent effects in the tissue and organ scales. Similarly, reentrant and triggered ventricular arrhythmias are inherently emergent tissue scale phenomena that are strongly influenced by the intracellular electrical coupling because of the ~mm electrical space constant of myocardium. No single cell model or experiment can recapitulate the in-vivo electrocardiographic phenotype.

Recently, drugs that block a non-inactivating component of the cardiac Na current (late Na current, $I_{NaL}$) have been suggested as therapeutics in inherited and acquired cardiac diseases (Bennett, P. B. et al. (1995) Nature 376:683-685; Wang, Q. et al. (1995) Cell 80:805-811; Maltsev, V. A. et al. (1998) Circulation 98:2545-2552; Maltsev, V. A. et al. (2006) Cardiovascular Research 69:116-127; Song, Y. et al. (2006) J Pharmacol Exp Ther. 318:214-222; Sossalla, S. et al. (2010) J Am Coll Cardiol. 55:2330-2342; Hund, T. J. et al. (2008) Journal of Molecular and Cellular Cardiology 45:420-428). Increased $I_{NaL}$ leads to action potential prolongation, disruption of normal cellular repolarization, development of arrhythmia triggers, and propensity to ventricular arrhythmia. $I_{NaL}$ is small in magnitude compared to peak ($I_{Napeak}$) (~1-3%), but alters cell action potentials and increases Na loading. With increasing recognition that multiple cardiac pathologies share $I_{NaL}$ upregulation, specific pharmacological inhibition of $I_{NaL}$ is desirable. The antianginal agent ranolazine shows selectivity for $I_{NaL}$ versus $I_{Napeak}$, representing a drug archetype for targeted reduction of $I_{NaL}$. However, like most drugs, ranolazine lacks specificity and also blocks the hERG current (IKr) causing QTc prolongation (Koren, M. J. et al. (2007) J Am Coll Cardiol. 49:1027-1034; Kaufman, E. S. (2008) J Cardiovasc Electrophysiol. 19:1294-1295). With its preferential targeting of INaL, ranolazine may be still an appropriate drug to target diseases marked by increased $I_{NaL}$ (Chaitman, B. R. (2006) Circulation 113:2462-2472; Moreno, J. D. et al. (2013) Circ Res. 113:e50-e61). In Aim 1 ranolazine can be compared to the pure Na channel blocker lidocaine in multiscale model simulations to predict and compare their effects on normal cardiac electrophysiology and in the setting of increased $I_{Na,L}$. A novel link between scales can be established in Aim 1: Atomic scale predictions can estimate drug docking sites and association and dissociation rates for lidocaine and ranolazine to closed, open and inactivated states of the cardiac Na and hERG K channels. As described herein, these simulations can inform kinetic parameters for functional scale Markov models of drug interactions with cardiac channels. Drug-channel models can be integrated into virtual cardiac cell, tissue and organ level models to predict emergent drug effects. Experiments at each scale can test and validate the model predictions.

Aim 2: To apply the multiscale model to screen preclinical compounds. Increases in $I_{NaL}$ can promote arrhythmias by prolonging APD, leading to early afterdepolarizations (EADs) and reducing repolarization reserve (Boutjdir, M. et al. (1991) Cardiovasc Res. 25:815-819; Sicouri, S. et al. (1997) J Cardiovasc Electrophysiol. 8:1280-1290; Undrovinas, A. et al. (2008) Cardiovascular & Hematological Agents in Medicinal Chemistry 6:348-359; Zaza, A. et al. (2008) Pharmacol Ther 119:326-339; January, C. et al. (1989) Circ Res. 64:977-990). The first studies on the preclinical compound GS-458967 in 2013 showed potent selective targeting of $I_{NaL}$ (GS967, IC50 for $I_{NaL}$=130 nM) allowing for specific therapeutic inhibition and study of the physiological and pathological role for $I_{NaL}$ in the heart. Thus, in Aim 2, the multiscale model can be applied to screen and predict effects of GS967 on cardiac cells, tissue and organ electrophysiology. Experiments can be carried out at all scales to validate the predictions. The multiscale model can also be applied to predict the GS967 binding site and the atomic determinants of GS967 potent selective block of $I_{Na,L}$. The GS967 analogs can be screened in the atomic model to identify those with even higher $I_{NaL}$ specificity. The most promising analog can be synthesized, screened in the multiscale model and experimentally validated.

Aim 3: To expand the multiscale model to screen for disease-specific drug therapy. In Aim 3, the multiscale model can be expanded to predict efficacy of ranolazine, lidocaine and GS967 as disease-specific therapies. Targeted pharmacological inhibition of $I_{NaL}$ has been suggested as therapeutic in a range of cardiac disorders from acquired (i.e., drug-induced) Long-QT syndrome (aLQTS) induced by $I_{Kr}$ block, to arrhythmogenic states marked by pathological late Na current including inherited Long-QT Syndrome. The multiscale model can be used to probe and comparatively predict effects of ranolazine, lidocaine and GS967 in pathological situations. Genotype-specific computational models of LQT3 mutations can be used to test drugs with varying specificity to target $I_{NaL}$. Risk of aLQTS has led to black box warnings limiting the use of otherwise promising drugs for treating cardiac dysrhythm, psychiatric disorders, gastrointestinal symptoms and infection (Drici, M. D. et al. (2000) Therapie 55:185-193). Hence, the multiscale model can be used to test the hypothesis that adjunctive $I_{NaL}$ block is a potential therapeutic strategy to reduce the incidence of acquired Long-QT. The efficacy of ranolazine, lidocaine, and GS967 can mitigate aLQTS caused by dofetilide. Patient-derived induced pluripotent stem cells (iPSCs) and cultured monolayers, and a rabbit model of acquired Long-QT can be used for model validation.

Despite attempts for more than 50 years, there is no way to predict how drugs can alter the emergent electrical behavior generated in the heart or other organs. The present disclosure describes a novel multiscale model that can be used to predict drug or agent effects on cardiac dynamics for 1) drug prediction (Lu, H. R. et al. (2010) Br J Pharmacol. 160:60-76), 2) preclinical screening and, 3) to predict therapy for specific arrhythmia syndromes. The present disclosure describes a system that brings together model simulations at the level of the atom—for the small molecule scale of the drug and the molecule scale of the channel—and simulations at the functional level of the protein, cell, tissue and organ. The power of combining these scales in a predictive framework is that it can allow, for the first time, a way to derive on and off rates of drugs from atomic scale simulations and to then use these values to inform and build functional level channel models. This approach can be used for varied genotypes, which can even be used to predict individual responses to drug or agent therapy. Although cardiac simulations at the channel, cell and tissue level have been long developed are not new techniques per se, they have been repeatedly proven, ensuring success of the plan to apply their predictive power to pharmacology. The novel linkages can connect mature approaches to emerging modeling approaches at the atomic and organ scales.

The multiscale model can be used to address key research questions in each Aim to drive model development and exemplify applications. Ultimately, the approach is a scalable framework that can be automated to interact with other developing technologies, including high-throughput electrophysiology measurements (such as PatchExpress (Penniman, J. R. et al. (2010) Journal of Pharmacological and Toxicological Methods 62:107-118; Mo, Z. L. et al. (2009) Journal of Pharmacological and Toxicological Methods 60:39-44; Zeng, H. et al. (2008) Assay Drug Dev Technol. 6:235-241; Trepakova, E. S. et al. (2007) Assay Drug Dev Technol. 5:617-627; Ly, J. Q. et al. (2007) Clin Lab Med. 27:201-208; Dubin, A. E. et al. (2005) J Biomol Screen. 10:168-181) and Ionworks (Bridal, T. R. et al. (2010) Assay Drug Dev Technol. 8:755-765; Jow, F. et al. (2007) J Biomol Screen 12:1059-1067; Harmer, A. R. et al. (2008) Journal of Pharmacological and Toxicological Methods 57:30-41;

Bridgland-Taylor, M. H. et al. (2006) Journal of Pharmacological and Toxicological Methods 54:189-199; Sorota, S. et al. (2005) Assay Drug Dev Technol 3:47-57; Schroeder, K. et al. (2003) 3 Biomol Screen 8:50-64), drug development via progress in synthetic biology (Nattel, S. et al. (2006) Nature Reviews Drug Discovery 5:1034-1049), and even personalized medicine via drug screening in patients' own induced pluripotent stem (iPS) cell-derived cardiomyocytes (Braam, S. R. et al. (2010) Stem Cell Res 4:107-116). These technologies in conjunction with the multiscale models described herein form an interactive multiscale modeling and simulation driven process that can be used in the regulatory process prior to drug approval, in academia for research, in industry for drug and disease screening, and for patient oriented medicine in the clinic. Expansion can also be facilitated through the Working Groups, which can allow shared resources to promote collaborative expansion of the multiscale approach to other key drug targets including other ion channels, GPCRs and subcellular signaling components. The Working Group can be critical to promote standards (C and CellML) that can bridge model codes and interface directly with existing tools that are available from the National Biomedical Computing Resource (NBCR), particularly "Continuity 6".

Specific Aim 1: To Develop a Multiscale Model for Predictive Pharmacology.

Aim 1 Rationale: Most antiarrhythmic drugs have complex interactions with multiple channels, conformational state specificity, bioactive metabolites and neutral and charged fractions, the latter of which has intrinsic voltage dependence. Drugs alter the action potential waveform, which in turn affects drug potency. Applicants' goal in this aim is to capture the complex features of drug channel interactions in a multiscale model to allow for computational prediction of drug effects on cardiac electrical activity. The predictive utility of the model is confirmed by simulating two cardiac Na channel drugs, lidocaine and ranolazine. While lidocaine is a pure Na channel blocker, ranolazine also blocks Ix, resulting in QTc prolongation (Koren, M. J. et al. (2007) J Am Coll Cardiol. 49:1027-1034; Kaufman, E. S. (2008) J Cardiovasc Electrophysiol. 19:1294-1295). However, with its $I_{NaL}$ targeting, ranolazine may be effective to treat disorders with inherited or acquired $I_{NaL}$ enhancement.

A prototype proof-of principle multiscale model has been developed for efficient prediction of: 1) Conformation state-specific atomic-scale determinants of drug interaction that cannot be determined experimentally without exhaustive crystallographic and/or mutagenesis experiments. 2) Rates from atomic scale simulations of interactions for Na channel blocking drugs at the protein function scale. 3) High throughput prediction of emergent drug effects on cell, tissue and organ cardiac electrical behavior for which no comparable experiment exists. 4) Emergent behaviors that can be mapped back to underlying parameters through component dissection, to reveal mechanisms of emergent behaviors, a function for which there is no experimental counterpart.

The present disclosure uses atomic scale molecular docking simulations in Rosetta and molecular dynamics (MD) simulations for wild-type (WT) and inactivation deficient ΔKPQ mutant human Nav1.5 channels to predict binding sites and affinity of charged and neutral fractions of lidocaine and ranolazine to closed, open and inactivated channel states. Aside from large $I_{NaL}$ (~1% of $I_{Napeak}$), the ΔKPQ channel is very similar to WT (Chandra, R. et al. (1998) Circulation 98:55; Fredj, S. et al. (2006) Circ Res. 99:1225-1232; Dumaine, R. et al. (1998) American Journal of Physiology-Heart and Circulatory Physiology 274:H477-H487; Chandra, R. et al. (1998) American Journal of Physiology-Heart and Circulatory Physiology 43: H1643-H1654), making ΔKPQ well suited for comparing efficacy of $I_{NaL}$ block. Atomic scale Rosetta predictions of free energy of drug binding can be translated to drug affinity ($IC_{50}$) through an existing molecular dynamics based approach (Buch, I. et al. (2011) Proc Natl Acad Sci USA 108:10184-10189). High yield batch predictions of drug trajectories in the binding site can allow calculation of an equilibrium distribution of free energies of interactions to inform kinetic rates of drug-channel interactions with discrete states in the Markov functional models. Free energy perturbation (FEP) simulations are performed by the system (such as the system 100) to determine the relative free energies of drugs with similar structures to pinpoint the molecular determinants of drug affinity for Nav channels. Drug-channel models can be integrated into virtual cardiac cellular, tissue and organ models to predict emergent drug effects. Predictions can be tested and validated experimentally in rabbit cells, tissues and organs.

Figure 34:
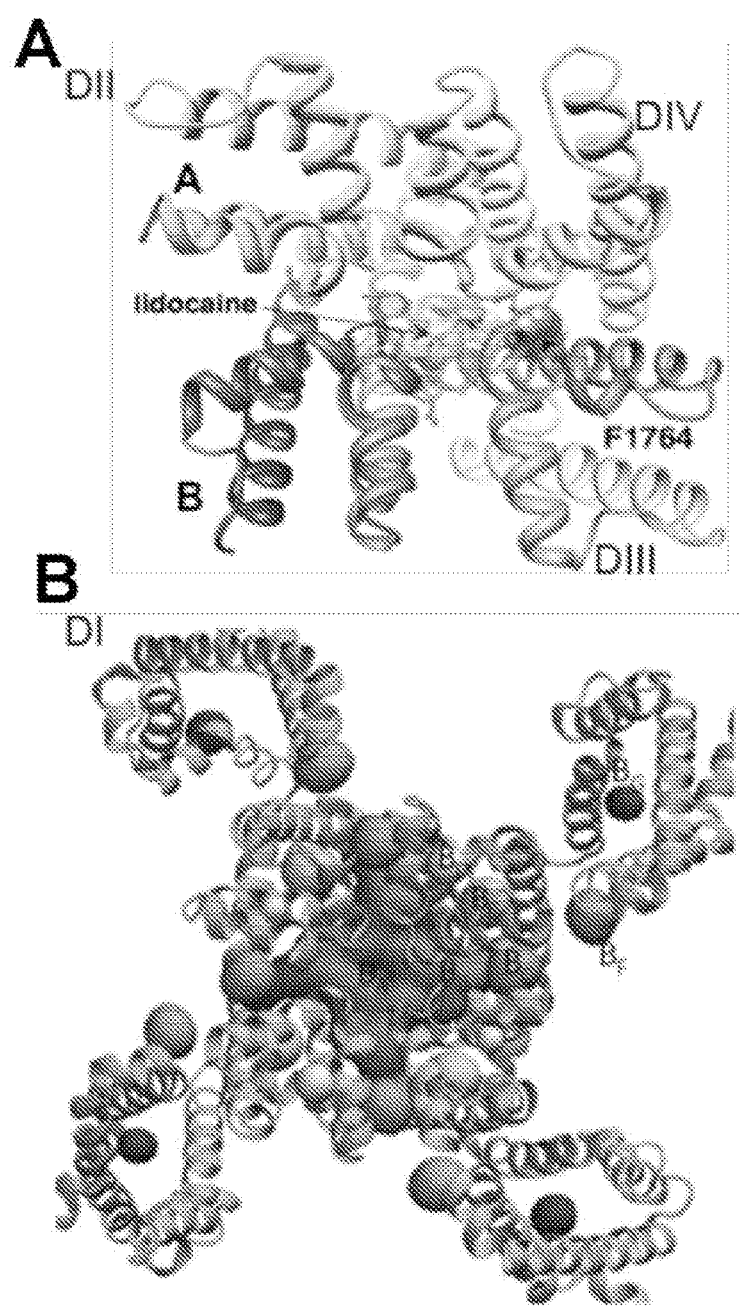
FIGS. 34A-34B.

Structure Atomic Scale: Rosetta modeling of cardiac voltage gated Na channel (Nav1.5) pore-forming domain (FIGS. 34A-34B). Homology, de novo, and full-atom modeling of the Nav1.5 and hERG K channels can be performed using Rosetta-Membrane and Rosetta symmetry methods developed by the Yarov-Yarovoy lab (Yarov-Yarovoy, V. et al. (2006) Proteins 62:1010-1025; Barth, P. et al. (2007) Proc Natl Acad Sci USA 104:15682-15687; Andre, I. et al. (2007) Proc Natl Acad Sci USA 104:17656-17661). The X-ray structures of NavAb (Payandeh, J. et al. (2012) Nature 486:135-139; Payandeh, J. et al. (2011) Nature 475:353-358), NavMs (McCusker, E. C. et al. (2012) Nat Commun 3:1102), NavRh (Zhang, X. et al. (2012) Nature 486:130-134), NavAe (Shaya, D. et al. (2014) J Mol Biol 426:467-483) and Kv1.2 (Long, S. B. et al. (2007) Nature 450:376-382), KvAP (Jiang, Y. et al. (2003) Nature 423:33-41), and KcsA (Zhou, Y. et al. (2001) Nature 414:43-48) channels can be used as templates, and pairwise sequence alignments with the Nav1.5 and hERG K channels generated using HHPred server (Soding, J. (2005) Bioinformatics 21:951-960) as described previously (Wang, C. et al. (2007) Journal of Molecular Biology 373:503-519; Mandell, D. J. et al. (2009) Nat Methods 6:551-552).

Rosetta-Ligand drug docking to Nav1.5 channels. Drug docking can be via the Rosetta-Ligand method as in (Davis, I. W. et al. (2009) Journal of Molecular Biology 385:381-392; Meiler, J. et al. (2006) Proteins 65:538-548) (preliminary data in FIG. 34A). Recent progress in determining high-resolution structures of closed, open, and inactivated states of the poreforming domain structures of bacterial Nav channels (Payandeh, J. et al. (2012) Nature 486:135-139; Payandeh, J. et al. (2011) Nature 475:353-358; Zhang, X. et al. (2012) Nature 486:130-134; McCusker, E. C. et al. (2012) Nat Commun 3:1102) now allows structural modeling of multiple states of Nav channels. The system 100 incorporates or uses a set of Nav channel complexes using Rosetta methods (Yarov-Yarovoy, V. et al. (2006) Proteins 62:1010-1025; Barth, P. et al. (2007) Proc Natl Acad Sci USA 104:15682-15687; Andre, I. et al. (2007) Proc Natl Acad Sci USA 104:17656-17661). Closed, open and inactivated state models of human Nav1.5 WT and inactivation deficient ΔKPQ mutant channels can be generated and used to predict closed, open, and inactivated state docking of lidocaine and ranolazine.

Molecular dynamics (MD) simulations. Starting with each of the lowest energy models for the drug-channel complex from Rosetta docking, the system an launch a library consisting of hundreds of long (100 ns) MD simulations. These simulations can allow for the observation of unbiased trajectories of drug binding and unbinding with the channel. In some implementations, the system 100 can utilize the approach used by Buch et al. (Buch, I. et al. (2011) Proc Natl Acad Sci USA 108:10184-10189) to estimate the kinetics of protein-ligand binding. The Standard free energy of binding ($\Delta G°$) can be calculated using $\Delta G° = -\Delta W - k_B T \log(V_b/V°)$, where $\Delta W$ is the depth of the potential of mean force (PMF), computed from the library of trajectories that have sampled an equilibrium distribution of drug-channel interactions, $k_B$ is the Boltzmann constant, T is the temperature, $V_b$ is bound volume calculated as the integral of the Boltzmann factor of the potential mean force over the binding site, and $V°$ is the standard state volume. The system can then carry out or execute a Markov State analysis (Noe, F. et al. (2012) Curr Opin Struct Biol 18:154-162) to determine the kinetically separated stable and metastable states. Analysis of successful state crossings can yield statistics from which the system can obtain kinetic rate constants (Buch, I. et al. (2011) Proc Natl Acad Sci USA 108:10184-10189). The system can do this by using the mean first passage time (MFPT) for the ON and OFF reactions as $k_{off}=1/\text{MFPToff}$ and $k_{on}=1/(C*\text{MFPT}_{on})$, where $k_{on}$ is inversely dependent on the ligand concentration, C. Knowledge of the free energies and rates of drug binding, combined with the extensive sampling of drug movements around the channel, can inform the mechanisms of drug interactions, understanding extents and rates of binding and unbinding of the different drugs. MD simulations can require the careful parameterization of new drug models consistent with the protein force field. In some implementations, work for prototypical drugs, benzocaine and phenytoin has already been performed (see preliminary data FIG. 34B). Initial guesses from the generalized CHARMM development software, CGENFF, can then be optimized to reproduce quantum mechanical calculations for internal coordinates, interactions with water molecules, adjustments to improve interactions in aqueous media, and dipole moments of the drugs in both neutral and charged forms, and through modifications to Lennard-Jones potentials to approach experimental partitioning data, such as from water to the membrane interface mimetic, n-octanol. The system can be configured to minimize statistical errors through exhaustive sampling of drug bound states, with the libraries of simulations and advanced Markov state analysis (Buch, I. et al. (2011) Proc Natl Acad Sci USA 108:10184-10189).

Free Energy Perturbation (FEP) Simulations: The structural similarity of lidocaine, benzocaine and phenytoin (all Sigma Aldrich) can be taken advantage of by employing FEP simulations that compute relative free energies of drug binding. Drugs can be alchemically transformed into analogs within the binding site, as well as in bulk electrolyte, with the free energy difference equal to the relative free energy of binding, via a thermodynamic cycle (e.g., Mobley, D. L. et al. (2012) J Chem Phys 137:230901). Relative drug binding affinities of similar ligands can be far more efficient and accurate than absolute binding affinities, due to a cancellation of errors (Wang, K. et al. (2013) J Comput Aided Mol Des 27:989-1007; Rocklin, G. J. et al. (2013) J Chem Phys 139:184103; Rocklin, G. J. et al. (2013) J Chem Theory Comput 9:3072-3083; Rocklin, G. J. et al. (2013) Journal of Molecular Biology 425; 4569-4583; Chodera, J. D. et al. (2013) Annu Rev Biophys. 42:121-142; Mobley, D. L. et al. (2007) Journal of Molecular Biology 371:1118-1134; Mobley, D. L. et al. (2006) J Chem Phys 125:084902; Deng, Y. et al. (2009) J Phys Chem B 113:2234-2246), and have become a valuable tool for accurate screening of candidate drug compounds (Mobley, D. L. et al. (2012) J Chem Phys 137:230901; Shirts, M. R. et al. (2010) Drug Design: Structure and Ligand-based Approaches. (Cambridge University Press, 2010).).

Model validation: Experimental data for mapping of key residues important for drug-channel interactions can be used to evaluate the accuracy of the drug-channel model predictions. Antiarrhythmic drug binding sites within $Na^+$ channel pore lumen have been mapped in detail previously (Ragsdale, D. S. et al. (1994) Science 265:1724-1728; Yarov-Yarovoy, V. et al. (2001) Journal of Biological Chemistry 276:20-27; Yarov-Yarovoy, V. et al. (2002) Journal of Biological Chemistry 277:35393-35401). The system can compare kinetic parameters estimated from MD simulations with drug affinities from electrophysiological data as follows: Ranolazine: Kd for tonic block of Late $I_{Na}$=6 µM (Wu, L. et al. (2004) J Pharmacol Exp Ther 310:599-605), tonic block of peak $I_{Na}$=165.2 µM*, use-dependent block of $I_{Na}$=100.5 µM* (*unpublished). K channel affinities: $K_d$ for $I_{Kr}$=12 µM (Rajamani, S. et al. (2008) J Cardiovasc Pharmacol 51:581-589). Metabolites: Four predominant metabolites (7 others have affinity outside of the therapeutic range) can be modeled (Chaitman, B. R. (2006) Circulation 113:2462-2472). All 11 metabolites potently inhibited $I_{Na,L}$ by 12-57% at 10 µM like ranolzine (Chaitman, B. R. (2006) Circulation 113:2462-2472) and do not require explicit modeling. Lidocaine is 60% charged at pH 7.4 (pKa=7.6 (Liu, H. et al. (2003) J. Gen. Physiol. 121:199-214)). Charged and neutral fractions have low open (Kd=318-400 µM (Abriel, H. et al. (2000) Circulation 102:921-925; Bennett, P. B. et al. (1995) Nature 376:683-685)) and closed state affinity (Kd=895 µM (Liu, H. et al. (2003) J. Gen. Physiol. 121:199-214)). Neutral drug has high inactivated state affinity (Kd=3.4 µM) (Liu, H. et al. (2003) J. Gen. Physiol. 121:199-214).

In some implementations If predictions deviate from experimentally determined affinities for specific Nav1.5 channel states, then alternative channel conformations can be explored with the Rosetta relax application.

These alternative states can be used to find alternate lowest energy binding conformation of drugs. Force field and statistical errors typically lead to kcal/mol-level errors in calculated free energies. However, these errors can be kept to a minimum by: 1) focusing on the calculation of relative drug binding affinities; 2) using force field models that target high level quantum mechanical and experimental data; and 3) sampling long times and using advanced methods for elucidating drug binding thermodynamics and kinetics, as described above.

Figure 35:
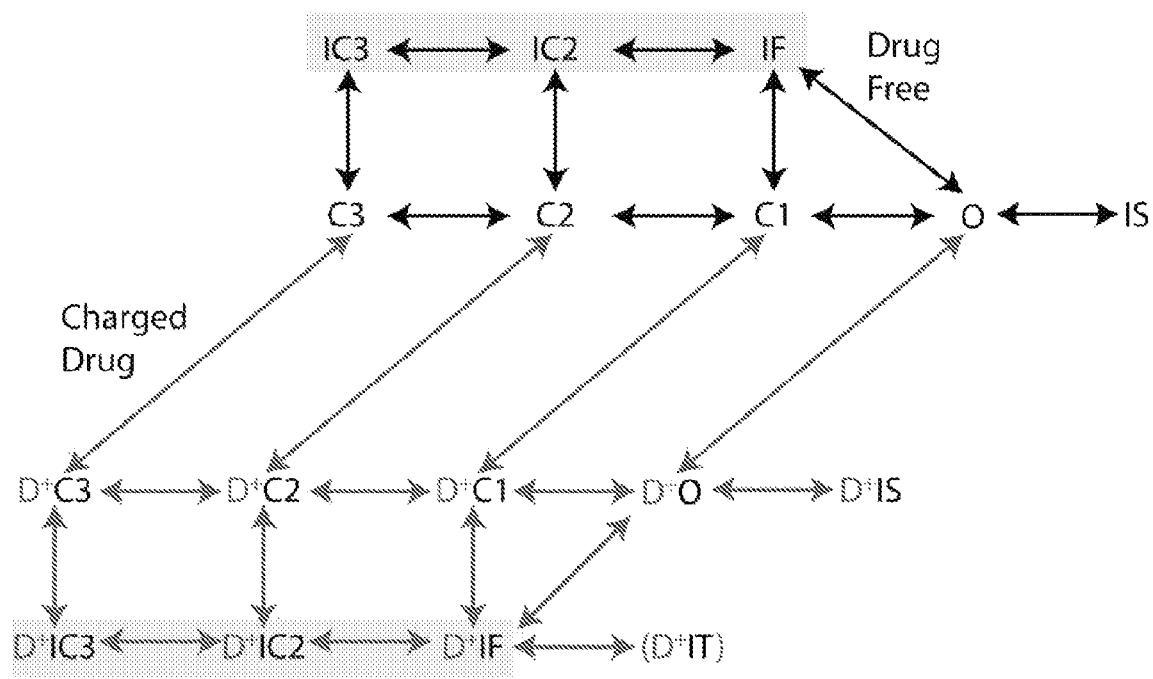
FIG. 35 shows the Markov model of Na channel-drug interaction. Drug free comprises 8 states (top rows in black). Red lines indicate entry or egress from drug bound states denoted by a red D+. Some arrows omitted for clarity (blue).
Figure 36:
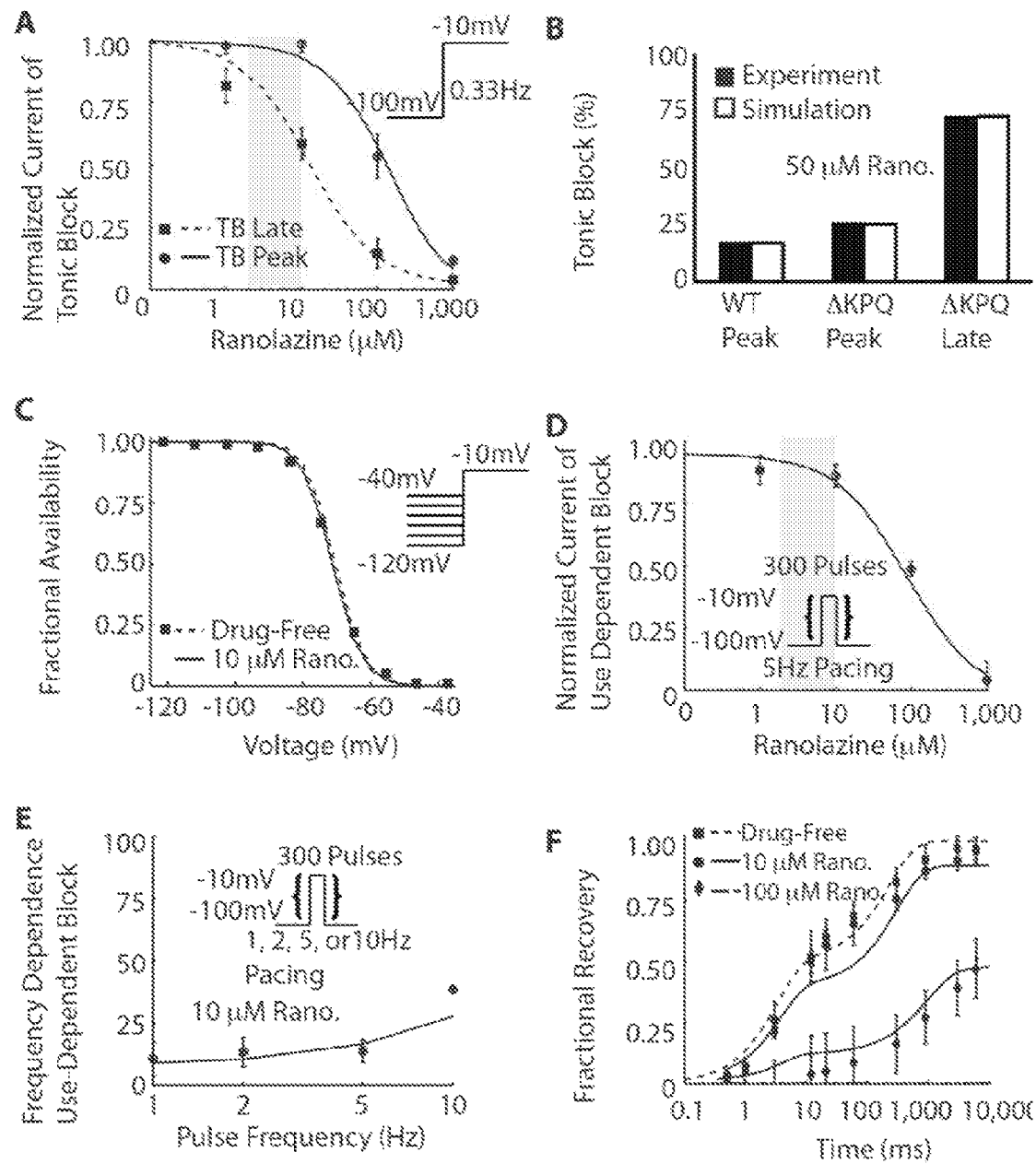
FIGS. 36A-36F show simulated (lines) and experimental symbols) ranolazine—ΔKPQ Mutant Na+channel interactions.

Protein Function Scale: Models for drug interaction with cardiac ion channels: Drug-bound states (Hille, B. (1977) Journal of General Physiology 69:497-515) for the Na channel model are shown in preliminary data FIG. 35 (red). To constrain drug rates for conformational states in the kinetic models, the system can determine drug concentration (a model variable) and diffusion rates (D) to formulate drug on rates "$k_{on}$"=[drug]*D. Affinity ($IC_{50}$) of the drug to discrete conformations determines drug off rates "$k_{off}$"=$IC_{50}$*D. Relative kinetic rates for the charged and neutral drug fractions can be derived from atomic scale simulations as described above. In some implementations, the system 100 can derive relative kinetic rates for the charged and neutral drug fractions from atomic scale simulations. These values can be used to constrain drug binding and unbinding rate constants in the Markov model. Drug "on" and "off" rates can be fixed to reduce the number of free parameters in the model. Rate constants can then be constrained via optimization to five pacing protocols including: steady state availability (Liu, H. et al. (2002) Journal of General Physiology 120:39-51), steady state activation (Rivolta, I. et al. (2001) J Biol Chem 276:30623-30630), recovery from inactivation at −90 mV (An, R. H. et al. (1996) Circ Res. 79:103-108), recovery from multi-pulse block at −100 mV, and time constant of inactivation from the open state (An, R. H. et al. (1996) Circ Res. 79:103-108). The system can be configured to adhere to microscopic reversibility (Colquhoun, D. et al. (2004) Biophysical Journal 86:3510-3518). Details are in recent studies (Moreno, J. D. et al. (2011) Science Translational Medicine 3:98ra83; Moreno, J. D. et al. (2013) Circ Res. 113:e50-e61) (and preliminary data FIGS. 36A-36F).

Figure 37:
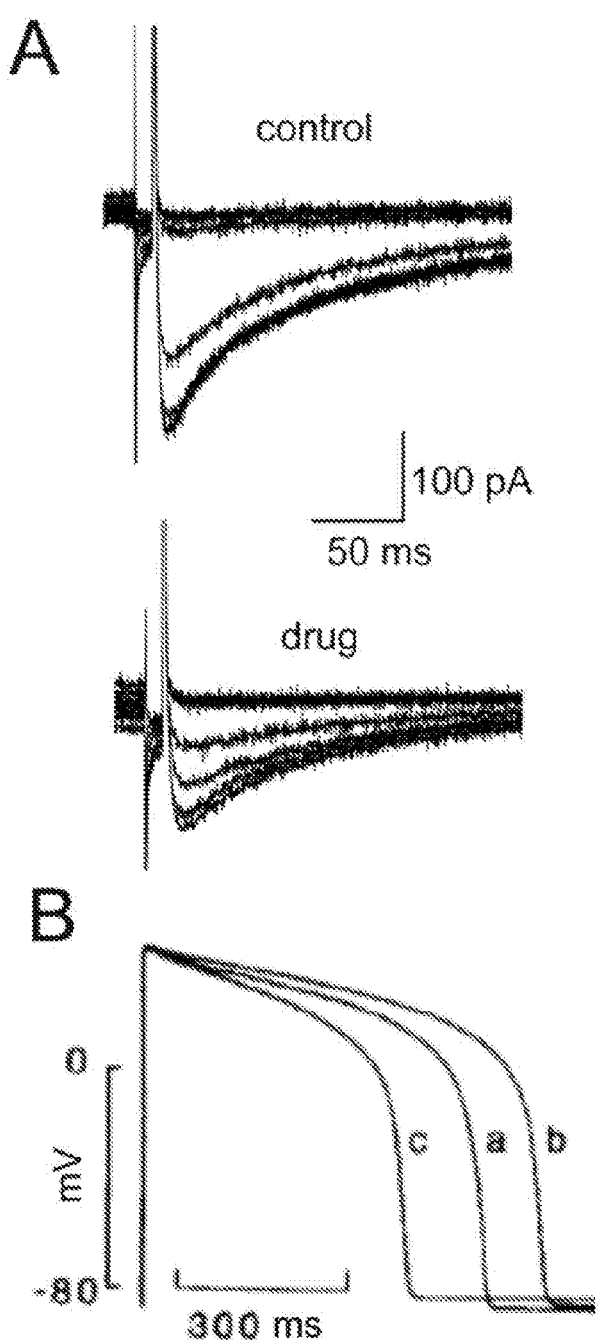
FIGS. 37A-37B.

Experiments to determine cardiac drug targets. Off-target effects of ranolazine and metabolites can be evaluated, for example, in the Harvey lab. Ventricular myocytes can be isolated from adult rabbits using enzymatic techniques described previously (Harvey, R. D. et al. (1989) The American Journal of Physiology 257:C1177-C1181). Evidence for off-target drug effects can be obtained using the AP clamp sequential dissection technique (Horvath, B. et al. (2013) Journal of Molecular and Cellular Cardiology 64:59-68; Banyasz, T. et al. (2011) Journal of Molecular and Cellular Cardiology 50:578-581). With this approach, the steady-state action potential recorded under current clamp conditions (see preliminary data FIGS. 37A-37B) is used to generate the command potential for voltage clamp experiments in the same cell. Subsequent application of the compound in question results in a drug-sensitive current. Presence of a drug-sensitive current in the presence of $I_{Na}$ inhibition with 30 µM TTX is evidence for an off-target effect. Reduction of the drug sensitive current in the presence of blockers of other known currents ($I_{CaL}$, 1 µM nifedipine; $I_{to}$, 200 µM 3,4-diaminopyridine; $I_{Ks}$, 10 µM chromanol-293B; $I_{Kr}$, 1 µM E4031; and $I_{K1}$, 50 µM Ba$^{2+}$) can be used to identify channels affected. Traditional voltage clamp techniques can be used to quantify specific drug actions on identified targets for model optimization (Harvey, R. D. et al. (1989) The American Journal of Physiology 257:C1177-C1181; Harvey, R. D. et al. (1988) The Journal of General Physiology 91:593-615) (FIGS. 36A-36F). Drug effects on ΔKPQ channels can be evaluated in HEK 293 cells expressing the variant engineered into wild type cDNA cloned in pcDNA3.1 as described in (Liu, H. et al. (2002) The Journal of General Physiology 120:39-51).

Models for drug-free normal or mutant channels: Gating models for WT and ΔKPQ cardiac Na channels have been developed (FIGS. 36A-36F) (Clancy, C. E. et al. (1999) Nature 400:566-569; Clancy, C. E. et al. (2003) Circulation 107:2233-2237; Clancy, C. E. et al. (2002) J Clin Invest 110:1251-1262; Clancy, C. E. et al. (2002) Circulation 105:1208-1213; Moreno, J. D. et al. (2011) Science Translational Medicine 3:98ra83). The Fink $I_{Kr}$ model can be used (FIG. 45) (Fink, M. et al. (2008) Prog Biophys Mol Biol 96:357-376; Clancy, C. E. et al. (2001) Cardiovascular Research 50:301-313; Bett, G. C. et al. (2011) Biophysical Journal 101:631-642).

Numerical methods and parameter optimization for drug-free channels: Implicit methods can be used to solve ODEs (Moreno, J. D. et al. (2011) Science Translational Medicine 3:98ra83). Nelder-Mead or Newton-Raphson optimization with random small (<10%) perturbations applied to local minimum can allow continued optimization to improve fits (Moreno, J. D. et al. (2011) Science Translational Medicine 3:98ra83). Simultaneous optimization to experimental data can be performed (e.g., ΔKPQ Na current in preliminary data FIGS. 36A-36F).

Limitations and alternatives: If the system is not able to fit experimental results with proposed model schemes, the system can be configured to perform an iterative process to reconcile simulations and experiments: Alternate model topologies can be explored to minimize differences between the model and experiment. For example, complex kinetics of drug recovery may indicate additional drug states (i.e., fast and slow unbinding to open channels). Experiments can be performed to better constrain the model topology and kinetics as needed.

Cell Scale: Simulations: The Soltis-Saucerman rabbit cardiac model (Soltis, A. R. et al. (2010) Biophysical Journal 99:2038-2047) can be used for all initial simulations. This allows experimental validation of model predictions to ensure drug-receptor interactions are modeled accurately, followed by simulations in human models. The models of drug-channel kinetics can be incorporated into the three human models of ventricular cells including O'Hara-Rudy (O'Hara, T. et al. (2011) PLoS Computational Biology 7:e1002061), ten Tusscher (ten Tusscher, K. H. W. J. et al. (2006) Am J Physiol Heart Circ Physiol. 291:H1088-H1100), and Grandi-Berl (Grandi, E. et al. (2009) J Mol Cell Cardiol. 48:112-121) to miminize model dependence of the findings. Cellular level protocols: drug effects on action potentials (APs) can be predicted by the system 100 for therapeutic concentration of ranolazine (5-10 µM (Chaitman, B. R. (2006) Circulation 113:2462-2472; Gordon, M. (2003) Medical Review of Safety (Ranolazine), www.fda.gov/ohrms/dockets/ac/03/briefing/4012B2_02_Division Dir Memo.htm)) and lidocaine (10-20 µM 113) at 60-220 beats per minute (BPM). Simulated parameter changes can be tracked: Cell excitability (max. upstroke velocity of the AP (V/s)), action potential duration (APD), early afterdepolarizations (EADs), cell refractoriness and APD restitution (Goldhaber, J. I. et al. (1997) Circulation 96:3756-3756). In WT cells, The system is expected to observe dose-dependent depression of cellular excitability observed as reduced upstroke velocity of the AP and dose-dependent reduction to APD. In the absence of drugs, it is expected the ΔKPQ inactivation deficient mutant cells to generate APD prolongation and, at slow frequencies, early afterdepolarizations (EADs). It is further expected that ranolazine and lidocaine can reduce APD in the mutant cells and dose-dependent depression of emergent EADs. Off-target drug effects (i.e., kr block by ranolazine) on cell parameters can be predicted in simulations with drug on primary targets alone and/or with off-target effects. Sensitivity analysis: Sensitivity analysis can be used to identify quantities underlying model dynamics, examine the limits on parameter estimation from experimental measurements, improve numerical stability, and test hypotheses. Variance based systematic sensitivity analysis using an orthonormal Hermite approximation (OHA) for reactions in response to parameter perturbations can produce sensitivity coefficients connecting parameters and outputs. The system can also conduct principal component analysis for parameter ranks (Wong, C. F. et al. (1991) Journal of Physical Chemistry 95:9628-9630). Error propagation: Model formulations represent "average" behavior. Variability exists in experimental data for each parameter, so the system can construct 10000 distinct models with random parameters combination chosen from within the standard deviation of the data, for example, from a recent paper (Yang, P. C. et al. (2012) Front Physiol 360). The effect of propagating errors in the 1000th paced beat at a cycle length of 1000 ms can be examined for APDs and maximum upstroke velocities (V/s). This is an additional test of sensitivity of the model behaviors to the underlying parameters.

Model Reduction: A reduced model (Tran, D. X. et al. (2009) Physical Review Letters 102:258103) can allow efficient prediction of drugs on cardiac parameters. A H-H scheme can be used to represent drug free Na current and for drug effects, an additional "inactivation" type gate (x) can be added of the form $dx/dt=(1/\tau_x)*(x_\infty-x)$, where x depends on $m^3h$. The time constant ($\tau$) can be fit to the simulated timecourse (in the full model) of drug buildup and drug unbinding. The reduced model allows: Quantitative simulations can identify parameter regimes of interest (i.e., drug dose to eliminate an arrhythmia trigger) and allows perturbation of "drug gate" kinetics to test for improved or reduced therapeutic potential. For example, a faster drug unbinding might allow lower dose to rectify an early afterdepolarization (EAD). However, this change in kinetics may increase vulnerability to proarrhythmic unidirectional conduction block. Key predictions in the reduced model can be simulated in the complex model. Qualitative analysis reveals fundamental dynamical mechanisms of emergent system behaviors, such as the dynamical mechanism of EADs revealed through bifurcation analysis (Tran, D. X. et al. (2009) Physical Review Letters 102:258103). In the reduced model the system can probe how perturbations to "drug gate" kinetics alter stability of the subsystem dynamics that drives EAD development. Although the "drug gate" is a simplified representation of drug channel kinetics, the analysis can link fundamental mechanisms back to specific biophysical properties of the drug channel interaction for design of improved therapeutics.

Validation of the model predictions in rabbit myocytes: Model predictions of changes to cell parameters after drug application can be experimentally tested in single rabbit ventricular myocytes in the Harvey lab. Dr. Harvey is an expert in measuring changes to cellular electrophysiology induced by drugs (preliminary data FIGS. 37A-37B) and can carry out experiments to validate key parameter changes predicted by the model simulations drug effects on action potentials (APs) for the therapeutically relevant concentration and pacing frequencies (60-220 beats per minute (BPM)). Parameters can be tracked: Cell excitability (maximum upstroke velocity of the AP (V/s)), action potential duration (APD), early afterdepolarizations (EADs), cell refractoriness and APD restitution (Goldhaber, J. I. et al. (1997) Circulation 96:3756-3756). Validation of model predictions can also benefit from the experimental literature characterizing effects of the antiarrhythmic drugs that can be studied (Belardinelli, L. et al. (2013) J Pharmacol Exp Ther. 344:23-32; Vizzardi, E. et al. (2012) Journal of Cardiovascular Pharmacology and Therapeutics 17:353-356; Antzelevitch, C. et al. (2011) Heart Rhythm 8:1281-1290). The established pharmacological model of LQT3 with ATX-II can be used in isolated rabbit ventricular myocytes with 5-10 nM ATX-II (Wu, L. et al. (2004) J Pharmacol Exp Ther 310:599-605) to validate the simulations in the ΔKPQ inactivation mutants.

Experimental validation of drug effects on intracellular calcium: The ΔKPQ mutation and ATX-II are expected to increase $[Na]_i$, and loading of $[Ca^{2+}]_i$, via the Na/Ca exchanger (Wasserstrom, J. A. et al. (2009) J Pharmacol Exp Ther. 331:382-391; Ver Donck, L. et al. (1993) Cardiovascular Research 27:349-357), thus the Bers lab can employ fluorescence microscopy with simultaneous measurement of membrane voltage, $[Na]_i$ and $[Ca^{2+}]_i$ to test the potential for lidocaine or ranolazine to normalize intracellular Ca by preventing Na overload (Despa, S. et al. (2012) Cardiovascular Research 95:480-486; Ginsburg, K. S. et al. (2013) J Physiol 591:2067-2086). Voltage, $[Na]_i$ and $[Ca^{2+}]_i$ can be measured in the presence of predicted combinations of ATX-II+/−lidocaine or ranolazine between 0.5 and 3 Hz. Dramatic Na (and $Ca^2$) loading at rapid frequencies is expected. Once conditions for Na and Ca loading are established, a fast-slow protocol to induce DADs can be initiated. the potential for drug pretreatment to prevent DAD emergence can then be tested.

Limitations and alternatives: Here multiple experiments can be used to test the accuracy of the model predictions. Simulations can be performed in rabbit so that the effects of drugs in the WT simulations can be directed compared to experiments in cell and tissue level rabbit cardiac preparations. But, significant deviation may be found from the rabbit model predictions and the experimental measurements. Thus, an iterative process can be undertaken to reconcile simulations and experiments: Experimentally measured parameters that do not validate model predictions can be used in a feedback process to further refine and constrain the models via an iterative approach linking disparities in measured and simulated cellular level parameter to lower level model parameters (i.e., channel conductance, voltage dependence, time constants) that can be re-tuned in the optimization process. For example, if it is found that lidocaine causes more depression of cellular excitability in experiments (as indicated by maximum upstroke velocity of the AP (V/s)), mine resting membrane potential and Na current amplitude before and after drug application can be examined and then these parameters can be used to additionally constrain the computational model.

Figure 38:
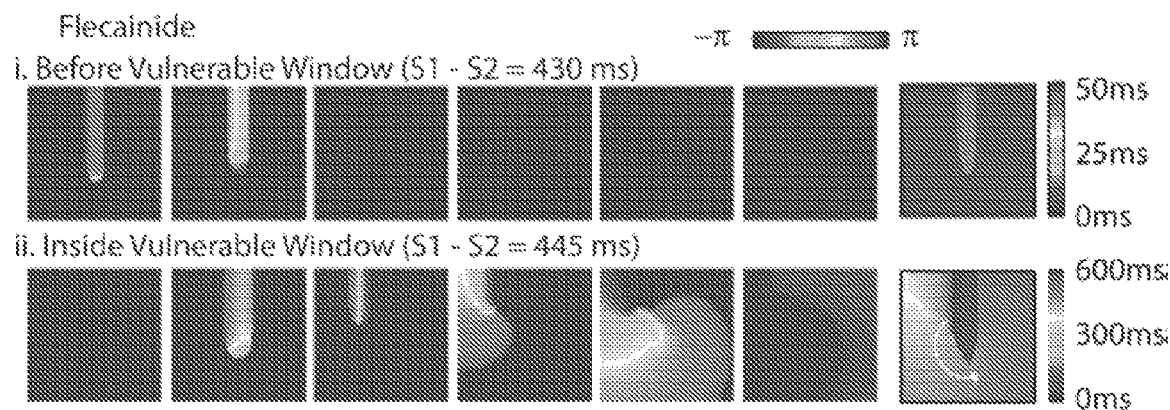
FIG. 38 shows flecainide in a 2D tissue model. Phase maps for flecainide (2 μM) (scale on top: red is wavefront, and blue is repolarized (though not necessarily recovered from drug block)). Right panels are activation isochrones. A premature impulse applied in the wake of the preceding wave (i) before or (ii) in the vulnerable window.

TISSUE SCALE: One-dimensional (1D) simulations: 1D simulations can be carried out to coarsely identify parameter regimes of interest with a computationally tractable model as described (Moreno, J. D. et al. (2011) Science Translational Medicine 3:98ra83). Regimes exhibiting compelling dynamics can be investigated in higher dimensions. The following parameter changes with drug application can be predicted: APD restitution, conduction velocity (CV): CV is calculated between cell 49 and 50 at dV/dtmax. Because conduction block promotes reentrant arrhythmias and wavebreak causing fibrillation (Weiss, J. N. et al. (2005) Circulation 112:1232-1240). The drug concentration can be predicted for conduction block over 60 BPM-220 BPM with escalating drug (0.5 μM increments) or until block occurs. A period of vulnerability exists when electrical stimulation can initiate self-sustaining spiral waves (Mines, G. (1914) Trans. Roy. Soc. Can:43-53; Allessie, M. A. et al. (1973) Circ Res. 33:54-62) capable of degeneration into fibrillatory rhythms. The "vulnerable window" to unidirectional block and retrograde conduction can be assessed, suggesting reentrant arrhythmia in higher dimensions (Starmer, C. F. et al. (1991) Circulation 84:1364-1377; Starmer, C. F. et al. (1993) Biophysical Journal 65:1775-1787; Starmer, C. F. (2002) International Journal of Bifurcation and Chaos 12:1953-1968; Moreno, J. D. et al. (2011) Science Translational Medicine 3:98ra83). The refractory period can also be used to quantify drug-induced increase in arrhythmia risk (Starmer, C. F. (2002) International Journal of Bifurcation and Chaos 12:1953-1968). Two-dimensional (2D) simulations: 2D simulations can determine if proarrhythmic phenomena observed in lower dimensions cause reentrant arrhythmias and/or spiral wave breakup. The change in voltage in space and time can be computed as in (ten Tusscher, K. H. W. J. et al. (2006) Am J Physiol Heart Circ Physiol. 291:H1088-H1100). Other parameters are as in 1D simulations. An example of 2D stable reentry induced by flecainide after static pacing (S1) followed by an S2 within the vulnerable window is shown in preliminary data in FIG. 38. APD restitution, dispersion of repolarization and reentry wavelength can be tracked and compared to experiments before and after drug. Sensitivity analysis: Because the PDE-based model is computationally expensive, the elementary effects method can be used for large perturbation combinations (Marino, S. et al. (2008) Journal of Theoretical Biology 254:178-196).

Figure 39:
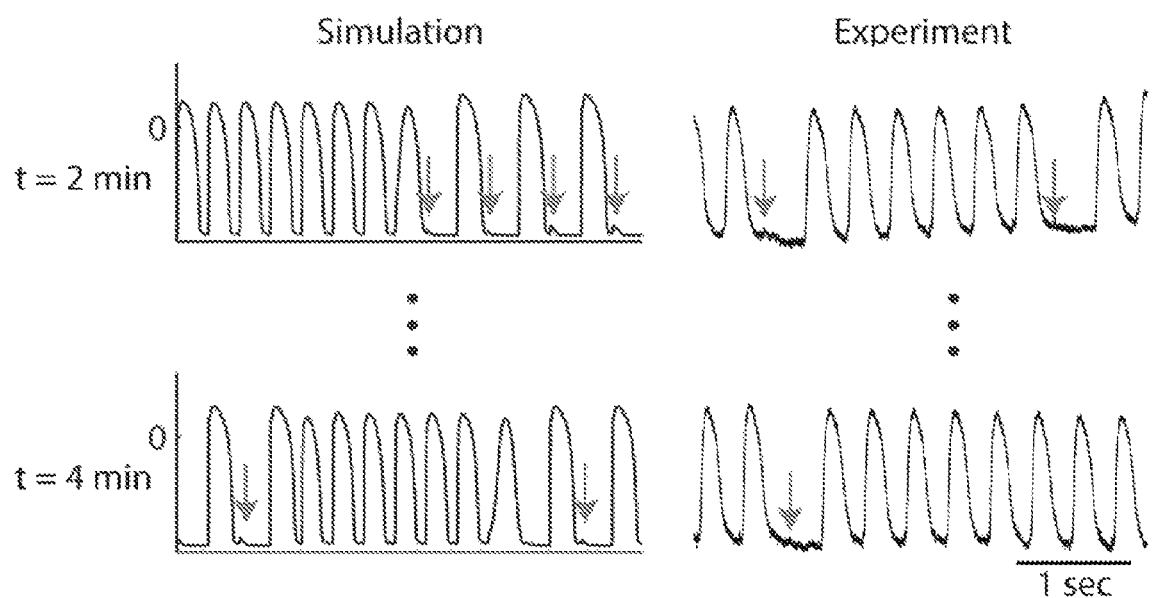
FIG. 39 shows an example of experimental validation of simulated tissue responses. During tachycardic pacing (160 beats per minute) Na channel block with 2 μM flecainide leads to conduction block of action potentials in simulated and experimental tissue preparations.
Figure 40:
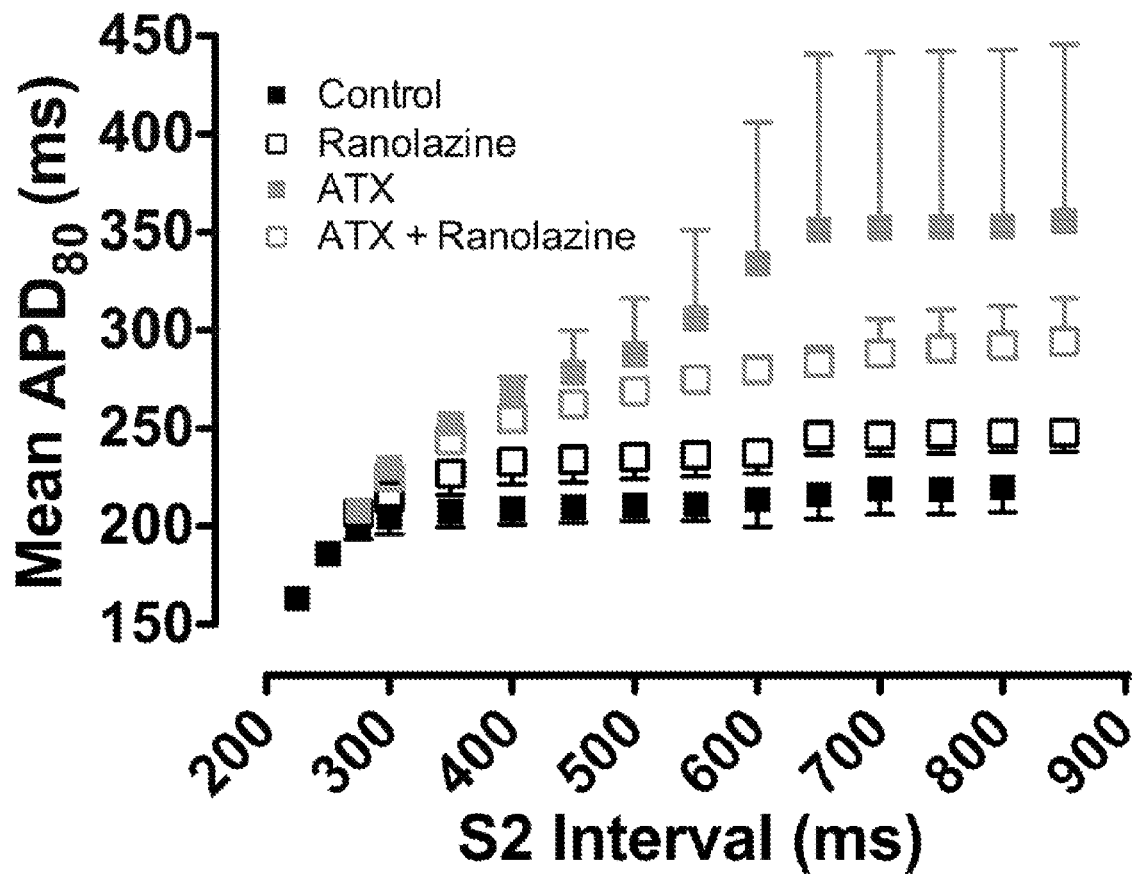
FIG. 40 shows ranolazine (10 uM), ATX-II (10 nM), and ranolazine+ATX-II were studied with optical mapping in n=3 rabbit hearts. Standard S1-S2 restitution protocol reveals drug/compound effect on APD. ATX-II at long S2 led to EADs.

Tissue level experimental validation of the model predictions: Optical mapping experiments in the Ripplinger lab can be performed in normal rabbit tissue+/−ATX-II (10 nM) to validate key parameter changes predicted by the tissue level simulations with WT and ΔKPQ channels with no drug, lidocaine or ranolazine. Arrhythmia vulnerability parameters can be tracked and compared to simulated parameters: Conduction velocity, conduction velocity restitution, APD restitution, dispersion of repolarization, and reentry wavelength. Optical mapping experiments in Langendorff-perfused rabbit hearts use voltage-(RH237) and calcium-(Rhod2-AM) sensitive dyes. Dyes are excited with LED light sources (~530 nm). Emitted light is collected with two MiCam Ultima-L CMOS cameras (SciMedia, USA) at a sampling rate of 1 kHz. The mapping field of view can be approximately 2.5×2.5 cm, resulting in a spatial resolution of ~250 μm/pixel. Pacing can be applied with a biopolar electrode on the epicardial surface. Examples of experimental validation of model predictions are shown in preliminary data in FIG. 39 (drug-induced conduction block) and FIG. 40 (ranolazine+/−ATX-II on APD restitution).

Limitations and alternatives: Optical mapping limitations include the use of pharmacological excitation-contraction uncouplers to prevent motion artifacts in the optical recordings. However, blebbistatin can be used, which has been shown to have minimal effects on action potential and Ca2+ handling characteristics. Optical signal recording is limited to a depth of ~1 mm, so it is not possible to record endocardial or transmural signals without excising portions of the heart tissue. Wide-field optical mapping signals represent average signals, so single-cell activities cannot be discerned.

Significant differences in tissue model predictions and the experimental measurements can be found. Thus, an iterative process to reconcile simulations and experiments can be undertaken: Experimentally measured parameters that do not validate model predictions can be used in a feedback process to further refine and constrain the models via an iterative approach linking disparities in measured and simulated tissue level parameter to lower level model parameters (i.e. cellular APDs, cell coupling, upstroke velocity of the AP) that can be re-tuned in the optimization process. For example, if it is found that lidocaine causes more depression of conduction velocity in experiments, action potential upstroke velocity and cell coupling parameters in the model before and after drug application can be examined and then used to retune these parameters in the computational model.

Figure 41:
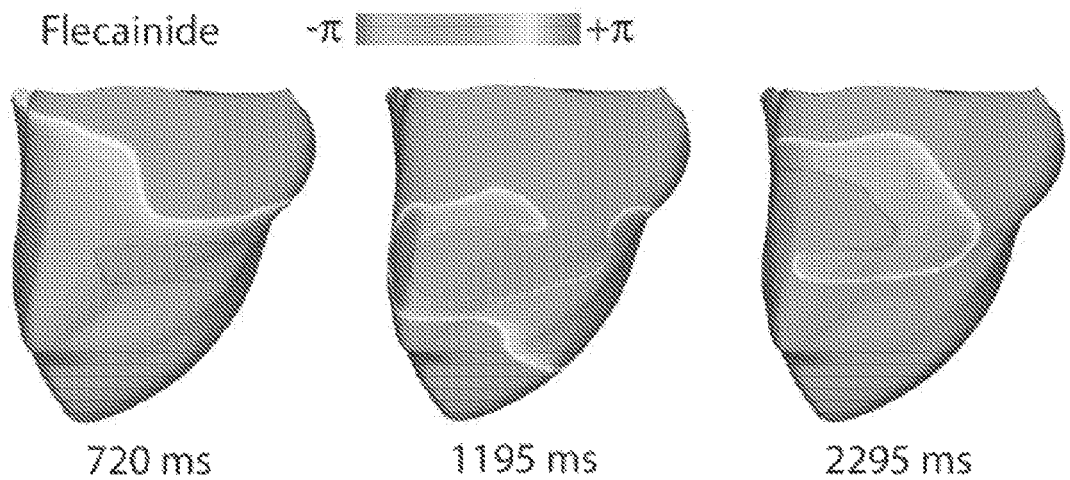
FIG. 41 shows reentry in 3D models of the ventricle. (A) Phase maps of a sustained Fig.-of-eight reentry with 2 μM flecainide at 120 BPM in response to an S2 within the vulnerable window

ORGAN SCALE: Simulation in geometrically realistic ventricular models: Finally, to ensure that model predictions in idealized two-dimensions can hold true in complex organ structures, Trayanova Lab can test drug effects in an MRI-based anatomically detailed 3-D models of the rabbit and human ventricles as described previously (Moreno, J. D. et al. (2011) Science Translational Medicine 3:98ra83). An example is shown for flecainide-induced reentry in preliminary data in FIG. 41. 3D ventricles were paced from the apex at a rate of 120 BPM with 2 μM flecainide. A stimulus inside the vulnerable window initiated persistent reentry with flecainide. It is expected to be able to readily induce reentrant arrhythmias with this S1-S2 protocol in the rabbit model only when the ΔKPQ mutation is present. It is expected to predict dose-dependent reduction in the vulnerable window for both ranolazine and lidocaine and, due to more reduction in APDs with lidocaine, it is expected to see the reduction in the time of sustained reentry.

Figure 42:
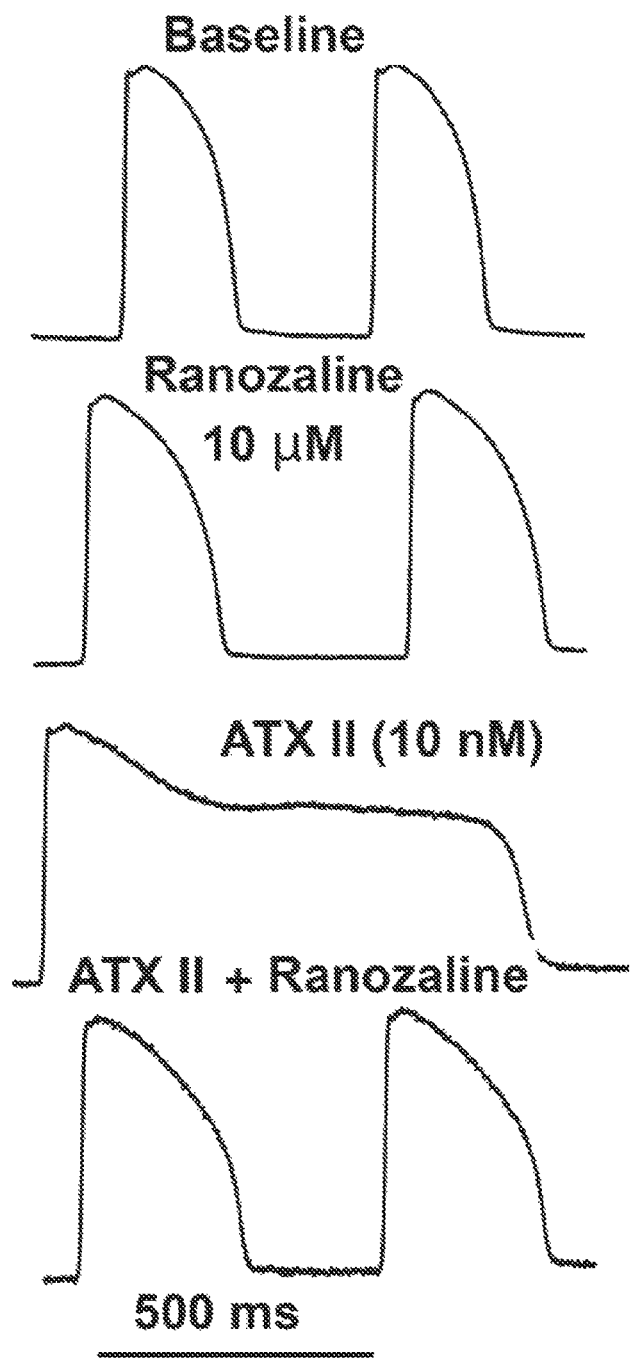
FIG. 42 shows an example optical Aps from a rabbit heart in normal sinus rhythm under baseline conditions (top). Ranolazine or ATX-II were added to the perfusate to test the effects of each drug/compound alone and in combination. Ranolazine prolonged APD via off-target effects on hERG. ATX-II greatly prolonged APD (due to increased $I_{NaL}$) and caused frequent EADs during sinus rhythm. The effect of ATX-II was reversed when ranolazine was added to the perfusate (bottom).

Organ level experimental validation of the model predictions: Experiments (Ripplinger lab) can be performed to validate key parameter changes predicted by the organ level simulations in WT channels and the pharmacological model of LQT3 with ATX-II (preliminary data in FIG. 42). Optical mapping experiments in Langendorff-perfused rabbit hearts can be performed as above. The AV node can be ablated to produce heart block, and hearts can be paced at rates of 60 BPM-220 BPM. APs can be recoded from the left ventricular epicardium and a lead I ECG can be continuously recorded. Pacing can be applied with a bipolar electrode on the epicardial surface. Arrhythmia incidence can be measured with a standard S1-S2 or S1-S2-S3 pacing protocol and can be compared to simulated arrhythmias. After a 10-20-minute period of equilibration, hearts can be exposed to vehicle (Tyrode's solution) or ATX-II and then to increasing concentrations of lidocaine or ranolazine.

Limitations and expectations: Because organ-scale simulations are computationally expensive, it can not be able to exhaustively test model prediction generated in lower dimensions in the whole organ. Thus it is prudent to test only key model predictions in the whole organ. These simulations can include a test of ranolazine efficacy in the most severe LQT3 mutant, ΔKPQ. Experimentally, it is possible (although unlikely in the presence of ATX-II) that arrhythmias can not be induced with either an S1-S2 or S1-S2-S3 pacing protocol. In this case the system can use an alternative burst pacing approach to induce reentrant arrhythmias.

Specific Aim 2: To apply the multiscale model for screening preclinical compounds. AIM 2 Rationale: Although INaL is small in healthy hearts, increased INaL is present in many pathologic conditions (Moreno, J. D. et al. (2011) Journal of Molecular and Cellular Cardiology 52:608-619). Increases in INaL can promote arrhythmias by prolonging APD, leading to early afterdepolarizations and reduced repolarization reserve (Boutjdir, M. et al. (1991) Cardiovasc Res. 25:815-819; Sicouri, S. et al. (1997) J Cardiovasc Electrophysiol. 8:1280-1290; Undrovinas, A. et al. (2008) Cardiovascular & Hematological Agents in Medicinal Chemistry 6:348-359; Zaza, A. et al. (2008) Pharmacol Ther 119:326-339; January, C. et al. (1989) Circ Res. 64:977-990). In 2013 the first publications on the preclinical compound GS967 showed potent targeting of $I_{NaL}$ ($IC_{50}$ for $I_{NaL}$=130 nM) 1. Preferential targeting of INaL is desirable, but the structural determinants of GS967 specificity and potency are unknown. Thus, the multiscale model can be applied to predict the GS967 binding site and atomic determinants of potent $I_{NaL}$ affinity.

Aim 2 Expected Outcomes: Upon completion of Aim 2, it is expected to have demonstrated the usefulness of the multiscale model for efficient prediction of: 1) Effects of modified drug functional groups to change GS967 affinity, allowing for improved understanding of the atomic determinants of drug affinity. 2) Novel pharmacological compounds that cannot be readily determined experimentally without exhaustive screening libraries. 3) High throughput preclinical drug screening for emergent effects on cell, tissue and organ cardiac electrical behavior for which no comparable experiment exists.

Aim 2 General Plan: Atomic-scale simulations for GS967 can be performed as described in Aim 1. These predictions can be used to inform rate constants of drug binding to discrete states of WT and ΔKPQ mutant Na channels in the channel function scale models.

As in Aim 1 drug-channel models can be integrated into rabbit and human cellular, tissue and organ level models to predict effects of GS967. Model predictions can be validated experimentally in normal and ATX-II challenged rabbit ventricular cells, tissues and hearts. GS967 can be modified in the atomic model to search for improved analogs with higher specificity to $I_{NaL}$ versus $I_{Napeak}$.

The most promising analog can be synthesized and modeled, followed by experimental tests of the predictions. Structure Atomic Scale: Structural modeling of Nav1.5 channel, ligand docking of GS967, and molecular dynamics (MD) simulations are as in Aim 1. Model validation: Kinetic parameters estimated from MD simulations can be compared with drug affinities from electrophysiological data for GS967: Kd for tonic block of Late $I_{Na}$=0.13 μM (Belardinelli, L. et al. (2013) J Pharmacol Exp Ther. 344:23-32), tonic block of peak $I_{Na}$=1500 μM 1. K channel: $I_{Kr}$=17% inhibition at 10 μM 1. Screening for drug analogs: The lowest interaction energy conformations of GS967 in the human Nav1.5 receptor site predicted by Rosetta can be used to identify additional receptor contact points. Drug analogs can be rationally designed guided by the specific environment of drug molecule within the receptor site. For example, open fenestrations within NaV channel pore-forming domain structure are near the antiarrhythmic receptor site (Payandeh, J. et al. (2012) Nature 486:135-139; Payandeh, J. et al. (2011) Nature 475:353-358) and may comprise specific novel interaction sites. During each round, drug analogs can be docked to Nav1.5 channel states. The lowest interaction energy analogs can undergo MD simulations to estimate standard free energy of ligand binding and kinetic parameters as in Aim 1. Predictions of specific channel-drug interactions from the large library of drug binding simulations can be tested using free energy perturbation (FEP) as in Aim 1. FEP can reveal affinity changes associated with modified drug functional groups or channel mutants, allowing for improved understanding of the determinants of drug affinity, with the potential to propose novel pharmacological compounds.

Synthesis of drug analogs: GS967 analogues suggested by simulations to have improved potencies (e.g., increase late $I_{Na}$ block) can be synthesized in the Wulff lab according to published procedures for phenyl substituted triazolo[4,3-a]pyridines. The lab is skilled in design and synthesis of ion channel modulators and has previously identified potent and selective $K_v1.3$ and $K_{Ca}$ channel modulators (Sankaranarayanan, A. et al. (2009) Mol Pharmacol 75:281-295; Wulff, H. et al. (2000) Proc Natl Acad Sci USA 97:8151-8156; Schmitz, A. et al. (2005) Mol Pharmacol. 68:1254-1270). The lab routinely synthesizes triarylmethanes, furocoumarines, benzothiazole, oxazole and other heteroaromatic systems and should therefore have no major difficulties in synthesizing triazolopyridines (Sankaranarayanan, A. et al. (2009) Mol Pharmacol 75:281-2951; Wulff, H. et al. (2000) Proc Natl Acad Sci USA 97:8151-8156; Schmitz, A. et al. (2005) Mol Pharmacol. 68:1254-1270; Bodendiek, S. B. et al. (2009) European Journal of Medicinal Chemistry 44:1838-1852; Harvey, A. J. et al. (2006) J Med Chem 49:1433-1441). The exact structures can depend on the model predictions, however, it is expected to 1) vary the substituents on the phenyl and triazolopyridine moieties (e.g., replacement of $CF_3$ with Cl, $NH_2$, $CH_3$ etc.) and 2) isosterically replace the phenyl ring and the triazolopyridine with thiophene or differently annulated triazolo systems. The synthesized analog can be tested using the methods as for GS967.

Limitations and alternatives: As described for Aim 1.

Figure 43:
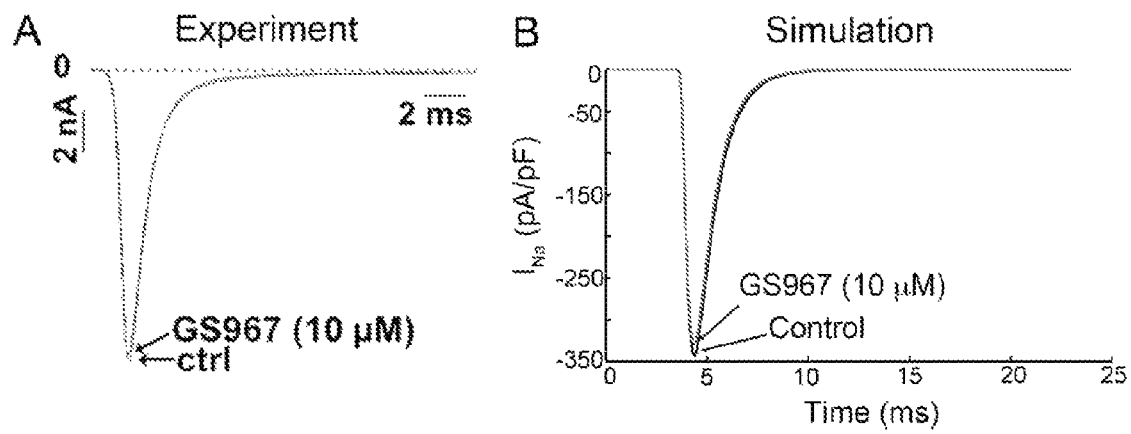
FIGS. 43A-43B show rabbit experiment (Belardinelli, L. et al. (2013) J Pharmacol Exp Ther. 344:23-32) and computational Na current model showing negligible effects of GS967 on peak current.

Protein Function Scale: Models for drug interaction with cardiac ion channels: The process for GS967 is as described in Aim 1. A preliminary model prediction with GS967 is shown in FIGS. 43A-43B.

Experiments to determine cardiac drug targets. Off-target effects of GS967 can be evaluated as in Aim 1 (Banyasz, T. et al. (2011) Journal of Molecular and Cellular Cardiology 50:578-581; Banyasz, T. et al. (2012) Heart Rhythm 9:134-142).

Models for drug-free normal or mutant channels: The models are as described in Aim 1.

Numerical methods and parameter optimization and Limitations and alternatives: As described in Aim 1.

Figure 44:
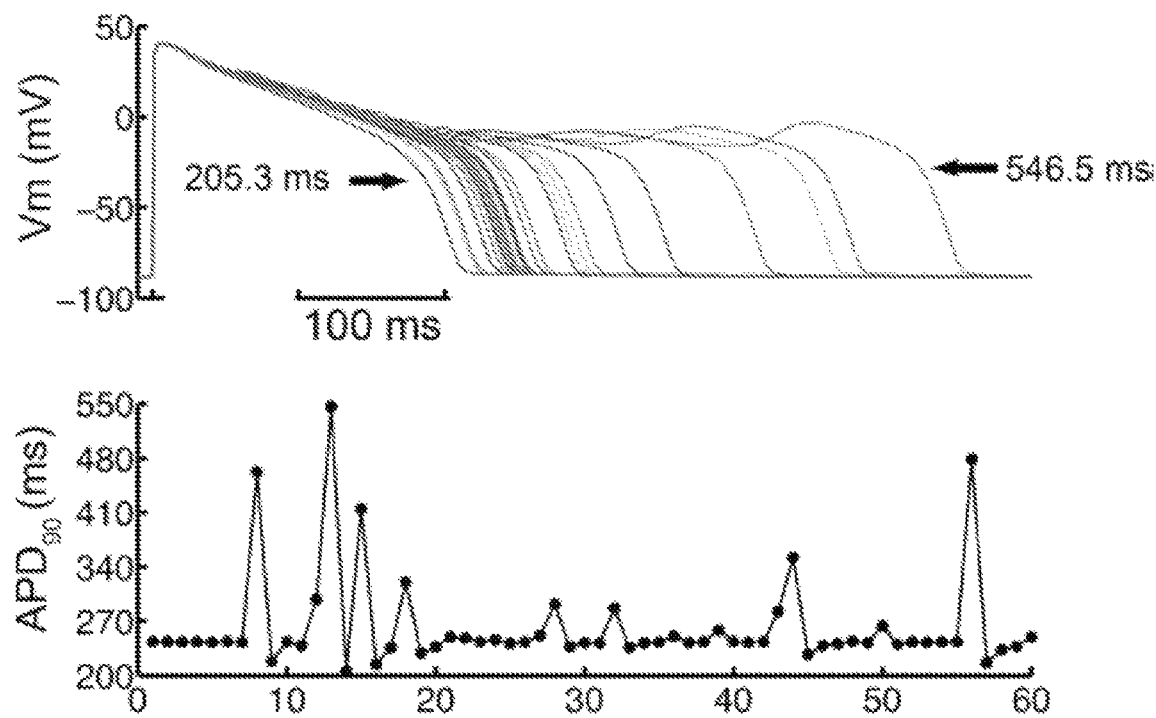
FIG. 44 shows APD variability in simulated normal cell induced by random injection of small current −0.1 to −0.2 pA/pF throughout the AP plateau (between 30 and 200 ms) during 1 Hz pacing. APD variability for successive beats in bottom.

Cell Scale: Simulations: As described in Aim 1. Additionally, it is expected to observe minimal dose dependent depression of cellular excitability with GS967 and substantial dose-dependent changes to APD and prevention of EADs. It is also expected that GS967 can reduce DAD occurrence elicited by short-long pacing protocols that lead to Na loading and resulting $Ca^{2+}$ overload (Moreno, J. D. et al. (2013) Circ Res. 113:e50-e61). The potential for GS967 to reduce cellular susceptibility to small electrical perturbations can be tested. The AP plateau is a phase of high resistance, rendering the cell vulnerable to perturbations that can arise from electrotonic influences of the surrounding tissue and arrhythmia triggers in the form of early and delayed afterdepolarizations. It is expected that GS967 to reduced APD90 variability and prevent emergent EADs virtual cells in response to small electrical perturbation (preliminary data FIG. 44).

Sensitivity analysis and error propagation: As in Aim 1.

Experimental Validation of the Model Predictions in Rabbit Myocytes:

Predictions of changes in the WT and ATX-II pharmacological model of LQT387 to rabbit cellular parameters after drug application can be as described in Aim 1. GS967 can be tested on APD variability in the WT and ATX-II pretreated cells compared to drug free as described in (Zaniboni, M. et al. (2000) Am J Physiol Heart Circ Physiol 278:H677-H687).

Action potentials can be recorded using non-dialyzing microelectrodes (Belevych, A. E. et al. (2000) Journal of Physiology (London) 528:279-289). For each cell, 10 consecutive APs recorded after >2 minutes 0.5 Hz pacing can be used to calculate the coefficient of variability (CV), which is defined as the standard deviation/mean APD90. APD variability, attributable to stochastic ion channel behavior, contributes to dispersion of refractoriness, a determinant of arrhythmogenesis (Zaniboni, M. et al. (2000) Am J Physiol Heart Circ Physiol 278:H677-H687). Inhibition of INaL is expected to reduce APD variability.

Experimental validation of GS967 effects on intracellular calcium: As in Aim 1. Limitations and alternatives: As in Aim 1. Iterative process to reconcile cellular simulations and experiments: Experimentally measured parameters that do not validate model predictions can be used in a feedback process as described in Aim 1. For example, if experiments show that GS967 confers more protection against small perturbations (i.e., less APD variability observed in experiments with GS967 than in simulations), this would suggest too little total current during simulated AP plateaus (membrane resistance is too high). Additional optimization would be performed to constrain current amplitudes to data from the AP clamp experiments as described in Aim 1.

Tissue Scale: One-dimensional (1D) simulations: 1D simulations can be carried in rabbit and human ventricular virtual tissues as described in Aim 1. Because GS967 exhibits potent INaL block, it is expected to predict dose-dependent reduction in APD, but negligible effects on conduction The hypothesis that GS967 reduces APD, but preserves conduction velocity at all pacing rates can be tested. Two-dimensional (2D) simulations: 2D simulations can be as described in Aim 1. It is determined that GS967 can be especially effective to reduce the size of the vulnerable window to unidirectional conduction block and reentry (Starmer, C. F. et al. (1991) Circulation 84:1364-1377; Starmer, C. F. et al. (1993) Biophysical Journal 65:1775-1787; Starmer, C. F. (2002) International Journal of Bifurcation and Chaos 12:1953-1968). Thus, "vulnerable window" as in Aim 1 with and without varying concentrations of GS967 can be assessed (Starmer, C. F. et al. (1991) Circulation 84:1364-1377; Starmer, C. F. et al. (1993) Biophysical Journal 65:1775-1787; Moreno, J. D. et al. (2011) Science Translational Medicine 3:98ra83). The refractory period (which is expected to be reduced to GS967 induced APD shortening) can be considered to quantify drug-induced increase in arrhythmia risk (129). Sensitivity analysis as for Aim 1131. Tissue level experimental validation of the model predictions: Optical mapping (Ripplinger lab) can be performed+/−GS96 as in Aim 1. Limitations and alternatives: Limitations are as in Aim 1.

Organ Scale: Simulation in geometrically realistic ventricular models: The drug GS967 is potentially therapeutic in the setting of ventricular tachyarrhythmias (Belardinelli, L. et al. (2013) J Pharmacol Exp Ther. 344:23-32). An attempt can be made to induce arrhythmia-linked phenomenon+/−GS967 in organ scale models in the Trayanova Lab as described in Aim 1. Organ level experimental validation of the model predictions: Experiments in the Ripplinger lab can be performed to validate predictions of GS967 organ level simulations as in Aim 1. Limitations and expectations: As in Aim 1.

Specific Aim 3: To Apply the Multiscale Model to Screen for Disease Specific Drug Therapy.

AIM 3 Rationale: Disease induced enhancement of late $I_{Na}$ promotes the development of arrhythmogenic afterdepolarizations, triggered arrhythmic activity, and torsades de pointer (TdP) in cardiac ventricular myocytes, cardiac tissue, and intact hearts (Boutjdir, M. et al. (1991) Cardiovasc Res. 25:815-819; Sicouri, S. et al. (1997) J Cardiovasc Electrophysiol. 8:1280-1290; Song, Y. et al. (2004) J Cardiovasc Pharmacol. 44:192-199; Wu, L. et al. (2006) J Pharmacol Exp Ther. 316:718-726; Clancy, C. E. et al. (1999) Nature 400:566-569). Pharmacological targeting of $I_{NaL}$ has been shown to improve cardiac electrical function in myocytes challenged by cardiac glycosides, hydrogen peroxide, pharmacological enhancement of late $I_{Na}$, and even with drugs that block hERG ($I_{Kr}$) and reduce repolarization reserve (Ver Donck, L. et al. (1993) Cardiovascular Research 27:349-357; Haigney, M. C. et al. (1994) Circulation 90:391-399; Le Grand, B. et al. (1995) American Journal of Physiology 269:H533-H540; Sicouri, S. et al. (1997) J Cardiovasc Electrophysiol. 8:1280-1290; Song, Y. et al. (2004) J Cardiovasc Pharmacol. 44:192-199; Song, Y. et al. (2006) J Pharmacol Exp Ther. 318:214-222; Wu, L. et al. (2006) J Pharmacol Exp Ther. 316:718-726; Sossalla, S. et al. (2010) J Am Coll Cardiol. 55:2330-2342; Undrovinas, A. et al. (2008) Cardiovascular & Hematological Agents in Medicinal Chemistry 6:348-359; Wu, L. et al. (2011) Circulation 123:1713-1720). In this Aim, the goal is to expand the multiscale models from Aims 1 and 2 to predict and compare the therapeutic efficacy of lidocaine, ranolazine and GS967 in the setting of inherited Long-QT Type 3 (LQT3) (Wang, D. W. et al. (1997) J Clin Invest 99:1714-1720; Wilde, A. A. et al. (2011) Circ Res. 108:884-897) and acquired Long-QT (aLQTS) induced by block of $I_{Kr}$.

Aim 3 Expected Outcomes: Upon completion of Aim 3, it is expected to have demonstrated the usefulness of the multiscale model for novel prediction of: 1) Atomic-scale effects of mutations on drug interactions that cannot be determined experimentally without onerous crystallographic and/or mutagenesis experiments. 2) Rates from atomic scale simulations of drug interactions with mutant Na channels at the protein function scale. 3) High throughput prediction of emergent drug effects in inherited and acquired disease-specific states on cell, tissue and organ cardiac electrical behavior for which no comparable experiment exists.

Aim 3 General Plan: The general approach to predict effects of antiarrhythmic drugs in diseased states is as follows: (1) the system can construct multiscale models to predict interactions of lidocaine, ranolazine and GS967 in aLQTS and for LQT3 mutations ΔKPQ, I1768V, Y1795insD and Y1795C (Clancy, C. E. et al. (1999) Nature 400:566-569; Clancy, C. E. et al. (2003) Circulation 107:2233-2237; Clancy, C. E. et al. (2002) J Clin Invest 110:1251-1262; Clancy, C. E. et al. (2002) Circulation 105:1208-1213). (2) Predictions to changes in arrhythmia vulnerability parameters. (3) Sensitivity analysis performed. (4) Experimental validation.

Protein Structure Scale: Rosetta modeling of cardiac voltage gated Na+ channel (Nav1.5) Long-QT 3 mutations. WT and ΔKPQ mutant channels can be as described in Aim 1. Closed, open and inactivated state models of LQT3 mutations I1768V, Y1795insD, and Y1795C can be generated and used to predict state affinities of ranolazine, lidocaine and GS967.

Molecular dynamics simulations: As described in Aims 1 and 2.

Model validation: Kinetic parameters estimated from MD simulations can be compared with drug affinities from electrophysiological data in WT and mutants as described in Aim 1. This is an important step to validate and show the predictive power during development of the model framework.

Limitations and alternatives: As described for Aim 1.

PROTEIN FUNCTION SCALE: Models for drug-free normal or mutant channels: Markov gating models for WT and mutant cardiac Na channels including LQT3 ΔKPQ can be developed (FIGS. 36A-36F), I1768V and Y1795insD and Y1795C (Clancy, C. E. et al. (1999) Nature 400:566-569; Clancy, C. E. et al. (2003) Circulation 107:2233-2237; Clancy, C. E. et al. (2002) J Clin Invest 110:1251-1262; Clancy, C. E. et al. (2002) Circulation 105:1208-1213; Moreno, J. D. et al. (2011) Science Translational Medicine 3:98ra83). Channel models can be fit to reproduce critical kinetics with drugs as described in Aim 1.

Models for dofetilide block of $I_{Kr}$: A model of dofetilide interaction with $I_{Kr}$ has been developed based on the five-state model from Fink et al. (Moreno, J. D. et al. (2011) Science Translational Medicine 3:98ra83). Measured affinities and diffusion rates were used to constrain dofetilide rates. (see preliminary model FIGS. 45 and 46).

Experiments to determine drug interactions with mutant channels: As described in Aim 1. Drug effects on LQT3 mutations can be evaluated in HEK 293 cells expressing either ΔKPQ, I1768V, Y1795insD, or Y1795C SCN5A variants engineered into wild type cDNA cloned in pcDNA3.1 (Invitrogen) as described in (Liu, H. et al. (2002) Journal of General Physiology 120:39-51).

Cell Scale: Simulations with Inherited Long QT Mutations:

To predict if ranolazine, lidocaine or GS967 improves LQT3 abnormal cellular electrical phenotypes, the effects of addition of mutations and/or drugs in the rabbit and human models can be simulated as in Aim 1. There is an expectation to see mutation specific APD prolongation worsening at low frequency (Fredj, S. et al. (2006) Circ Res. 99:1225-1232; Nuyens, D. et al. (2001) Nature Medicine 7:1021-1027; Fredj, S. et al. (2006) British Journal of Pharmacology 148:16-24). Cells can be paced for 500 stimuli between 50-120 BPM to predict rate dependent APD prolongation and emergence of early afterdepolarizations (EADs). Each drug in the therapeutic range (effective dose can predicted for GS967) can be tested to normalize mutant action potential morphology. The system can also screen for depression of cellular excitability. Pause-induced EADs: LQT3-linked arrhythmias are typically preceded by pauses and short-longshort sequences (Viswanathan, P. C. et al. (1999) Cardiovasc Res. 42:530-542; Jackman, W. M. et al. (1988) Progress in Cardiovascular Diseases 31:115-172; Leclercq, J. F. et al. (1988) Eur Heart J. 9:1276-1283; Kay, G. N. et al. (1983) J Am Coll Cardiol. 2:806-817; Viskin, S. et al. (2000) Heart 83:661-666). Drug therapy for LQT3 patients must normalize arrhythmia triggers subsequent to pauses. Concentrations of ranolazine, lidocaine and GS967 can be predicted to prevent pause-induced arrhythmia triggers over pause intervals for fast (100 BPM) and slow (60 BPM) S1 pacing frequencies (Moreno, J. D. et al. (2013) Circ Res. 113:e50-e61). It is difficult to know a priori what to expect from model simulations with individual drugs and mutations—simulations are likely to reveal complex non-intuitive relationships between mutant channels emergent effects of interacting drugs. Modeling acquired Long-QT: The system can predict if selective INaL block would make cells less susceptible to acquired Long-QT by APD prolongation induced by simulated clinical dose of dofetilide (8.2 nM (Demolis, J. L. et al. (1996) Circulation 94:1592-1599)) in the computational cell models (rabbit and human models) with and without lidocaine, ranolazine and GS967 pretreatment. Applicants expect to observe concentration-dependent reductions in APD after dofetilide.

Validation of predictions for drug treatment of acquired Long-QT in rabbit myocytes: Drug effects on cell models of acquired Long-QT can be tested as in Aims 1 and 2 in rabbit myocytes with dofetilide (10-100 nM) (Kiehn, J. et al. (1996) Circulation 94:2572-2579).

Experimental testing of the model predictions in human iPSCs: There is access to patient-specific human-induced pluripotent stem cell (hiPSC)-derived cardiomyocytes (hiPSC-CMs) containing WT and mutant Na channels (LQT3 ΔKPQ, I1768V and Y1795insD and Y1795C) to qualitatively validate the model predictions. The goal is to test the predicted emergent behavior of drug-channel interaction in native milieu using the mutant channels expressed in hiPSC-CMs. There is an awareness of the quantitative differences between rabbit model and hiPSC-CMs, however, the goal is to allow qualitative comparison between the rabbit model and human cardiomyocytes. The proposed experiments also allow future translation of the findings to patients. Culture and Directed Differentiation of hiPSC into hiPSC-CMs. Feeder-free hiPSCs (iPS-D19-9-T7, WiCell) can be cultured with mTeSR on hESC-qualified matrigel. HiPSCs can be differentiated into hiPSC-derived cardiomyocytes (CMs) using the recently published method (Lian, X. et al. (2013) Nat Protoc. 8:162-175; Lian, X. et al. (2012) Proc Natl Acad Sci USA 109:E1848-E1857). Using directed differentiation (DD)-medium specific for each differentiation stage, observe ~90% beating clusters of cardiomyocyte subtypes comprising heterogeneous cardiomyocyte subtypes as shown by myosin light chain (MLC)2a staining for all immature cardiomyocytes and MLC2v for ventricular-specific cardiomyocytes. Day 40 (maturing cardiomyocytes) can be used for experiments described below. Experimental effects of drugs to suppress arrhythmogenic afterdepolarizations can be assessed in patient derived hiPSC-CM with WT and mutant Na channels. In parallel to the rabbit model, the hiPSC-CMs can also be used to investigate drug effects on APs, peak and late Na current kinetics for ranolazine (5-10 μM (Chaitman, B. R. (2006) Circulation 113:2462-2472; Gordon, M. (2003) Medical Review of Safety (Ranolazine), www.fda.gov/ohrms/dockets/ac/03/briefing/4012B2_02_ Division Dir Memo.htm)) and lidocaine (10-20 μM (Brunton L L, L. J., Parker K L. Goodman & Gilman's The Pharmacological Basis of Therapeutics, 11th edition. (McGraw-Hill).)) at frequencies (60-150 BPM). Maximum upstroke velocity of the AP (V/s)), APD, early afterdepolarizations (EADs), cell refractoriness and APD restitution (Goldhaber, J. I. et al. (1997) Circulation 96:3756-3756) can be quantified.

Limitations and alternatives: hiPSCCMs exhibit immaturities including electrophysiological instability, inefficient excitation-contraction (EC) coupling, and small cell size (Boheler, K. R. et al. (2002) Circ Res. 91:189-201; Ieda, M. et al. (2010) Cell 142:375-386; Itzhaki, I. et al. (2006) Ann N Y Acad Sci 1080:207-215; Kamp, T. J. et al. (2009) Circulation Research 105:617-619; Lieu, D. K. et al. (2009) Stem Cells Dev 18:1493-1500; Liu, J. et al. (2007) Stem Cells 25:3038-3044; Sartiani, L. et al. (2007) Stem Cells 25:1136-1144). Nonetheless, the system offers advantages over expression cell lines by providing the interacting and cytoskeletal proteins, and regulatory machinery. It also allows determination of differences in drug-channel interactions between WT and mutant channels. Recent studies have shown that the hiPSC-CMs can be manipulated to increase their maturity. (Kim, C. et al. (2013) Nature 494: 105-110) If discrepancies in the model predictions compared to measurements in hiPSC-CMs are found, the Paci computational model of human stem cell derived cardiomyocytes can be deployed (Paci, M. et al. (2012) Biomed Eng Online 11:61).

Tissue Scale: One-dimensional (JD) simulations: 1D simulations can be carried out as described in Aims 1 and 2. Pause-induced or short-long-short arrhythmia trigger: Computational one-dimensional tissue models can be used to predict if ranolazine, lidocaine and GS967 can normalize APs following pauses as in Aim 2.

Applicants can test the effect of pretreatment with clinical doses of ranolazine and lidocaine and GS967. Drug concentration for conduction block can also be predicted.

Two-dimensional (2D) simulations: As in Aim 2 for prediction of all combinations of mutations and drugs.

Tissue level experimental validation of the model predictions in cultured iPSC cells: Dr. Chiamvimonvat's group has recently published the conduction velocity measurement of monolayers of human pluripotent stem cell derived-CMs using optical mapping with MiCAM Ultima (Chen, A. et al. (2011) Adv Mater 23:5785-5791). Optical mapping experiments in the Ripplinger lab in 2D cultured iPSCs (Sondergaard, C. S. et al. (2012) Annals of Thoracic Surgery 94:1241-1248, discussion 1249; Feinberg, A. W. et al.

(2013) Stem Cell Reports 1:387-396) with WT and mutant channels can be used to validate key parameter changes predicted by the tissue level simulations as described in Aims 1 and 2. Optical mapping experiments can be as described in Aims 1 and 2, but can be performed at higher magnification (1.63-10×). Pacing via a platinum bipolar pacing lead located in the culture medium −0.5-1 mm above the edge of the 2D culture can stimulate the CMs at 8 V, 1.5 Hz for 20 ms. After a 10-20-minute period of equilibration, cultures can be exposed to lidocaine, GS967 or ranolazine until a steady-state effect is reached. Reentrant arrhythmias can be induced with an S1-S2 or burst pacing protocol and can be compared to simulated arrythmias.

Experimental validation for drug treatment of acquired Long-QT in rabbit tissue: Tissue level model predictions of drug effects on acquired Long-QT can be tested as in Aims 1 and 2 in rabbit epicardium with dofetilide (10-100 nM) (Kiehn, J. et al. (1996) Circulation 94:2572-2579). Limitations and alternatives: If the iPSC culture is not large enough to sustain reentrant arrhythmias (wavelength is larger than the tissue area), then larger cultures (more cells) can be billed, or focus on arrhythmogenic behavior (i.e., the arrhythmia vulnerability parameters described above).

Organ Scale: Simulation in geometrically realistic ventricular models: Simulations can be undertaken in the Travanova lab. Clancy Lab can transfer computational based cell models of mutations and drugs in the Soltis-Saucerman rabbit ventricular cell model. Drug-mutation combinations and the effects of lidocaine, ranolazine and GS967 to prevent LQT3 and dofetilide promoted reentry can be tested in the Trayanova model as in (Moreno, J. D. et al. (2011) Science Translational Medicine 3:98ra83).

Experimental validation of predictions for drug treatment of acquired Long-QT in rabbit heart: Tissue level model predictions of drug effects on acquired Long-QT can be tested as in Aims 1 and 2 in rabbit hearts with dofetilide using well established methods (Kiehn, J. et al. (1996) Circulation 94:2572-2579; D'Alonzo, A. J. et al. (1999) Eur J Pharmacol 369:57-64; Nalos, L. et al. (2012) Br J Pharmacol 165:467-478).

Limitations and expectations: The limitations are the same as described for other Aims. there are limitation at this juncture by the inability to experimentally validate the inherited mutation organ scale model predictions.

The present technology illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the present technology claimed.

Thus, it should be understood that the materials, methods, and examples provided here are representative of preferred aspects, are exemplary, and are not intended as limitations on the scope of the present technology.

The present technology has been described broadly and generically herein. Each of the narrower species and sub-generic groupings falling within the generic disclosure also form part of the present technology. This includes the generic description of the present technology with a proviso or negative limitation removing any subject matter from the genus, regardless of whether or not the excised material is specifically recited herein.

In addition, where features or aspects of the present technology are described in terms of Markush groups, those skilled in the art can recognize that the present technology is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, can control.

H. Computing Environment

FIGS. 47A and 47B depict block diagrams of a computing device 2400. As shown in FIGS. 47A and 47B, each computing device 2400 includes a central processing unit 2421, and a main memory unit 2422. As shown in FIG. 47A, a computing device 2400 can include a storage device 2428, an installation device 2416, a network interface 2418, an I/O controller 2423, display devices 2424a-2424n, a keyboard 2426 and a pointing device 2427, e.g. a mouse. The storage device 2428 can include, without limitation, an operating system, software, and software of system 100. As shown in FIG. 47B, each computing device 2400 can also include additional optional elements, e.g. a memory port 2403, a bridge 2470, one or more input/output devices 2430a-2430n (generally referred to using reference numeral 2430), and a cache memory 2440 in communication with the central processing unit 2421.

The central processing unit 2421 is any logic circuitry that responds to and processes instructions fetched from the main memory unit 2422. In many embodiments, the central processing unit 2421 is provided by a microprocessor unit, e.g.: those manufactured by Intel Corporation of Mountain View, Calif.; those manufactured by Motorola Corporation of Schaumburg, Ill.; the ARM processor (from, e.g., ARM Holdings and manufactured by ST, TI, ATMEL, etc.) and TEGRA system on a chip (SoC) manufactured by Nvidia of Santa Clara, Calif.; stand-alone ARM processors; the POWER7 processor, those manufactured by International Business Machines of White Plains, N.Y.; or those manufactured by Advanced Micro Devices of Sunnyvale, Calif.; or field programmable gate arrays ("FPGAs") from Altera in San Jose, Calif., Intel Corporation, Xlinix in San Jose, Calif., or MicroSemi in Aliso Viejo, Calif., etc. The computing device 2400 can be based on any of these processors, or any other processor capable of operating as described herein. The central processing unit 2421 can utilize instruction level parallelism, thread level parallelism, different levels of cache, and multi-core processors. A multi-core processor can include two or more processing units on a single computing component. Examples of multi-core processors include the AMD PHENOM IIX2, INTEL CORE i5 and INTEL CORE i7.

Main memory unit 2422 can include one or more memory chips capable of storing data and allowing any storage location to be directly accessed by the microprocessor 2421. Main memory unit 2422 can be volatile and faster than storage 2428 memory. Main memory units 2422 can be Dynamic random access memory (DRAM) or any variants, including static random access memory (SRAM), Burst SRAM or SynchBurst SRAM (BSRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Single Data Rate Synchronous DRAM (SDR SDRAM), Double Data Rate SDRAM (DDR SDRAM), Direct Rambus DRAM (DRDRAM), or Extreme Data Rate DRAM (XDR DRAM). In some embodiments, the main memory 2422 or the storage 2428 can be non-volatile; e.g., non-volatile read access memory (NVRAM), flash memory non-volatile static RAM (nvSRAM), Ferro-electric RAM (FeRAM), Magnetoresistive RAM (MRAM), Phase-change memory (PRAM), conductive-bridging RAM (CBRAM), Silicon-Oxide-Nitride-Oxide-Silicon (SONOS), Resistive RAM (RRAM), Racetrack, Nano-RAM (NRAM), or Millipede memory. The main memory 2422 can be based on any of the above described memory chips, or any other available memory chips capable of operating as described herein. In the embodiment shown in FIG. 47A, the processor 2421 communicates with main memory 2422 via a system bus 2450 (described in more detail below). FIG. 47B depicts an embodiment of a computing device 2400 in which the processor communicates directly with main memory 2422 via a memory port 2403. For example, in FIG. 47B the main memory 2422 can be DRDRAM.

FIG. 47B depicts an embodiment in which the main processor 2421 communicates directly with cache memory 2440 via a secondary bus, sometimes referred to as a backside bus. In other embodiments, the main processor 2421 communicates with cache memory 2440 using the system bus 2450. Cache memory 2440 typically has a faster response time than main memory 2422 and is typically provided by SRAM, BSRAM, or EDRAM. In the embodiment shown in FIG. 47B, the processor 2421 communicates with various I/O devices 2430 via a local system bus 2450. Various buses can be used to connect the central processing unit 2421 to any of the I/O devices 2430, including a PCI bus, a PCI-X bus, or a PCI-Express bus, or a NuBus. For embodiments in which the I/O device is a video display 2424, the processor 2421 can use an Advanced Graphics Port (AGP) to communicate with the display 2424 or the I/O controller 2423 for the display 2424. FIG. 47B depicts an embodiment of a computer 2400 in which the main processor 2421 communicates directly with I/O device 2430b or other processors 2421' via HYPERTRANSPORT, RAPIDIO, or INFINIBAND communications technology. FIG. 47B also depicts an embodiment in which local busses and direct communication are mixed: the processor 2421 communicates with I/O device 2430a using a local interconnect bus while communicating with I/O device 2430b directly.

A wide variety of I/O devices 2430a-2430n can be present in the computing device 2400. Input devices can include keyboards, mice, trackpads, trackballs, touchpads, touch mice, multi-touch touchpads and touch mice, microphones (analog or MEMS), multi-array microphones, drawing tablets, cameras, single-lens reflex camera (SLR), digital SLR (DSLR), CMOS sensors, CCDs, accelerometers, inertial measurement units, infrared optical sensors, pressure sensors, magnetometer sensors, angular rate sensors, depth sensors, proximity sensors, ambient light sensors, gyroscopic sensors, or other sensors. Output devices can include video displays, graphical displays, speakers, headphones, inkjet printers, laser printers, and 3D printers.

Devices 2430a-2430n can include a combination of multiple input or output devices, including, e.g., Microsoft KINECT, Nintendo Wiimote for the WII, Nintendo WII U GAMEPAD, or Apple IPHONE. Some devices 2430a-2430n allow gesture recognition inputs through combining some of the inputs and outputs. Some devices 2430a-2430n provides for facial recognition which can be utilized as an input for different purposes including authentication and other commands. Some devices 2430a-2430n provides for voice recognition and inputs, including, e.g., Microsoft KINECT, SIRI for IPHONE by Apple, Google Now or Google Voice Search.

Additional devices 2430a-2430n have both input and output capabilities, including, e.g., haptic feedback devices, touchscreen displays, or multi-touch displays. Touchscreen, multi-touch displays, touchpads, touch mice, or other touch sensing devices can use different technologies to sense touch, including, e.g., capacitive, surface capacitive, projected capacitive touch (PCT), in-cell capacitive, resistive, infrared, waveguide, dispersive signal touch (DST), in-cell optical, surface acoustic wave (SAW), bending wave touch (BWT), or force-based sensing technologies. Some multi-touch devices can allow two or more contact points with the surface, allowing advanced functionality including, e.g., pinch, spread, rotate, scroll, or other gestures. Some touchscreen devices, including, e.g., Microsoft PIXELSENSE or Multi-Touch Collaboration Wall, can have larger surfaces, such as on a table-top or on a wall, and can also interact with other electronic devices. Some I/O devices 2430a-2430n, display devices 2424a-2424n or group of devices can be augmented reality devices. The I/O devices can be controlled by an I/O controller 2421 as shown in FIG. 47A. The I/O controller 2421 can control one or more I/O devices, such as, e.g., a keyboard 126 and a pointing device 2427, e.g., a mouse or optical pen. Furthermore, an I/O device can also provide storage and/or an installation medium 116 for the computing device 2400. In still other embodiments, the computing device 2400 can provide USB connections (not shown) to receive handheld USB storage devices. In further embodiments, an I/O device 2430 can be a bridge between the system bus 2450 and an external communication bus, e.g. a USB bus, a SCSI bus, a FireWire bus, an Ethernet bus, a Gigabit Ethernet bus, a Fibre Channel bus, or a Thunderbolt bus.

In some embodiments, display devices 2424a-2424n can be connected to I/O controller 2421. Display devices can include, e.g., liquid crystal displays (LCD), thin film transistor LCD (TFT-LCD), blue phase LCD, electronic papers (e-ink) displays, flexile displays, light emitting diode displays (LED), digital light processing (DLP) displays, liquid crystal on silicon (LCOS) displays, organic light-emitting diode (OLED) displays, active-matrix organic light-emitting diode (AMOLED) displays, liquid crystal laser displays, time-multiplexed optical shutter (TMOS) displays, or 3D displays. Examples of 3D displays can use, e.g. stereoscopy, polarization filters, active shutters, or autostereoscopy. Display devices 2424a-2424n can also be a head-mounted display (HMD). In some embodiments, display devices 2424a-2424n or the corresponding I/O controllers 2423 can be controlled through or have hardware support for OPENGL or DIRECTX API or other graphics libraries.

In some embodiments, the computing device 2400 can include or connect to multiple display devices 2424a-2424n, which each can be of the same or different type and/or form. As such, any of the I/O devices 2430a-2430n and/or the I/O controller 2423 can include any type and/or form of suitable hardware, software, or combination of hardware and software to support, enable or provide for the connection and use of multiple display devices 2424a-2424n by the computing device 2400. For example, the computing device 2400 can include any type and/or form of video adapter, video card, driver, and/or library to interface, communicate, connect or otherwise use the display devices 2424a-2424n. In one embodiment, a video adapter can include multiple connectors to interface to multiple display devices 2424a-2424n. In other embodiments, the computing device 2400 can include multiple video adapters, with each video adapter connected to one or more of the display devices 2424a-2424n. In some embodiments, any portion of the operating system of the computing device 2400 can be configured for using multiple displays 2424a-2424n. In other embodiments, one or more of the display devices 2424a-2424n can be provided by one or more other computing devices 2400a or 2400b connected to the computing device 2400, via the network 140. In some embodiments software can be designed and constructed to use another computer's display device as a second display device 2424a for the computing device 2400. For example, in one embodiment, an Apple iPad can connect to a computing device 2400 and use the display of the device 2400 as an additional display screen that can be used as an extended desktop. One ordinarily skilled in the art can recognize and appreciate the various ways and embodiments that a computing device 2400 can be configured to have multiple display devices 2424a-2424n.

Referring again to FIG. 47A, the computing device 2400 can comprise a storage device 2428 (e.g. one or more hard disk drives or redundant arrays of independent disks) for storing an operating system or other related software, and for storing application software programs such as any program related to the software for the system 100. Examples of storage device 2428 include, e.g., hard disk drive (HDD); optical drive including CD drive, DVD drive, or BLU-RAY drive; solid-state drive (SSD); USB flash drive; or any other device suitable for storing data. Some storage devices can include multiple volatile and non-volatile memories, including, e.g., solid state hybrid drives that combine hard disks with solid state cache. Some storage device 2428 can be non-volatile, mutable, or read-only. Some storage device 2428 can be internal and connect to the computing device 2400 via a bus 2450. Some storage device 2428 can be external and connect to the computing device 2400 via a I/O device 2430 that provides an external bus. Some storage device 2428 can connect to the computing device 2400 via the network interface 2418 over a network, including, e.g., the Remote Disk for MACBOOK AIR by APPLE. Some client devices 2400 may not require a non-volatile storage device 2428 and can be thin clients or zero clients 202. Some storage device 2428 can also be used as an installation device 2416, and can be suitable for installing software and programs. Additionally, the operating system and the software can be run from a bootable medium, for example, a bootable CD, e.g. KNOPPIX, a bootable CD for GNU/Linux that is available as a GNU/Linux distribution from knoppix.net.

Computing device 2400 can also install software or applications from an application distribution platform. Examples of application distribution platforms include the App Store for iOS provided by Apple, Inc., the Mac App Store provided by Apple, Inc., GOOGLE PLAY for Android OS provided by Google Inc., Chrome Webstore for CHROME OS provided by Google Inc., and Amazon Appstore for Android OS and KINDLE FIRE provided by Amazon.com, Inc.

Furthermore, the computing device 2400 can include a network interface 2418 to interface to the network 140 through a variety of connections including, but not limited to, standard telephone lines LAN or WAN links (e.g., 802.11, T1, T3, Gigabit Ethernet, Infiniband), broadband connections (e.g., ISDN, Frame Relay, ATM, Gigabit Ethernet, Ethernet-over-SONET, ADSL, VDSL, BPON, GPON, fiber optical including FiOS), wireless connections, or some combination of any or all of the above. Connections can be established using a variety of communication protocols (e.g., TCP/IP, Ethernet, ARCNET, SONET, SDH, Fiber Distributed Data Interface (FDDI), IEEE 802.11a/b/g/n/ac CDMA, GSM, WiMax and direct asynchronous connections). In one embodiment, the computing device 2400 communicates with other computing devices 2400' via any type and/or form of gateway or tunneling protocol e.g. Secure Socket Layer (SSL) or Transport Layer Security (TLS), or the Citrix Gateway Protocol manufactured by Citrix Systems, Inc. of Ft. Lauderdale, Florida. The network interface 118 can comprise a built-in network adapter, network interface card, PCMCIA network card, EXPRESSCARD network card, card bus network adapter, wireless network adapter, USB network adapter, modem or any other device suitable for interfacing the computing device 2400 to any type of network capable of communication and performing the operations described herein.

A computing device 2400 of the sort depicted in FIG. 47A can operate under the control of an operating system, which controls scheduling of tasks and access to system resources. The computing device 2400 can be running any operating system such as any of the versions of the MICROSOFT WINDOWS operating systems, the different releases of the Unix and Linux operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: WINDOWS 24000, WINDOWS Server 2012, WINDOWS CE, WINDOWS Phone, WINDOWS XP, WINDOWS VISTA, and WINDOWS 24, WINDOWS RT, and WINDOWS 8 all of which are manufactured by Microsoft Corporation of Redmond, Wash.; MAC OS and iOS, manufactured by Apple, Inc. of Cupertino, Calif.; and Linux, a freely-available operating system, e.g. Linux Mint distribution ("distro") or Ubuntu, distributed by Canonical Ltd. of London, United Kingdom; or Unix or other Unix-like derivative operating systems; and Android, designed by Google, of Mountain View, Calif., among others. Some operating systems, including, e.g., the CHROME OS by Google, can be used on zero clients or thin clients, including, e.g., CHROMEBOOKS.

The computer system 2400 can be any workstation, telephone, desktop computer, laptop or notebook computer, netbook, ULTRABOOK, tablet, server, handheld computer, mobile telephone, smartphone or other portable telecommunications device, media playing device, a gaming system, mobile computing device, or any other type and/or form of computing, telecommunications or media device that is capable of communication. The computer system 2400 has sufficient processor power and memory capacity to perform the operations described herein. In some embodiments, the computing device 2400 can have different processors, operating systems, and input devices consistent with the device. The Samsung GALAXY smartphones, e.g., operate under the control of Android operating system developed by Google, Inc. GALAXY smartphones receive input via a touch interface.

In some embodiments, the computing device 2400 is a gaming system. For example, the computer system 2400 can comprise a PLAYSTATION 3, or PERSONAL PLAYSTATION PORTABLE (PSP), or a PLAYSTATION VITA device manufactured by the Sony Corporation of Tokyo, Japan, a NINTENDO DS, NINTENDO 3DS, NINTENDO WII, or a NINTENDO WII U device manufactured by Nintendo Co., Ltd., of Kyoto, Japan, or an XBOX 360 device manufactured by the Microsoft Corporation of Redmond, Wash., or an OCULUS RIFT or OCULUS VR device manufactured by OCULUS VR, LLC of Menlo Park, Calif.

In some embodiments, the computing device 2400 is a digital audio player such as the Apple IPOD, IPOD Touch, and IPOD NANO lines of devices, manufactured by Apple Computer of Cupertino, Calif. Some digital audio players can have other functionality, including, e.g., a gaming system or any functionality made available by an application from a digital application distribution platform. For example, the IPOD Touch can access the Apple App Store. In some embodiments, the computing device 2400 is a portable media player or digital audio player supporting file formats including, but not limited to, MP3, WAV, M4A/AAC, WMA Protected AAC, AIFF, Audible audiobook, Apple Lossless audio file formats and .mov, .m4v, and .mp4 MPEG-4 (H.264/MPEG-4 AVC) video file formats.

In some embodiments, the computing device 2400 is a tablet e.g. the IPAD line of devices by Apple; GALAXY TAB family of devices by Samsung; or KINDLE FIRE, by Amazon.com, Inc. of Seattle, Wash. In other embodiments, the computing device 2400 is an eBook reader, e.g. the KINDLE family of devices by Amazon.com, or NOOK family of devices by Barnes & Noble, Inc. of New York City, N.Y.

In some embodiments, the communications device 2400 includes a combination of devices, e.g. a smartphone combined with a digital audio player or portable media player. For example, one of these embodiments is a smartphone, e.g. the IPHONE family of smartphones manufactured by Apple, Inc.; a Samsung GALAXY family of smartphones manufactured by Samsung, Inc.; or a Motorola DROID family of smartphones. In yet another embodiment, the communications device 2400 is a laptop or desktop computer equipped with a web browser and a microphone and speaker system, e.g. a telephony headset. In these embodiments, the communications devices 2400 are web-enabled and can receive and initiate phone calls. In some embodiments, a laptop or desktop computer is also equipped with a webcam or other video capture device that enables video chat and video call.

In some embodiments, the status of one or more machines 2400 in the network are monitored, generally as part of network management. In one of these embodiments, the status of a machine can include an identification of load information (e.g., the number of processes on the machine, CPU and memory utilization), of port information (e.g., the number of available communication ports and the port addresses), or of session status (e.g., the duration and type of processes, and whether a process is active or idle). In another of these embodiments, this information can be identified by a plurality of metrics, and the plurality of metrics can be applied at least in part towards decisions in load distribution, network traffic management, and network failure recovery as well as any aspects of operations of the present solution described herein. Aspects of the operating environments and components described above can become apparent in the context of the systems and methods disclosed herein.

The scope of the claims should not be limited by the embodiments set forth in the above examples, but should be given the broadest interpretation consistent with the description as a whole.

While this specification contains many specific implementation details, these should not be construed as limitations on the scope of any disclosures or of what can be claimed, but rather as descriptions of features specific to particular embodiments of particular aspects. Certain features described in this specification in the context of separate embodiments can also be implemented in combination in a single embodiment. Conversely, various features described in the context of a single embodiment can also be implemented in multiple embodiments separately or in any suitable subcombination. Moreover, although features can be described above as acting in certain combinations and even initially claimed as such, one or more features from a claimed combination can in some cases be excised from the combination, and the claimed combination can be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing can be advantageous. Moreover, the separation of various system components in the embodiments described above should not be understood as requiring such separation in all embodiments, and it should be understood that the described program components and systems can generally be integrated in a single software product or packaged into multiple software products.

References to "or" may be construed as inclusive so that any terms described using "or" may indicate any of a single, more than one, and all of the described terms. References to at least one of a conjunctive list of terms may be construed as an inclusive OR to indicate any of a single, more than one, and all of the described terms. For example, a reference to "at least one of 'A' and 'B'" can include only 'A', only 'B', as well as both 'A' and 'B'.

Thus, particular embodiments of the subject matter have been described. In some cases, the actions recited in the claims can be performed in a different order and still achieve desirable results. In addition, the processes depicted in the accompanying figures do not necessarily require the particular order shown, or sequential order, to achieve desirable results.

Aspects are set forth within the following claims.

What is claimed is:

1. A method of determining one or more effects induced by an agent if the agent were administered to patients, the method comprising:

determining, by a computing system including one or more processors, based on an atomic structure of the agent, one or more kinetic rates corresponding to one or more states of an ion channel in the presence of the agent;

determining, by the computing system, a channel open probability based on states of pore-forming and voltage sensing domains of the ion channel using agent concentration and agent diffusion rates and the one or more kinetic rates;

determining, by the computing system, using the channel open probability, an action potential characteristic induced by the agent on a cellular level;

determining, by the computing system, a spacial dispersion of an action potential based upon the agent concentration and a tissue composition;

generating, by the computing system, using any combination of (i) the one or more kinetic rates, (ii) the channel open probability, (iii) the action potential characteristic, or (iv) the spacial dispersion, an output indicating a likelihood that the agent induces an organ-level pharmacological effect in patients; and providing, by the computing system, via a network interface or output device of a computing device, the output to a pre-clinical drug screen in a drug safety pipeline.

2. The method of claim 1, wherein determining the channel open probability based on states of pore-forming and voltage sensing domains of the ion channel comprises performing modeling of multiple states of pore-forming and voltage sensing domains.

3. The method of claim 1, wherein determining the action potential characteristic induced by the agent on the cellular level comprises:
   calculating the triangulation of an action potential based upon the agent concentration;
   calculating the temporal dispersion of the action potential based on the agent concentration;
   simulating ventricular myocytes using action potential duration (APD) adaptation curves based on a plurality of agent concentrations to determine reverse use dependent agent effects; and
   determining beat-to-beat instability for a duration of time.

4. The method of claim 1, wherein determining the spacial dispersion comprises performing a one-dimensional simulation to calculate the spacial dispersion of the action potential based upon the agent concentration and the tissue composition.

5. The method of claim 1, wherein determining the spacial dispersion comprises performing a two-dimensional simulation or a three-dimensional simulation.

6. The method of claim 1, further comprising simulating a transmural fiber or tissue.

7. The method of claim 1, further comprising modifying discrete transition rates of ion channels.

8. The method of claim 1, wherein the output indicating a likelihood that the agent induces the particular effect includes a likelihood score.

9. The method of claim 1, wherein the one or more ion channels is a cardiac ion channel, a hERG channel, or one of a Potassium ion channel, a Sodium ion channel or a Calcium ion channel.

10. The method of claim 1, wherein the agent is an agent that blocks hERG and prolongs a QT interval and does not cause Torsades de pointes (TdP) or other arrhythmia.

11. The method of claim 1, wherein the agent is a drug, an antibody, a small molecule agent, or a pharmaceutical composition.

\* \* \* \* \*